US009745296B2

(12) United States Patent
Flynn et al.

(10) Patent No.: US 9,745,296 B2
(45) Date of Patent: Aug. 29, 2017

(54) SALTS, CO-CRYSTALS, AND POLYMORPHS OF AN ANXIOLYTIC COMPOUND

(71) Applicants: Bionomics Limited, Thebarton, South Australia (AU); Ironwood Pharmaceuticals, Inc., Cambridge, MA (US)

(72) Inventors: Bernard Luke Flynn, Donvale (AU); Dharam Paul, Flinders Park (AU); Andrew John Harvey, Goodwood (AU); Vasu V. Sethuraman, Waltham, MA (US); Raymond E. Forslund, Natick, MA (US); Song Xue, Newton, MA (US); Rob Livingston, Cambridge, MA (US); Ahmad Hashash, Cambridge, MA (US)

(73) Assignees: BIONOMICS LIMITED, Thebarton, South Australia (AU); IRONWOOD PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/776,643

(22) PCT Filed: Mar. 14, 2014

(86) PCT No.: PCT/AU2014/000272
§ 371 (c)(1),
(2) Date: Sep. 14, 2015

(87) PCT Pub. No.: WO2014/138812
PCT Pub. Date: Sep. 18, 2014

(65) Prior Publication Data
US 2016/0185770 A1    Jun. 30, 2016

Related U.S. Application Data

(60) Provisional application No. 61/798,926, filed on Mar. 15, 2013.

(51) Int. Cl.
*C07D 471/04* (2006.01)
*A61K 31/4375* (2006.01)
*C07C 55/10* (2006.01)

(52) U.S. Cl.
CPC ............ *C07D 471/04* (2013.01); *C07C 55/10* (2013.01)

(58) Field of Classification Search
CPC ................ C07D 471/04; C07D 413/06; C07C 2102/08; A61K 31/5375; A61K 31/4375
USPC ................ 544/127; 514/234.5, 300; 546/122
See application file for complete search history.

(56) References Cited

FOREIGN PATENT DOCUMENTS

| WO | WO 2008/046135 A1 | 4/2008 |
| WO | WO2012/116410 A1 | 9/2012 |
| WO | WO 2012/151640 A1 | 11/2012 |

*Primary Examiner* — Alicia L Otton
*Assistant Examiner* — Sagar Patel
(74) *Attorney, Agent, or Firm* — Knobbe, Martens, Olson & Bear, LLP

(57) ABSTRACT

The present invention provides amorphous arid crystalline forms of 1-ethyl-6-(indan-2-ylamino)-3-(morpholine-4-carbonyl)-1,8-naphthyridin-4-one (compound 1), and salts, co-crystals, and pharmaceutical compositions thereof. The invention also provides methods of treating and/or preventing a disease, such as a central nervous system disease (e.g., an anxiety disorder), using the amorphous and crystalline forms, and salts, co-crystals, and pharmaceutical compositions thereof.

15 Claims, 89 Drawing Sheets

SALTS, CO-CRYSTALS, AND POLYMORPHS OF AN ANXIOLYTIC COMPOUND

BACKGROUND OF THE INVENTION

U.S. Pat. No. 8,293,737, the entirety of which is incorporated herein by reference, describes certain 1,8-naphthyridin-4(1H)-one compounds which are useful as anxiolytic agents. Such compounds include 1-ethyl-6-(indan-2-ylamino)-3-(morpholine-4-carbonyl)-1,8-naphthyridin-4-one (compound 1).

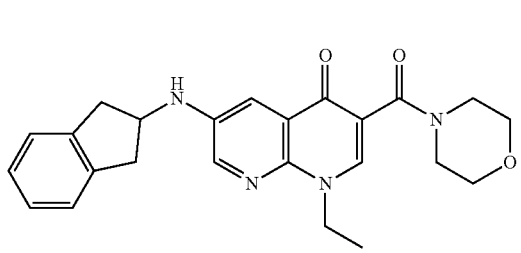

Compound 1 possesses anxiolytic activity without sedative side effects and therefore represents an attractive alternative to the 1,4-benzodiazepine class of anxiolytics such as diazepam.

SUMMARY OF THE INVENTION

It has now been found that salt forms and polymorphs described herein, and compositions thereof, are useful as therapeutic agents and in the preparation of pharmaceutical compositions and exhibit desirable characteristics for such purposes. In general, these salt forms and polymorphs, and pharmaceutically acceptable compositions thereof, are useful for treating or lessening the severity of a variety of diseases or disorders described herein (e.g., an anxiety disorder).

Provided herein are various crystalline forms of compound 1. In some embodiments, the crystalline form of compound 1 is substantially anhydrous. In some embodiments, the crystalline form of compound 1 is a solvate (e.g., a hydrate). In some embodiments, the crystalline form of compound 1 is a hydrate. In some embodiments, the crystalline form of compound 1 is Form C in some embodiments, the crystalline from of compound 1 is Form D in some embodiments, the crystalline form of compound 1 is Form B in some embodiments, the crystalline form of compound 1 is Form F. In some embodiments, the crystalline form of compound 1 is Form G. In some embodiments, the crystalline form of compound 1 is Form H. In some embodiments, the crystalline form of compound 1 is Form I. In some embodiments, the crystalline form of compound 1 is Form J. In some embodiments, the crystalline form of compound 1 is Form K. In some embodiments, the crystalline form of compound 1 is Form L. In some embodiments, the crystalline form of compound 1 is Form M.

In some embodiments, provided herein is a pharmaceutically acceptable salt of compound 1, wherein the pharmaceutically acceptable salt is an acid addition salt. In some embodiments, the salt is amorphous. In some embodiments, the salt is crystalline. In some embodiments, the salt is substantially anhydrous. In some embodiments, the salt is a solvate (e.g., a hydrate). In some embodiments, provided herein are fumarate, L-malate, D-malate, succinate, maleate, thiocyanate, oxalate, benzoate, 2-oxoglutarate, and tartrate salts of compound 1. In some embodiments, provided herein are fumaric acid, L-malic acid, D-malic acid, succinic acid, maleic acid, hydrogen thiocyanate, oxalic acid, benzoic acid, 2-oxoglutaric acid, and tartaric acid co-crystals of compound 1.

In another aspect, the present invention provides additional solid forms, such as Form FUM-P3, Form FUM-P4, Form MLA-P3, Form MLA-P4, Form SUC-P3, Form SUC-P4, Form SUC-P5, Form MLE-P4, and Form MLE-P6. In some embodiments, Form FUM-P3 is a fumarate salt of compound 1. In some embodiments, Form FUM-P4 is a fumarate salt of compound 1. In some embodiments, Form FUM-P5 is a fumarate salt of compound 1. In some embodiments, Form MLA-P3 is an L-malate salt of compound 1. In some embodiments, Form MLA-P4 is an L-malate salt of compound 1. In some embodiments, Form SUC-P3 is a succinate salt of compound 1. In some embodiments, Form SUC-P4 is a succinate salt of compound 1. In some embodiments, Form MLE-P4 is a maleate salt of compound 1. In some embodiments, Form MLE-P6 is a maleate salt of compound 1.

The present invention also provides co-crystals formed from compound 1 and an additional compound. In certain embodiments, the co-crystal is a complex of compound 1 and the additional compound. In certain embodiments, the additional compound is a coformer, such as a solvent and an additional pharmaceutical agent (e.g., an additional therapeutic or prophylactic agent described herein). In some embodiments, Form FUM-P3 is a co-crystal of compound 1 and an additional compound. In some embodiments, Form FUM-P4 is a co-crystal of compound 1 and an additional compound. In some embodiments, Form MLA-P3 is a co-crystal of compound 1 and an additional compound. In some embodiments, Form MLA-P4 is a co-crystal of compound 1 and an additional compound. In some embodiments, Form SUC-P3 is a co-crystal of compound 1 and an additional compound. In some embodiments, Form SUC-P4 is a co-crystal of compound 1 and an additional compound. In some embodiments, Form SUC-P5 is a co-crystal of compound 1 and an additional compound. In some embodiments, Form MLE-P4 is a co-crystal of compound 1 and an additional compound. In some embodiments, Form MLE-P6 is a co-crystal of compound 1 and an additional compound.

The present invention also provides amorphous forms of compound 1. In certain embodiments, the amorphous form is Form A.

In some embodiments, provided herein are pharmaceutical compositions comprising a crystalline form of compound 1 and optionally an additional ingredient selected from pharmaceutically acceptable carriers, diluents, and excipients. In some embodiments, the pharmaceutical composition comprises Form C of compound 1. In some embodiments, the pharmaceutical composition comprises Form D of compound 1. In some embodiments, the pharmaceutical composition comprises Form E of compound 1. In some embodiments, the pharmaceutical composition comprises Form F of compound 1. In some embodiments, the pharmaceutical composition comprises Form G of compound 1. In some embodiments, the pharmaceutical composition comprises Form H of compound 1. In some embodiments, the pharmaceutical composition comprises Form I of compound 1. In some embodiments, the pharmaceutical composition comprises Form J of compound 1. In some embodiments, the pharmaceutical composition comprises Form K of compound 1. In some embodiments, the pharmaceutical composition comprises Form L of compound 1. In some embodiments, the pharmaceutical composition comprises Form M of compound 1. In some embodiments, provided herein is a pharmaceutical composition comprising a fumarate, L-malate, D-malate, succinate, maleate, thiocyanate, oxalate, benzoate, 2-oxoglutarate, or tartrate salt of compound 1, and optionally an additional ingredient selected from pharmaceutically acceptable carriers, diluents, and excipients. In some embodiments, the pharmaceutical composition comprises Form FUM-P3. In some embodiments, the pharmaceutical composition includes Form FUM-P4. In some embodiments, the pharmaceutical composition comprises Form MLA-P4. In some embodiments, the pharmaceutical composition comprises Form SUC-P3. In some embodiments, the pharmaceutical composition comprises Form MLE-P4. In some embodiments, the pharmaceutical composition comprises Form MLE-P6.

In some embodiments, provided herein are pharmaceutical compositions comprising an amorphous form of compound 1 and optionally an additional ingredient selected from pharmaceutically acceptable carriers, diluents, and excipients. In some embodiments, the pharmaceutical composition comprises Form A.

Also provided herein are methods of preventing and/or treating various diseases, disorders, or conditions comprising administering to a subject a pharmaceutical composition described herein. Pharmaceutical compositions and uses described herein comprises one or more of the polymorphs (e.g., Form C to Form M) or salts (e.g., fumarate, L-malate, D-malate, succinate, maleate, thiocyanate, oxalate, benzoate, 2-oxoglutarate, or tartrate salt) of Compound 1 described herein.

Definitions

The following definitions are more general terms used throughout the present application:

The term "solvate" refers to forms of a compound (e.g., compound 1) that are associated with a solvent, usually by a solvolysis reaction. This physical association may include hydrogen bonding. Conventional solvents include water, methanol, ethanol, acetic acid, DMSO, THF, diethyl ether, and the like. In certain embodiments, solvates are formed using Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). A compound may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate," refers to a compound (e.g., compound 1) which is associated with water. Typically, the number of the water molecules contained in a hydrate of a compound is in a definite ratio to the number of the compound molecules in the hydrate. Hydrates include both stoichiometric hydrates and non-stoichiometric hydrates. Therefore, a hydrate of a compound may be represented, for example, by the general formula $R.xH_2O$, wherein R is the compound and wherein x is a number greater than 0. A given compound may form more than one type of hydrates, including, e.g., monohydrates (stoichiometric, x is 1), lower hydrates (non-stoichiometric, x is a number greater than 0 and smaller than 1, e.g., hemihydrates ($R.0.5H_2O$)), and polyhydrates (non-stoichiometric, x is a number greater than 1, e.g., dihydrates ($R.2H_2O$) and hexahydrates ($R.6H_2O$)).

It is also to be understood that compounds that have the same molecular formula but differ in the nature or sequence of bonding of their atoms or the arrangement of their atoms in space are termed "isomers".

The term "polymorphs" refers to a crystalline form of a compound (e.g., compound 1), or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystalline form to dominate. Various polymorphs of a compound, or a salt, hydrate, or solvate thereof, can be prepared by crystallization under different conditions.

As used herein "co-crystals" consist of two or more components that form a unique crystalline structure having unique properties. The only difference between a crystalline salt and a co-crystal lies in the transfer of a proton. The transfer of protons from one component to another in a crystal is dependent on the environment. For this reason, crystalline salts and co-crystals may be thought of as two ends of a proton transfer spectrum, where the salt has completed the proton transfer at one end and an absence of proton transfer exists for co-crystals at the other end.

As used herein, the term "impurity" refers to extraneous matter included in a compound (e.g., compound 1), or a pharmaceutically acceptable salt, solvate, hydrate, tautomer, or polymorph thereof. Extraneous matter includes one or more substances that are different from the compound, or the pharmaceutically acceptable salt, solvate, hydrate, tautomer, or polymorph thereof. In certain embodiments, the extraneous matter is undesired extraneous matter. For example, when an anhydrous compound is desired, the solvent (e.g., water) included in the compound is an impurity. When a crystalline compound is desired, an amorphous form of the compound included in the compound is an impurity. When certain polymorph of a compound is desired, a different polymorph of the compound included in the compound is an impurity. The term "substantially free of impurities" means that a compound (e.g., compound 1), or a pharmaceutically acceptable salt, solvate, hydrate, tautomer, or polymorph thereof, contains no significant amount of extraneous matter (e.g., undesired extraneous matter). What amount of the extraneous matter constitutes a significant amount depends on the subject matter and is understood in the art. In certain embodiments, about 1 wt %, about 2 wt %, about 3 wt %, about 5 wt %, about 7 wt %, or about 10 wt % of extraneous matter in a compound, or a pharmaceutically acceptable salt, solvate, hydrate, tautomer, or polymorph thereof, is a significant amount of extraneous matter.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is fish.

The terms "administer," "administering," or "administration," as used herein, refers to implanting, absorbing, ingesting, injecting, inhaling, or otherwise introducing a compound, or a pharmaceutically acceptable salt, solvate, hydrate, tautomer, polymorph, or pharmaceutical composition thereof, in or on a subject.

As used herein, the terms "in combination" and "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms. Treatment may also be continued after symptoms have resolved, for example, to delay or prevent recurrence.

The terms "prevention," "prevent," and "preventing," as used herein, refer to administering a medicament (e.g., compound 1, or a pharmaceutically acceptable salt, solvate, hydrate, tautomer, polymorph, or pharmaceutical composition thereof) beforehand to avert or forestall the appearance of one or more symptoms of a disease or disorder. The person of ordinary skill in the medical art recognizes that the terms "prevention," "prevent," and "preventing" are not absolute terms. In the medical art these terms are understood to refer to the prophylactic administration of a medicament to substantially diminish the likelihood or seriousness of a condition, or symptom of the condition, and this is the sense intended in this disclosure.

As used herein, the terms "condition," "disease," and "disorder" are used interchangeably.

An "effective amount" of a compound described herein refers to an amount sufficient to elicit the desired biological response, e.g., treating a condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating an anxiety disorder, an effective amount of an inventive compound may provide a therapeutic and/or prophylactic benefit in the treatment and/or prevention of the anxiety disorder or to delay or minimize one or more symptoms associated with the anxiety disorder.

A "therapeutically effective amount" of a compound described herein is an amount sufficient to provide a therapeutic benefit in the treatment of a condition (e.g., an anxiety disorder) or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound described herein is an amount sufficient to prevent a condition (e.g., an anxiety disorder), or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neurite" refers to any projection from the cell body of a neuron. This projection can be either an axon or a dendrite. Neurites are often packed with microtubule bundles, the growth of which is stimulated by Nerve Growth Factor (NGF), as well as tau proteins, MAP1, and MAP2. The neural cell adhesion molecule N-CAM simultaneously combines with another N-CAM and a fibroblast growth factor receptor to stimulate the tyrosine kinase activity of that receptor to induce the growth of neurites.

A disease"responsive to neurite outgrowth" is a disease, disorder, or condition which may be ameliorated by enhancement of neurite outgrowth. Diseases responsive to neurite outgrowth include neurodegenerative diseases (e.g., multiple sclerosis and a Parkinsonian related disorder) and diseases that involve neural damage that include wound healing, spinal cord injury, and peripheral nerve disorders.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

DETAILED DESCRIPTION OF CERTAIN EMBODIMENTS

Figure 1:
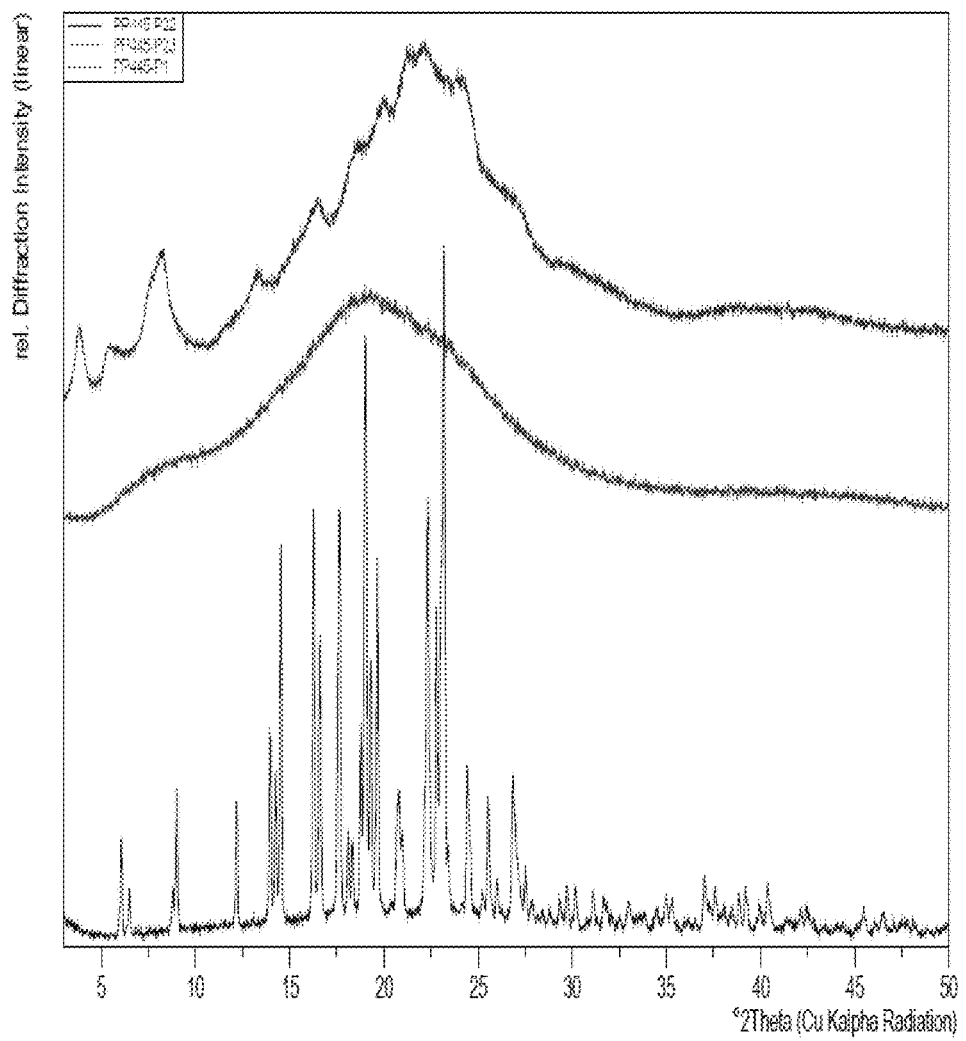
FIG. 1 depicts an X-Ray Powder Diffraction (XRPD) pattern of Form A (middle curve).

Compound 1 (1-ethyl-6-(indan-2-ylamino)-3-(morpholine-4-carbonyl)-1,8-naphthyridin-4-one) has been reported to elicit an anxiolytic effect. Compound 1 has shown significant potential for the treatment of a variety of disorders of the central nervous system (CNS), such as anxiety disorders. See, e.g., U.S. Pat. No. 8,293,737.

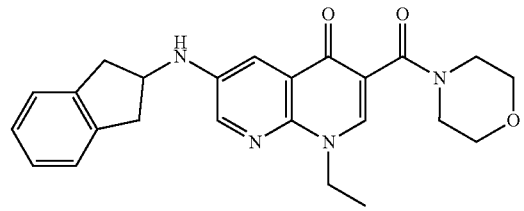

In some embodiments, it would be desirable to provide a crystalline polymorph of compound 1 that, as compared to the amorphous compound 1, imparts improved physical characteristics such as improved aqueous solubility, stability, and/or ease of formulation. Accordingly, provided herein are various crystalline forms of compound 1.

In some embodiments, a provided crystalline form of compound 1 is substantially anhydrous. In some embodiments, a provided crystalline form of compound 1 is a hydrate. In some embodiments, a provided crystalline form of compound 1 is a hemihydrate. In some embodiments, a provided crystalline form of compound 1 is a non-stoichiometric hydrate. In some embodiments, a provided crystalline form of compound 1 is a solvate. In some embodiments, a provided crystalline form of compound 1 is a hemisolvate. In some embodiments, a provided crystalline form of compound 1 is a non-stoichiometric solvate.

In some embodiments, it would be desirable to provide a salt form of compound 1 that, as compared to compound 1, imparts characteristics such as improved aqueous solubility, stability, and ease of formulation. Accordingly, the present disclosure also provides salts of compound 1. In certain embodiments, a provided salt of compound 1 is an acid addition salt. Also provided herein are crystalline polymorphs of certain acid addition salts of compound 1. Also provided herein are amorphous forms of compound 1 (such as amorphous Form A) and amorphous forms of certain acid addition salts of compound 1.

In certain embodiments, the present disclosure provides a fumarate salt of compound 1. In certain embodiments, the present disclosure provides an L-malate salt of compound 1. In certain embodiments, the present disclosure provides an D-malate salt of compound 1. In certain embodiments, the present disclosure provides a succinate salt of compound 1. In certain embodiments, the present disclosure provides a maleate salt of compound 1. In certain embodiments, the present disclosure provides a thiocyanate salt of compound 1. In certain embodiments, the present disclosure provides an oxalate salt of compound 1. In certain embodiments, the present disclosure provides a benzoate salt of compound 1. In certain embodiments, the present disclosure provides a 2-oxoglutarate salt of compound 1. In certain embodiments, the present disclosure provides a tartrate salt of compound 1.

It will be appreciated by one of ordinary skill in the art that the acid (e.g., fumaric acid, L-malic acid, D-malic acid, succinic acid, maleic acid, thiocyanic acid, oxalic acid, benzoic acid, or 2-oxoglutaric acid) and compound 1 are ionically bonded to form an acid addition salt. It will also be appreciated that various stoichiometries of compound 1 to a provided acid are possible. It is contemplated that salts of compound 1 can exist in a variety of physical forms. For example, a salt of compound 1 (e.g., a fumarate, L-malate, D-malate, succinate, maleate, thiocyanate, oxalate, benzoate, 2-oxoglutarate, or tartrate salt) can be in solution, suspension, or in solid form. In certain embodiments, a salt of compound 1 (e.g., a fumarate, L-malate, D-malate, succinate, maleate, thiocyanate, oxalate, benzoate, 2-oxoglutarate, or tartrate salt) is in solid form. When a salt of compound 1 (e.g., a fumarate, L-malate, D-malate, succinate, maleate, thiocyanate, oxalate, benzoate, 2-oxoglutarate, or tartrate salt) is in solid form, said compound may be amorphous, crystalline, or a mixture thereof. A solid form of a salt of compound 1 (e.g., a fumarate, L-malate, D-malate, succinate, maleate, thiocyanate, oxalate, benzoate, 2-oxoglutarate, or tartrate salt) may exist in neat (non-solvated) form, or as a solvate (e.g., a hydrate). Exemplary solid forms are described in more detail below.

In certain embodiments, the present invention provides compound 1, or a fumarate, L-malate, D-malate, succinate, maleate, thiocyanate, oxalate, benzoate, 2-oxoglutarate, or tartrate salt thereof, substantially free of impurities. Such extraneous matter may include excess salt forming acid, excess compound 1, residual solvents, or any other impurities that may result from the preparation, and/or isolation, of compound 1, or a fumarate, L-malate, D-malate, succinate, maleate, thiocyanate, oxalate, benzoate, 2-oxoglutarate, or tartrate salt thereof. In certain embodiments, at least about 95% by weight of compound 1 is present. In certain embodiments, at least about 95% by weight of a fumarate, L-malate, D-malate, succinate, maleate, thiocyanate, oxalate, benzoate, 2-oxoglutarate, or tartrate salt of compound 1 is present. In certain embodiments, at least about 99% by weight of compound 1 is present. In certain embodiments, at least about 99% by weight of a fumarate, L-malate, D-malate, succinate, maleate, thiocyanate, oxalate, benzoate, 2-oxoglutarate, or tartrate salt of compound 1 is present.

In certain embodiments, compound 1 is present in an amount of at least about 97, 97.5, 98, 98.5, 99, 99.5, 99.8 weight percent where the percentages are based on the total weight of the composition. In certain embodiments, a fumarate, L-malate, D-malate, succinate, maleate, thiocyanate, oxalate, benzoate, 2-oxoglutarate, or tartrate salt of compound 1 is present in an amount of at least about 97, 97.5, 98, 98.5, 99, 99.5, 99.8 weight percent where the percentages are based on the total weight of the composition. In certain embodiments, compound 1 contains no more than about 3.0 area percent HPLC of total organic impurities and, in certain embodiments, no more than about 1.5 area percent HPLC total organic impurities relative to the total area of the HPLC chromatogram. In certain embodiments, a fumarate, L-malate, D-malate, succinate, maleate, thiocyanate, oxalate, benzoate, 2-oxoglutarate, or tartrate salt of compound 1 contains no more than about 3.0 area percent HPLC of total organic impurities and, in certain embodiments, no more than about 1.5 area percent HPLC total organic impurities relative to the total area of the HPLC chromatogram. In other embodiments, compound 1 contains no more than about 1.0 area percent HPLC of any single impurity, and, in certain embodiments, no more than about 0.6 area percent HPLC of any single impurity, and, in certain embodiments, no more than about 0.5 area percent HPLC of any single impurity, relative to the total area of the HPLC chromatogram. In other embodiments, a fumarate, L-malate, D-malate, succinate, maleate, thiocyanate, oxalate, benzoate, 2-oxoglutarate, or tartrate salt of compound 1 contains no more than about 1.0 area percent HPLC of any single impurity, and, in certain embodiments, no more than about 0.6 area percent HPLC of any single impurity, and, in certain embodiments, no more than about 0.5 area percent HPLC of any single impurity, relative to the total area of the HPLC chromatogram.

The structure depicted for compound 1, or a salt thereof, are also meant to include all tautomeric forms of compound 1 or salts thereof. Additionally, structures depicted herein are also meant to include compounds that differ only in the presence of one or more isotopically enriched atoms. For example, compounds having the structure of compound 1, or a fumarate, L-malate, D-malate, succinate, maleate, thiocyanate, oxalate, benzoate, 2-oxoglutarate, or tartrate salt thereof, except for the replacement of hydrogen by deuterium or tritium, or the replacement of a carbon by a $^{13}$C- or $^{14}$C-enriched carbon are within the scope of the present invention.

Solid Forms

Compound 1, or a fumarate, L-malate, D-malate, succinate, maleate, thiocyanate, oxalate, benzoate, 2-oxoglutarate, or tartrate salt thereof, has been found to exist in a variety of solid forms. Such forms include polymorphs, solvates, hydrates, and amorphous forms. All such forms are contemplated herein. In certain embodiments, the present invention provides compound 1 as a composition of one or more solid forms selected from polymorphs, solvates, hydrates, and amorphous forms of compound 1. In certain embodiments, the present invention provides a fumarate salt of compound 1 as a composition of one or more solid forms selected from polymorphs, solvates, hydrates, and amorphous forms of a fumarate salt of compound 1. In certain embodiments, the present invention provides an L-malate salt of compound 1 as a composition of one or more solid forms selected from polymorphs, solvates, hydrates, and amorphous forms of an L-malate salt of compound 1. In certain embodiments, the present invention provides an D-malate salt of compound 1 as a composition of one or more solid forms selected from polymorphs, solvates, hydrates, and amorphous forms of a D-malate salt of compound 1. In certain embodiments, the present invention provides a succinate salt of compound 1 as a composition of one or more solid forms selected from polymorphs, solvates, hydrates, and amorphous forms of a succinate salt of compound 1. In certain embodiments, the present invention provides a maleate salt of compound 1 as a composition of one or more solid forms selected from polymorphs, solvates, hydrates, and amorphous forms of a maleate salt of compound 1. In certain embodiments, the present invention provides a thiocyanate salt of compound 1 as a composition of one or more solid forms selected from polymorphs, solvates, hydrates, and amorphous forms of a thiocyanate salt of compound 1. In certain embodiments, the present invention provides an oxalate salt of compound 1 as a composition of one or more solid forms selected from polymorphs, solvates, hydrates, and amorphous forms of an oxalate salt of compound 1. In certain embodiments, the present invention provides a benzoate salt of compound 1 as a composition of one or more solid forms selected from polymorphs, solvates, hydrates, and amorphous forms of a benzoate salt of compound 1. In certain embodiments, the present invention provides a 2-oxoglutarate salt of compound 1 as a composition of one or more solid forms selected from polymorphs, solvates, hydrates, and amorphous forms of a 2-oxoglutarate salt of compound 1. In certain embodiments, the present invention provides a tartrate salt of compound 1 as a composition of one or more solid forms selected from polymorphs, solvates, hydrates, and amorphous forms of a tartrate salt of compound 1.

Different solid forms of a compound typically differ in their physical and chemical properties based on the arrangement of the molecules in the solid form (e.g., the arrangement of the molecule in the crystal lattice). A given substance may give rise to a variety of solid forms, in particular a variety of crystalline forms, wherein each form has different and distinct physical and chemical properties, such as solubility profiles, thermodynamic and chemical stabilities, melting points, Raman spectra, and/or x-ray diffraction peaks.

Different solid forms of a compound can be typically distinguished by X-ray diffraction, in particular X-ray powder diffraction (XRPD) and by other methods, such as, for example, differential scanning calorimetry (DSC), infrared spectroscopy, and/or Raman spectroscopy.

Form A

Compound 1 may be present in an amorphous solid form. Amorphous solids are well known to those of ordinary skill in the art and are typically prepared by such methods as lyophilization, melting, and precipitation from supercritical fluid, among others. In some embodiments, the present invention provides an amorphous form of compound 1 referred to herein as amorphous Form A (Form A). In certain embodiments, Form A is substantially free of impurities. In certain embodiments, Form A is 99% free of impurities by weight. In certain embodiments, Form A is 97% free of impurities by weight. In certain embodiments, Form A is 95% free of impurities by weight. In certain embodiments, Form A is substantially free of crystalline compound 1. In certain embodiments, Form A is substantially free of a salt of compound 1. In certain embodiments, Form A is substantially free of a solvate of compound 1. In certain embodiments, amorphous Form A is substantially anhydrous. In certain embodiments, Form A comprises at least about 95% by weight of amorphous compound 1. In certain embodiments, Form A comprises at least about 97% by weight of amorphous compound 1. In certain embodiments, Form A comprises at least about 99% by weight of amorphous compound 1.

Form A can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In certain embodiments, Form A is characterized by an X-ray powder diffraction pattern substantially similar to the one depicted in FIG. 1. In certain embodiments, Form A is characterized by a Raman spectrum substantially similar to the one depicted in FIG. 2.

In certain embodiments, Form A has an observed melting point of about 148-156° C.

In certain embodiments, Form A is obtained from quench cooling of melt. In certain embodiments, Form A is obtained from fast evaporation from a halogenated hydrocarbon solvent (e.g., dichloromethane (DCM)).

Form C

Compound 1 may also be present in a solid crystalline form. In certain embodiments, compound 1 is present as a crystalline solid substantially free of amorphous compound 1. In certain embodiments, at least 95% by weight of crystalline compound 1 is present. In certain embodiments, at least 99% by weight of crystalline compound 1 is present.

In certain embodiments, compound 1 is a neat crystal form and thus does not have any water or solvent incorporated into the crystal structure. It has been found that compound 1 can exist in at least two distinct neat (i.e., anhydrous) crystalline forms, i.e., Form C and Form D. In some embodiments, the present invention provides a polymorphic form of compound 1 referred to herein as Form C.

In certain embodiments, Form C is substantially free of impurities. In certain embodiments, Form C is 99% free of impurities by weight. In certain embodiments, Form C is 97% free of impurities by weight. In certain embodiments, Form C is 95% free of impurities by weight. In certain embodiments, Form C is substantially free of amorphous compound 1. In certain embodiments, Form C is substantially free of other crystalline forms of compound 1. In certain embodiments, Form C is substantially free of a salt of compound 1. Form C is not a solvate or hydrate of compound 1.

Form C can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form C of compound 1 is characterized by an X-ray powder diffraction pattern substantially similar to the one depicted in FIG. 3. In some embodiments, Form C of compound 1 is characterized in that it has one or more peaks in its X-ray powder diffraction pattern selected from those in Table 2. In some embodiments, Form C of compound 1 is characterized by at least one, at least two, at least three, at least four, at least five, at least six, at least seven, at least eight, at least nine, at least ten, at least eleven, at least twelve, at least thirteen, at least fourteen, at least fifteen, or at least sixteen peaks in its X-ray powder diffraction pattern selected from those in Table 2. In some embodiments, Form C of compound 1 is characterized in that it has one or more peaks in its X-ray powder diffraction pattern selected from the strong and very strong peaks in Table 2.

TABLE 2

X-ray powder diffraction pattern of Form C.

| Angle 2-Theta ° | d value Angstrom | Intensity (relative) | Intensity % |
|---|---|---|---|
| 4.05 | 21.8 | w | 15 |
| 5.89 | 15.0 | s | 37 |

TABLE 2-continued

X-ray powder diffraction pattern of Form C.

| Angle 2-Theta ° | d value Angstrom | Intensity (relative) | Intensity % |
|---|---|---|---|
| 8.33 | 10.6 | s | 41 |
| 9.33 | 9.5 | s | 40 |
| 11.82 | 7.5 | m | 26 |
| 12.53 | 7.1 | w | 13 |
| 15.09 | 5.86 | vs | 100 |
| 17.29 | 5.12 | s | 49 |
| 17.78 | 4.99 | w | 14 |
| 18.75 | 4.73 | m | 27 |
| 20.97 | 4.23 | w | 15 |
| 21.44 | 4.14 | w | 14 |
| 22.04 | 4.03 | w | 14 |
| 4.05 | 21.8 | w | 15 |
| 22.66 | 3.92 | m | 17 |
| 26.69 | 3.34 | w | 12 |
| 27.11 | 3.29 | w | 14 |

The terms used in the tables with XRPD data herein have the following meanings: The term "vs" stands for "very strong." The term "s" stands for "strong." The term "m" stands for "medium." The term "w" stands for "weak." The term "vw" stands for "very weak."

In some embodiments, Form C of compound 1 is characterized by one or more peaks in its X-ray powder diffraction pattern selected from those in Table 3. In some embodiments, Form C of compound 1 is characterized by at least one, at least two, at least three, at least four, at least five, or at least six peaks in its X-ray powder diffraction pattern selected from those in Table 3.

TABLE 3

Select characteristic peaks of the X-ray powder diffraction pattern of Form C.

| Angle 2-Theta ° | d value Angstrom | Intensity (relative) | Intensity % |
|---|---|---|---|
| 8.33 | 10.6 | s | 41 |
| 9.33 | 9.5 | s | 40 |
| 11.82 | 7.5 | m | 26 |
| 15.09 | 5.86 | vs | 100 |
| 17.29 | 5.12 | s | 49 |
| 18.75 | 4.73 | m | 27 |

Figure 4:
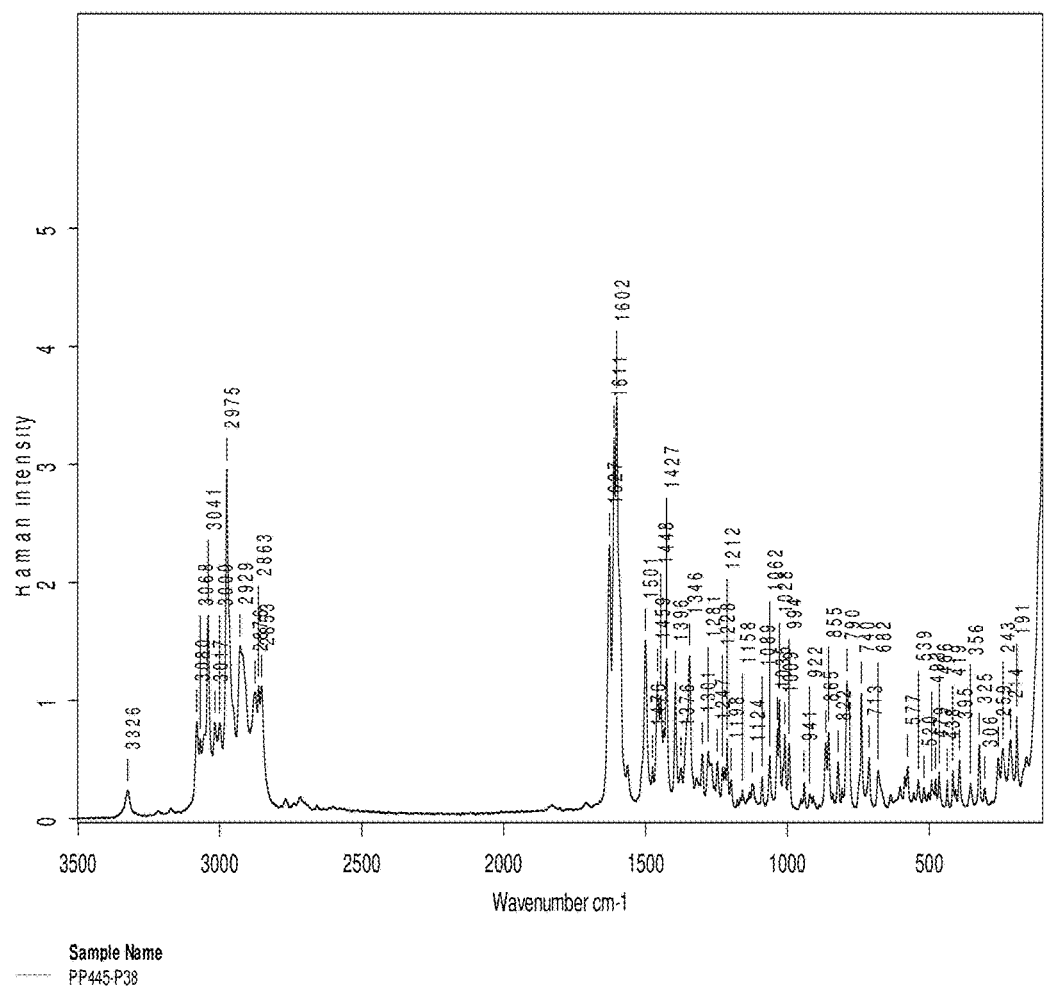
FIG. 4 depicts an FT-Raman spectrum of Form C.

In some embodiments, Form C of compound 1 is characterized by a Raman spectrum substantially similar to the one depicted in FIG. 4. In some embodiments, Form C of compound 1 is characterized by one or more peaks in its Raman spectrum selected from those in Table 4. In some embodiments, Form C of compound 1 is characterized by having a Raman spectrum with characteristic peaks at about those in Table 4.

TABLE 4

Raman spectrum of Form C.

| Wavenumber (cm$^{-1}$) | Absolute Intensity | Normalized Intensity (%) |
|---|---|---|
| 3326 | 0.236 | 6.6 |
| 3080 | 0.816 | 22.8 |
| 3068 | 0.675 | 18.9 |
| 3041 | 1.734 | 48.5 |
| 3017 | 0.812 | 22.7 |
| 3000 | 0.810 | 22.7 |
| 2975 | 2.952 | 82.6 |
| 2929 | 1.466 | 41.0 |
| 2876 | 1.069 | 29.9 |
| 2863 | 1.127 | 31.6 |
| 2853 | 1.119 | 31.3 |
| 1627 | 2.316 | 64.8 |
| 1611 | 3.220 | 90.1 |
| 1602 | 3.572 | 100.0 |
| 1501 | 1.513 | 42.4 |
| 1476 | 0.435 | 12.2 |
| 1459 | 1.170 | 32.8 |
| 1448 | 1.046 | 29.3 |
| 1427 | 1.357 | 38.0 |
| 1396 | 1.153 | 32.3 |
| 1376 | 0.431 | 12.1 |
| 1346 | 1.383 | 38.7 |
| 1301 | 0.548 | 15.3 |
| 1281 | 0.569 | 15.9 |
| 1247 | 0.484 | 13.5 |
| 1228 | 0.438 | 12.3 |
| 1212 | 0.670 | 18.8 |
| 1198 | 0.325 | 9.1 |
| 1158 | 0.241 | 6.7 |
| 1124 | 0.301 | 8.4 |
| 1089 | 0.355 | 9.9 |
| 1062 | 0.531 | 14.9 |
| 1035 | 0.753 | 21.1 |
| 1028 | 1.016 | 28.4 |
| 1009 | 0.714 | 20.0 |
| 994 | 0.639 | 17.9 |
| 941 | 0.307 | 8.6 |
| 922 | 0.210 | 5.9 |
| 865 | 0.642 | 18.0 |
| 855 | 0.732 | 20.5 |
| 822 | 0.479 | 13.4 |
| 790 | 1.165 | 32.6 |
| 739 | 1.061 | 29.7 |
| 713 | 0.519 | 14.5 |
| 682 | 0.412 | 11.5 |
| 577 | 0.442 | 12.4 |
| 539 | 0.330 | 9.2 |
| 520 | 0.261 | 7.3 |
| 493 | 0.321 | 9.0 |
| 479 | 0.335 | 9.4 |
| 466 | 0.386 | 10.8 |
| 438 | 0.320 | 9.0 |
| 418 | 0.405 | 11.3 |
| 395 | 0.494 | 13.8 |
| 356 | 0.296 | 8.3 |
| 325 | 0.624 | 17.5 |
| 306 | 0.254 | 7.1 |
| 258 | 0.518 | 14.5 |
| 242 | 0.590 | 16.5 |
| 214 | 0.667 | 18.7 |
| 191 | 0.865 | 24.2 |

In some embodiments, Form C of compound 1 is characterized by one or more peaks in its Raman spectrum selected from those in Table 5. In some embodiments, Form C of compound 1 is characterized by at least one, at least two, at least three, at least four, at least five, at least six, at least seven, at least eight, or at least nine peaks in its Raman spectrum selected from those in Table 5.

TABLE 5

Select characteristic peaks of the Raman spectrum of Form C

| Wavenumber (cm$^{-1}$) | Absolute Intensity | Normalized Intensity (%) |
|---|---|---|
| 1627 | 2.316 | 64.8 |
| 1611 | 3.220 | 90.1 |

TABLE 5-continued

Select characteristic peaks of the Raman spectrum of Form C

| Wavenumber (cm$^{-1}$) | Absolute Intensity | Normalized Intensity (%) |
|---|---|---|
| 1602 | 3.572 | 100.0 |
| 1501 | 1.513 | 42.4 |
| 1459 | 1.170 | 32.8 |
| 1427 | 1.357 | 38.0 |
| 1396 | 1.153 | 32.3 |
| 1346 | 1.383 | 38.7 |
| 790 | 1.165 | 32.6 |

Figure 5:
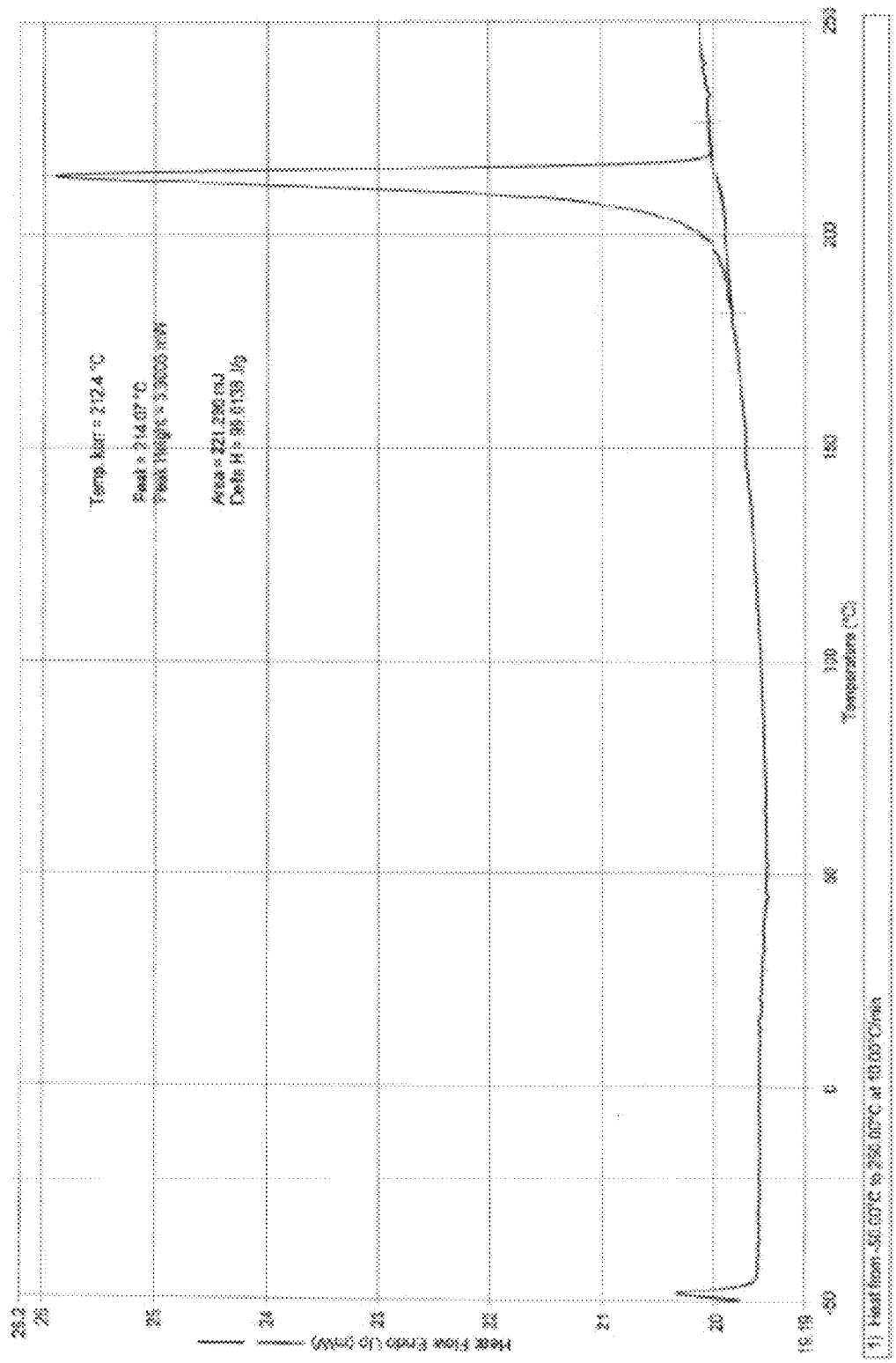
FIG. 5 depicts a Differential Scanning Calorimetry (DSC) thermogram of Form C.

In some embodiments, Form C has a DSC thermogram substantially similar to the one depicted in FIG. 5. In some embodiments, Form C is characterized in that it has a DSC thermogram with an endotherm having a peak temperature ($T_{max}$) of about 212° C. In some embodiments, Form C is characterized in that it has a DSC thermogram with a ΔH of about 99 J/g.

Figure 6:
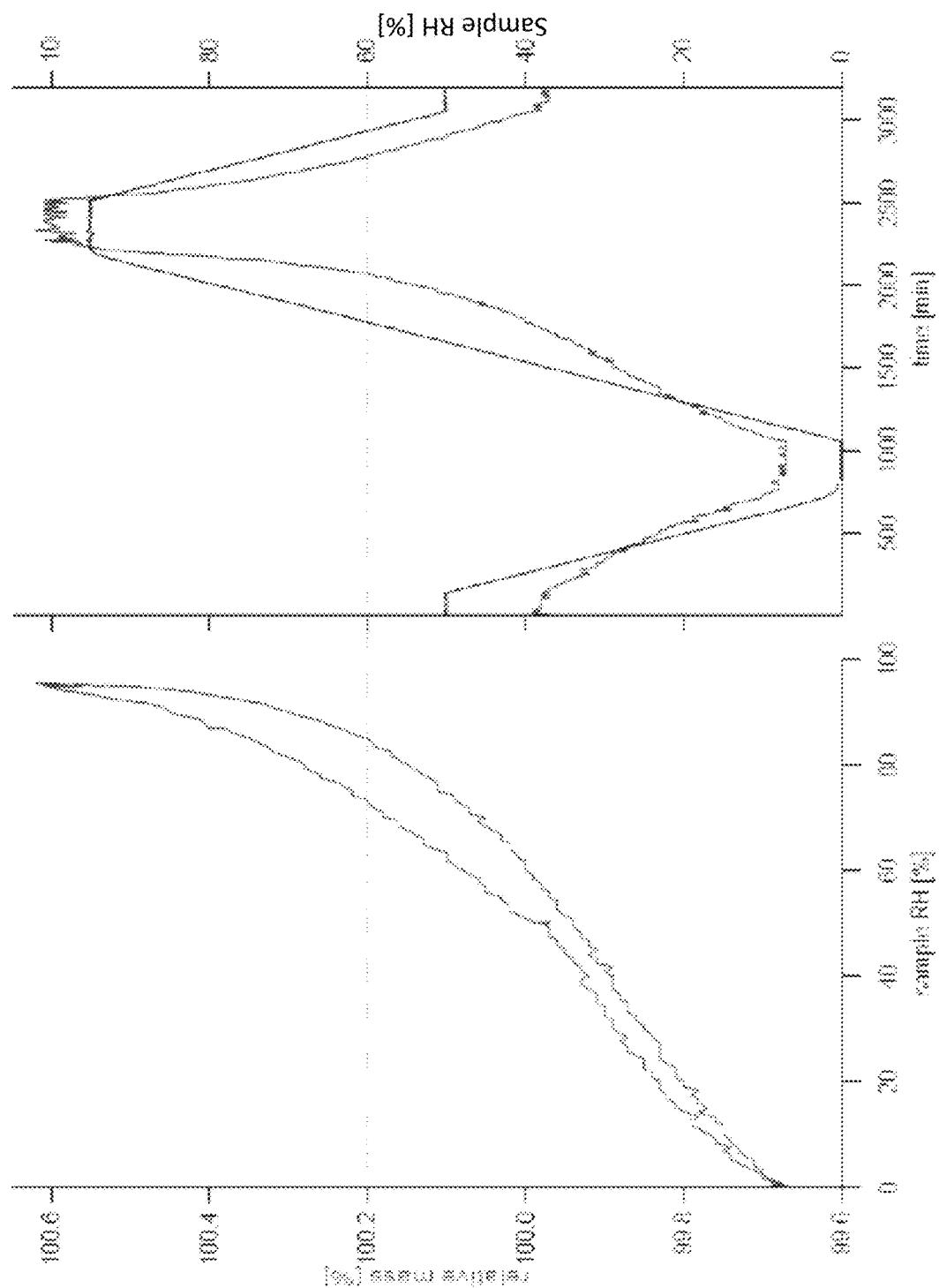
FIG. 6 depicts a Dynamic Vapor Sorption (DVS) isotherm of Form C.

In some embodiments, Form C has a DVS isotherm substantially similar to the one depicted in FIG. 6.

Figure 7:
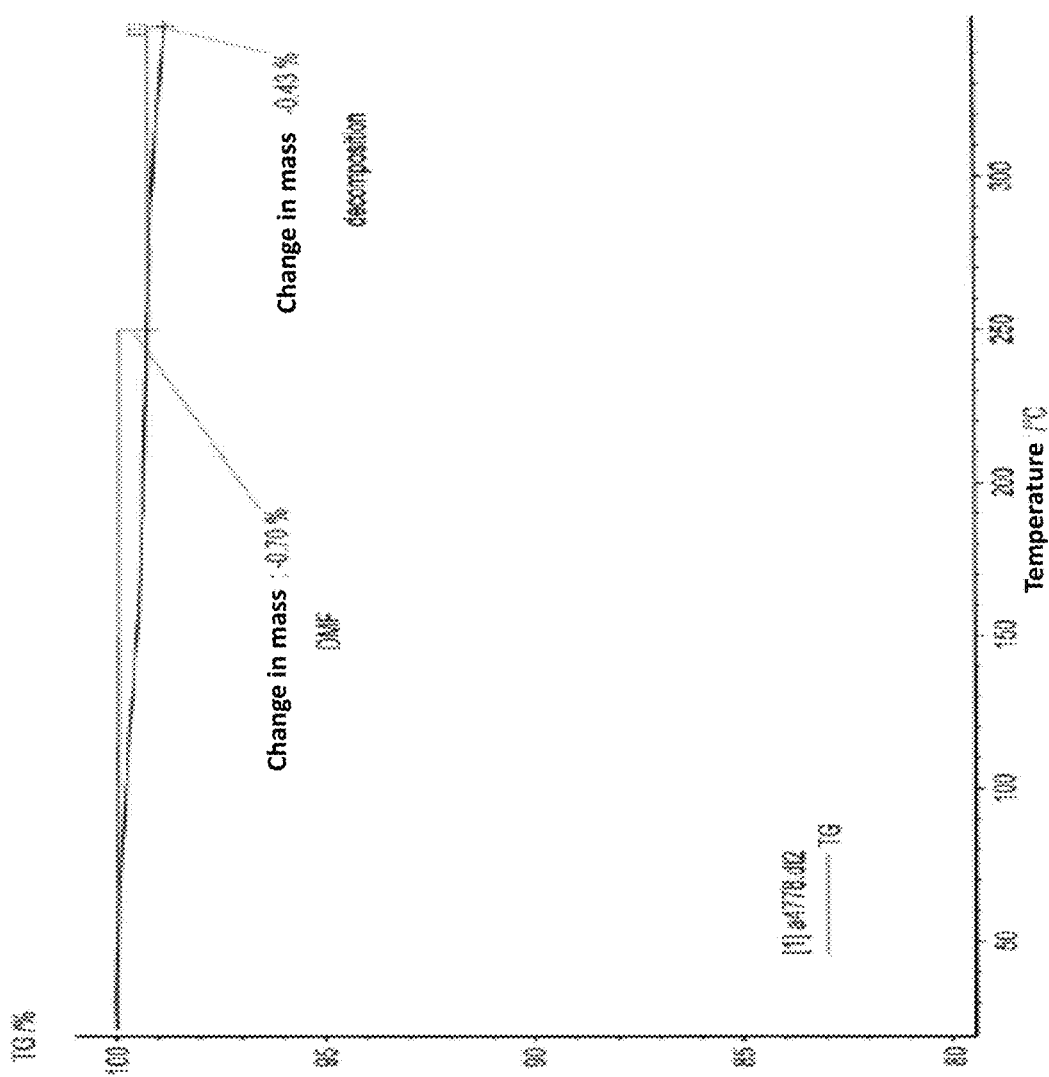
FIG. 7 depicts a Thermogravimetric Fourier-Transform Infrared (TG-FTIR) thermogram of Form C.

In some embodiments, Form C has a TG-FTIR thermogram substantially similar to the one depicted in FIG. 7.

Figure 85A:
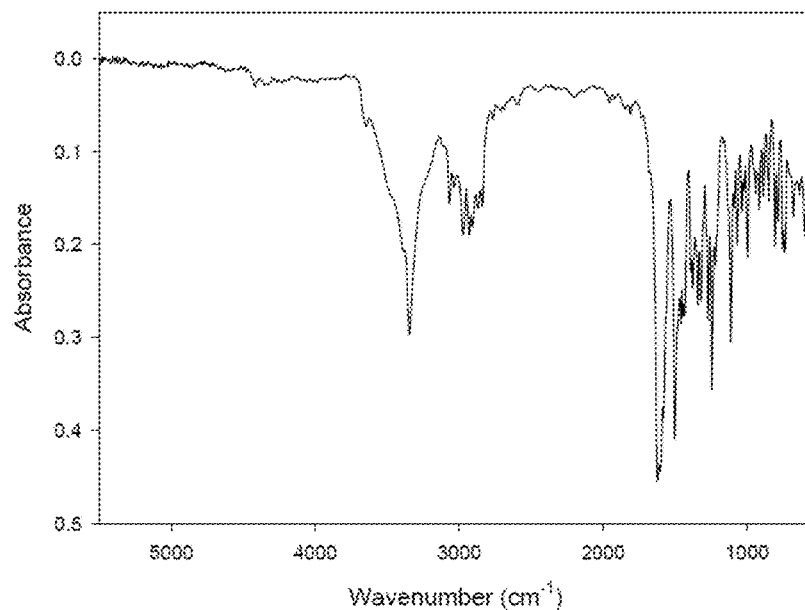
FIGS. 85A-85B depict an infrared (IR) spectrum of Form C.
Figure 85B:
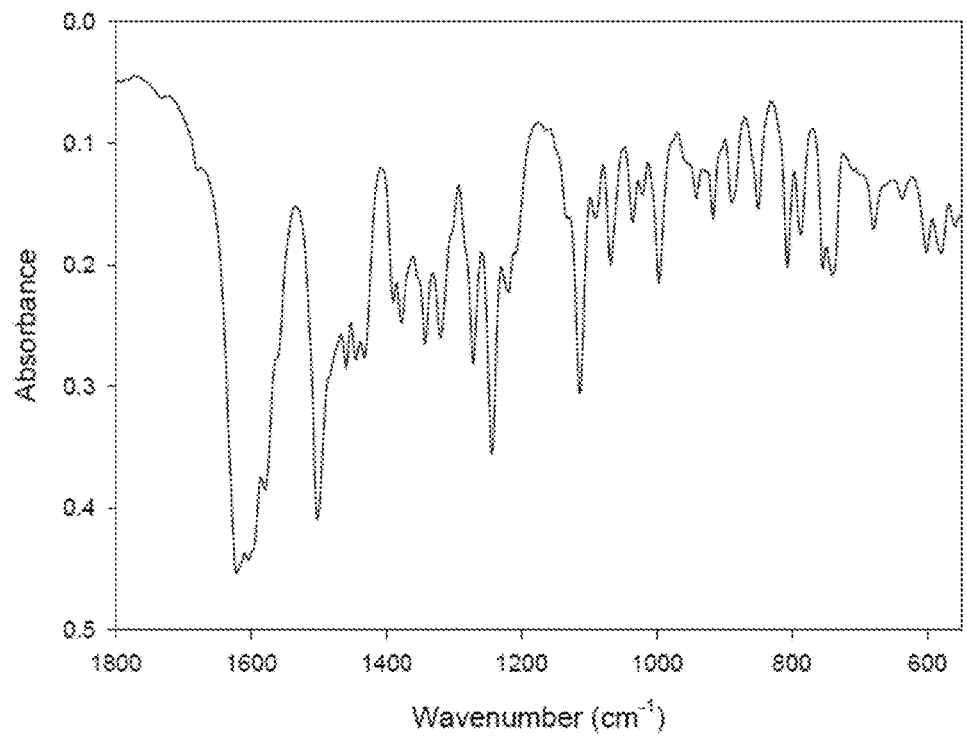
Figure 86:
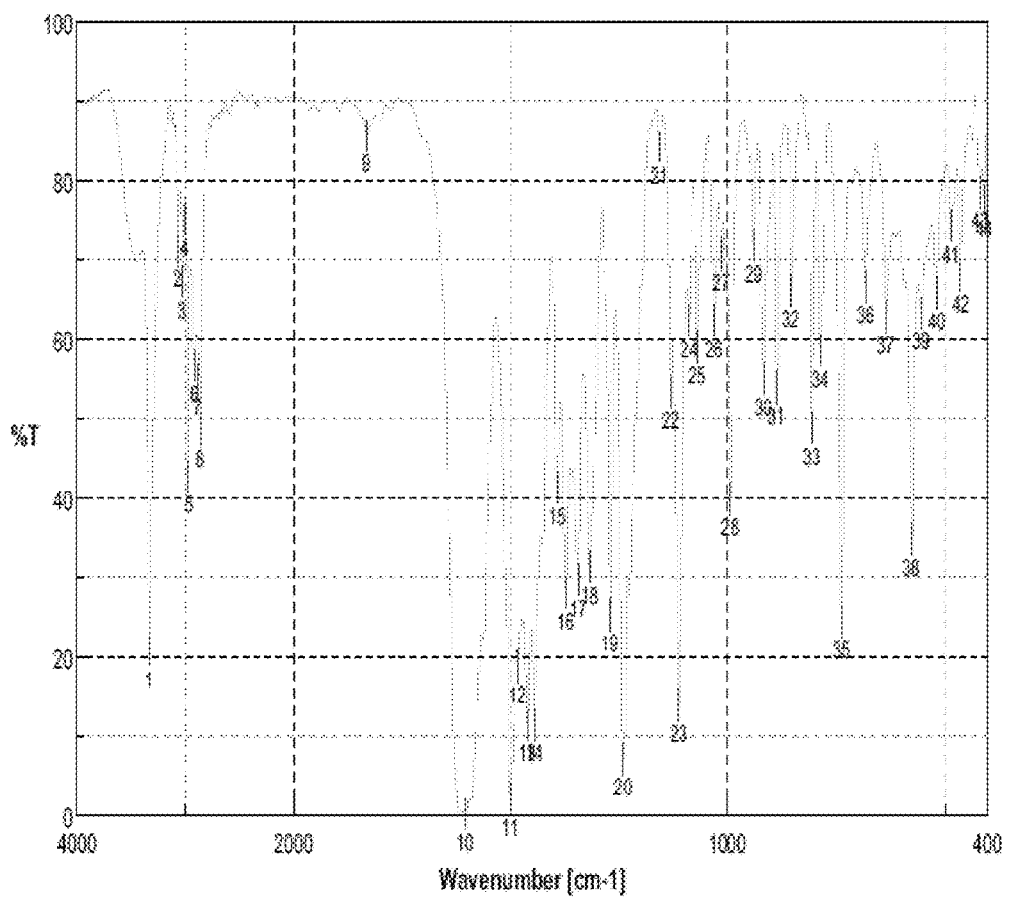
FIG. 86 depict another IR spectrum of Form C.

In some embodiments, Form C of compound 1 is characterized by an IR spectrum substantially similar to the one depicted in FIGS. 85A and 85B. In some embodiments, Form C of compound 1 is characterized by an IR spectrum substantially similar to the one depicted in FIG. 86. In some embodiments, Form C of compound 1 is characterized by one or more peaks in its IR spectrum selected from those in Table 85.

TABLE 85

IR spectrum

| No. | cm−1 | % T | No. | cm−1 | % T | No. | cm−1 | % T |
|---|---|---|---|---|---|---|---|---|
| 1 | 3324.68 | 20.8781 | 2 | 3066.26 | 71.334 | 3 | 3023.84 | 67.3925 |
| 4 | 2996.84 | 75.1349 | 5 | 2968.87 | 42.8261 | 6 | 2915.84 | 56.8473 |
| 7 | 2878.24 | 54.994 | 8 | 2859.92 | 48.5373 | 9 | 1832.04 | 85.8173 |
| 10 | 1603.52 | 0.306526 | 11 | 1499.38 | 2.08717 | 12 | 1482.99 | 18.9158 |
| 13 | 1461.78 | 11.4636 | 14 | 1445.39 | 11.5874 | 15 | 1394.28 | 41.3824 |
| 16 | 1373.07 | 28.15 | 17 | 1345.11 | 29.8025 | 18 | 1318.11 | 31.4519 |
| 19 | 1270.86 | 25.2928 | 20 | 1240.97 | 7.18615 | 21 | 1157.08 | 84.3949 |
| 22 | 1131.05 | 53.4389 | 23 | 1113.69 | 13.9215 | 24 | 1087.66 | 62.5416 |
| 25 | 1070.3 | 59.1501 | 26 | 1031.73 | 62.5165 | 27 | 1015.34 | 70.778 |
| 28 | 993.16 | 39.8618 | 29 | 940.128 | 71.7559 | 30 | 916.022 | 55.1066 |
| 31 | 887.095 | 54.0377 | 32 | 853.347 | 66.128 | 33 | 806.099 | 48.9103 |
| 34 | 785.85 | 58.69 | 35 | 737.639 | 24.5861 | 36 | 682.677 | 66.7085 |
| 37 | 635.43 | 62.8494 | 38 | 576.612 | 34.7937 | 39 | 554.434 | 63.3669 |
| 40 | 519.722 | 65.9416 | 41 | 485.009 | 74.4132 | 42 | 464.761 | 67.9772 |
| 43 | 417.513 | 78.5559 | 44 | 408.835 | 77.593 | | | |

Figure 8:
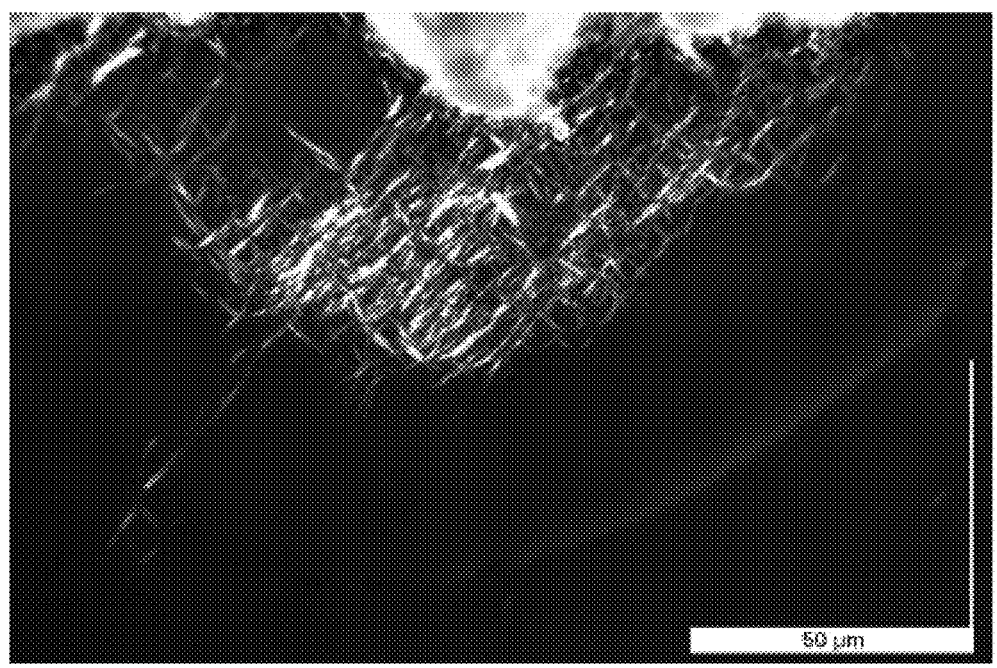
FIG. 8 depicts a microscopic image with crossed polarizers of Form C.

In certain embodiments, Form C is fine hairs or needles. In certain embodiments, Form C has a microscopic image with crossed polarizers substantially similar to the one depicted in FIG. 8.

In certain embodiments, Form C has an observed melting point from about 204° C. to about 211° C. In some embodiments, Form C has an observed aqueous solubility of about 0.04 mg/mL at about 25° C. In some embodiments, Form C is obtained from ethanol/water. In some embodiments, Form C is obtained from ethanol/water (1:1 v/v). In some embodiments, Form C is stable for at least about 1 month, at least about 2 months, at least about 4 months, at least about 6 months, at least about 12 months, at least about 18 months, at least about 24 months, or at least about 3 years at about 25° C. and about 60% relative humidity. In some embodiments, Form C has substantially the same XRPD pattern post storage for at least about 1 month, at least about 2 months, at least about 4 months, at least about 6 months, at least about 12 months, at least about 18 months, at least about 24 months, or at least about 3 years at about 25° C. and about 60% relative humidity. In some embodiments, Form C has substantially the same IR spectrum post storage for at least about 1 month, at least about 2 months, at least about 4 months, at least about 6 months, at least about 12 months, at least about 18 months, at least about 24 months, or at least about 3 years at about 25° C. and about 60% relative humidity.

In some embodiments, Form C is stable for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity. In some embodiments, Form C has substantially the same XRPD pattern post storage for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity. In some embodiments, Form C has substantially the same IR spectrum post storage for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity.

Form D

In some embodiments, the present invention provides a polymorphic form of compound 1 referred to herein as crystalline Form D (Form D). In certain embodiments, Form D is substantially anhydrous. In certain embodiments, Form D is 99% anhydrous by weight. In certain embodiments, Form D is 97% anhydrous by weight. In certain embodiments, Form D is 95% anhydrous by weight. In certain embodiments, Form D is substantially free of impurities. In certain embodiments, Form D is 99% free of impurities by weight. In certain embodiments, Form D is 97% free of impurities by weight. In certain embodiments, Form D is 95% free of impurities by weight. In certain embodiments, crystalline Form D is substantially free of amorphous compound 1. In certain embodiments, crystalline Form D is substantially free of other crystalline forms of compound 1. In certain embodiments, crystalline Form D is substantially free of a salt of compound 1. In certain embodiments, crystalline Form D is substantially free of a solvate of compound 1.

Figure 9:
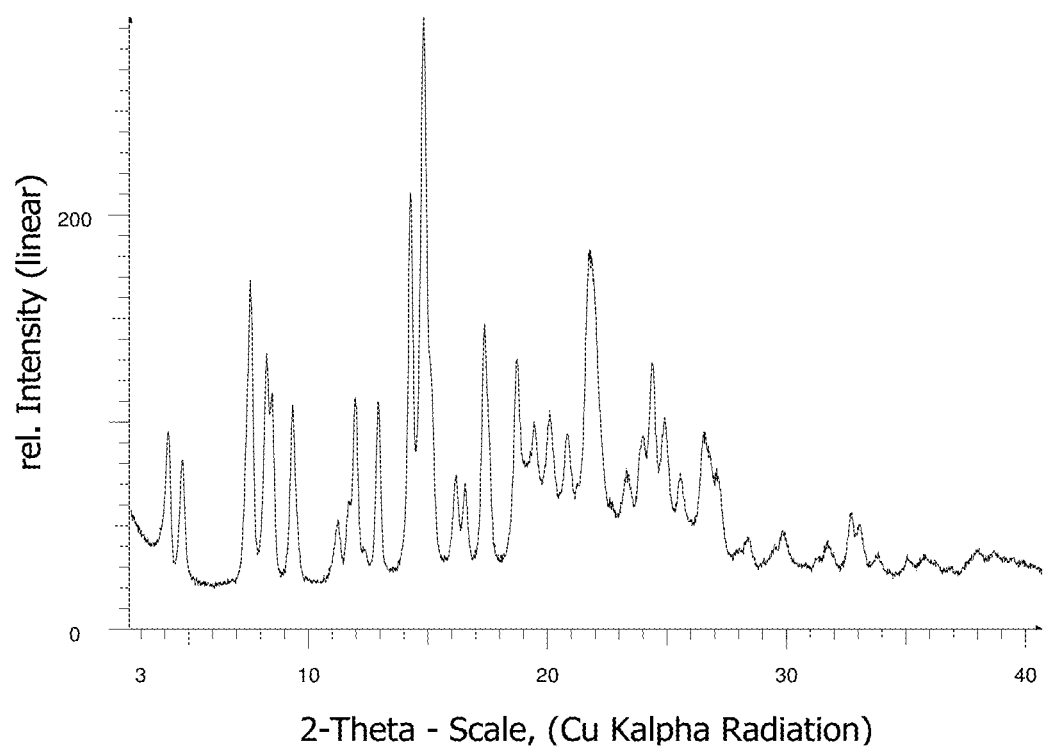
FIG. 9 depicts an XRPD pattern of Form D.

Form D can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, crystalline Form D of compound 1 is characterized by an X-ray powder diffraction pattern substantially similar to the one depicted in FIG. 9. In some embodiments, crystalline Form D of compound 1 is characterized in that it has one or more peaks in its X-ray powder diffraction pattern selected from those in Table 6. In some embodiments, crystalline Form D of compound 1 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, or at least twenty-eight peaks in its X-ray powder diffraction pattern selected from those in Table 6. In some embodiments, Form D of compound 1 is characterized in that it has one or more peaks in its X-ray powder diffraction pattern selected from the strong and very strong peaks in Table 6.

TABLE 6

X-ray powder diffraction pattern of Form D.

| Angle 2-Theta ° | d value Angstrom | Intensity (relative) | Intensity % |
|---|---|---|---|
| 4.10 | 21.5 | m | 29 |
| 4.69 | 18.8 | m | 25 |
| 7.54 | 11.7 | s | 56 |
| 8.22 | 10.7 | s | 46 |
| 8.43 | 10.5 | s | 38 |
| 9.31 | 9.5 | s | 36 |
| 11.20 | 7.9 | m | 18 |
| 11.94 | 7.4 | s | 38 |
| 12.90 | 6.9 | s | 38 |
| 14.25 | 6.2 | vs | 72 |
| 14.80 | 5.98 | vs | 100 |
| 16.15 | 5.48 | m | 25 |
| 16.54 | 5.36 | m | 24 |
| 17.34 | 5.11 | s | 49 |
| 18.71 | 4.74 | s | 44 |
| 19.43 | 4.57 | s | 34 |
| 20.08 | 4.42 | s | 36 |
| 20.82 | 4.26 | s | 32 |
| 21.75 | 4.08 | s | 62 |
| 23.31 | 3.81 | m | 26 |
| 23.99 | 3.71 | s | 32 |
| 24.39 | 3.65 | s | 45 |
| 24.91 | 3.57 | s | 35 |
| 25.54 | 3.49 | m | 25 |
| 26.52 | 3.36 | s | 31 |
| 27.08 | 3.29 | m | 27 |
| 32.72 | 2.73 | m | 20 |
| 33.08 | 2.71 | m | 17 |

In some embodiments, crystalline Form D of compound 1 is characterized by one or more peaks in its X-ray powder diffraction pattern selected from those in Table 7. In some embodiments, crystalline Form D of compound 1 is characterized by at least one, at least two, at least three, at least four, at least five, at least six, at least seven, or at least eight in its X-ray powder diffraction pattern selected from those in Table 7.

TABLE 7

Select characteristic peaks of the X-ray powder diffraction pattern of Form D.

| Angle 2-Theta ° | d value Angstrom | Intensity (relative) | Intensity % |
|---|---|---|---|
| 7.54 | 11.7 | s | 56 |
| 8.22 | 10.7 | s | 46 |
| 14.25 | 6.2 | vs | 72 |
| 14.80 | 5.98 | vs | 100 |
| 17.34 | 5.11 | s | 49 |
| 18.71 | 4.74 | s | 44 |
| 21.75 | 4.08 | s | 62 |
| 24.39 | 3.65 | s | 45 |

Figure 10:
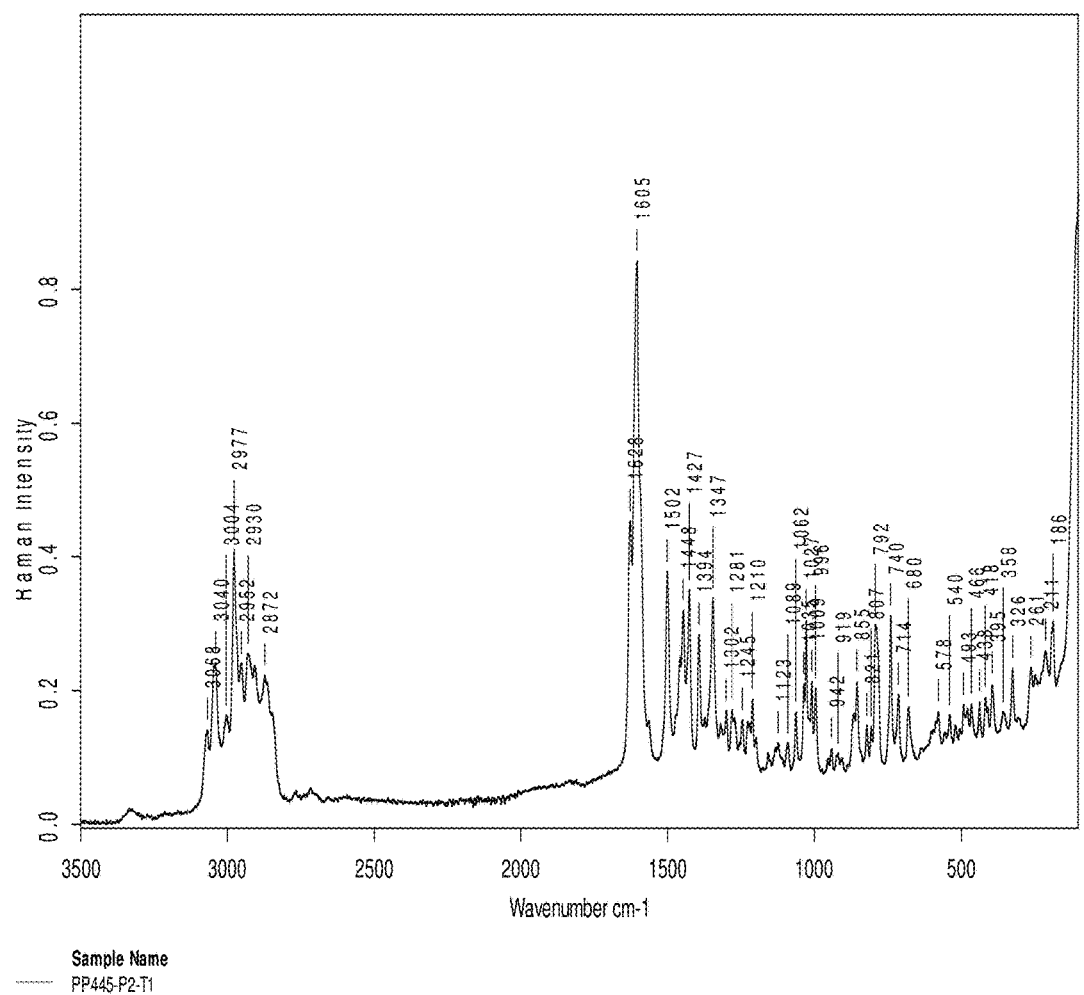
FIG. 10 depicts an FT-Raman spectrum of Form D.

In some embodiments, crystalline Form D of compound 1 is characterized by a Raman spectrum substantially similar to the one depicted in FIG. 10. In some embodiments, crystalline Form D of compound 1 is characterized by one or more peaks in its Raman spectrum selected from those in Table 8. In some embodiments, crystalline Form D of compound 1 is characterized by having a Raman spectrum with characteristic peaks at about those in Table 8.

TABLE 8

Raman spectrum of Form D.

| Wavenumber (cm$^{-1}$) | Absolute Intensity | Normalized Intensity (%) |
|---|---|---|
| 3068 | 0.141 | 16.7 |
| 3040 | 0.241 | 28.6 |
| 3004 | 0.163 | 19.4 |
| 2977 | 0.410 | 48.7 |
| 2952 | 0.241 | 28.6 |
| 2929 | 0.255 | 30.3 |
| 2872 | 0.223 | 26.5 |
| 1628 | 0.453 | 53.8 |
| 1605 | 0.842 | 100.0 |
| 1502 | 0.378 | 44.9 |
| 1448 | 0.319 | 37.9 |
| 1427 | 0.350 | 41.6 |
| 1394 | 0.284 | 33.7 |
| 1347 | 0.338 | 40.1 |
| 1302 | 0.171 | 20.3 |
| 1281 | 0.172 | 20.4 |
| 1245 | 0.157 | 18.6 |
| 1210 | 0.187 | 22.2 |
| 1123 | 0.122 | 14.5 |
| 1089 | 0.122 | 14.5 |
| 1062 | 0.168 | 20.0 |
| 1035 | 0.210 | 24.9 |
| 1027 | 0.304 | 36.1 |
| 1009 | 0.213 | 25.3 |
| 996 | 0.204 | 24.2 |
| 942 | 0.113 | 13.4 |
| 919 | 0.106 | 12.6 |
| 855 | 0.213 | 25.3 |
| 821 | 0.148 | 17.6 |
| 807 | 0.146 | 17.3 |
| 792 | 0.299 | 35.5 |
| 740 | 0.312 | 37.1 |
| 714 | 0.194 | 23.0 |
| 680 | 0.176 | 20.9 |
| 578 | 0.169 | 20.1 |
| 540 | 0.164 | 19.5 |
| 493 | 0.179 | 21.3 |
| 466 | 0.180 | 21.4 |
| 438 | 0.183 | 21.7 |
| 418 | 0.190 | 22.6 |
| 395 | 0.210 | 24.9 |

TABLE 8-continued

Raman spectrum of Form D.

| Wavenumber (cm$^{-1}$) | Absolute Intensity | Normalized Intensity (%) |
|---|---|---|
| 358 | 0.168 | 20.0 |
| 326 | 0.233 | 27.7 |
| 261 | 0.235 | 27.9 |
| 211 | 0.259 | 30.8 |
| 186 | 0.303 | 36.0 |

In some embodiments, crystalline Form D of compound 1 is characterized by one or more peaks in its Raman spectrum selected from those in Table 9. In some embodiments, crystalline Form D of compound 1 is characterized by at least one, at least two, at least three, at least four, at least five, at least six, at least seven, at least eight, at least nine, or at least ten peaks in its Raman spectrum selected from those in Table 9.

TABLE 9

Select characteristic peaks of the Raman spectrum of Form D.

| Wavenumber (cm$^{-1}$) | Absolute Intensity | Normalized Intensity (%) |
|---|---|---|
| 1628 | 0.453 | 53.8 |
| 1605 | 0.842 | 100.0 |
| 1502 | 0.378 | 44.9 |
| 1448 | 0.319 | 37.9 |
| 1427 | 0.350 | 41.6 |
| 1394 | 0.284 | 33.7 |
| 1347 | 0.338 | 40.1 |
| 1027 | 0.304 | 36.1 |
| 792 | 0.299 | 35.5 |
| 740 | 0.312 | 37.1 |

Figure 11:
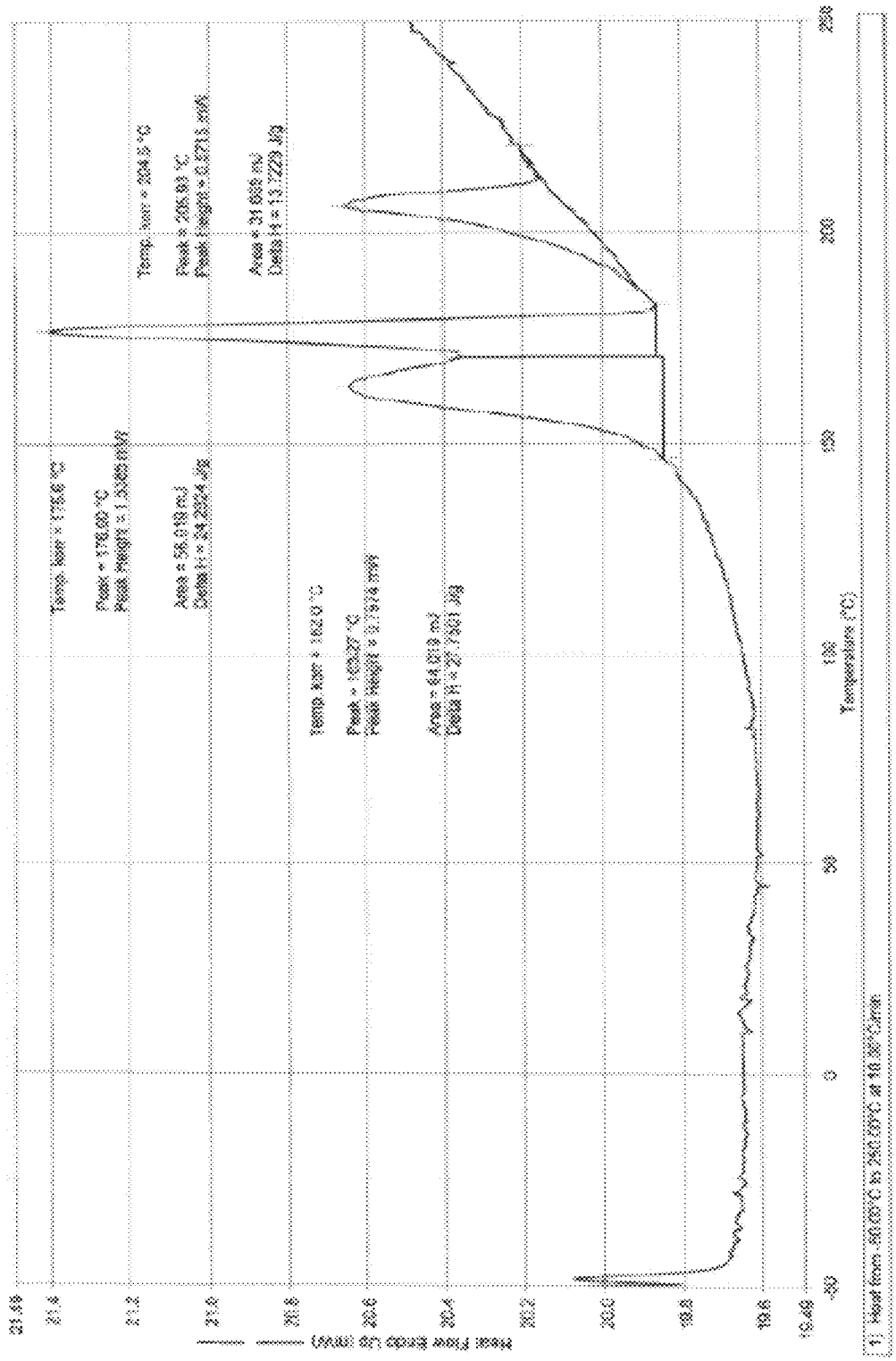
FIG. 11 depicts a DSC thermogram of Form D.

In some embodiments, Form D has a DSC thermogram substantially similar to the one depicted in FIG. 11. In some embodiments, Form D is characterized in that it has a DSC thermogram with endotherm peak temperatures ($T_{max}$) of about 162° C., about 176° C., and about 205° C. In some embodiments, Form D is characterized in that it has a DSC thermogram with ΔH values of about 27.8 J/g, about 24.3 J/g, and about 13.7 J/g.

Figure 12:
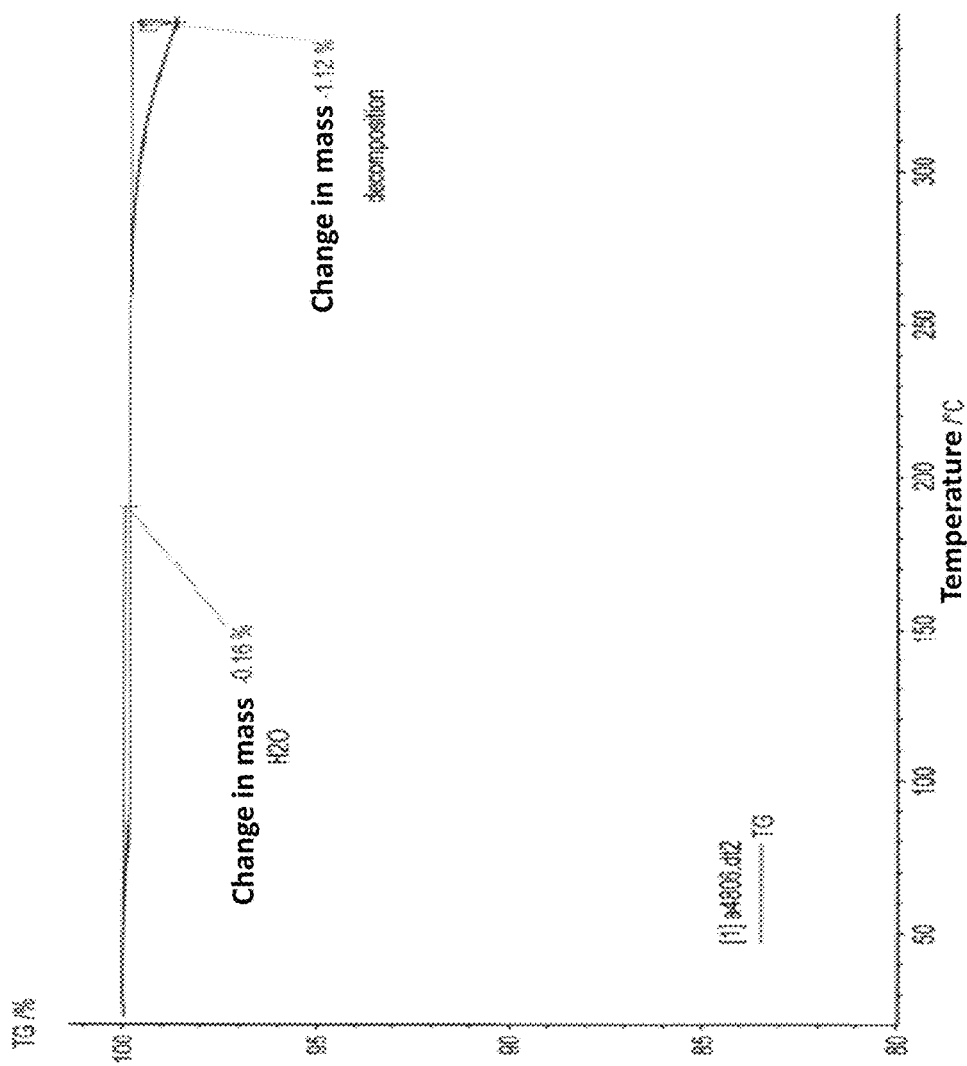
FIG. 12 depicts a TG-FTIR thermogram of Form D.

In some embodiments, Form D is characterized by a TG-FTIR thermogram substantially similar to the one depicted in FIG. 12.

In some embodiments, Form D is obtained from drying Form E under vacuum. In some embodiments, Form D is obtained from drying Form E at a pressure of lower than about 5 mbar for about 12 hours, about 1 day, about 2 days, or about 3 days. In some embodiments, Form D is stable for at least about 1 month, at least about 2 months, at least about 4 months, at least about 6 months, at least about 12 months, at least about 18 months, at least about 2 years, or at least about 3 years at about 25° C. and about 60% relative humidity.

In certain embodiments, compound 1 is a solvated crystal form and thus has solvent (e.g., MeOH, EtOH, 2-PrOH, 1-BuOH, THF, EtOAc, dioxane, pyridine, or DMSO) incorporated into the crystal structure. It has been found that compound 1 can exist in multiple solvate crystal forms, or polymorphs. In some embodiments, the present invention provides a polymorphic form of compound 1 referred to herein as crystalline Form E.

In certain embodiments, Form E is substantially free of impurities. In certain embodiments, Form E is 99% free of impurities by weight. In certain embodiments, Form E is 97% free of impurities by weight. In certain embodiments, Form E is 95% free of impurities by weight. In certain embodiments, Form E is substantially free of amorphous compound 1. In certain embodiments, Form E is substantially free of other crystalline forms of compound 1. In certain embodiments, Form E is substantially free of a salt of compound 1.

Form E can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form E is characterized by an X-ray powder diffraction pattern substantially similar to the one depicted in FIG. 13. In some embodiments, Form E is characterized in that it has one or more peaks in its X-ray powder diffraction pattern selected from those in Table 10. In some embodiments, Form E is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven peaks in its X-ray powder diffraction pattern selected from those in Table 10. In some embodiments, Form E of compound 1 is characterized in that it has one or more peaks in its X-ray powder diffraction pattern selected from the strong and very strong peaks in Table 10.

TABLE 10

X-ray powder diffraction pattern of Form E.

| Angle 2-Theta ° | d value Angstrom | Intensity (relative) | Intensity % |
|---|---|---|---|
| 4.02 | 22.0 | s | 32 |
| 4.43 | 19.9 | w | 14 |
| 7.26 | 12.2 | s | 55 |
| 7.88 | 11.2 | vs | 100 |
| 8.75 | 10.1 | m | 19 |
| 11.14 | 7.9 | s | 36 |
| 11.36 | 7.8 | s | 32 |
| 12.02 | 7.4 | s | 36 |
| 13.38 | 6.6 | s | 31 |
| 14.29 | 6.2 | s | 48 |
| 15.69 | 5.64 | s | 37 |
| 16.33 | 5.42 | m | 27 |
| 17.82 | 4.97 | s | 42 |
| 18.23 | 4.86 | s | 40 |
| 18.63 | 4.76 | m | 28 |
| 19.76 | 4.49 | s | 35 |
| 20.11 | 4.41 | s | 42 |
| 20.52 | 4.32 | m | 30 |
| 20.97 | 4.23 | s | 30 |
| 21.34 | 4.16 | s | 32 |
| 22.25 | 3.99 | s | 46 |
| 22.66 | 3.92 | s | 37 |
| 23.54 | 3.78 | m | 29 |
| 24.01 | 3.70 | m | 27 |
| 25.05 | 3.55 | m | 30 |
| 27.39 | 3.25 | m | 26 |
| 29.25 | 3.05 | m | 17 |

In some embodiments, Form E is characterized by one or more peaks in its X-ray powder diffraction pattern selected from those in Table 11. In some embodiments, Form E is characterized by at least one, at least two, at least three, at least four, at least five, or at least seven peaks in its X-ray powder diffraction pattern selected from those in Table 11.

TABLE 11

Select characteristic peaks of the X-ray powder diffraction pattern of Form E.

| Angle 2-Theta ° | d value Angstrom | Intensity (relative) | Intensity % |
|---|---|---|---|
| 7.26 | 12.2 | s | 55 |
| 7.88 | 11.2 | vs | 100 |
| 14.29 | 6.2 | s | 48 |
| 17.82 | 4.97 | s | 42 |
| 18.23 | 4.86 | s | 40 |
| 20.11 | 4.41 | s | 42 |
| 22.25 | 3.99 | s | 46 |

Figure 14:
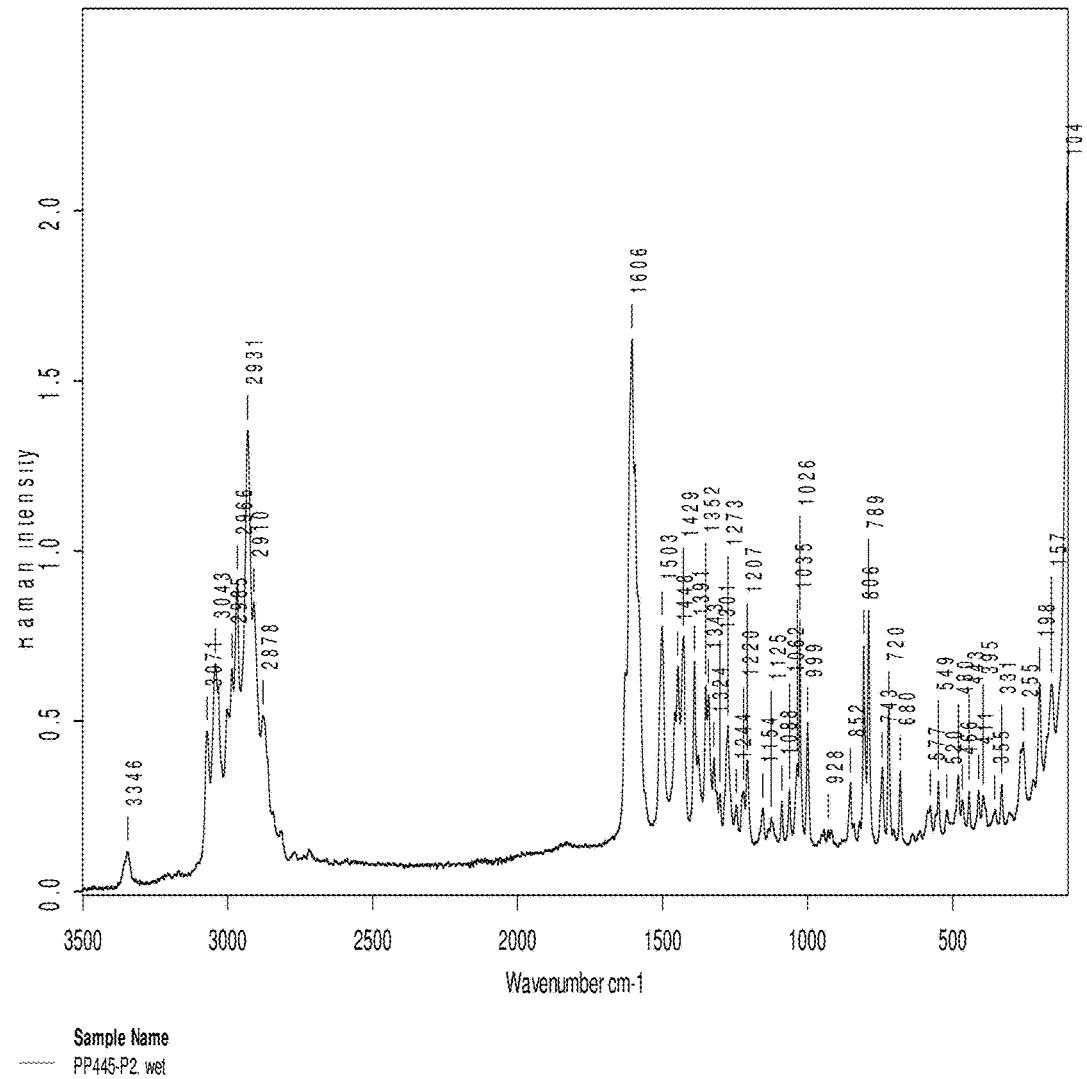
FIG. 14 depicts an FT-Raman spectrum of Form E.

In some embodiments, Form E is characterized by a Raman spectrum substantially similar to the one depicted in FIG. 14. In some embodiments, Form E is characterized by one or more peaks in its Raman spectrum selected from those in Table 12. In some embodiments, Form E is characterized by having a Raman spectrum with characteristic peaks at about those in Table 12.

TABLE 12

Raman spectrum of Form E.

| Wavenumber (cm$^{-1}$) | Absolute Intensity | Normalized Intensity (%) |
|---|---|---|
| 3346 | 0.116 | 5.7 |
| 3071 | 0.469 | 23.1 |
| 3043 | 0.668 | 33.0 |
| 2985 | 0.654 | 32.3 |
| 2966 | 0.913 | 45.1 |
| 2931 | 1.355 | 66.9 |
| 2910 | 0.848 | 41.9 |
| 2878 | 0.517 | 25.5 |
| 1606 | 1.621 | 80.0 |
| 1503 | 0.780 | 38.5 |
| 1448 | 0.661 | 32.6 |
| 1429 | 0.749 | 37.0 |
| 1391 | 0.676 | 33.4 |
| 1352 | 0.605 | 29.9 |
| 1343 | 0.578 | 28.5 |
| 1324 | 0.391 | 19.3 |
| 1301 | 0.287 | 14.2 |
| 1273 | 0.485 | 23.9 |
| 1244 | 0.254 | 12.5 |
| 1220 | 0.294 | 14.5 |
| 1207 | 0.383 | 18.9 |
| 1153 | 0.243 | 12.0 |
| 1125 | 0.216 | 10.7 |
| 1088 | 0.265 | 13.1 |
| 1062 | 0.298 | 14.7 |
| 1035 | 0.376 | 18.6 |
| 1026 | 0.795 | 39.2 |
| 999 | 0.495 | 24.4 |
| 928 | 0.181 | 8.9 |
| 852 | 0.318 | 15.7 |
| 806 | 0.723 | 35.7 |
| 789 | 0.826 | 40.8 |
| 742 | 0.362 | 17.9 |
| 720 | 0.544 | 26.9 |
| 680 | 0.354 | 17.5 |
| 577 | 0.250 | 12.3 |
| 549 | 0.323 | 15.9 |
| 520 | 0.238 | 11.7 |
| 480 | 0.342 | 16.9 |
| 466 | 0.267 | 13.2 |
| 443 | 0.294 | 14.5 |
| 411 | 0.296 | 14.6 |
| 395 | 0.280 | 13.8 |
| 355 | 0.238 | 11.7 |

TABLE 12-continued

Raman spectrum of Form E.

| Wavenumber (cm$^{-1}$) | Absolute Intensity | Normalized Intensity (%) |
|---|---|---|
| 331 | 0.312 | 15.4 |
| 255 | 0.437 | 21.6 |
| 198 | 0.613 | 30.3 |
| 157 | 0.609 | 30.1 |
| 104 | 2.026 | 100.0 |

In some embodiments, Form E is characterized by one or more peaks in its Raman spectrum selected from those in Table 13. In some embodiments, Form E is characterized by at least one, at least two, at least three, at least four, at least five, at least six, at least seven, or at least eight peaks in its Raman spectrum selected from those in Table 13.

TABLE 13

Select characteristic peaks of the Raman spectrum of Form E.

| Wavenumber (cm$^{-1}$) | Absolute Intensity | Normalized Intensity (%) |
|---|---|---|
| 1606 | 1.621 | 80.0 |
| 1503 | 0.780 | 38.5 |
| 1448 | 0.661 | 32.6 |
| 1429 | 0.749 | 37.0 |
| 1391 | 0.676 | 33.4 |
| 1026 | 0.795 | 39.2 |
| 806 | 0.723 | 35.7 |
| 789 | 0.826 | 40.8 |

Figure 15:
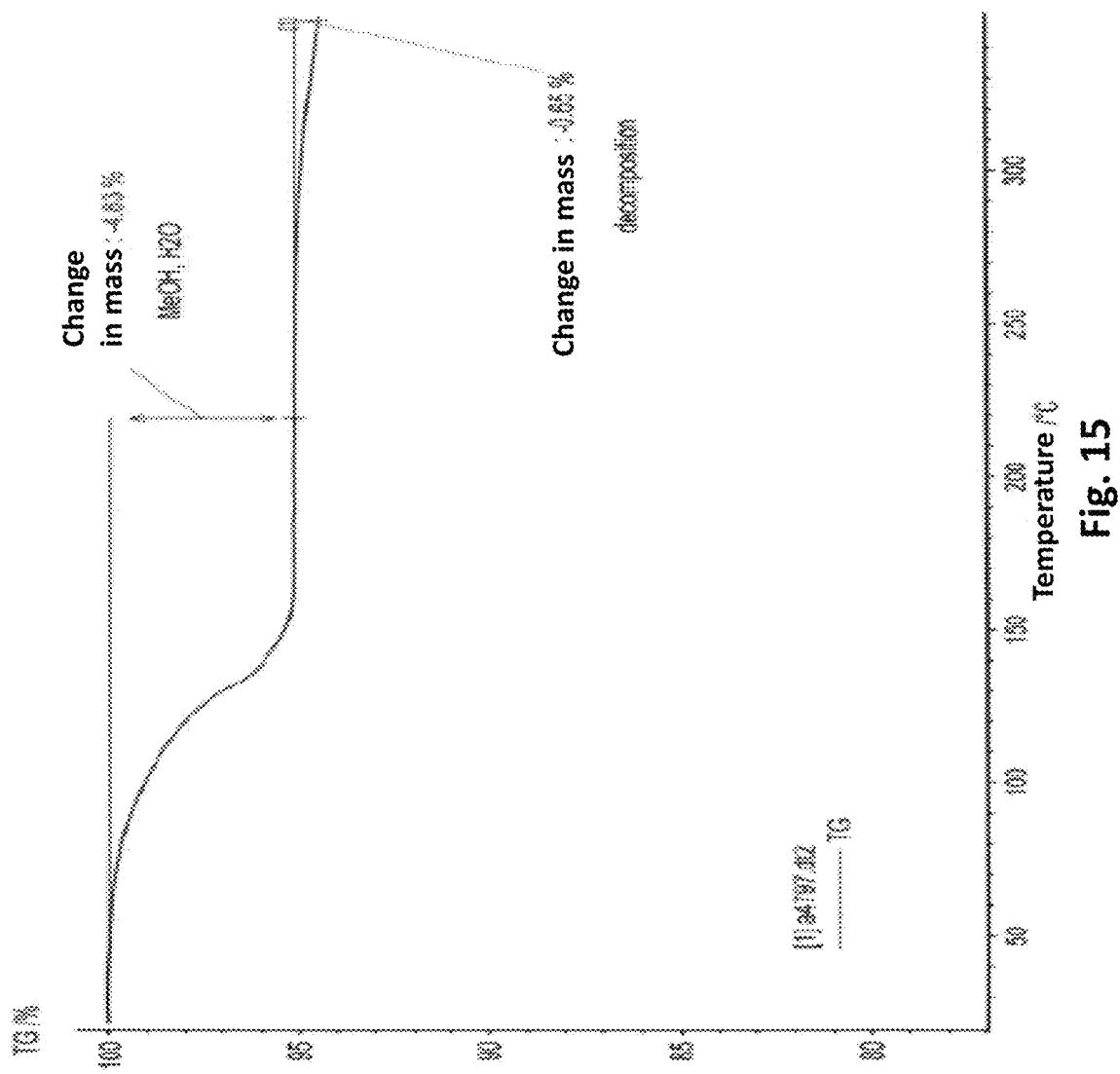
FIG. 15 depicts a TG-FTIR thermogram of Form E.

In some embodiments, Form E has a TG-FTIR thermogram substantially similar to the one depicted in FIG. 15.

In some embodiments, Form E is obtained from methanol. In some embodiments, Form E is a methanol solvate. In some embodiments, Form E is a non-stoichiometric solvate. In some embodiments, Form E is a non-stoichiometric methanol solvate.

Form F

In certain embodiments, the present invention provides crystalline Form F (Form F) of compound 1. In certain embodiments, Form F is substantially free of impurities. In certain embodiments, Form F is 99% free of impurities by weight. In certain embodiments, Form F is 97% free of impurities by weight. In certain embodiments, Form F is 95% free of impurities by weight. In certain embodiments, Form F is substantially free of amorphous compound 1. In certain embodiments, Form F is substantially free of other crystalline forms of compound 1. In certain embodiments, Form F is substantially free of a salt of compound 1.

Form F can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form F is characterized by an X-ray powder diffraction pattern substantially similar to the one depicted in FIG. 16. In some embodiments, Form F is characterized in that it has one or more peaks in its X-ray powder diffraction pattern selected from those in Table 14. In some embodiments, Form F is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, or at least thirty-four peaks in its X-ray powder diffraction pattern selected from those in Table 14. In some embodiments, Form F of compound 1 is characterized in that it has one or more peaks in its X-ray powder diffraction pattern selected from the strong and very strong peaks in Table 14.

TABLE 14

X-ray powder diffraction pattern of Form F.

| Angle 2-Theta ° | d value Angstrom | Intensity (relative) | Intensity % |
|---|---|---|---|
| 3.84 | 23.0 | s | 41 |
| 5.70 | 15.5 | m | 17 |
| 5.97 | 14.8 | m | 19 |
| 7.02 | 12.6 | vs | 100 |
| 8.26 | 10.7 | s | 38 |
| 9.19 | 9.6 | s | 35 |
| 10.21 | 8.7 | w | 8 |
| 10.62 | 8.3 | w | 13 |
| 10.98 | 8.1 | w | 11 |
| 11.34 | 7.8 | m | 22 |
| 12.07 | 7.3 | m | 25 |
| 12.47 | 7.1 | w | 13 |
| 13.79 | 6.4 | m | 15 |
| 14.72 | 6.0 | m | 18 |
| 15.11 | 5.86 | s | 34 |
| 16.47 | 5.38 | m | 22 |
| 16.70 | 5.31 | m | 26 |
| 17.81 | 4.98 | m | 23 |
| 18.41 | 4.82 | s | 47 |
| 19.74 | 4.49 | m | 24 |
| 20.27 | 4.38 | m | 24 |
| 20.84 | 4.26 | m | 26 |
| 21.32 | 4.16 | m | 26 |
| 21.76 | 4.08 | m | 28 |
| 23.15 | 3.84 | s | 44 |
| 24.04 | 3.70 | m | 27 |
| 24.43 | 3.64 | m | 15 |
| 24.87 | 3.58 | m | 16 |
| 25.60 | 3.48 | m | 27 |
| 26.04 | 3.42 | m | 18 |
| 26.94 | 3.31 | m | 18 |
| 30.11 | 2.97 | w | 11 |
| 30.55 | 2.92 | w | 13 |
| 31.06 | 2.88 | w | 12 |

In some embodiments, Form F is characterized by one or more peaks in its X-ray powder diffraction pattern selected from those in Table 15. In some embodiments, Form F is characterized by at least one, at least two, at least three, at least four, at least five, or at least six peaks in its X-ray powder diffraction pattern selected from those in Table 15.

TABLE 15

Select characteristic peaks of the X-ray powder diffraction pattern of Form F.

| Angle 2-Theta ° | d value Angstrom | Intensity (relative) | Intensity % |
|---|---|---|---|
| 7.02 | 12.6 | vs | 100 |
| 8.26 | 10.7 | s | 38 |
| 9.19 | 9.6 | s | 35 |
| 15.11 | 5.86 | s | 34 |
| 18.41 | 4.82 | s | 47 |
| 23.15 | 3.84 | s | 44 |

Figure 17:
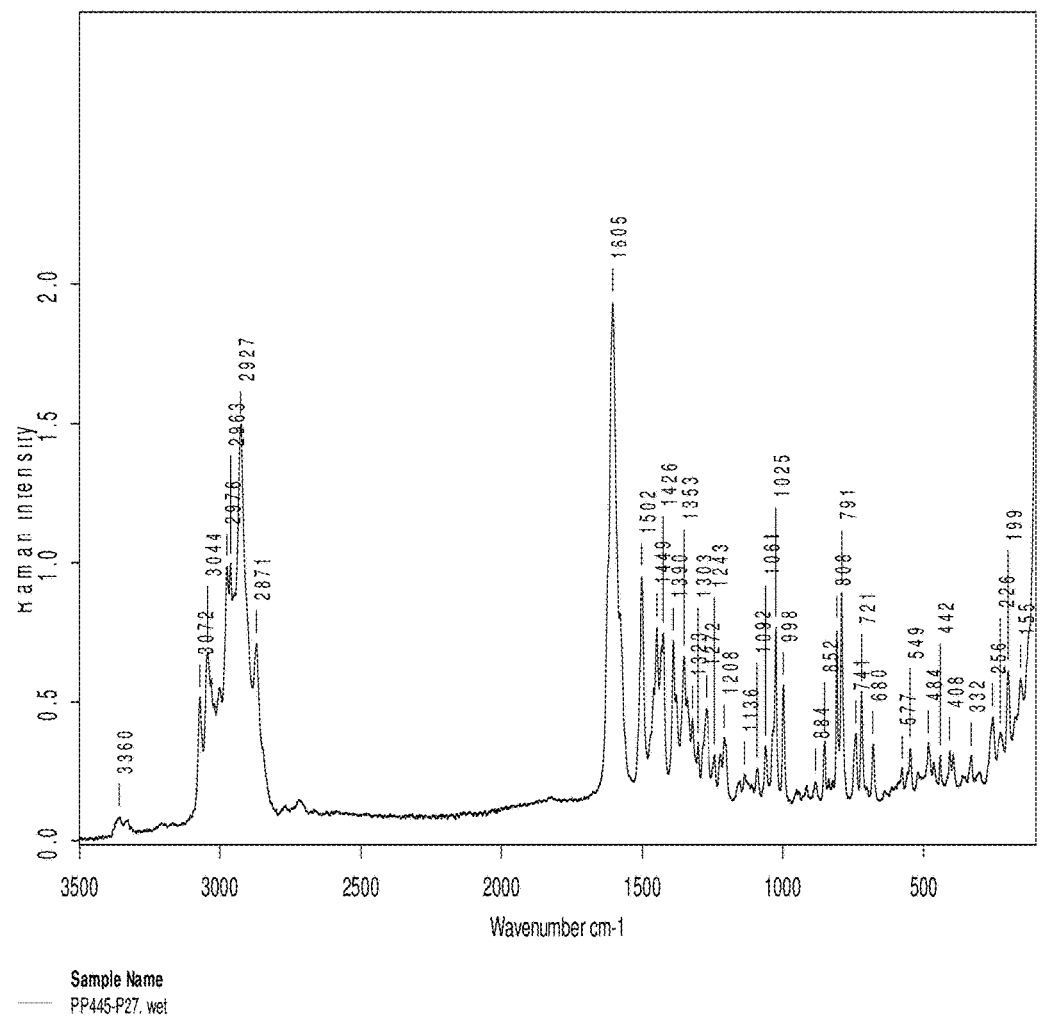
FIG. 17 depicts an FT-Raman spectrum of Form F.

In some embodiments, Form F is characterized by a Raman spectrum substantially similar to the one depicted in FIG. 17. In some embodiments, Form F is characterized by one or more peaks in its Raman spectrum selected from those in Table 16. In some embodiments, Form F is characterized by at least one, at least two, at least three, at least four, at least five, at least six, at least seven, at least eight, at least nine, or at least ten peaks in its Raman spectrum selected from those in Table 16.

TABLE 16

Raman spectrum of Form F.

| Wavenumber (cm$^{-1}$) | Absolute Intensity | Normalized Intensity (%) |
|---|---|---|
| 3360 | 0.087 | 4.5 |
| 3072 | 0.516 | 26.7 |
| 3044 | 0.678 | 35.0 |
| 2976 | 0.985 | 50.9 |
| 2963 | 0.996 | 51.4 |
| 2927 | 1.498 | 77.4 |
| 2871 | 0.709 | 36.6 |
| 1605 | 1.936 | 100.0 |
| 1502 | 0.950 | 49.1 |
| 1449 | 0.768 | 39.7 |
| 1426 | 0.746 | 38.5 |
| 1390 | 0.719 | 37.1 |
| 1352 | 0.662 | 34.2 |
| 1323 | 0.439 | 22.7 |
| 1302 | 0.354 | 18.3 |
| 1272 | 0.476 | 24.6 |
| 1243 | 0.310 | 16.0 |
| 1208 | 0.372 | 19.2 |
| 1135 | 0.239 | 12.3 |
| 1092 | 0.264 | 13.6 |
| 1061 | 0.342 | 17.7 |
| 1024 | 0.769 | 39.7 |
| 998 | 0.560 | 28.9 |
| 884 | 0.214 | 11.1 |
| 852 | 0.359 | 18.5 |
| 808 | 0.763 | 39.4 |
| 791 | 0.896 | 46.3 |
| 741 | 0.387 | 20.0 |
| 721 | 0.538 | 27.8 |
| 680 | 0.348 | 18.0 |
| 577 | 0.263 | 13.6 |
| 548 | 0.335 | 17.3 |
| 484 | 0.351 | 18.1 |
| 442 | 0.309 | 16.0 |
| 408 | 0.325 | 16.8 |
| 332 | 0.308 | 15.9 |
| 256 | 0.446 | 23.0 |
| 226 | 0.389 | 20.1 |
| 199 | 0.613 | 31.7 |
| 155 | 0.585 | 30.2 |

In some embodiments, Form F is characterized by one or more peaks in its Raman spectrum selected from those in Table 17. In some embodiments, Form F is characterized by at least one, at least two, at least three, at least four, at least five, at least six, at least seven, at least eight, or at least nine peaks in its Raman spectrum selected from those in Table 17.

TABLE 17

Select characteristic peaks of the Raman spectrum of Form F.

| Wavenumber (cm$^{-1}$) | Absolute Intensity | Normalized Intensity (%) |
|---|---|---|
| 1605 | 1.936 | 100.0 |
| 1502 | 0.950 | 49.1 |
| 1449 | 0.768 | 39.7 |
| 1426 | 0.746 | 38.5 |
| 1390 | 0.719 | 37.1 |
| 1352 | 0.662 | 34.2 |
| 1024 | 0.769 | 39.7 |

TABLE 17-continued

Select characteristic peaks of the Raman spectrum of Form F.

| Wavenumber (cm$^{-1}$) | Absolute Intensity | Normalized Intensity (%) |
|---|---|---|
| 808 | 0.763 | 39.4 |
| 791 | 0.896 | 46.3 |

Figure 18:
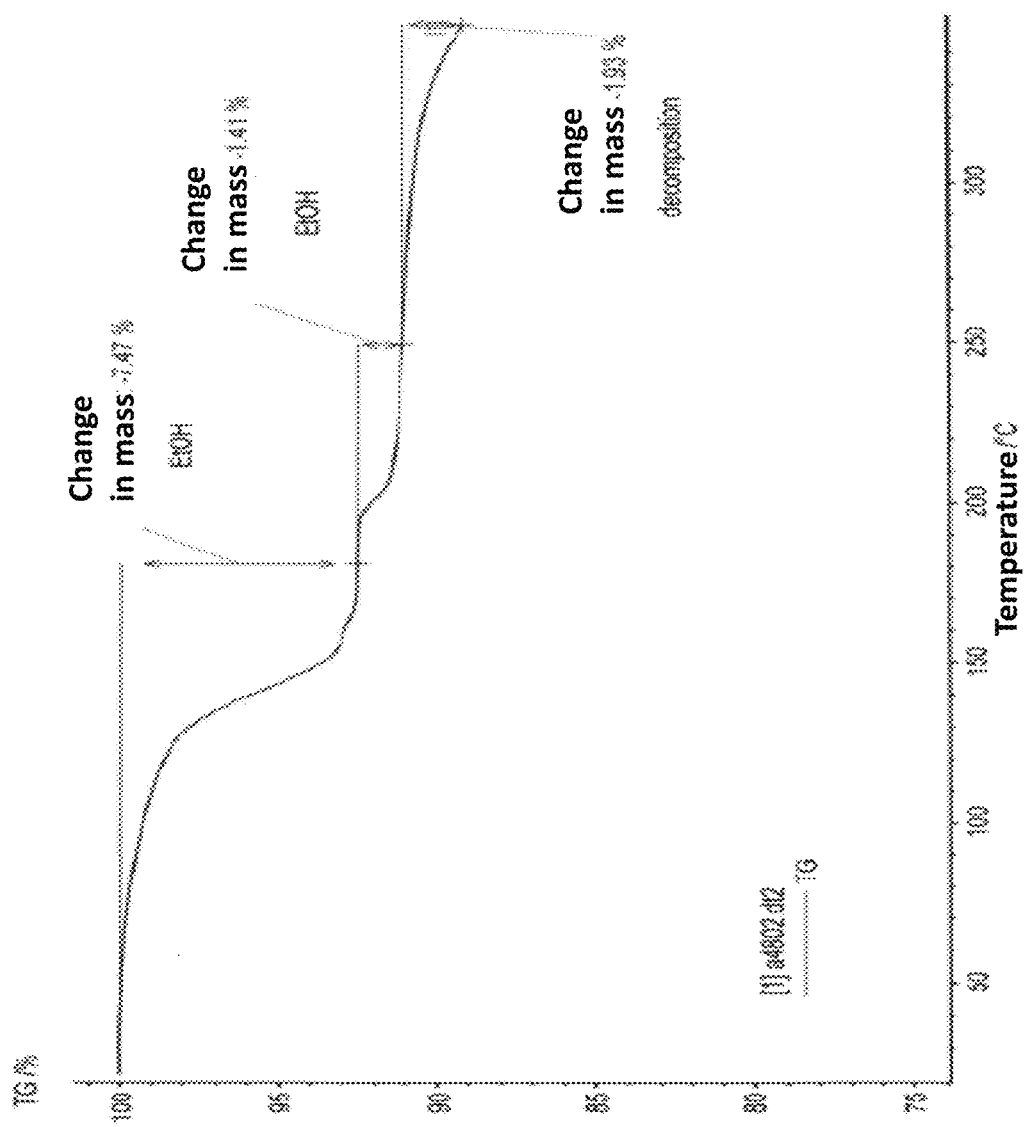
FIG. 18 depicts a TG-FTIR thermogram of Form F.

In some embodiments, Form F has a TG-FTIR thermogram substantially similar to the one depicted in FIG. 18.

In some embodiments, Form F is obtained from ethanol. In some embodiments, Form F is an ethanol solvate. In some embodiments, Form F is a non-stoichiometric solvate. In some embodiments, Form F is a non-stoichiometric ethanol solvate.

In some embodiments, Form F is stable for at least about 1 month, at least about 2 months, at least about 4 months, at least about 6 months, at least about 12 months, at least about 18 months, at least about 2 years, or at least about 3 years at about 25° C. and about 60% relative humidity.

Form G

In certain embodiments, the present invention provides crystalline Form G (Form G) of compound 1. In certain embodiments, Form G is substantially free of impurities. In certain embodiments, Form G is 99% free of impurities by weight. In certain embodiments, Form G is 97% free of impurities by weight. In certain embodiments, Form G is 95% free of impurities by weight. In certain embodiments, Form G is substantially free of amorphous compound 1. In certain embodiments, Form G is substantially free of other crystalline forms of compound 1. In certain embodiments, Form G is substantially free of a salt of compound 1.

Form G can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form G is characterized by an X-ray powder diffraction pattern substantially similar to the one depicted in FIG. 19. In some embodiments, Form G is characterized in that it has one or more peaks in its X-ray powder diffraction pattern selected from those in Table 18. In some embodiments, Form G is characterized by at least one, at least two, at least three, at least four, at least five, at least six, at least seven, at least eight, at least nine, at least ten, at least eleven, at least twelve, at least thirteen, or at least fourteen peaks in its X-ray powder diffraction pattern selected from those in Table 18. In some embodiments, Form G of compound 1 is characterized in that it has one or more peaks in its X-ray powder diffraction pattern selected from the strong and very strong peaks in Table 18.

TABLE 18

X-ray powder diffraction pattern of Form G.

| Angle 2-Theta ° | d value Angstrom | Intensity (relative) | Intensity % |
|---|---|---|---|
| 3.54 | 24.9 | vs | 100 |
| 5.00 | 17.7 | m | 27 |
| 6.12 | 14.4 | m | 16 |
| 7.08 | 12.5 | m | 21 |
| 7.89 | 11.2 | vs | 93 |
| 11.18 | 7.9 | m | 24 |
| 12.75 | 6.9 | m | 16 |

TABLE 18-continued

X-ray powder diffraction pattern of Form G.

| Angle 2-Theta ° | d value Angstrom | Intensity (relative) | Intensity % |
|---|---|---|---|
| 14.17 | 6.2 | m | 25 |
| 14.60 | 6.1 | s | 55 |
| 15.82 | 5.60 | s | 31 |
| 17.73 | 5.00 | s | 42 |
| 18.07 | 4.91 | s | 48 |
| 21.13 | 4.20 | m | 27 |
| 23.93 | 3.72 | s | 30 |

In some embodiments, Form G is characterized by one or more peaks in its X-ray powder diffraction pattern selected from those in Table 19. In some embodiments, Form G is characterized by at least one, at least two, at least three, or at least four peaks in its X-ray powder diffraction pattern selected from those in Table 19.

TABLE 19

Select characteristic peaks of the X-ray powder diffraction pattern of Form G.

| Angle 2-Theta ° | d value Angstrom | Intensity (relative) | Intensity % |
|---|---|---|---|
| 7.89 | 11.2 | vs | 93 |
| 14.60 | 6.1 | s | 55 |
| 17.73 | 5.00 | s | 42 |
| 18.07 | 4.91 | s | 48 |

Figure 20:
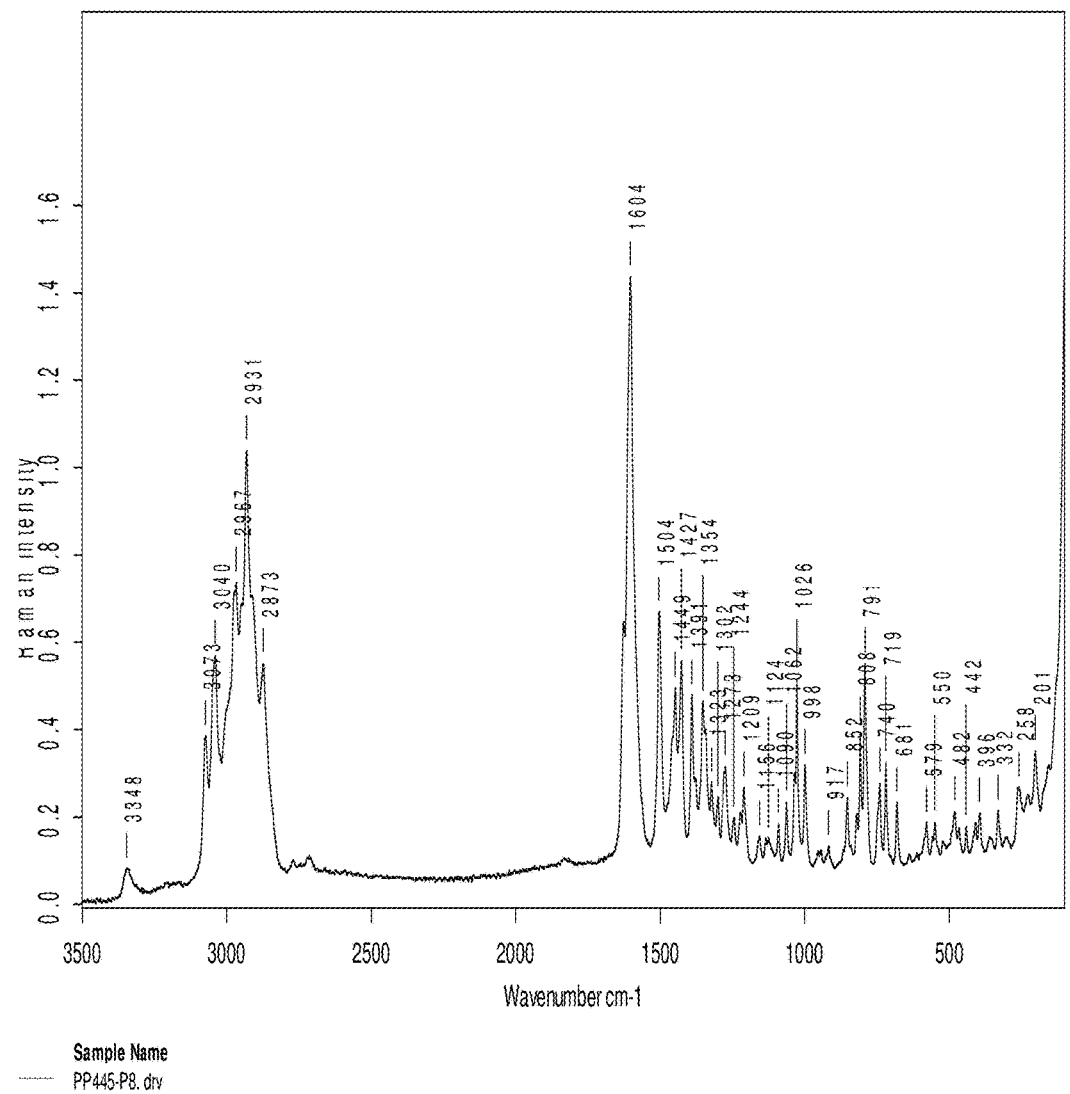
FIG. 20 depicts an FT-Raman spectrum of Form G.

In some embodiments, Form G is characterized by a Raman spectrum substantially similar to the one depicted in FIG. 20. In some embodiments, Form G is characterized by one or more peaks in its Raman spectrum selected from those in Table 20. In some embodiments, Form G is characterized by having a Raman spectrum with characteristic peaks at about those in Table 20.

TABLE 20

Raman spectrum of Form G.

| Wavenumber (cm$^{-1}$) | Absolute Intensity | Normalized Intensity (%) |
|---|---|---|
| 3348 | 0.083 | 5.8 |
| 3073 | 0.385 | 26.8 |
| 3039 | 0.568 | 39.5 |
| 2967 | 0.738 | 51.4 |
| 2931 | 1.038 | 72.2 |
| 2873 | 0.551 | 38.3 |
| 1604 | 1.437 | 100.0 |
| 1504 | 0.670 | 46.6 |
| 1449 | 0.496 | 34.5 |
| 1427 | 0.558 | 38.8 |
| 1391 | 0.480 | 33.4 |
| 1354 | 0.464 | 32.3 |
| 1323 | 0.281 | 19.6 |
| 1302 | 0.247 | 17.2 |
| 1273 | 0.316 | 22.0 |
| 1244 | 0.199 | 13.8 |
| 1209 | 0.268 | 18.6 |
| 1155 | 0.157 | 10.9 |
| 1124 | 0.152 | 10.6 |
| 1090 | 0.185 | 12.9 |
| 1062 | 0.235 | 16.4 |
| 1026 | 0.515 | 35.8 |
| 998 | 0.319 | 22.2 |
| 917 | 0.134 | 9.3 |
| 852 | 0.245 | 17.0 |
| 808 | 0.395 | 27.5 |

TABLE 20-continued

Raman spectrum of Form G.

| Wavenumber (cm$^{-1}$) | Absolute Intensity | Normalized Intensity (%) |
|---|---|---|
| 791 | 0.552 | 38.4 |
| 740 | 0.278 | 19.3 |
| 719 | 0.325 | 22.6 |
| 680 | 0.234 | 16.3 |
| 579 | 0.187 | 13.0 |
| 550 | 0.188 | 13.1 |
| 482 | 0.213 | 14.8 |
| 442 | 0.179 | 12.5 |
| 396 | 0.209 | 14.5 |
| 332 | 0.215 | 15.0 |
| 258 | 0.268 | 18.6 |
| 201 | 0.351 | 24.4 |

In some embodiments, Form G is characterized by one or more peaks in its Raman spectrum selected from those in Table 21. In some embodiments, Form G is characterized by at least one, at least two, at least three, at least four, at least five, at least six, at least seven, or at least eight peaks in its Raman spectrum selected from those in Table 21.

TABLE 21

Select characteristic peaks of the Raman spectrum of Form G.

| Wavenumber (cm$^{-1}$) | Absolute Intensity | Normalized Intensity (%) |
|---|---|---|
| 1604 | 1.437 | 100.0 |
| 1504 | 0.670 | 46.6 |
| 1449 | 0.496 | 34.5 |
| 1427 | 0.558 | 38.8 |
| 1391 | 0.480 | 33.4 |
| 1354 | 0.464 | 32.3 |
| 1026 | 0.515 | 35.8 |
| 791 | 0.552 | 38.4 |

Figure 21:
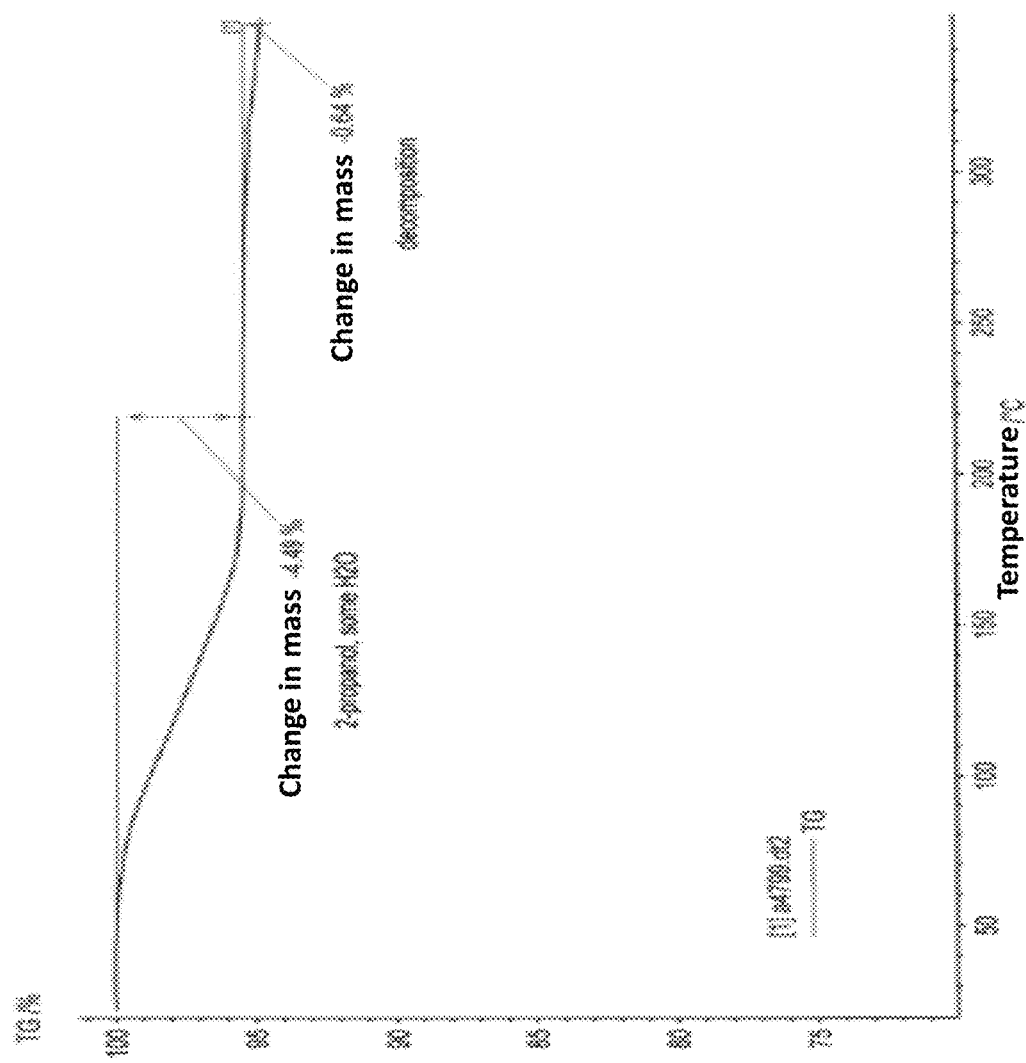
FIG. 21 depicts a TG-FTIR thermogram of Form G.

In some embodiments, Form G has a TG-FTIR thermogram substantially similar to the one depicted in FIG. 21.

In some embodiments, Form G is obtained from isopropanol. In some embodiments, Form G is an isopropanol solvate. In some embodiments, Form G is a non-stoichiometric solvate. In some embodiments, Form G is a non-stoichiometric isopropanol solvate.

Form H

In certain embodiments, the present invention provides crystalline Form H (Form H) of compound 1.

In certain embodiments, Form H is substantially free of impurities. In certain embodiments, Form H is 99% free of impurities by weight. In certain embodiments, Form H is 97% free of impurities by weight. In certain embodiments, Form H is 95% free of impurities by weight. In certain embodiments, Form H is substantially free of amorphous compound 1. In certain embodiments, Form H is substantially free of other crystalline forms of compound 1. In certain embodiments, Form H is substantially free of a salt of compound 1.

Form H can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form H is characterized by an X-ray powder diffraction pattern substantially similar to the one depicted in FIG. 22. In some embodiments, Form H is characterized in that it has one or more peaks in its X-ray powder diffraction pattern selected from those in Table 22. In some embodiments, Form H is characterized by at least one, at least two, at least three, at least four, at least five, at least six, at least seven, at least eight, at least nine, at least ten, at least eleven, at least twelve, or at least thirteen peaks in its X-ray powder diffraction pattern selected from those in Table 22. In some embodiments, Form H of compound 1 is characterized in that it has one or more peaks in its X-ray powder diffraction pattern selected from the strong and very strong peaks in Table 22.

TABLE 22

X-ray powder diffraction pattern of Form H.

| Angle 2-Theta ° | d value Angstrom | Intensity (relative) | Intensity % |
|---|---|---|---|
| 3.58 | 24.7 | vs | 100 |
| 6.13 | 14.4 | s | 52 |
| 7.50 | 11.8 | s | 68 |
| 7.87 | 11.2 | vs | 81 |
| 9.96 | 8.9 | m | 29 |
| 11.17 | 7.9 | s | 31 |
| 12.73 | 6.9 | s | 50 |
| 14.10 | 6.3 | s | 41 |
| 14.59 | 6.1 | s | 56 |
| 15.68 | 5.65 | vs | 85 |
| 17.69 | 5.01 | s | 66 |
| 18.79 | 4.72 | s | 57 |
| 21.84 | 4.07 | s | 61 |

In some embodiments, Form H is characterized by one or more peaks in its X-ray powder diffraction pattern selected from those in Table 23. In some embodiments, Form H is characterized by at least one, at least two, at least three, at least four, or at least five peaks in its X-ray powder diffraction pattern selected from those in Table 23.

TABLE 23

Select characteristic peaks of the X-ray powder diffraction pattern of Form H.

| Angle 2-Theta ° | d value Angstrom | Intensity (relative) | Intensity % |
|---|---|---|---|
| 6.13 | 14.4 | s | 52 |
| 7.87 | 11.2 | vs | 81 |
| 12.73 | 6.9 | s | 50 |
| 15.68 | 5.65 | vs | 85 |
| 17.69 | 5.01 | s | 66 |

Figure 23:
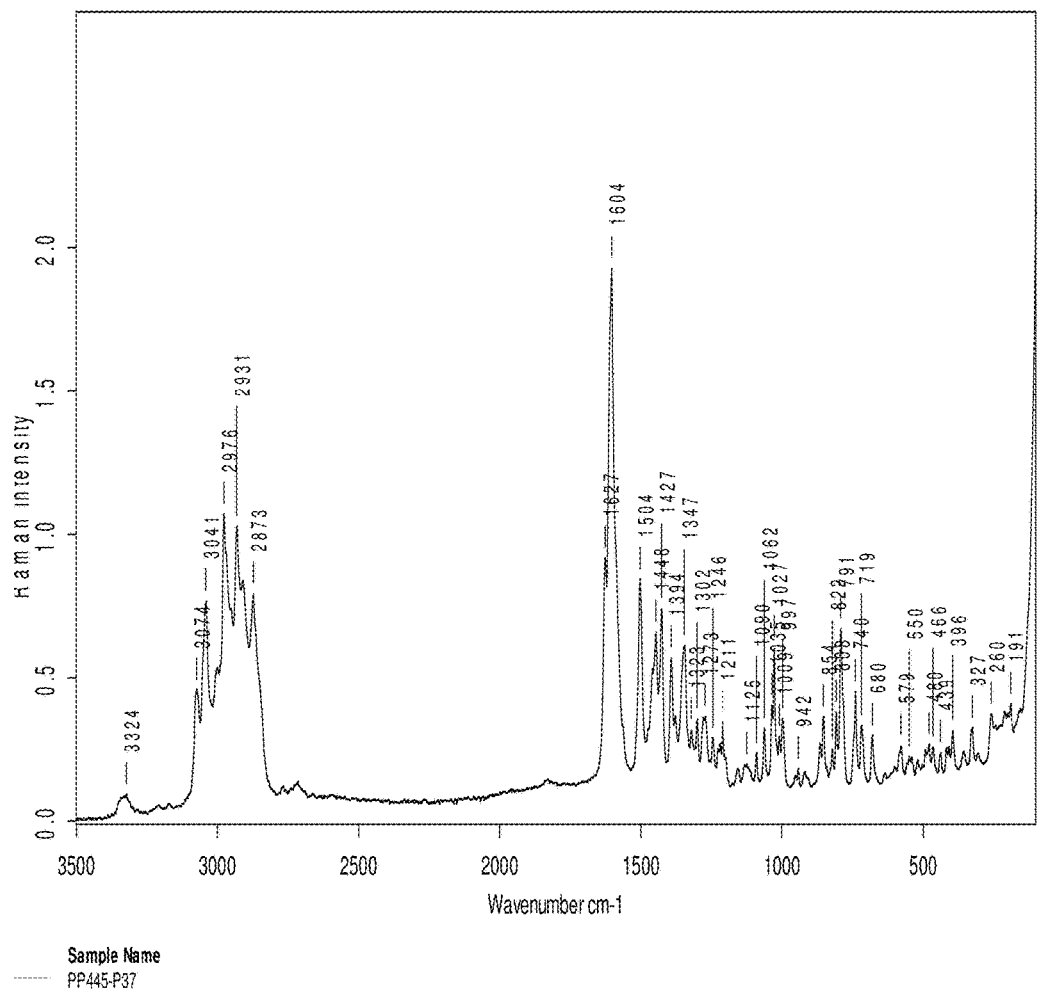
FIG. 23 depicts an FT-Raman spectrum of Form H.

In some embodiments, Form H is characterized by a Raman spectrum substantially similar to the one depicted in FIG. 23. In some embodiments, Form H is characterized by one or more peaks in its Raman spectrum selected from those in Table 24. In some embodiments, Form H is characterized by having a Raman spectrum with characteristic peaks at about those in Table 24,

TABLE 24

Raman spectrum of Form H.

| Wavenumber (cm$^{-1}$) | Absolute Intensity | Normalized Intensity (%) |
|---|---|---|
| 3324 | 0.093 | 4.8 |
| 3074 | 0.457 | 23.7 |
| 3041 | 0.769 | 39.8 |
| 2976 | 1.070 | 55.4 |

TABLE 24-continued

Raman spectrum of Form H.

| Wavenumber (cm⁻¹) | Absolute Intensity | Normalized Intensity (%) |
|---|---|---|
| 2931 | 1.027 | 53.2 |
| 2873 | 0.793 | 41.1 |
| 1627 | 0.918 | 47.5 |
| 1604 | 1.931 | 100.0 |
| 1503 | 0.845 | 43.8 |
| 1448 | 0.659 | 34.1 |
| 1427 | 0.743 | 38.5 |
| 1394 | 0.570 | 29.5 |
| 1347 | 0.614 | 31.8 |
| 1323 | 0.317 | 16.4 |
| 1302 | 0.356 | 18.4 |
| 1273 | 0.364 | 18.9 |
| 1246 | 0.289 | 15.0 |
| 1211 | 0.346 | 17.9 |
| 1125 | 0.197 | 10.2 |
| 1090 | 0.237 | 12.3 |
| 1062 | 0.322 | 16.7 |
| 1035 | 0.403 | 20.9 |
| 1027 | 0.606 | 31.4 |
| 1009 | 0.295 | 15.3 |
| 997 | 0.358 | 18.5 |
| 942 | 0.182 | 9.4 |
| 854 | 0.364 | 18.9 |
| 822 | 0.250 | 12.9 |
| 808 | 0.378 | 19.6 |
| 791 | 0.671 | 34.7 |
| 740 | 0.455 | 23.6 |
| 719 | 0.333 | 17.2 |
| 680 | 0.298 | 15.4 |
| 579 | 0.262 | 13.6 |
| 550 | 0.224 | 11.6 |
| 480 | 0.268 | 13.9 |
| 466 | 0.258 | 13.4 |
| 439 | 0.238 | 12.3 |
| 396 | 0.315 | 16.3 |
| 327 | 0.324 | 16.8 |
| 260 | 0.373 | 19.3 |
| 191 | 0.409 | 21.2 |

In some embodiments, Form H is characterized by one or more peaks in its Raman spectrum selected from those in Table 25. In some embodiments, Form H is characterized by at least one, at least two, at least three, at least four, at least five, at least six, at least seven, or at least eight peaks in its Raman spectrum selected from those in Table 25.

TABLE 25

Select characteristic peaks of the Raman spectrum of Form H.

| Wavenumber (cm⁻¹) | Absolute Intensity | Normalized Intensity (%) |
|---|---|---|
| 1627 | 0.918 | 47.5 |
| 1601 | 1.931 | 100.0 |
| 1503 | 0.845 | 43.8 |
| 1448 | 0.659 | 34.1 |
| 1427 | 0.743 | 38.5 |
| 1347 | 0.614 | 31.8 |
| 1027 | 0.606 | 31.4 |
| 791 | 0.671 | 34.7 |

Figure 24:
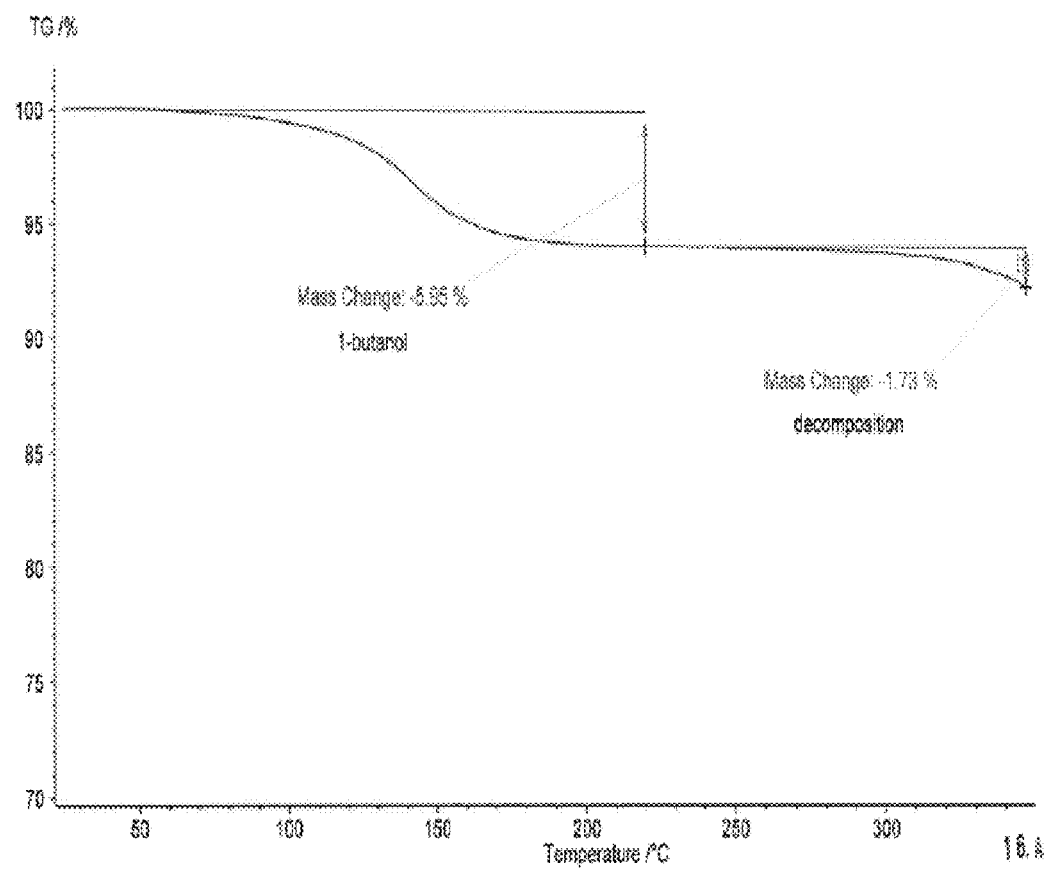
FIG. 24 depicts a TG-FTIR thermogram of Form H.

In some embodiments, Form H has a TG-FTIR thermogram substantially similar to the one depicted in FIG. 24.

In some embodiments, Form H is obtained from 1-butanol. In some embodiments, Form H is a 1-butanol solvate. In some embodiments, Form H is a non-stoichiometric solvate. In some embodiments, Form H is a non-stoichiometric 1-butanol solvate Form I In certain embodiments, the present invention provides crystalline Form I of compound 1. In certain embodiments, Form I is substantially free of impurities. In certain embodiments, Form I is 99% free of impurities by weight. In certain embodiments, Form I is 97% free of impurities by weight. In certain embodiments, Form I is 95% free of impurities by weight. In certain embodiments, Form I is substantially free of amorphous compound 1. In certain embodiments, Form I is substantially free of other crystalline forms of compound 1. In certain embodiments, Form I is substantially free of a salt of compound 1.

Form I can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form I is characterized by an X-ray powder diffraction pattern substantially similar to the one depicted in FIG. 25. In some embodiments, Form I is characterized in that it has one or more peaks in its X-ray powder diffraction pattern selected from those in Table 26. In some embodiments, Form I is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or at least nineteen peaks in its X-ray powder diffraction pattern selected from those in Table 26. In some embodiments, Form I of compound 1 is characterized in that it has one or more peaks in its X-ray powder diffraction pattern selected from the strong and very strong peaks in Table 26.

TABLE 26

X-ray powder diffraction pattern of Form I.

| Angle 2-Theta ° | d value Angstrom | Intensity (relative) | Intensity % |
|---|---|---|---|
| 3.81 | 23.1 | vs | 99 |
| 5.23 | 16.9 | s | 33 |
| 6.24 | 14.2 | vs | 83 |
| 7.57 | 11.7 | vs | 85 |
| 8.02 | 11.0 | s | 47 |
| 8.74 | 10.1 | s | 64 |
| 9.34 | 9.5 | s | 38 |
| 10.01 | 8.8 | s | 32 |
| 12.45 | 7.1 | s | 42 |
| 12.88 | 6.9 | s | 64 |
| 14.09 | 6.3 | s | 58 |
| 16.03 | 5.52 | vs | 100 |
| 17.48 | 5.07 | vs | 75 |
| 18.70 | 4.74 | vs | 81 |
| 21.40 | 4.15 | s | 43 |
| 21.90 | 4.05 | s | 46 |
| 22.48 | 3.95 | s | 47 |
| 24.12 | 3.69 | s | 44 |
| 25.71 | 3.46 | s | 34 |

In some embodiments, Form I is characterized by one or more peaks in its X-ray powder diffraction pattern selected from those in Table 27. In some embodiments, Form I is characterized by at least one, at least two, at least three, at least four, at least five, or at least six peaks in its X-ray powder diffraction pattern selected from those in Table 27.

TABLE 27

Select characteristic peaks of the X-ray
powder diffraction pattern of Form I.

| Angle 2-Theta ° | d value Angstrom | Intensity (relative) | Intensity % |
|---|---|---|---|
| 6.24 | 14.2 | vs | 83 |
| 7.57 | 11.7 | vs | 85 |
| 8.74 | 10.1 | s | 64 |
| 16.03 | 5.52 | vs | 100 |
| 17.48 | 5.07 | vs | 75 |
| 18.70 | 4.74 | vs | 81 |

Figure 26:
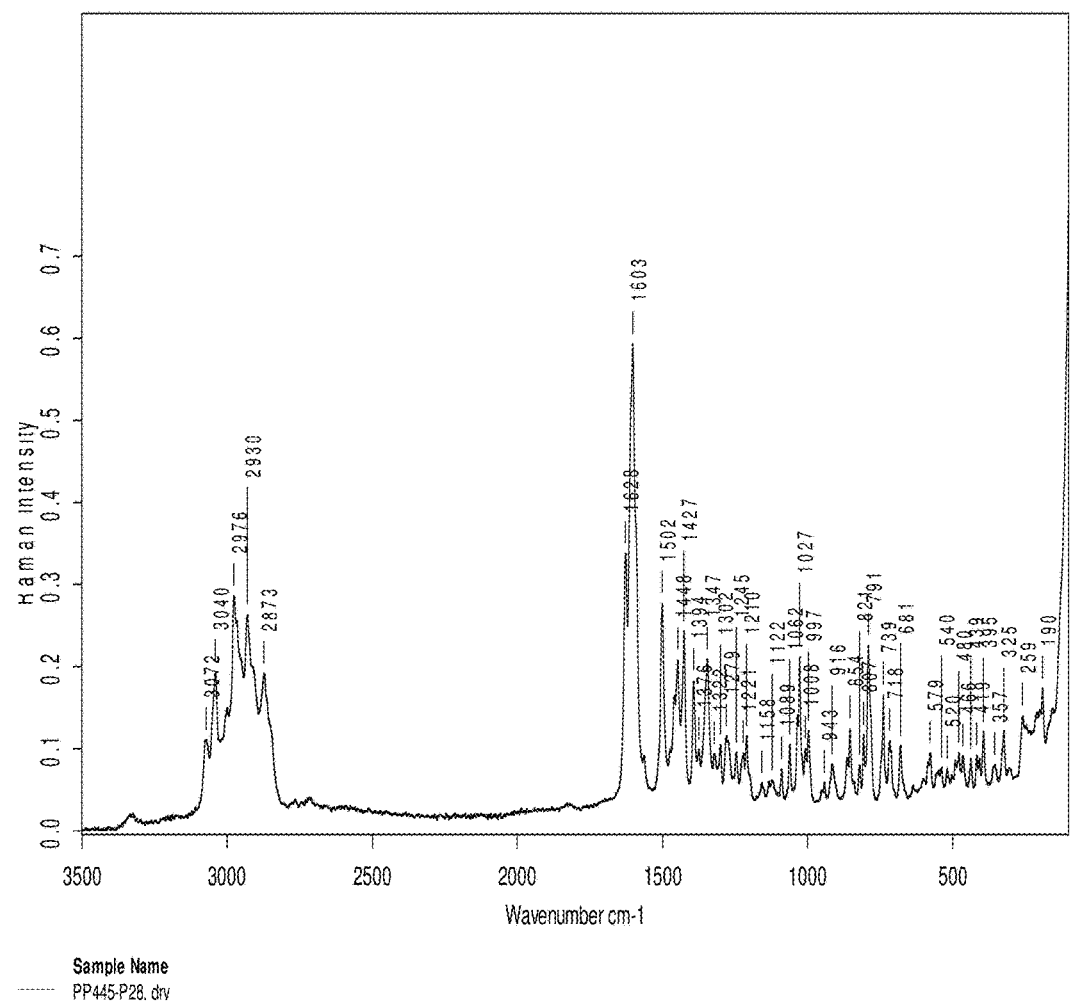
FIG. 26 depicts an FT-Raman spectrum of Form I.

In some embodiments, Form I is characterized by a Raman spectrum substantially similar to the one depicted in FIG. 26. In some embodiments, Form I is characterized by one or more peaks in its Raman spectrum selected from those in Table 28. In some embodiments, Form I is characterized by having a Raman spectrum with characteristic peaks at about those in Table 28.

TABLE 28

Raman spectrum of Form I.

| Wavenumber (cm$^{-1}$) | Absolute Intensity | Normalized Intensity (%) |
|---|---|---|
| 3072 | 0.111 | 18.7 |
| 3040 | 0.193 | 32.5 |
| 2976 | 0.286 | 48.2 |
| 2930 | 0.263 | 44.4 |
| 2873 | 0.191 | 32.2 |
| 1628 | 0.338 | 57.0 |
| 1603 | 0.593 | 100.0 |
| 1502 | 0.277 | 46.7 |
| 1448 | 0.208 | 35.1 |
| 1427 | 0.243 | 41.0 |
| 1394 | 0.183 | 30.9 |
| 1376 | 0.099 | 16.7 |
| 1347 | 0.209 | 35.2 |
| 1322 | 0.094 | 15.9 |
| 1302 | 0.105 | 17.7 |
| 1279 | 0.116 | 19.6 |
| 1245 | 0.095 | 16.0 |
| 1221 | 0.095 | 16.0 |
| 1210 | 0.116 | 19.6 |
| 1158 | 0.058 | 9.8 |
| 1122 | 0.062 | 10.5 |
| 1089 | 0.076 | 12.8 |
| 1062 | 0.105 | 17.7 |
| 1027 | 0.212 | 35.8 |
| 1008 | 0.100 | 16.9 |
| 997 | 0.122 | 20.6 |
| 943 | 0.059 | 9.9 |
| 916 | 0.081 | 13.7 |
| 854 | 0.124 | 20.9 |
| 821 | 0.080 | 13.5 |
| 807 | 0.117 | 19.7 |
| 791 | 0.226 | 38.1 |
| 739 | 0.166 | 28.0 |
| 718 | 0.110 | 18.5 |
| 681 | 0.104 | 17.5 |
| 579 | 0.095 | 16.0 |
| 540 | 0.077 | 13.0 |
| 520 | 0.076 | 12.8 |
| 480 | 0.095 | 16.0 |
| 466 | 0.092 | 15.5 |
| 439 | 0.088 | 14.8 |
| 419 | 0.092 | 15.5 |
| 395 | 0.121 | 20.4 |
| 357 | 0.081 | 13.7 |
| 325 | 0.122 | 20.6 |
| 259 | 0.140 | 23.6 |
| 190 | 0.173 | 29.2 |

In some embodiments, Form I is characterized by one or more peaks in its Raman spectrum selected from those in Table 29. In some embodiments, Form I is characterized by at least one, at least two, at least three, at least four, at least five, at least six, at least seven, at least eight, or at least nine peaks in its Raman spectrum selected from those in Table 29.

TABLE 29

Select characteristic peaks of the Raman spectrum of Form I.

| Wavenumber (cm$^{-1}$) | Absolute Intensity | Normalized Intensity (%) |
|---|---|---|
| 1628 | 0.338 | 57.0 |
| 1603 | 0.593 | 100.0 |
| 1502 | 0.277 | 46.7 |
| 1448 | 0.208 | 35.1 |
| 1427 | 0.243 | 41.0 |
| 1394 | 0.183 | 30.9 |
| 1347 | 0.209 | 35.2 |
| 1027 | 0.212 | 35.8 |
| 791 | 0.226 | 38.1 |

Figure 27:
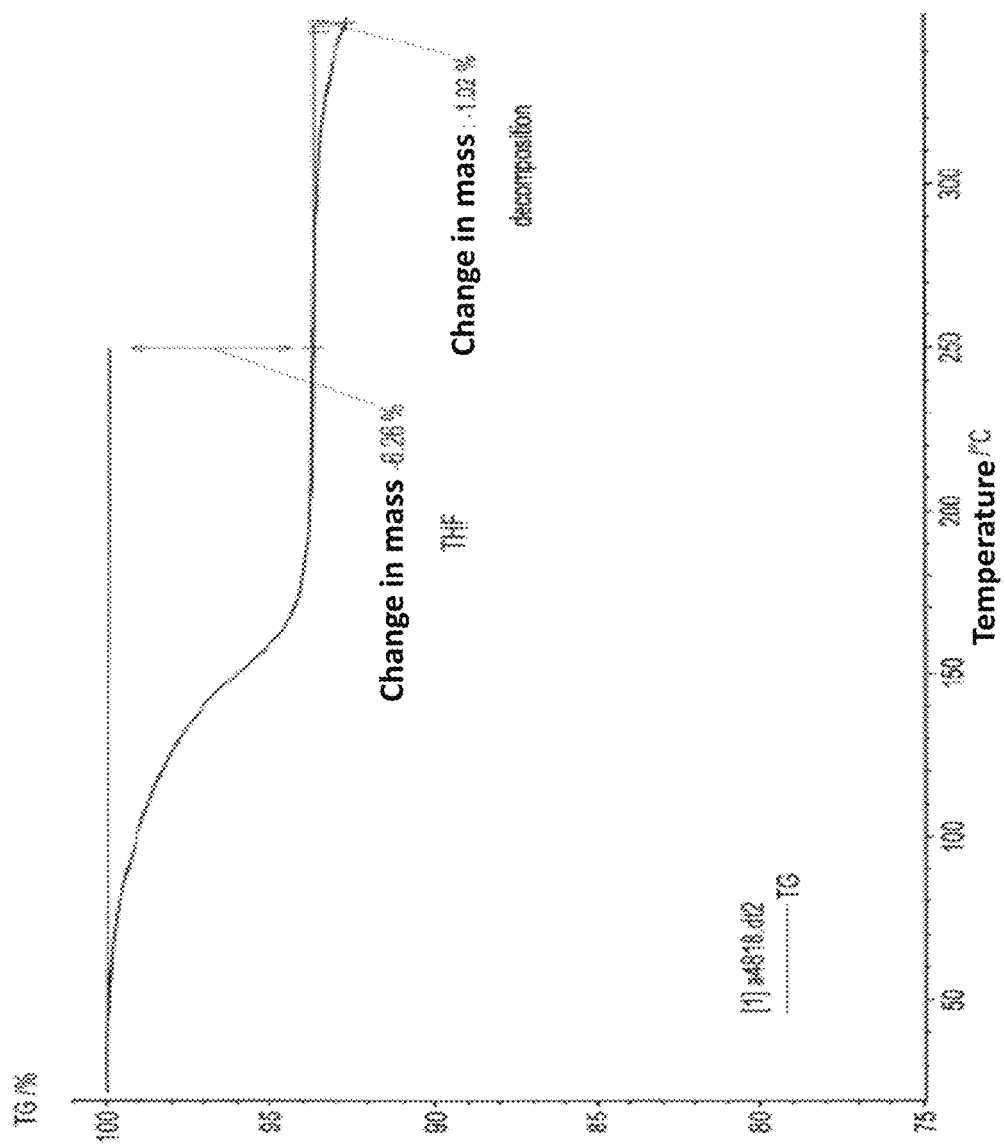
FIG. 27 depicts a TG-FTIR thermogram of Form I.

In some embodiments, Form I has a TG-FTIR thermogram substantially similar to the one depicted in FIG. 27.

In some embodiments, Form I is obtained from tetrahydrofuran. In some embodiments, Form I is a tetrahydrofuran solvate. In some embodiments, Form I is a non-stoichiometric solvate. In some embodiments, Form I is a non-stoichiometric tetrahydrofuran solvate.

Form J

In certain embodiments, the present invention provides crystalline Form J of compound 1. In certain embodiments, Form J is substantially free of impurities. In certain embodiments, Form J is 99% free of impurities by weight. In certain embodiments, Form J is 97% free of impurities by weight. In certain embodiments, Form J is 95% free of impurities by weight. In certain embodiments, Form J is substantially free of amorphous compound 1. In certain embodiments, Form J is substantially free of other crystalline forms of compound 1. In certain embodiments, Form J is substantially free of a salt of compound 1.

Form J can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form J is characterized by an X-ray powder diffraction pattern substantially similar to the one depicted in FIG. 28. In some embodiments, Form J is characterized in that it has one or more peaks in its X-ray powder diffraction pattern selected from those in Table 30. In some embodiments, Form J is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty-seven, at least thirty-eight, at least thirty-nine, at least forty, at least forty-one, at least forty-two, at least forty-three, at least forty-four, at least forty-five, at least forty-six, at least forty-seven, at least forty-eight, at least forty-nine, at least fifty, fifty-one, at least fifty-two, at least fifty-three, at least fifty-four, at least fifty-five, at least fifty-six, at least fifty-seven, at least fifty-eight, at least fifty-nine, at least sixty peaks in its X-ray powder diffraction pattern selected from those in Table 30. In some embodiments, Form J of compound 1 is characterized in that it has one or more peaks in its X-ray powder diffraction pattern selected from the strong and very strong peaks in Table 30.

TABLE 30

X-ray powder diffraction pattern of Form J.

| Angle 2-Theta ° | d value Angstrom | Intensity (relative) | Intensity % |
|---|---|---|---|
| 6.26 | 14.1 | vs | 100 |
| 8.12 | 10.9 | vw | 3 |
| 8.83 | 10.0 | vw | 2 |
| 9.12 | 9.7 | vw | 2 |
| 9.33 | 9.5 | w | 5 |
| 10.04 | 8.8 | m | 21 |
| 12.21 | 7.2 | vw | 5 |
| 12.57 | 7.0 | vw | 2 |
| 12.80 | 6.9 | vw | 2 |
| 12.97 | 6.8 | vw | 4 |
| 13.20 | 6.7 | m | 17 |
| 14.54 | 6.1 | w | 9 |
| 14.73 | 6.0 | vw | 4 |
| 15.38 | 5.76 | w | 6 |
| 15.75 | 5.62 | vw | 4 |
| 16.32 | 5.43 | w | 5 |
| 16.46 | 5.38 | vw | 4 |
| 16.90 | 5.24 | vw | 4 |
| 17.11 | 5.18 | vw | 2 |
| 17.50 | 5.06 | vw | 2 |
| 17.76 | 4.99 | vw | 4 |
| 18.13 | 4.89 | w | 8 |
| 18.38 | 4.82 | w | 13 |
| 18.62 | 4.76 | w | 8 |
| 18.88 | 4.70 | w | 13 |
| 19.07 | 4.65 | vw | 4 |
| 19.98 | 4.44 | vw | 5 |
| 20.21 | 4.39 | w | 14 |
| 20.62 | 4.30 | w | 5 |
| 21.15 | 4.20 | w | 7 |
| 21.48 | 4.13 | vw | 3 |
| 21.93 | 4.05 | vw | 4 |
| 22.24 | 3.99 | vw | 4 |
| 22.75 | 3.91 | vw | 3 |
| 23.16 | 3.84 | vw | 4 |
| 23.34 | 3.81 | w | 9 |
| 23.67 | 3.76 | vw | 2 |
| 24.10 | 3.69 | w | 6 |
| 24.54 | 3.62 | w | 7 |
| 24.84 | 3.58 | vw | 2 |
| 25.11 | 3.54 | vw | 3 |
| 25.28 | 3.52 | vw | 3 |
| 25.60 | 3.48 | w | 8 |
| 25.87 | 3.44 | w | 6 |
| 26.10 | 3.41 | vw | 3 |
| 26.59 | 3.35 | vw | 2 |
| 27.25 | 3.27 | vw | 2 |
| 27.67 | 3.22 | vw | 2 |
| 28.05 | 3.18 | vw | 3 |
| 28.60 | 3.12 | vw | 2 |
| 28.95 | 3.08 | vw | 2 |
| 29.28 | 3.05 | vw | 3 |
| 29.59 | 3.02 | vw | 2 |
| 29.86 | 2.99 | vw | 2 |
| 30.63 | 2.92 | vw | 2 |
| 31.78 | 2.81 | vw | 3 |
| 32.53 | 2.75 | vw | 2 |
| 32.80 | 2.73 | vw | 2 |
| 32.96 | 2.72 | vw | 2 |
| 33.23 | 2.69 | vw | 3 |

In some embodiments, Form J is characterized by one or more peaks in its X-ray powder diffraction pattern selected from those in Table 31. In some embodiments, Form J is characterized by at least one, at least two, at least three, at least four, at least five, or at least six peaks in its X-ray powder diffraction pattern selected from those in Table 31.

TABLE 31

Select characteristic peaks of the X-ray powder diffraction pattern of Form J.

| Angle 2-Theta ° | d value Angstrom | Intensity (relative) | Intensity % |
|---|---|---|---|
| 6.26 | 14.1 | vs | 100 |
| 10.04 | 8.8 | m | 21 |
| 13.20 | 6.7 | m | 17 |
| 18.38 | 4.82 | w | 13 |
| 18.88 | 4.70 | w | 13 |
| 20.21 | 4.39 | w | 14 |

Figure 29:
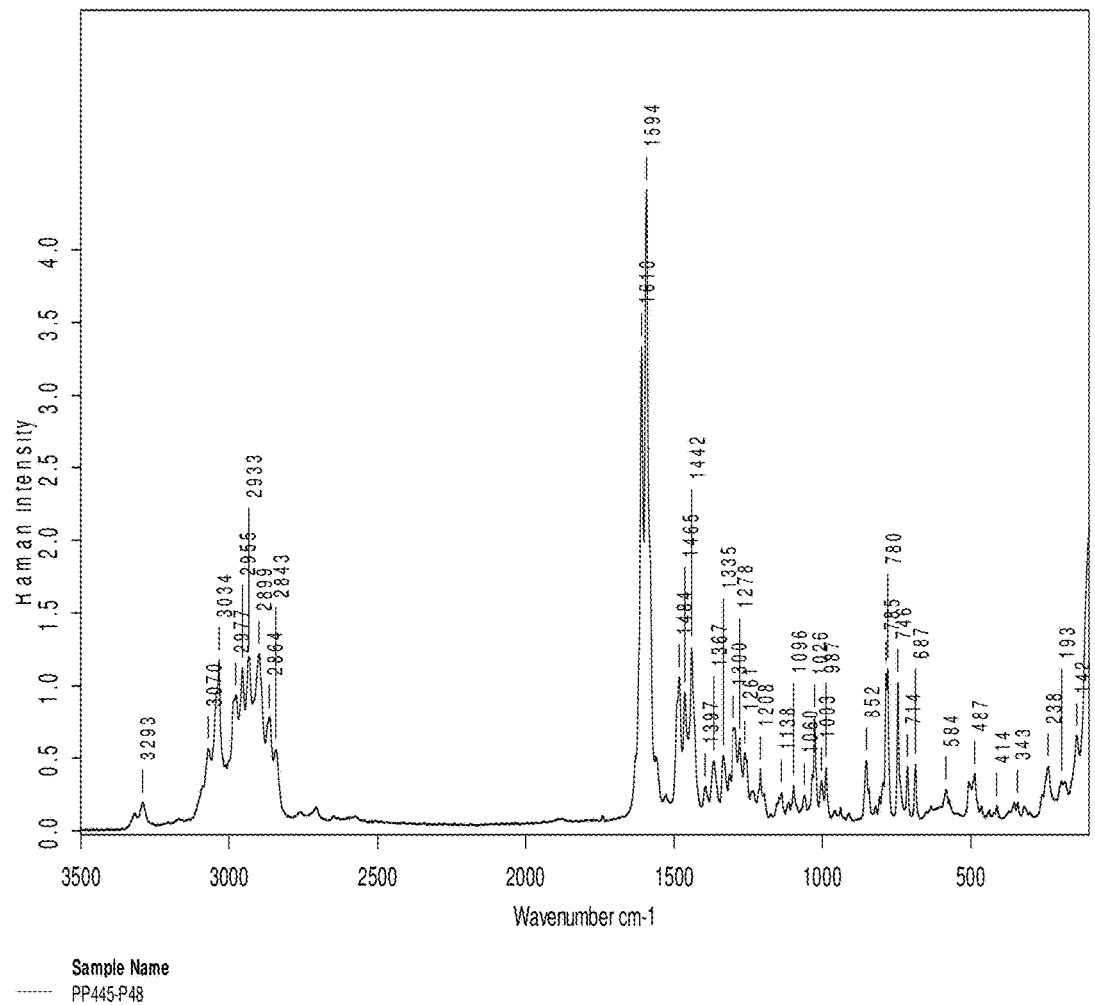
FIG. 29 depicts an FT-Raman spectrum of Form J.

In some embodiments, Form J is characterized by a Raman spectrum substantially similar to the one depicted in FIG. 29. In some embodiments, Form J is characterized by one or more peaks in its Raman spectrum selected from those in Table 32. In some embodiments, Form J is characterized by having a Raman spectrum with characteristic peaks at about those in Table 32.

TABLE 32

Raman spectrum of Form J.

| Wavenumber (cm$^{-1}$) | Absolute Intensity | Normalized Intensity (%) |
|---|---|---|
| 3293 | 0.192 | 4.3 |
| 3070 | 0.563 | 12.8 |
| 3034 | 1.175 | 26.6 |
| 2977 | 0.934 | 21.2 |
| 2955 | 1.121 | 25.4 |
| 2933 | 1.197 | 27.1 |
| 2899 | 1.219 | 27.6 |
| 2864 | 0.780 | 17.7 |
| 2843 | 0.558 | 12.6 |
| 1610 | 3.336 | 75.6 |
| 1593 | 4.414 | 100.0 |
| 1483 | 1.059 | 24.0 |
| 1465 | 0.954 | 21.6 |
| 1442 | 1.264 | 28.6 |
| 1397 | 0.304 | 6.9 |
| 1367 | 0.479 | 10.9 |
| 1335 | 0.516 | 11.7 |
| 1300 | 0.707 | 16.0 |
| 1278 | 0.633 | 14.3 |
| 1261 | 0.536 | 12.1 |
| 1208 | 0.422 | 9.6 |
| 1138 | 0.260 | 5.9 |
| 1096 | 0.310 | 7.0 |
| 1060 | 0.241 | 5.5 |
| 1026 | 0.781 | 17.7 |
| 1003 | 0.342 | 7.7 |
| 987 | 0.432 | 9.8 |
| 852 | 0.483 | 10.9 |
| 785 | 1.087 | 24.6 |
| 780 | 1.120 | 25.4 |
| 746 | 1.028 | 23.3 |
| 713 | 0.438 | 9.9 |
| 687 | 0.460 | 10.4 |
| 584 | 0.284 | 6.4 |
| 487 | 0.390 | 8.8 |
| 413 | 0.170 | 3.9 |
| 343 | 0.191 | 4.3 |
| 238 | 0.441 | 10.0 |
| 193 | 0.340 | 7.7 |
| 142 | 0.655 | 14.8 |

In some embodiments, Form J is characterized by one or more peaks in its Raman spectrum selected from those in Table 33. In some embodiments, Form J is characterized by at least one, at least two, at least three, at least four, at least five, at least six, at least seven, or at least eight peaks in its Raman spectrum selected from those in Table 33.

TABLE 33

Select characteristic peaks of the Raman spectrum of Form J.

| Wavenumber (cm$^{-1}$) | Absolute Intensity | Normalized Intensity (%) |
|---|---|---|
| 1610 | 3.336 | 75.6 |
| 1593 | 4.414 | 100.0 |
| 1483 | 1.059 | 24.0 |
| 1465 | 0.954 | 21.6 |
| 1442 | 1.264 | 28.6 |
| 785 | 1.087 | 24.6 |
| 780 | 1.120 | 25.4 |
| 746 | 1.028 | 23.3 |

Figure 30:
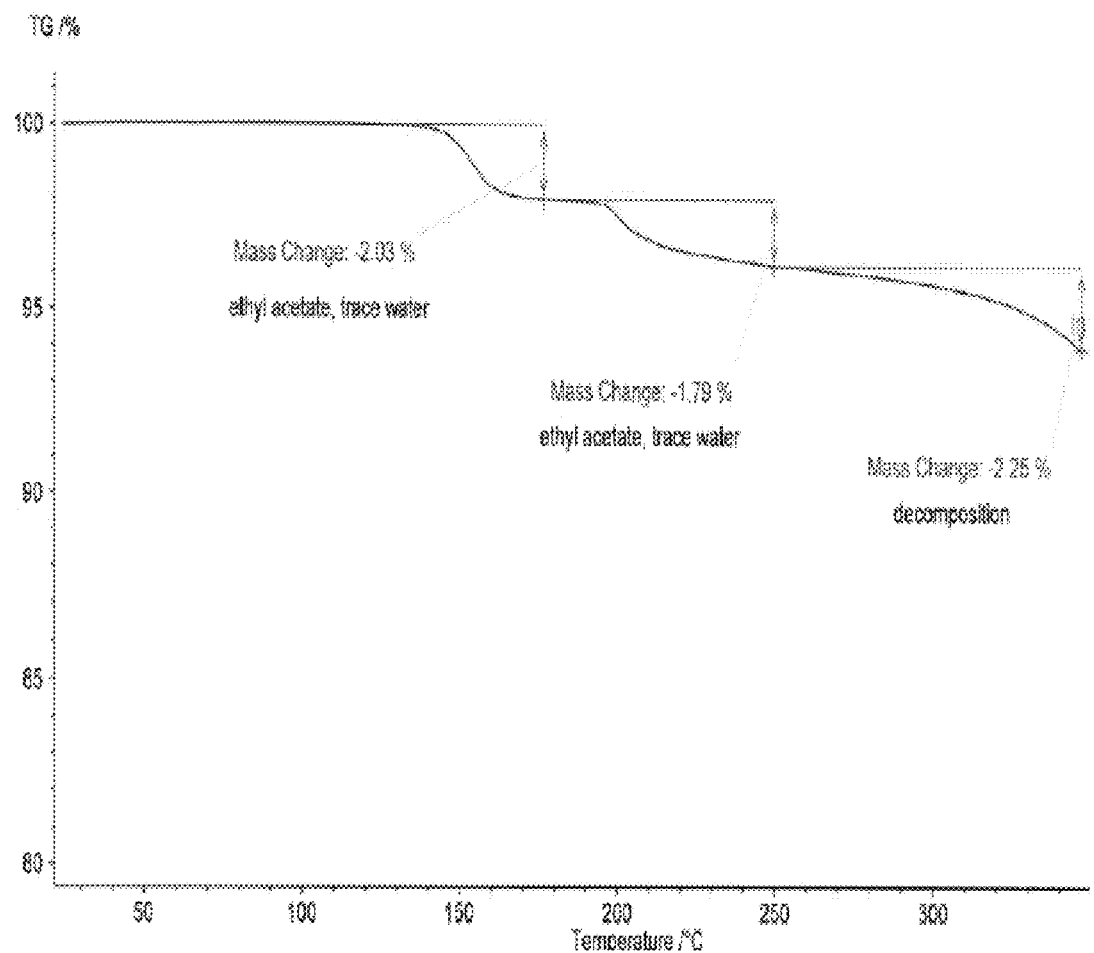
FIG. 30 depicts a TG-FTIR thermogram of Form J.

In some embodiments, Form J has a TG-FTIR thermogram substantially similar to the one depicted in FIG. 30. In some embodiments, Form J is obtained from ethyl acetate. In some embodiments, Form J is an ethyl acetate solvate. In some embodiments, Form J is a non-stoichiometric solvate. In some embodiments, Form J is a non-stoichiometric ethyl acetate solvate.

Form K

In certain embodiments, the present invention provides crystalline Form K (Form K) of compound 1. In certain embodiments, Form K is substantially free of impurities. In certain embodiments, Form K is 99% free of impurities by weight. In certain embodiments, Form K is 97% free of impurities by weight. In certain embodiments, Form K is 95% free of impurities by weight. In certain embodiments, Form K is substantially free of amorphous compound 1. In certain embodiments, Form K is substantially free of other crystalline forms of compound 1. In certain embodiments, Form K is substantially free of a salt of compound 1.

Form K can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form K is characterized by an X-ray powder diffraction pattern substantially similar to the one depicted in FIG. 31. In some embodiments, Form K is characterized in that it has one or more peaks in its X-ray powder diffraction pattern selected from those in Table 34. In some embodiments, Form K is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty peaks in its X-ray powder diffraction pattern selected from those in Table 34. In some embodiments, Form K of compound 1 is characterized in that it has one or more peaks in its X-ray powder diffraction pattern selected from the strong and very strong peaks in Table 34.

TABLE 34

X-ray powder diffraction pattern of Form K.

| Angle 2-Theta ° | d value Angstrom | Intensity (relative) | Intensity % |
|---|---|---|---|
| 3.55 | 24.9 | s | 42 |
| 5.89 | 15.0 | s | 43 |

TABLE 34-continued

X-ray powder diffraction pattern of Form K.

| Angle 2-Theta ° | d value Angstrom | Intensity (relative) | Intensity % |
|---|---|---|---|
| 6.94 | 12.7 | s | 43 |
| 7.18 | 12.3 | s | 53 |
| 8.47 | 10.4 | s | 39 |
| 9.00 | 9.8 | m | 22 |
| 10.20 | 8.7 | m | 22 |
| 10.82 | 8.2 | m | 17 |
| 12.55 | 7.0 | m | 23 |
| 14.11 | 6.3 | s | 34 |
| 14.67 | 6.0 | s | 54 |
| 15.36 | 5.77 | s | 43 |
| 15.87 | 5.58 | s | 51 |
| 17.19 | 5.16 | vs | 77 |
| 17.82 | 4.97 | vs | 86 |
| 18.08 | 4.90 | s | 69 |
| 19.68 | 4.51 | vs | 100 |
| 20.78 | 4.27 | s | 44 |
| 21.97 | 4.04 | s | 45 |
| 22.27 | 3.99 | s | 45 |

In some embodiments, Form K is characterized by one or more peaks in its X-ray powder diffraction pattern selected from those in Table 35. In some embodiments, Form K is characterized by at least one, at least two, at least three, at least four, at least five, at least six, or at least seven peaks in its X-ray powder diffraction pattern selected from those in Table 35.

TABLE 35

Select characteristic peaks of the X-ray powder diffraction pattern of Form K.

| Angle 2-Theta ° | d value Angstrom | Intensity (relative) | Intensity % |
|---|---|---|---|
| 7.18 | 12.3 | s | 53 |
| 14.67 | 6.0 | s | 54 |
| 15.87 | 5.58 | s | 51 |
| 17.19 | 5.16 | vs | 77 |
| 17.82 | 4.97 | vs | 86 |
| 18.08 | 4.90 | s | 69 |
| 19.68 | 4.51 | vs | 100 |

Figure 32:
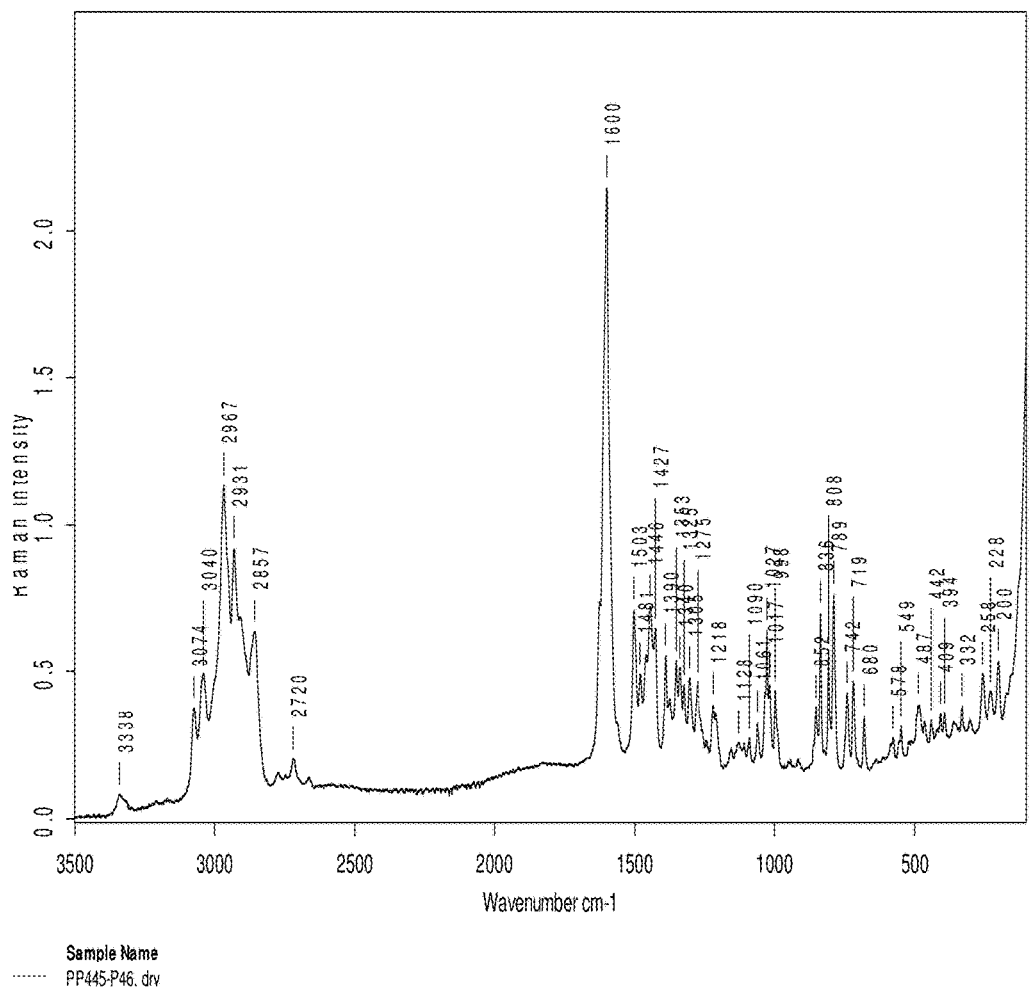
FIG. 32 depicts an FT-Raman spectrum of Form K.

In some embodiments, Form K is characterized by a Raman spectrum substantially similar to the one depicted in FIG. 32. In some embodiments, Form K is characterized by one or more peaks in its Raman spectrum selected from those in Table 36. In some embodiments, Form K is characterized by having a Raman spectrum with characteristic peaks at about those in Table 36.

TABLE 36

Raman spectrum of Form K.

| Wavenumber (cm$^{-1}$) | Absolute Intensity | Normalized Intensity (%) |
|---|---|---|
| 3338 | 0.082 | 3.8 |
| 3074 | 0.375 | 17.5 |
| 3040 | 0.492 | 22.9 |
| 2967 | 1.134 | 52.8 |
| 2931 | 0.919 | 42.8 |
| 2857 | 0.638 | 29.7 |
| 2720 | 0.202 | 9.4 |
| 1600 | 2.148 | 100.0 |
| 1503 | 0.711 | 33.1 |
| 1481 | 0.490 | 22.8 |
| 1446 | 0.723 | 33.7 |

TABLE 36-continued

Raman spectrum of Form K.

| Wavenumber (cm$^{-1}$) | Absolute Intensity | Normalized Intensity (%) |
|---|---|---|
| 1427 | 0.648 | 30.2 |
| 1390 | 0.555 | 25.8 |
| 1352 | 0.537 | 25.0 |
| 1340 | 0.512 | 23.8 |
| 1325 | 0.453 | 21.1 |
| 1305 | 0.479 | 22.3 |
| 1275 | 0.463 | 21.6 |
| 1218 | 0.386 | 18.0 |
| 1128 | 0.258 | 12.0 |
| 1090 | 0.273 | 12.7 |
| 1061 | 0.326 | 15.2 |
| 1027 | 0.642 | 29.9 |
| 1017 | 0.455 | 21.2 |
| 998 | 0.434 | 20.2 |
| 852 | 0.376 | 17.5 |
| 836 | 0.701 | 32.6 |
| 808 | 0.570 | 26.5 |
| 789 | 0.765 | 35.6 |
| 742 | 0.426 | 19.8 |
| 719 | 0.467 | 21.7 |
| 680 | 0.346 | 16.1 |
| 578 | 0.274 | 12.8 |
| 549 | 0.315 | 14.7 |
| 487 | 0.386 | 18.0 |
| 442 | 0.335 | 15.6 |
| 409 | 0.356 | 16.6 |
| 394 | 0.357 | 16.6 |
| 332 | 0.381 | 17.7 |
| 258 | 0.492 | 22.9 |
| 228 | 0.431 | 20.1 |
| 199 | 0.536 | 25.0 |

In some embodiments, Form K is characterized by one or more peaks in its Raman spectrum selected from those in Table 37. In some embodiments, Form K is characterized by at least one, at least two, at least three, at least four, at least five, or at least six peaks in its Raman spectrum selected from those in Table 37.

TABLE 37

Select characteristic peaks of the Raman spectrum of Form K.

| Wavenumber (cm$^{-1}$) | Absolute Intensity | Normalized Intensity (%) |
|---|---|---|
| 1600 | 2.148 | 100.0 |
| 1503 | 0.711 | 33.1 |
| 1446 | 0.723 | 33.7 |
| 1427 | 0.648 | 30.2 |
| 836 | 0.701 | 32.6 |
| 789 | 0.765 | 35.6 |

Figure 33:
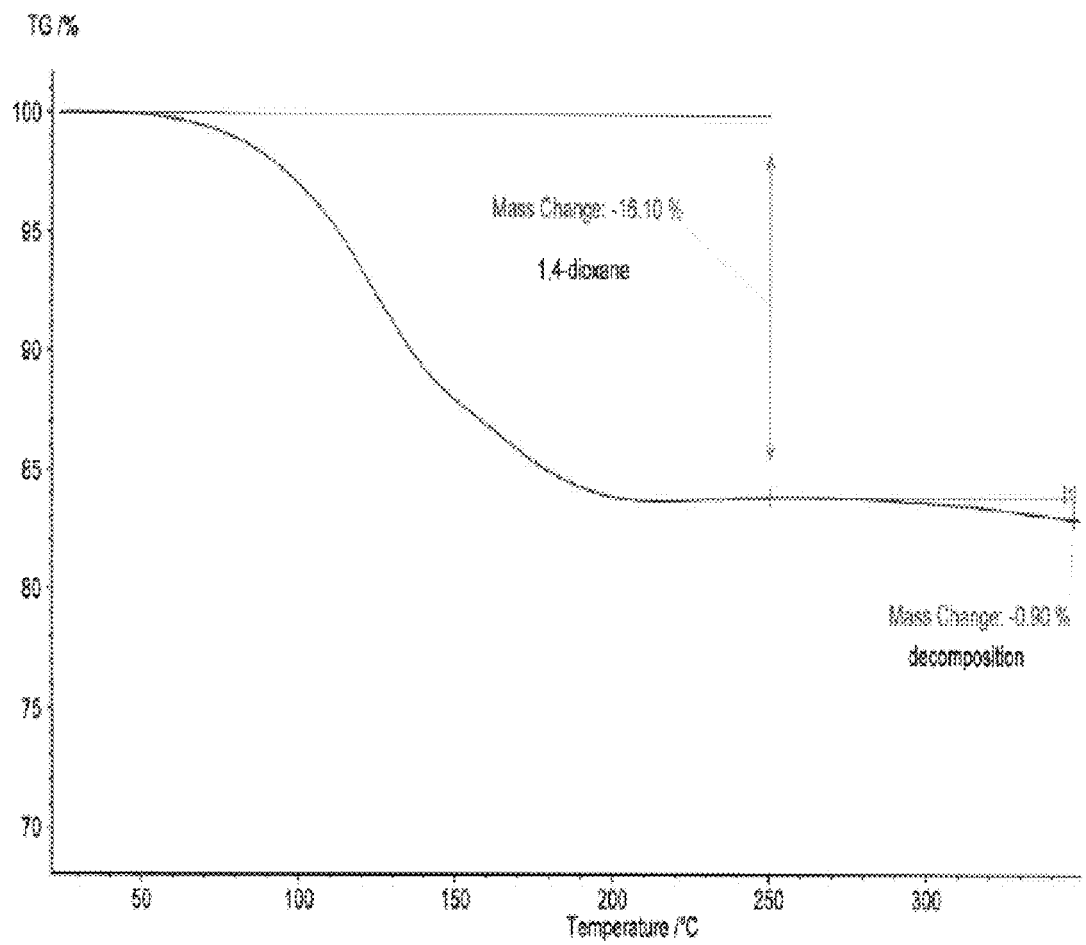
FIG. 33 depicts a TG-FTIR thermogram of Form K.

In some embodiments, Form K has a TG-FTIR thermogram substantially similar to the one depicted in FIG. 33. In some embodiments, Form K is obtained from dioxane. In some embodiments, Form K is a dioxane solvate. In some embodiments, Form K is a non-stoichiometric solvate. In some embodiments, Form K is a non-stoichiometric dioxane solvate.

Form L

In certain embodiments, the present invention provides crystalline Form L of compound 1. In certain embodiments, Form L is substantially free of impurities. In certain embodiments, Form L is 99% free of impurities by weight. In certain embodiments, Form L is 97% free of impurities by weight. In certain embodiments, Form L is 95% free of impurities by weight. In certain embodiments, Form L is substantially free of amorphous compound 1. In certain embodiments, Form L is substantially free of other crystalline forms of compound 1. In certain embodiments, Form L is substantially free of a salt of compound 1.

Form L can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form L is characterized by an X-ray powder diffraction pattern substantially similar to the one depicted in FIG. 34. In some embodiments, Form L is characterized in that it has one or more peaks in its X-ray powder diffraction pattern selected from those in Table 38. In some embodiments, Form L is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or at least nineteen peaks in its X-ray powder diffraction pattern selected from those in Table 38. In some embodiments, Form L of compound 1 is characterized in that it has one or more peaks in its X-ray powder diffraction pattern selected from the strong and very strong peaks in Table 38.

TABLE 38

X-ray powder diffraction pattern of Form L.

| Angle 2-Theta ° | d value Angstrom | Intensity (relative) | Intensity % |
|---|---|---|---|
| 4.07 | 21.7 | m | 20 |
| 5.98 | 14.8 | s | 59 |
| 8.31 | 10.6 | s | 37 |
| 8.54 | 10.3 | s | 34 |
| 9.39 | 9.4 | s | 55 |
| 12.02 | 7.4 | s | 34 |
| 15.31 | 5.78 | vs | 100 |
| 17.27 | 5.13 | s | 31 |
| 17.76 | 4.99 | s | 44 |
| 18.84 | 4.71 | s | 37 |
| 19.28 | 4.60 | s | 55 |
| 20.13 | 4.41 | m | 19 |
| 21.19 | 4.19 | s | 36 |
| 21.49 | 4.13 | s | 49 |
| 21.91 | 4.05 | s | 35 |
| 23.04 | 3.86 | m | 25 |
| 23.68 | 3.75 | m | 30 |
| 24.45 | 3.64 | m | 26 |
| 26.98 | 3.30 | m | 29 |

In some embodiments, Form L is characterized by one or more peaks in its X-ray powder diffraction pattern selected from those in Table 39. In some embodiments, Form L is characterized by at least one, at least two, at least three, at least four, at least five, or at least six peaks in its X-ray powder diffraction pattern selected from those in Table 39,

TABLE 39

Select characteristic peaks of the X-ray powder diffraction pattern of Form L.

| Angle 2-Theta ° | d value Angstrom | Intensity (relative) | Intensity % |
|---|---|---|---|
| 5.98 | 14.8 | s | 59 |
| 9.39 | 9.4 | s | 55 |
| 15.31 | 5.78 | vs | 100 |

TABLE 39-continued

Select characteristic peaks of the X-ray powder diffraction pattern of Form L.

| Angle 2-Theta ° | d value Angstrom | Intensity (relative) | Intensity % |
|---|---|---|---|
| 17.76 | 4.99 | s | 44 |
| 19.28 | 4.60 | s | 55 |
| 21.49 | 4.13 | s | 49 |

Figure 35:
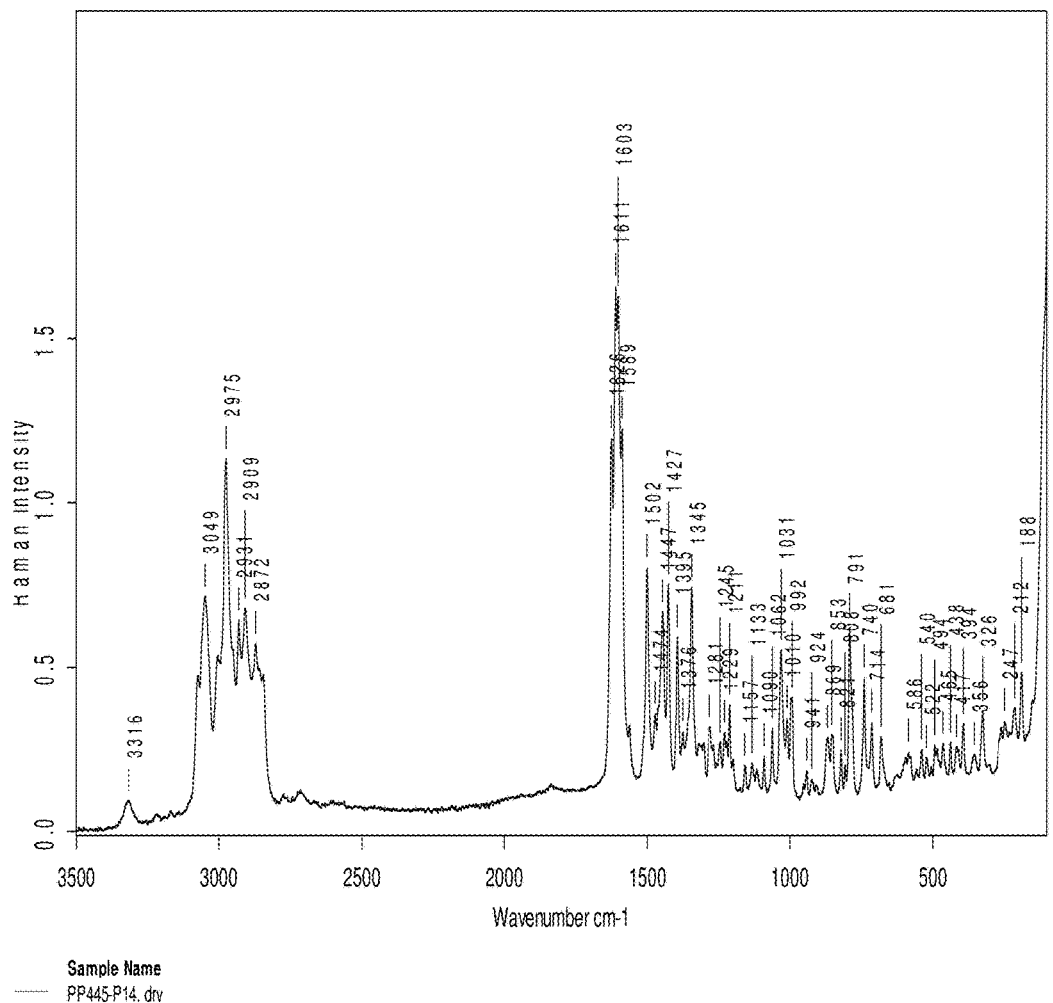
FIG. 35 depicts an FT-Raman spectrum of Form L.

In some embodiments, Form L is characterized by a Raman spectrum substantially similar to the one depicted in FIG. 35. In some embodiments, Form L is characterized by one or more peaks in its Raman spectrum selected from those in Table 40. In some embodiments, Form L is characterized by having a Raman spectrum with characteristic peaks at about those in Table 40.

TABLE 40

Raman spectrum of Form L.

| Wavenumber (cm$^{-1}$) | Absolute Intensity | Normalized Intensity (%) |
|---|---|---|
| 3316 | 0.093 | 5.6 |
| 3049 | 0.715 | 43.1 |
| 2975 | 1.133 | 68.3 |
| 2931 | 0.643 | 38.8 |
| 2909 | 0.680 | 41.0 |
| 2872 | 0.572 | 34.5 |
| 1626 | 1.197 | 72.2 |
| 1611 | 1.659 | 100.0 |
| 1603 | 1.630 | 98.3 |
| 1589 | 1.224 | 73.8 |
| 1502 | 0.803 | 48.4 |
| 1474 | 0.357 | 21.5 |
| 1447 | 0.667 | 40.2 |
| 1427 | 0.752 | 45.3 |
| 1395 | 0.592 | 35.7 |
| 1376 | 0.303 | 18.3 |
| 1345 | 0.743 | 44.8 |
| 1281 | 0.316 | 19.0 |
| 1245 | 0.271 | 16.3 |
| 1229 | 0.300 | 18.1 |
| 1211 | 0.383 | 23.1 |
| 1157 | 0.200 | 12.1 |
| 1133 | 0.207 | 12.5 |
| 1090 | 0.228 | 13.7 |
| 1061 | 0.313 | 18.9 |
| 1031 | 0.553 | 33.3 |
| 1010 | 0.342 | 20.6 |
| 992 | 0.406 | 24.5 |
| 941 | 0.184 | 11.1 |
| 924 | 0.158 | 9.5 |
| 869 | 0.284 | 17.1 |
| 853 | 0.293 | 17.7 |
| 821 | 0.246 | 14.8 |
| 808 | 0.201 | 12.1 |
| 791 | 0.625 | 37.7 |
| 740 | 0.469 | 28.3 |
| 714 | 0.331 | 20.0 |
| 681 | 0.288 | 17.4 |
| 586 | 0.241 | 14.5 |
| 540 | 0.248 | 14.9 |
| 522 | 0.224 | 13.5 |
| 493 | 0.261 | 15.7 |
| 464 | 0.267 | 16.1 |
| 438 | 0.270 | 16.3 |
| 417 | 0.257 | 15.5 |
| 394 | 0.326 | 19.7 |
| 356 | 0.234 | 14.1 |
| 326 | 0.365 | 22.0 |
| 247 | 0.334 | 20.1 |
| 212 | 0.375 | 22.6 |
| 188 | 0.485 | 29.2 |

In some embodiments, Form L is characterized by one or more peaks in its Raman spectrum selected from those in Table 41. In some embodiments, Form L is characterized by at least one, at least two, at least three, at least four, at least five, at least six, at least seven, at least eight, at least nine, at least ten, or at least eleven peaks in its Ramnan spectrum selected from those in Table 41.

TABLE 41

Select characteristic peaks of the Raman spectrum of Form L.

| Wavenumber (cm$^{-1}$) | Absolute Intensity | Normalized Intensity (%) |
|---|---|---|
| 1626 | 1.197 | 72.2 |
| 1611 | 1.659 | 100.0 |
| 1603 | 1.630 | 98.3 |
| 1589 | 1.224 | 73.8 |
| 1502 | 0.803 | 48.4 |
| 1447 | 0.667 | 40.2 |
| 1427 | 0.752 | 45.3 |
| 1395 | 0.592 | 35.7 |
| 1345 | 0.743 | 44.8 |
| 1031 | 0.553 | 33.3 |
| 791 | 0.625 | 37.7 |

Figure 36:
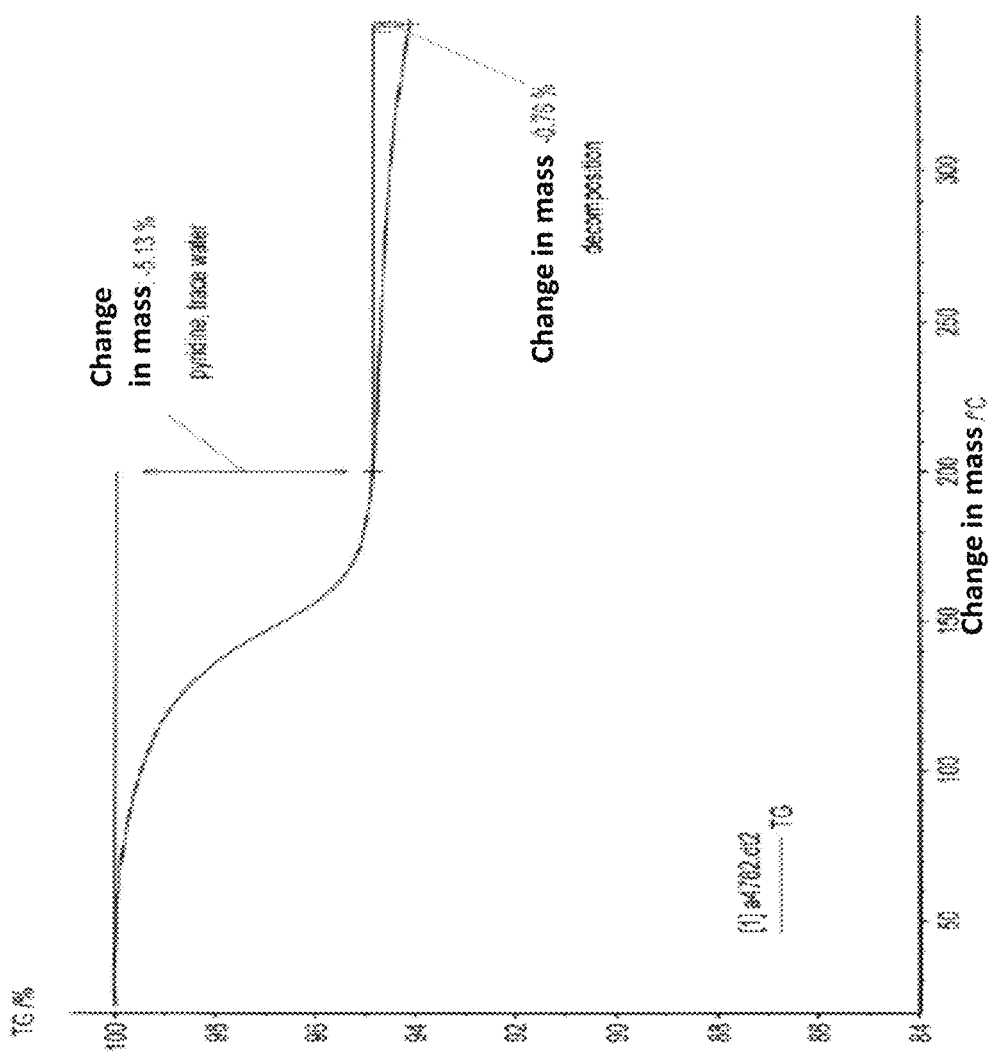
FIG. 36 depicts a TG-FTIR thermogram of Form L.

In some embodiments, Form L has a TG-FTIR thermogram substantially similar to the one depicted in FIG. 36. In some embodiments, Form L is obtained from pyridine/hexane. In some embodiments, Form L is a pyridine solvate. In some embodiments, Form L is a non-stoichiometric solvate. In some embodiments, Form L is a non-stoichiometric pyridine solvate.

Form M

In certain embodiments, the present invention provides crystalline Form M of compound 1. In certain embodiments, Form M is substantially free of impurities. In certain embodiments, Form M is 99% free of impurities by weight. In certain embodiments, Form M is 97% free of impurities by weight. In certain embodiments, Form M is 95% free of impurities by weight. In certain embodiments, Form M is substantially free of amorphous compound 1. In certain embodiments, Form M is substantially free of other crystalline forms of compound 1. In certain embodiments, Form M is substantially free of a salt of compound 1.

Form M can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form M is characterized by an X-ray powder diffraction pattern substantially similar to the one depicted in FIG. 37. In some embodiments, Form M is characterized in that it has one or more peaks in its X-ray powder diffraction pattern selected from those in Table 42. In some embodiments, Form M is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty-seven, at least thirty-eight, at least thirty-nine, or at least forty peaks in its X-ray powder diffraction pattern selected from those in Table 42. In some embodiments, Form M of compound 1 is characterized in that it has one or more peaks in its X-ray powder diffraction pattern selected from the strong and very strong peaks in Table 42.

TABLE 42

X-ray powder diffraction pattern of Form M.

| Angle 2-Theta ° | d value Angstrom | Intensity (relative) | Intensity % |
|---|---|---|---|
| 5.64 | 15.7 | w | 6 |
| 6.13 | 14.4 | vw | 2 |
| 7.67 | 11.5 | vw | 5 |
| 11.26 | 7.8 | vs | 100 |
| 11.98 | 7.4 | vw | 3 |
| 12.26 | 7.2 | vw | 2 |
| 13.66 | 6.5 | vw | 2 |
| 14.27 | 6.2 | vw | 2 |
| 15.35 | 5.77 | w | 13 |
| 16.61 | 5.33 | w | 5 |
| 16.94 | 5.23 | s | 61 |
| 17.12 | 5.17 | m | 20 |
| 17.96 | 4.94 | s | 36 |
| 18.45 | 4.80 | w | 10 |
| 18.92 | 4.69 | vw | 5 |
| 19.38 | 4.58 | m | 16 |
| 19.80 | 4.48 | vw | 4 |
| 20.13 | 4.41 | m | 16 |
| 20.87 | 4.25 | m | 16 |
| 21.28 | 4.17 | w | 8 |
| 21.81 | 4.07 | vw | 4 |
| 21.96 | 4.04 | w | 8 |
| 22.64 | 3.92 | s | 51 |
| 23.14 | 3.84 | w | 11 |
| 24.43 | 3.64 | m | 16 |
| 24.78 | 3.59 | w | 12 |
| 25.30 | 3.52 | vw | 5 |
| 25.56 | 3.48 | w | 5 |
| 27.04 | 3.29 | w | 8 |
| 27.37 | 3.26 | vw | 4 |
| 27.65 | 3.22 | vw | 4 |
| 28.15 | 3.17 | vw | 4 |
| 28.50 | 3.13 | vw | 4 |
| 29.32 | 3.04 | vw | 3 |
| 30.06 | 2.97 | vw | 4 |
| 32.41 | 2.76 | vw | 2 |
| 32.85 | 2.72 | vw | 3 |
| 33.90 | 2.64 | vw | 2 |
| 34.33 | 2.61 | vw | 4 |
| 34.70 | 2.58 | vw | 3 |

In some embodiments, Form M is characterized by one or more peaks in its X-ray powder diffraction pattern selected from those in Table 43. In some embodiments, Form M is characterized by at least one, at least two, at least three, at least four, at least five, at least six, or at least seven peaks in its X-ray powder diffraction pattern selected from those in Table 43.

TABLE 43

Select characteristic peaks of the X-ray powder diffraction pattern of Form M.

| Angle 2-Theta ° | d value Angstrom | Intensity (relative) | Intensity % |
|---|---|---|---|
| 11.26 | 7.8 | vs | 100 |
| 16.94 | 5.23 | s | 61 |
| 17.96 | 4.94 | s | 36 |
| 19.38 | 4.58 | m | 16 |
| 20.13 | 4.41 | m | 16 |
| 20.87 | 4.25 | m | 16 |
| 22.64 | 3.92 | s | 51 |

Figure 38:
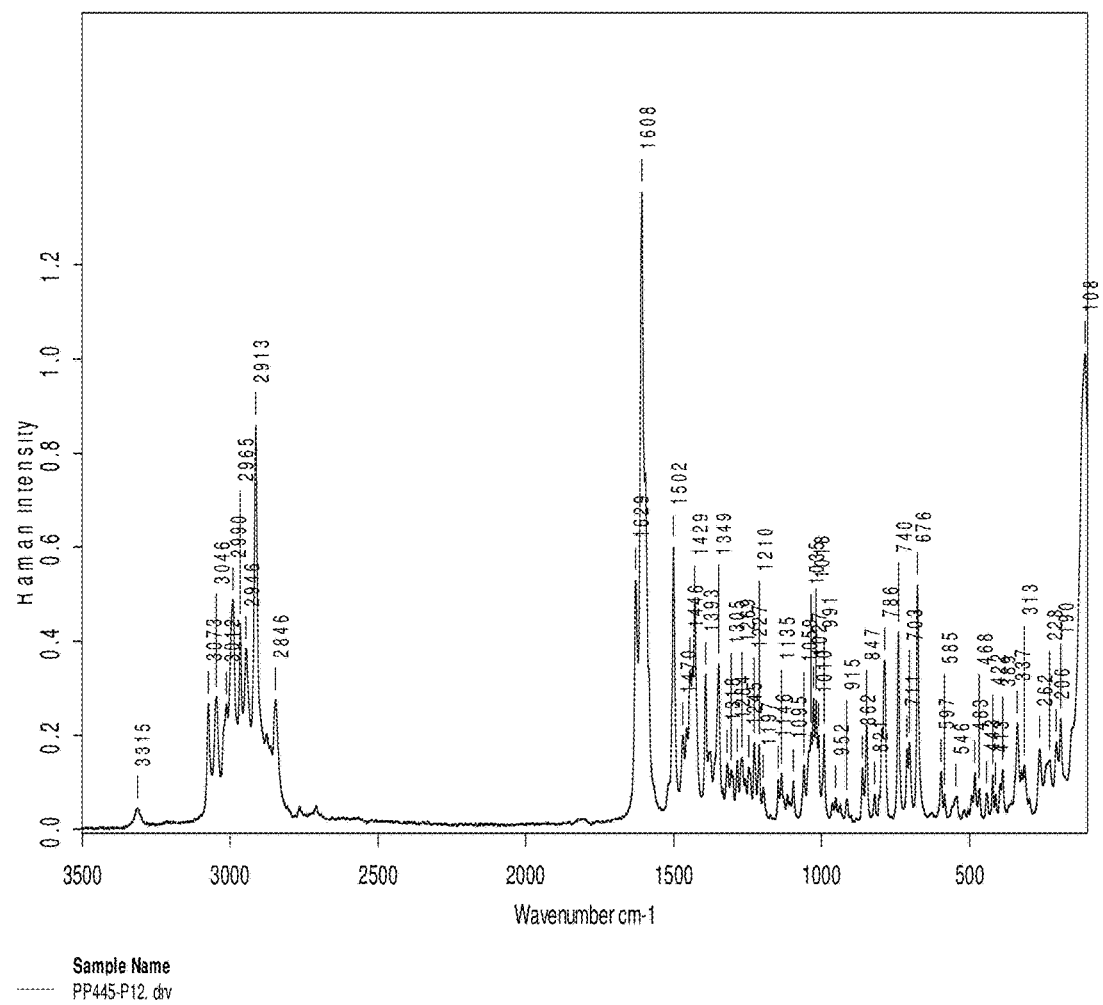
FIG. 38 depicts an FT-Raman spectrum of Form M.

In some embodiments, Form M is characterized by a Raman spectrum substantially similar to the one depicted in FIG. 38. In some embodiments, Form M is characterized by one or more peaks in its Raman spectrum selected from those in Table 44. In some embodiments, Form M is characterized by having a Raman spectrum with characteristic peaks at about those in Table 44.

TABLE 44

Raman spectrum of Form M.

| Wavenumber (cm$^{-1}$) | Absolute Intensity | Normalized Intensity (%) |
|---|---|---|
| 3315 | 0.044 | 3.2 |
| 3073 | 0.267 | 19.7 |
| 3046 | 0.282 | 20.8 |
| 3012 | 0.266 | 19.6 |
| 2990 | 0.487 | 35.9 |
| 2965 | 0.436 | 32.2 |
| 2946 | 0.384 | 28.3 |
| 2913 | 0.860 | 63.4 |
| 2846 | 0.275 | 20.3 |
| 1629 | 0.529 | 39.0 |
| 1608 | 1.356 | 100.0 |
| 1501 | 0.600 | 44.2 |
| 1470 | 0.200 | 14.7 |
| 1446 | 0.338 | 24.9 |
| 1429 | 0.491 | 36.2 |
| 1393 | 0.329 | 24.3 |
| 1349 | 0.352 | 26.0 |
| 1318 | 0.141 | 10.4 |
| 1305 | 0.126 | 9.3 |
| 1284 | 0.146 | 10.8 |
| 1269 | 0.152 | 11.2 |
| 1245 | 0.132 | 9.7 |
| 1227 | 0.184 | 13.6 |
| 1210 | 0.181 | 13.3 |
| 1197 | 0.089 | 6.6 |
| 1146 | 0.107 | 7.9 |
| 1135 | 0.120 | 8.8 |
| 1095 | 0.103 | 7.6 |
| 1059 | 0.138 | 10.2 |
| 1035 | 0.206 | 15.2 |
| 1027 | 0.279 | 20.6 |
| 1018 | 0.274 | 20.2 |
| 1010 | 0.199 | 14.7 |
| 991 | 0.203 | 15.0 |
| 952 | 0.067 | 4.9 |
| 915 | 0.064 | 4.7 |
| 862 | 0.131 | 9.7 |
| 847 | 0.222 | 16.4 |
| 821 | 0.075 | 5.5 |
| 786 | 0.359 | 26.5 |
| 740 | 0.420 | 31.0 |
| 711 | 0.172 | 12.7 |
| 703 | 0.185 | 13.6 |
| 676 | 0.519 | 38.3 |
| 597 | 0.123 | 9.1 |
| 585 | 0.075 | 5.5 |
| 546 | 0.070 | 5.2 |
| 483 | 0.121 | 8.9 |
| 468 | 0.087 | 6.4 |
| 443 | 0.077 | 5.7 |
| 422 | 0.116 | 8.6 |
| 413 | 0.074 | 5.5 |
| 389 | 0.127 | 9.4 |
| 337 | 0.226 | 16.7 |
| 313 | 0.137 | 10.1 |
| 262 | 0.172 | 12.7 |
| 228 | 0.148 | 10.9 |
| 206 | 0.186 | 13.7 |
| 190 | 0.236 | 17.4 |
| 108 | 1.010 | 74.5 |

In some embodiments, Form M is characterized by one or more peaks in its Raman spectrum selected from those in Table 45. In some embodiments, Form M is characterized by at least one, at least two, at least three, at least four, at least five, or at least six peaks in its Raman spectrum selected from those in Table 45.

TABLE 45

Select characteristic peaks of the Raman spectrum of Form M.

| Wavenumber (cm⁻¹) | Absolute Intensity | Normalized Intensity (%) |
|---|---|---|
| 1629 | 0.529 | 39.0 |
| 1608 | 1.356 | 100.0 |
| 1501 | 0.600 | 44.2 |
| 1429 | 0.491 | 36.2 |
| 740 | 0.420 | 31.0 |
| 676 | 0.519 | 38.3 |

Figure 39:
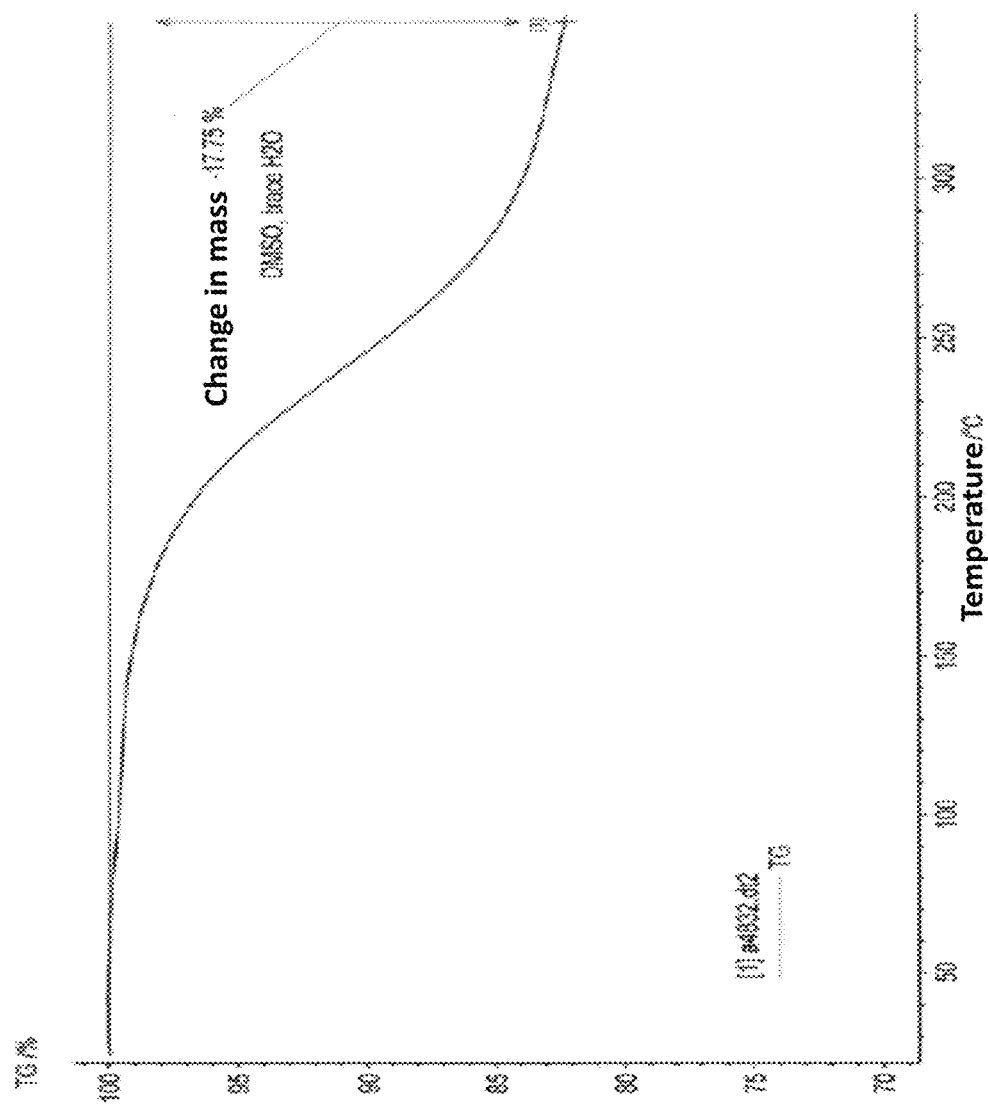
FIG. 39 depicts a TG-FTIR thermogram of Form M.

In some embodiments, Form M has a TG-FTIR thermogram substantially similar to the one depicted in FIG. 39. In some embodiments, Form M is obtained from dimethylsulfoxide/tert-butyl methyl ether. In some embodiments, Form M is a dimethylsulfoxide (DMSO) solvate. In some embodiments, Form M is a non-stoichiometric solvate. In some embodiments, Form M is a non-stoichiometric DMSO solvate.

Fumarate Salt, Co-Crystal, and Form FUM-P3

The present invention also provides various salts or salt forms of compound 1. In certain embodiments, provided is a fumarate salt form of compound 1. The fumarate salt may be amorphous or exist in one or more crystalline forms. In certain embodiments, the present invention provides a crystalline form of compound 1, designated Form FUM-P3. In some embodiments, Form FUM-P3 is a salt of compound 1. In some embodiments, Form FUM-P3 is a fumarate salt of compound 1. In some embodiments, Form FUM-P3 is a hemifumarate salt of compound 1.

The present invention also provides co-crystals of compound 1 and fumaric acid. The primary distinction between a salt form of compound 1 and a co-crystal of compound 1 and an additional compound is that in the salt form compound 1 is ionized and complexed with the salt former in a way that proton transfer can easily occur. In the co-crystal, however, compound 1 is complexed with the additional compound in a way that ionization of compound 1 and proton transfer are not required. Co-crystals described herein may be useful to improve the properties (e.g., aqueous solubility, stability, and ease of formulation) of compound 1. In some embodiments, Form FUM-P3 is a co-crystal of compound 1 and fumaric acid.

In certain embodiments, Form FUM-P3 is substantially free of impurities. In certain embodiments, the impurity is compound 1 in free base form. In certain embodiments, Form FUM-P3 is 99% free of impurities by weight. In certain embodiments, Form FUM-P3 is 97% free of impurities by weight. In certain embodiments, Form FUM-P3 is 95% free of impurities by weight. In certain embodiments, Form FUM-P3 is substantially free of amorphousfumarate salt of compound 1. In certain embodiments, Form FUM-P3 is substantially free of other crystalline forms of the fumarate salt of compound 1.

Figure 40:
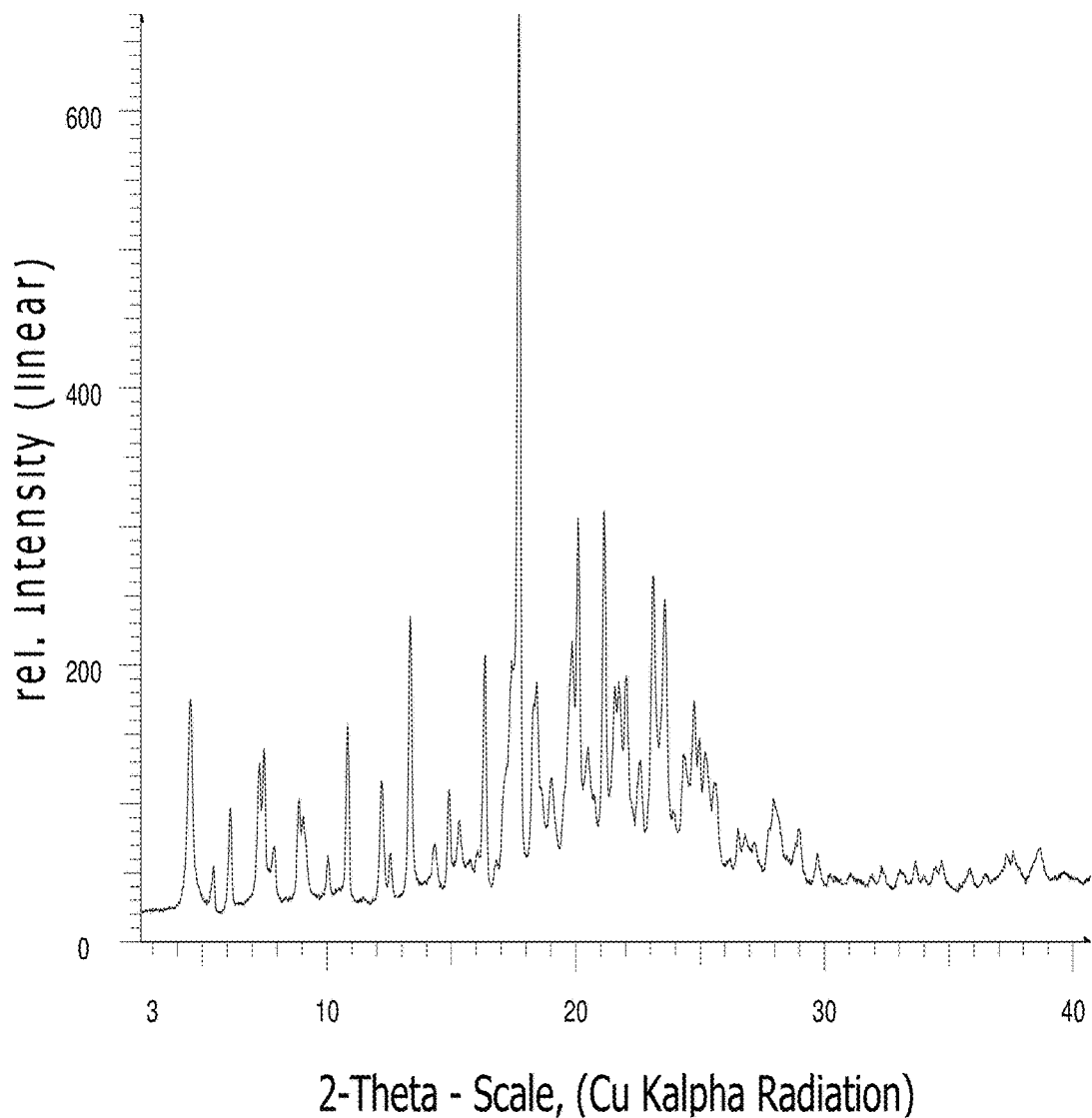
FIG. 40 depicts an XRPD pattern of Form FUM-P3.

Form FUM-P3 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form FUM-P3 is characterized by an X-ray powder diffraction pattern substantially similar to the one depicted in FIG. 40.

In some embodiments, Form FUM-P3 is characterized in that it has one or more peaks in its X-ray powder diffraction pattern selected from those in Table 46. In some embodiments, Form FUM-P3 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty-seven, at least thirty-eight, or at least thirty-nine peaks in its X-ray powder diffraction pattern selected from those in Table 46. In some embodiments, Form FUM-P3 of compound 1 is characterized in that it has one or more peaks in its X-ray powder diffraction pattern selected from the strong and very strong peaks in Table 46.

TABLE 46

Peaks from X-ray powder diffraction pattern.

| Angle 2-Theta ° | d value Angstrom | Intensity (relative) | Intensity % |
|---|---|---|---|
| 4.48 | 19.7 | m | 23 |
| 5.39 | 16.4 | w | 7 |
| 6.08 | 14.5 | w | 13 |
| 7.25 | 12.2 | m | 18 |
| 7.43 | 11.9 | m | 20 |
| 7.84 | 11.3 | w | 10 |
| 8.84 | 10.0 | w | 15 |
| 9.02 | 9.8 | w | 13 |
| 10.00 | 8.8 | w | 9 |
| 10.79 | 8.2 | m | 23 |
| 12.16 | 7.3 | m | 17 |
| 12.51 | 7.1 | w | 9 |
| 13.31 | 6.6 | s | 34 |
| 14.32 | 6.2 | w | 10 |
| 14.89 | 5.94 | m | 16 |
| 15.31 | 5.78 | w | 13 |
| 16.32 | 5.43 | s | 30 |
| 17.70 | 5.01 | vs | 100 |
| 18.41 | 4.82 | m | 27 |
| 19.00 | 4.67 | m | 17 |
| 19.84 | 4.47 | s | 32 |
| 20.08 | 4.42 | s | 46 |
| 20.47 | 4.34 | m | 20 |
| 21.13 | 4.20 | s | 48 |
| 21.56 | 4.12 | m | 27 |
| 21.73 | 4.09 | m | 28 |
| 22.02 | 4.03 | m | 28 |
| 22.57 | 3.94 | m | 19 |
| 23.10 | 3.85 | s | 40 |
| 23.56 | 3.77 | s | 37 |
| 24.33 | 3.66 | m | 20 |
| 24.75 | 3.59 | m | 26 |
| 24.94 | 3.57 | m | 22 |
| 25.19 | 3.53 | m | 20 |
| 25.57 | 3.48 | m | 17 |
| 26.54 | 3.36 | w | 12 |
| 27.97 | 3.19 | m | 15 |
| 28.99 | 3.08 | w | 12 |
| 29.74 | 3.00 | w | 9 |

In some embodiments, Form FUM-P3 is characterized by one or more peaks in its X-ray powder diffraction pattern selected from those in Table 47. In some embodiments, Form FUM-P3 is characterized by at least one, at least two, at least three, at least four, at least five, at least six, or at least seven peaks in its X-ray powder diffraction pattern selected from those in Table 47.

TABLE 47

Selected characteristic peaks from X-ray powder diffraction pattern of Form FUM-P3

| Angle 2-Theta ° | d value Angstrom | Intensity (relative) | Intensity % |
|---|---|---|---|
| 13.31 | 6.6 | s | 34 |
| 17.70 | 5.01 | vs | 100 |
| 19.84 | 4.47 | s | 32 |
| 20.08 | 4.42 | s | 46 |
| 21.13 | 4.20 | s | 48 |
| 23.10 | 3.85 | s | 40 |
| 23.56 | 3.77 | s | 37 |

Figure 41:
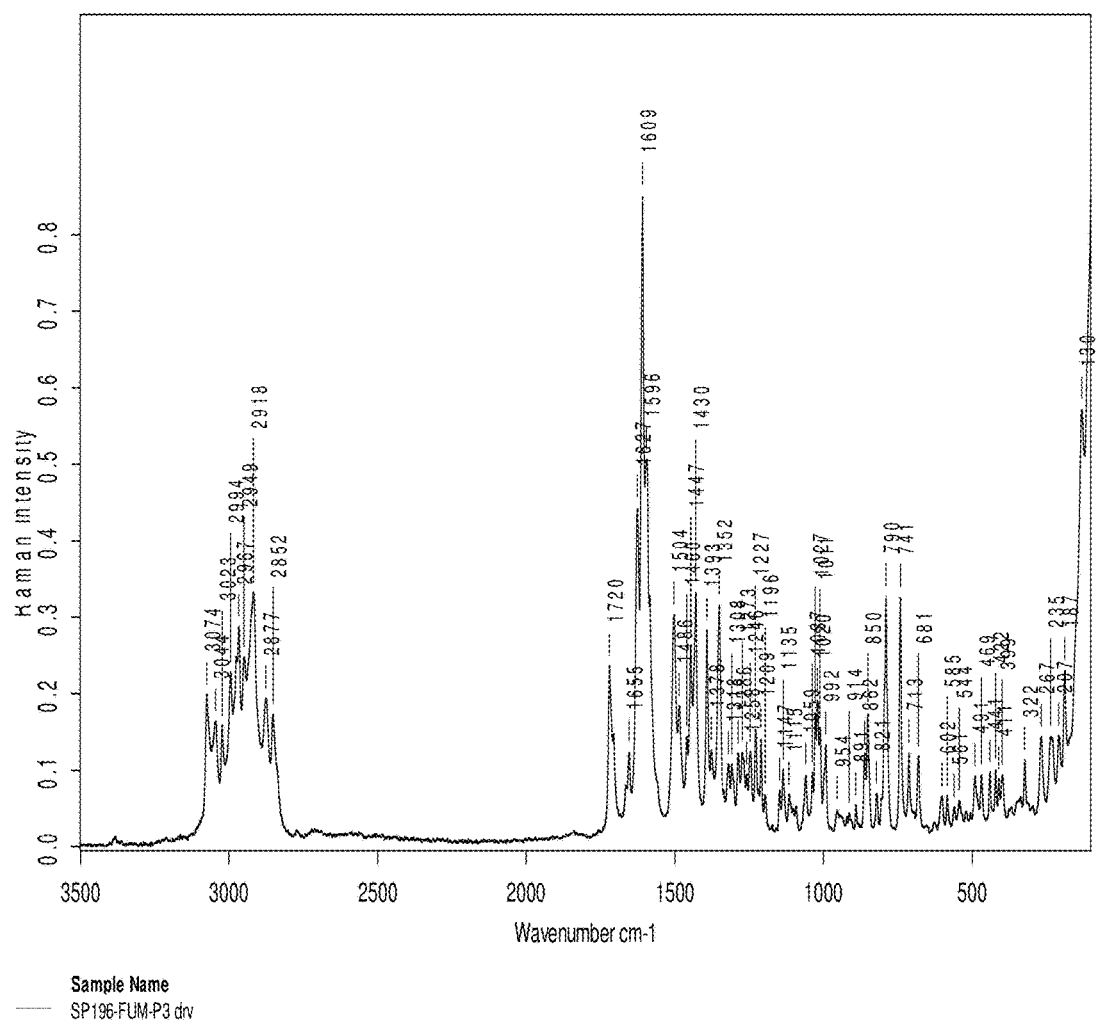
FIG. 41 depicts an FT-Raman spectrum of Form FUM-P3.

In some embodiments, Form FUM-P3 is characterized by a Raman spectrum substantially similar to the one depicted in FIG. 41. In some embodiments, Form FUM-P3 is characterized by one or more peaks in its Raman spectrum selected from those in Table 48. In some embodiments, Form FUM-P3 is characterized by having a Raman spectrum with characteristic peaks at about those wavenumbers listed in Table 48.

TABLE 48

Raman spectrum.

| Wavenumber (cm$^{-1}$) | Absolute Intensity | Normalized Intensity (%) |
|---|---|---|
| 3074 | 0.199 | 23.4 |
| 3044 | 0.164 | 19.3 |
| 3023 | 0.158 | 18.6 |
| 2994 | 0.228 | 26.8 |
| 2966 | 0.287 | 33.7 |
| 2949 | 0.248 | 29.1 |
| 2917 | 0.332 | 39.0 |
| 2877 | 0.194 | 22.8 |
| 2852 | 0.173 | 20.3 |
| 1720 | 0.237 | 27.8 |
| 1655 | 0.124 | 14.6 |
| 1627 | 0.443 | 52.1 |
| 1609 | 0.851 | 100.0 |
| 1596 | 0.506 | 59.5 |
| 1504 | 0.303 | 35.6 |
| 1486 | 0.184 | 21.6 |
| 1460 | 0.145 | 17.0 |
| 1447 | 0.264 | 31.0 |
| 1430 | 0.332 | 39.0 |
| 1393 | 0.283 | 33.3 |
| 1378 | 0.126 | 14.8 |
| 1352 | 0.316 | 37.1 |
| 1318 | 0.108 | 12.7 |
| 1308 | 0.108 | 12.7 |
| 1286 | 0.123 | 14.5 |
| 1272 | 0.124 | 14.6 |
| 1258 | 0.095 | 11.2 |
| 1246 | 0.124 | 14.6 |
| 1227 | 0.153 | 18.0 |
| 1209 | 0.141 | 16.6 |
| 1196 | 0.068 | 8.0 |
| 1147 | 0.074 | 8.7 |
| 1135 | 0.101 | 11.9 |
| 1115 | 0.069 | 8.1 |
| 1059 | 0.094 | 11.0 |
| 1037 | 0.098 | 11.5 |
| 1027 | 0.175 | 20.6 |
| 1020 | 0.191 | 22.4 |
| 1011 | 0.156 | 18.3 |
| 992 | 0.133 | 15.6 |
| 954 | 0.049 | 5.8 |
| 913 | 0.044 | 5.2 |
| 891 | 0.055 | 6.5 |
| 862 | 0.122 | 14.3 |
| 850 | 0.174 | 20.4 |
| 821 | 0.070 | 8.2 |
| 789 | 0.328 | 38.5 |
| 741 | 0.326 | 38.3 |
| 713 | 0.123 | 14.5 |
| 681 | 0.118 | 13.9 |
| 602 | 0.066 | 7.8 |
| 584 | 0.067 | 7.9 |
| 561 | 0.052 | 6.1 |
| 544 | 0.060 | 7.1 |
| 491 | 0.093 | 10.9 |
| 469 | 0.094 | 11.0 |
| 441 | 0.098 | 11.5 |
| 422 | 0.101 | 11.9 |
| 411 | 0.089 | 10.5 |
| 399 | 0.094 | 11.0 |
| 322 | 0.113 | 13.3 |
| 267 | 0.144 | 16.9 |
| 234 | 0.144 | 16.9 |
| 207 | 0.146 | 17.2 |
| 187 | 0.231 | 27.1 |
| 130 | 0.571 | 67.1 |

In some embodiments, Form FUM-P3 is characterized by one or more peaks in its Raman spectrum selected from those in Table 49. In some embodiments, Form FUM-P3 is characterized by at least one, at least two, at least three, at least four, at least five, at least six, at least seven, at least eight, at least nine, or at least ten peaks in its Raman spectrum selected from those in Table 49.

TABLE 49

Select characteristic peaks of the Raman spectrum of Form FUM-P3.

| Wavenumber (cm$^{-1}$) | Absolute Intensity | Normalized Intensity (%) |
|---|---|---|
| 1627 | 0.443 | 52.1 |
| 1609 | 0.851 | 100.0 |
| 1596 | 0.506 | 59.5 |
| 1504 | 0.303 | 35.6 |
| 1447 | 0.264 | 31.0 |
| 1430 | 0.332 | 39.0 |
| 1393 | 0.283 | 33.3 |
| 1352 | 0.316 | 37.1 |
| 789 | 0.328 | 38.5 |
| 741 | 0.326 | 38.3 |

Figure 42:
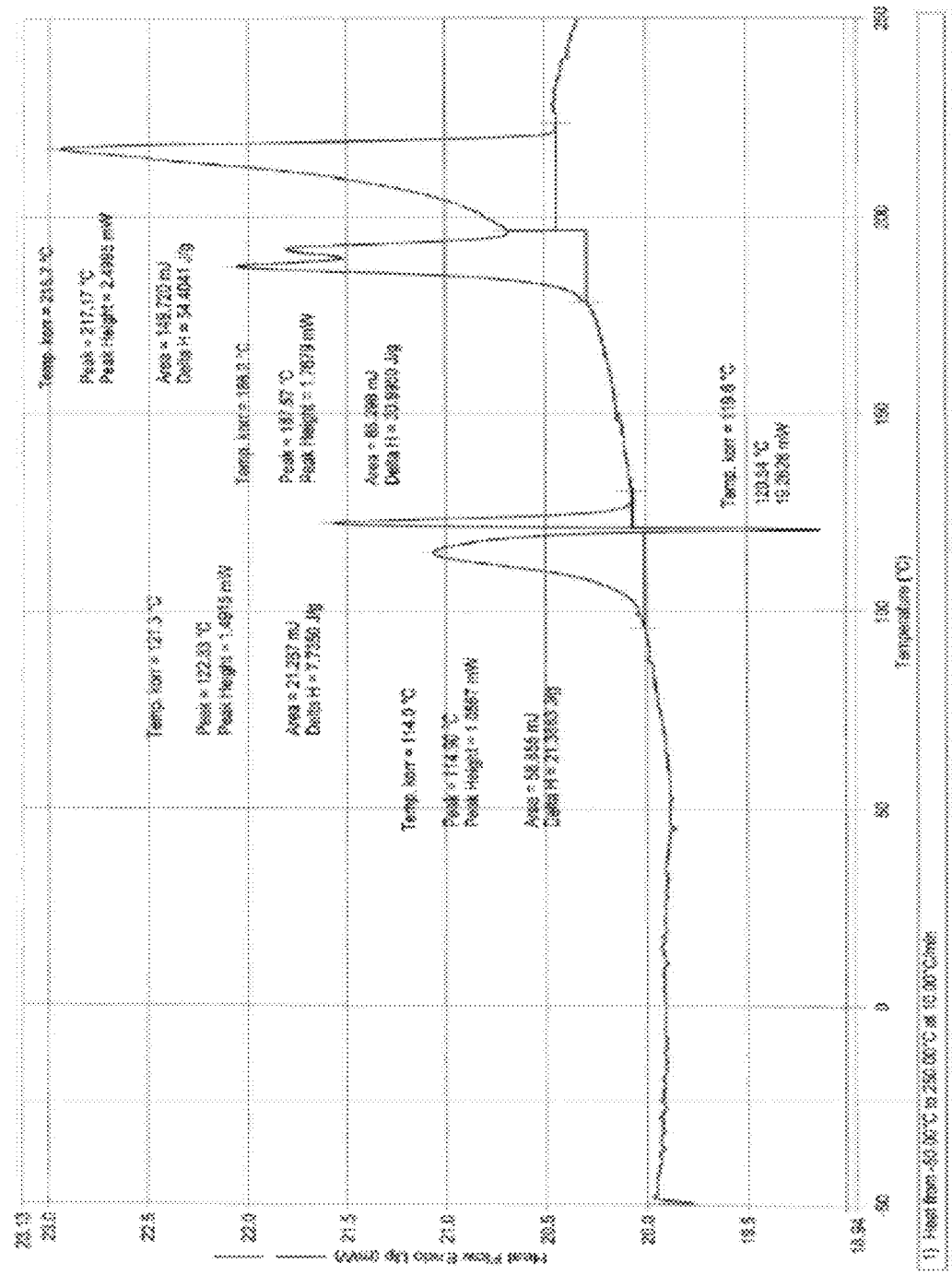
FIG. 42 depicts a DSC thermogram of Form FUM-P3.

In some embodiments, Form FUM-P3 is characterized by a DSC thermogram substantially similar to the one depicted in FIG. 42.

Figure 43:
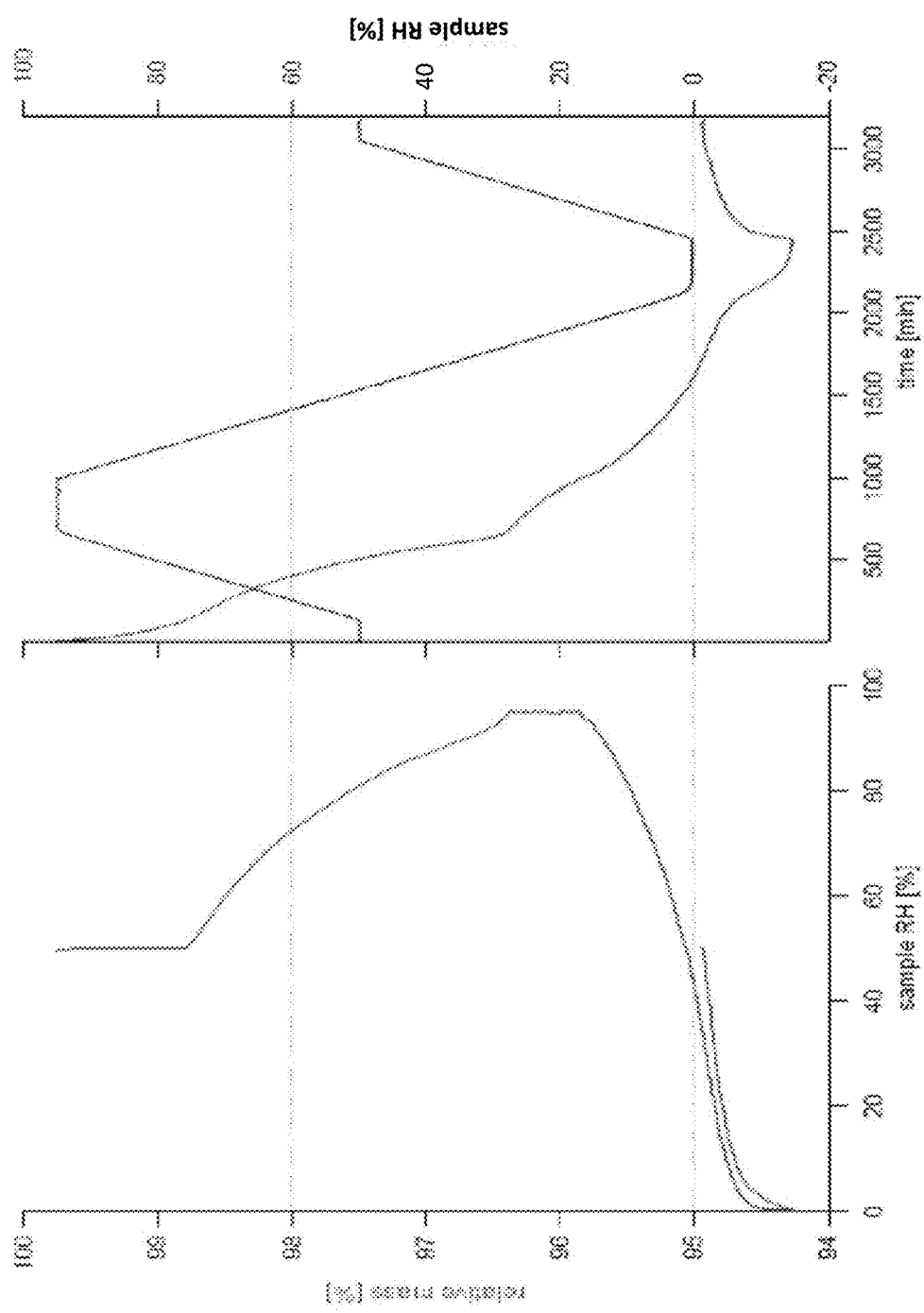
FIG. 43 depicts a DVS isotherm of Form FUM-P3.

In some embodiments, Form FUM-P3 is characterized by a DVS isotherm substantially similar to the one depicted in FIG. 43.

Figure 44:
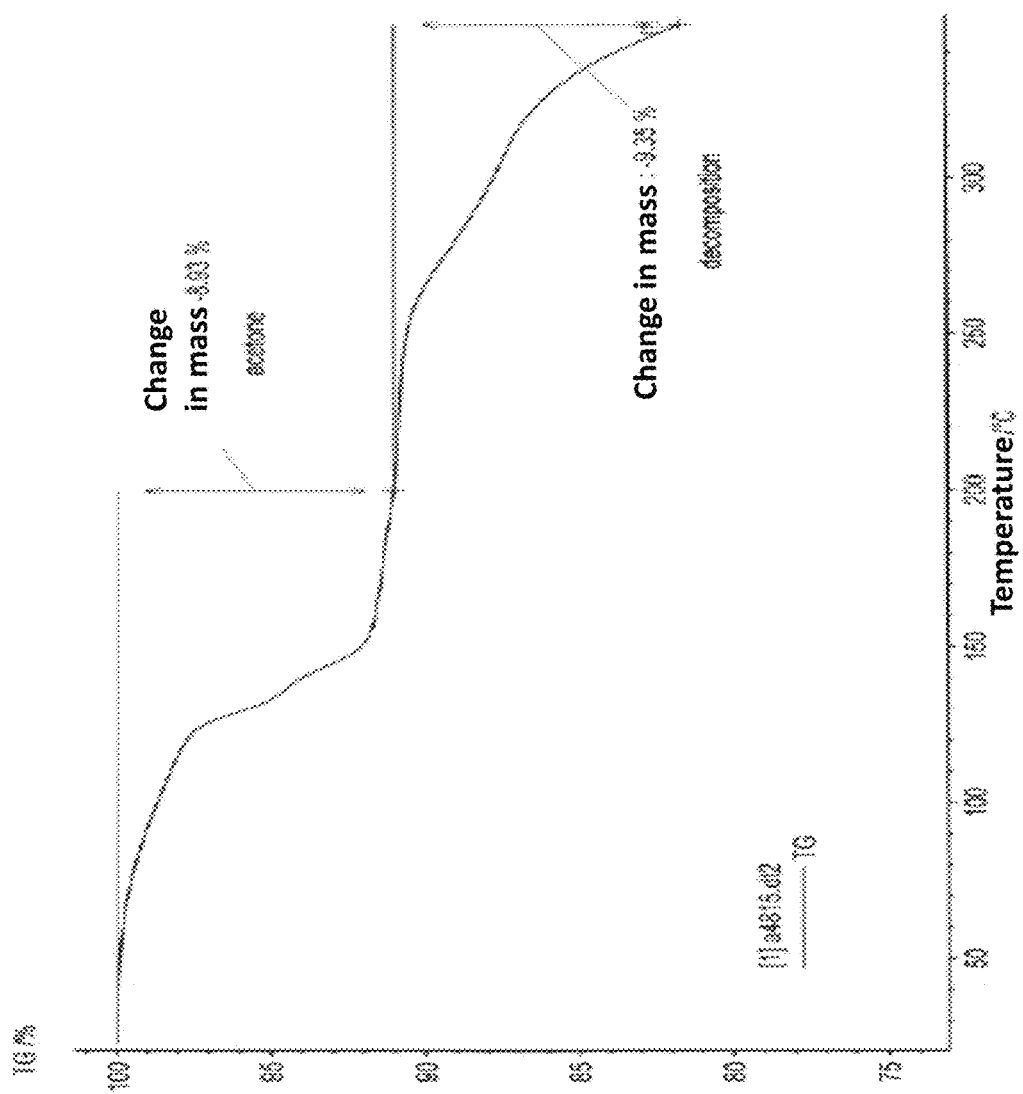
FIG. 44 depicts a TG-FTIR thermogram of Form FUM-P3.

In some embodiments, Form FUM-P3 is characterized by a TG-FTIR thermogram substantially similar to the one depicted in FIG. 44.

In some embodiments, Form FUM-P3 is a solvate. In some embodiments, Form FUM-P3 is a hemisolvate. In some embodiments, Form FUM-P3 is a non-stoichiometric solvate. In some embodiments, Form FUM-P3 is obtained by recrystallization of the fumarate salt of compound 1 from acetone. In some embodiments, Form FUM-P3 is an acetone solvate.

Form FUM-P4

In certain embodiments, the present invention provides crystalline Form FUM-P4 (Form FUM-P4) of compound 1. In some embodiments, Form FUM-P4 is a salt of compound 1. In some embodiments, Form FUM-P4 is a fumarate salt of compound 1. In some embodiments, Form FUM-P4 is a mono-fumarate salt of compound 1. In some embodiments, Form FUM-P4 is a co-crystal of compound 1 and fumaric acid.

In certain embodiments, Form FUM-P4 is substantially free of impurities. In certain embodiments, the impurity is compound 1 in free base form. In certain embodiments, Form FUM-P4 is 99% free of impurities by weight. In certain embodiments, Form FUM-P4 is 97% free of impurities by weight. In certain embodiments, Form FUM-P4 is 95% free of impurities by weight. In certain embodiments, Form FUM-P4 is substantially free of amorphous compound 1. In certain embodiments, Form FUM-P4 is substantially free of other crystalline forms of compound 1.

Form FUM-P4 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form FUM-P4 is characterized by an X-ray powder diffraction pattern substantially similar to the one depicted in FIG. 45. In some embodiments, Form FUM-P4 is characterized in that it has one or more peaks in its X-ray powder diffraction pattern selected from those in Table 50. In some embodiments, Form FUM-P4 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, or at least twenty-four peaks in its X-ray powder diffraction pattern selected from those in Table 50. In some embodiments, Form FUM-P4 of compound 1 is characterized in that it has one or more peaks in its X-ray powder diffraction pattern selected from the strong and very strong peaks in Table 50.

TABLE 50

X-ray powder diffraction pattern.

| Angle 2-Theta ° | d value Angstrom | Intensity (relative) | Intensity % |
|---|---|---|---|
| 4.50 | 19.6 | w | 13 |
| 5.25 | 16.8 | w | 9 |
| 6.04 | 14.6 | w | 12 |
| 7.40 | 11.9 | m | 21 |
| 8.80 | 10.0 | w | 14 |
| 10.66 | 8.3 | m | 18 |
| 12.13 | 7.3 | m | 17 |
| 13.25 | 6.7 | m | 25 |
| 14.84 | 5.97 | m | 17 |
| 16.11 | 5.50 | m | 25 |
| 17.17 | 5.16 | m | 26 |
| 17.64 | 5.02 | vs | 100 |
| 18.29 | 4.85 | m | 26 |
| 18.45 | 4.80 | s | 38 |
| 20.10 | 4.42 | s | 49 |
| 21.10 | 4.21 | s | 40 |
| 21.53 | 4.12 | s | 40 |
| 23.26 | 3.82 | s | 44 |
| 24.36 | 3.65 | m | 25 |
| 24.68 | 3.60 | m | 30 |
| 25.18 | 3.53 | m | 24 |
| 26.94 | 3.31 | m | 16 |
| 28.04 | 3.18 | m | 19 |
| 28.82 | 3.10 | m | 17 |

In some embodiments, Form FUM-P4 is characterized by one or more peaks in its X-ray powder diffraction pattern selected from those in Table 51. In some embodiments, Form FUM-P4 is characterized by at least one, at least two, at least three, at least four, at least five, at least six, or at least seven peaks in its X-ray powder diffraction pattern selected from those in Table 51.

TABLE 51

X-ray powder diffraction pattern.

| Angle 2-Theta ° | d value Angstrom | Intensity (relative) | Intensity % |
|---|---|---|---|
| 17.64 | 5.02 | vs | 100 |
| 18.45 | 4.80 | s | 38 |
| 20.10 | 4.42 | s | 49 |
| 21.10 | 4.21 | s | 40 |
| 21.53 | 4.12 | s | 40 |
| 23.26 | 3.82 | s | 44 |
| 24.68 | 3.60 | m | 30 |

Figure 46:
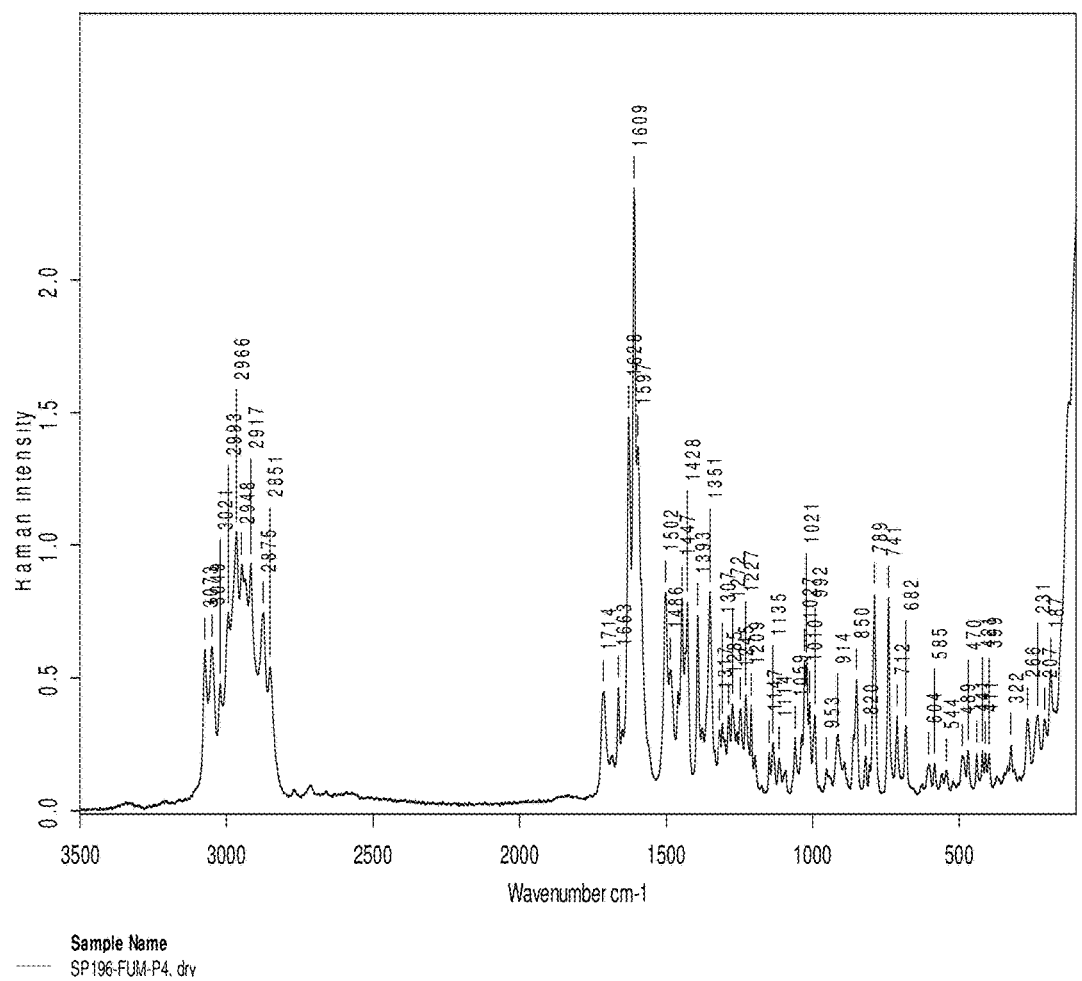
FIG. 46 depicts an FT-Raman spectrum of Form FUM-P4.

In some embodiments, Form FUM-P4 is characterized by a Raman spectrum substantially similar to the one depicted in FIG. 46. In some embodiments, Form FUM-P4 is characterized by one or more peaks in its Raman spectrum selected from those in Table 52. In some embodiments, Form FUM-P4 is characterized by having a Raman spectrum with characteristic peaks at about those in Table 52.

TABLE 52

Raman spectrum.

| Wavenumber (cm$^{-1}$) | Absolute Intensity | Normalized Intensity (%) |
|---|---|---|
| 3073 | 0.607 | 25.9 |
| 3049 | 0.617 | 26.3 |
| 3021 | 0.478 | 20.4 |
| 2993 | 0.745 | 31.8 |
| 2966 | 1.052 | 44.8 |
| 2948 | 0.926 | 39.5 |
| 2917 | 0.930 | 39.6 |
| 2875 | 0.743 | 31.7 |
| 2851 | 0.541 | 23.1 |
| 1714 | 0.448 | 19.1 |
| 1663 | 0.465 | 19.8 |
| 1628 | 1.482 | 63.2 |
| 1609 | 2.346 | 100.0 |
| 1597 | 1.374 | 58.6 |
| 1502 | 0.821 | 35.0 |
| 1486 | 0.529 | 22.5 |
| 1447 | 0.804 | 34.3 |
| 1428 | 0.785 | 33.5 |
| 1393 | 0.736 | 31.4 |
| 1351 | 0.825 | 35.2 |
| 1317 | 0.303 | 12.9 |
| 1307 | 0.328 | 14.0 |
| 1285 | 0.361 | 15.4 |
| 1272 | 0.402 | 17.1 |
| 1245 | 0.383 | 16.3 |
| 1227 | 0.434 | 18.5 |
| 1209 | 0.396 | 16.9 |
| 1147 | 0.219 | 9.3 |
| 1135 | 0.254 | 10.8 |
| 1114 | 0.195 | 8.3 |
| 1059 | 0.273 | 11.6 |
| 1027 | 0.565 | 24.1 |
| 1020 | 0.559 | 23.8 |
| 1010 | 0.405 | 17.3 |
| 992 | 0.361 | 15.4 |
| 953 | 0.156 | 6.6 |
| 914 | 0.286 | 12.2 |
| 850 | 0.493 | 21.0 |
| 820 | 0.205 | 8.7 |

TABLE 52-continued

Raman spectrum.

| Wavenumber (cm⁻¹) | Absolute Intensity | Normalized Intensity (%) |
|---|---|---|
| 789 | 0.815 | 34.7 |
| 741 | 0.800 | 34.1 |
| 712 | 0.357 | 15.2 |
| 682 | 0.319 | 13.6 |
| 604 | 0.174 | 7.4 |
| 585 | 0.178 | 7.6 |
| 544 | 0.151 | 6.4 |
| 489 | 0.207 | 8.8 |
| 470 | 0.226 | 9.6 |
| 441 | 0.218 | 9.3 |
| 421 | 0.225 | 9.6 |
| 411 | 0.216 | 9.2 |
| 399 | 0.213 | 9.1 |
| 322 | 0.247 | 10.5 |
| 266 | 0.346 | 14.7 |
| 231 | 0.358 | 15.3 |
| 207 | 0.344 | 14.7 |
| 187 | 0.532 | 22.7 |

In some embodiments, Form FUM-P4 is characterized by one or more peaks in its Raman spectrum selected from those in Table 53. In some embodiments, Form FUM-P4 is characterized by at least one, at least two, at least three, at least four, at least five, at least six, at least seven, at least eight, at least nine, or at least ten peaks in its Raman spectrum selected from those in Table 53.

TABLE 53

Raman spectrum.

| Wavenumber (cm⁻¹) | Absolute Intensity | Normalized Intensity (%) |
|---|---|---|
| 1628 | 1.482 | 63.2 |
| 1609 | 2.346 | 100.0 |
| 1597 | 1.374 | 58.6 |
| 1502 | 0.821 | 35.0 |
| 1447 | 0.804 | 34.3 |
| 1428 | 0.785 | 33.5 |
| 1393 | 0.736 | 31.4 |
| 1351 | 0.825 | 35.2 |
| 789 | 0.815 | 34.7 |
| 741 | 0.800 | 34.1 |

Figure 47:
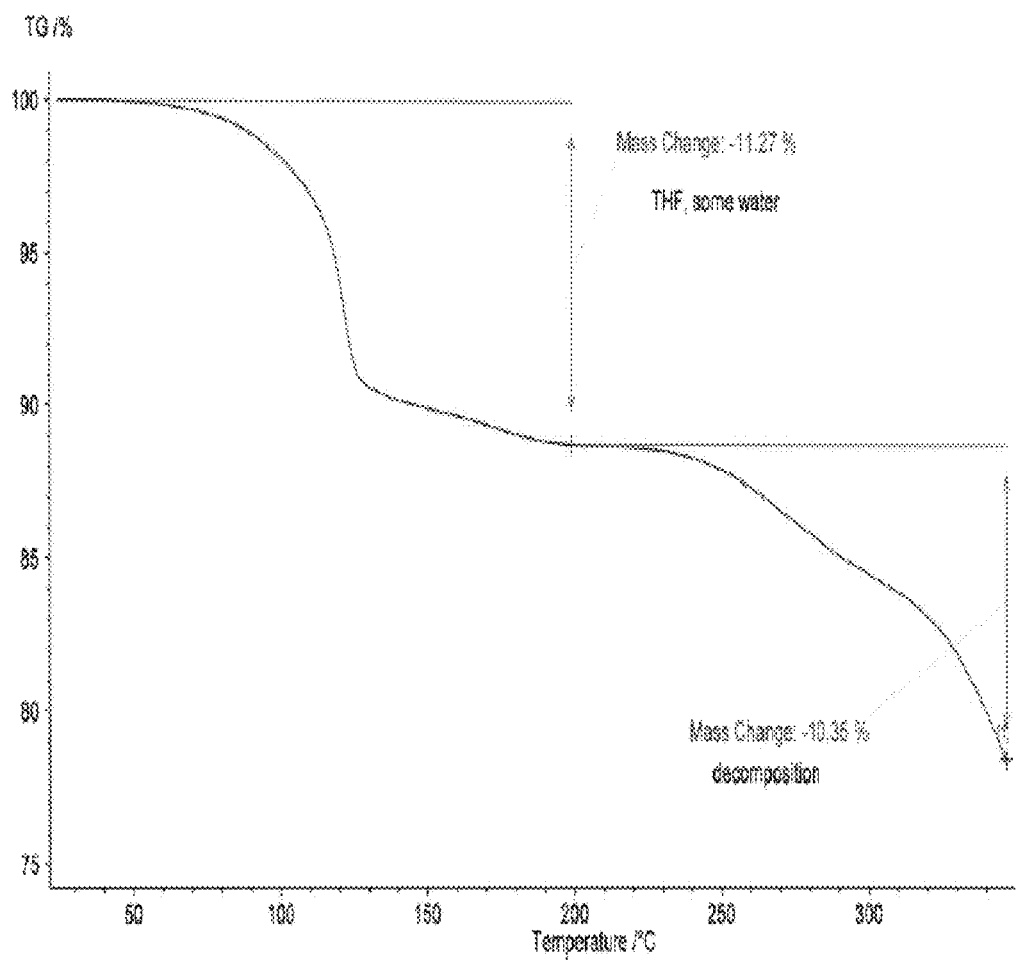
FIG. 47 depicts a TG-FTIR thermogram of Form FUM-P4.

In some embodiments, Form FUM-P4 is characterized by a TG-FTIR thermogram substantially similar to the one depicted in FIG. 47.

In some embodiments, Form FUM-P4 is a solvate. In some embodiments, Form FUM-P4 is a non-stoichiometric solvate. In some embodiments, Form FUM-P4 is obtained from tetrahydrofuran. In some embodiments, Form FUM-P4 is a tetrahydrofuran solvate.

Malate Salt, Co-Crystal, and Form MLA-P3

The invention also provides a malate (e.g., L-malate and D-malate) salt form of compound 1. The malate salt may be amorphous or exist in one or more crystalline forms. In certain embodiments, the present invention provides crystalline Form MLA-P3 (Form MLA-P3) of compound 1. In some embodiments, Form MLA-P3 is a salt of compound 1. In some embodiments, Form MLA-P3 is an L-malate salt of compound 1. In some embodiments, Form MLA-P3 is a mono-L-malate salt of compound 1. In some embodiments, Form MLA-P3 is a co-crystal of compound 1 and L-malic acid.

In certain embodiments, Form MLA-P3 is substantially free of impurities. In certain embodiments, the impurity is compound 1 in free base form. In certain embodiments, Form MLA-P3 is 99% free of impurities by weight. In certain embodiments, Form MLA-P3 is 97% free of impurities by weight. In certain embodiments, Form MLA-P3 is 95% free of impurities by weight. In certain embodiments, Form MLA-P3 is substantially free of amorphous L-malic acid salt of compound 1. In certain embodiments, Form MLA-P3 is substantially free of other crystalline forms of compound 1.

Figure 48:
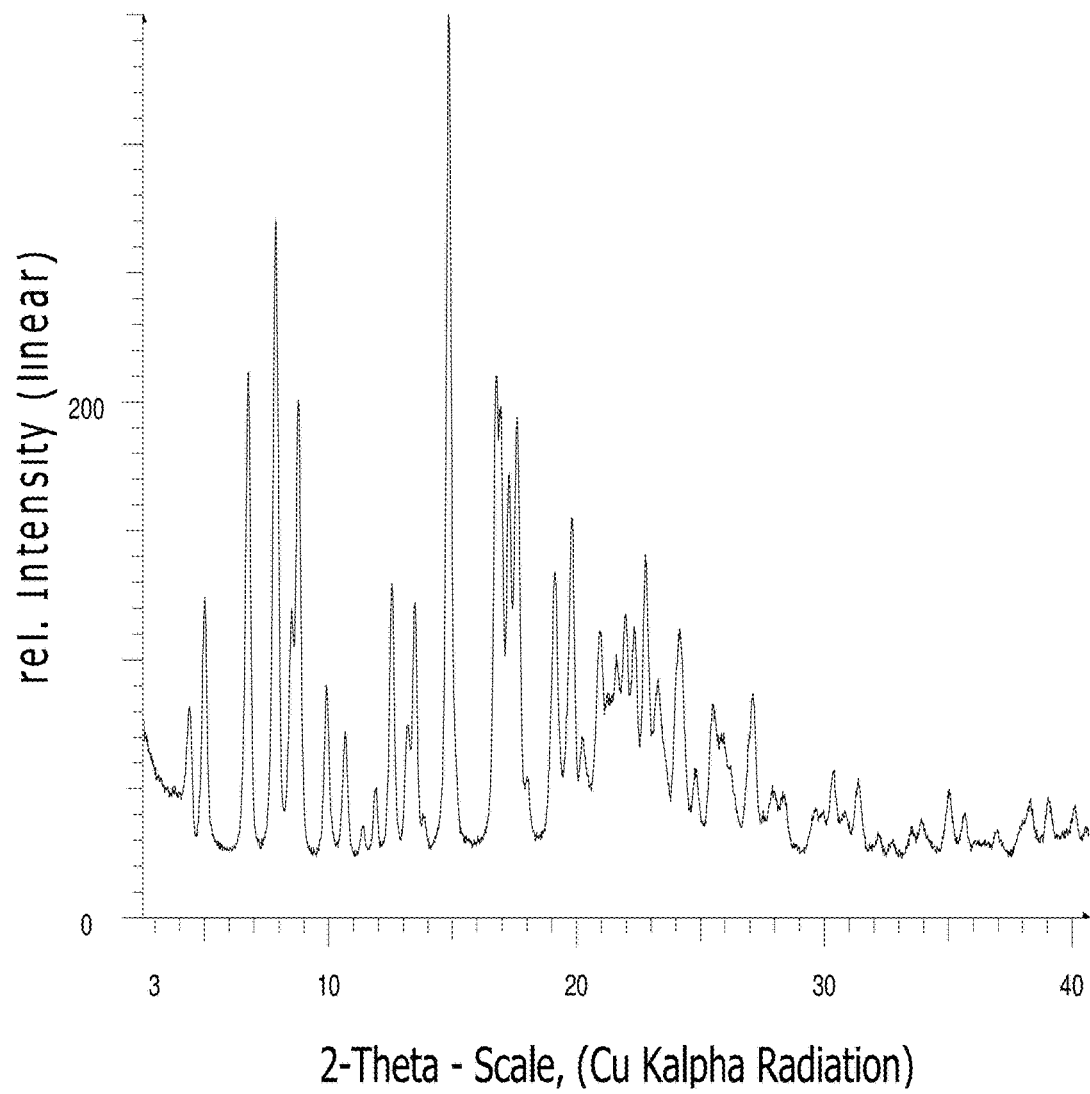
FIG. 48 depicts an XRPD pattern of Form MLA-P3.

Form MLA-P3 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form MLA-P3 is characterized by an X-ray powder diffraction pattern substantially similar to the one depicted in FIG. 48. In some embodiments, Form MLA-P3 is characterized in that it has one or more peaks in its X-ray powder diffraction pattern selected from those in Table 54. In some embodiments, Form MLA-P3 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, or at least thirty-three peaks in its X-ray powder diffraction pattern selected from those in Table 54. In some embodiments, Form MLA-P3 of compound 1 is characterized in that it has one or more peaks in its X-ray powder diffraction pattern selected from the strong and very strong peaks in Table 54.

TABLE 54

X-ray powder diffraction pattern.

| Angle 2-Theta ° | d value Angstrom | Intensity (relative) | Intensity % |
|---|---|---|---|
| 4.35 | 20.3 | m | 22 |
| 4.97 | 17.8 | s | 35 |
| 6.72 | 13.1 | s | 62 |
| 7.83 | 11.3 | vs | 82 |
| 8.48 | 10.4 | s | 36 |
| 8.75 | 10.1 | s | 61 |
| 9.89 | 8.9 | m | 28 |
| 10.64 | 8.3 | m | 22 |
| 11.35 | 7.8 | w | 11 |
| 11.86 | 7.5 | w | 15 |
| 12.52 | 7.1 | s | 39 |
| 13.15 | 6.7 | m | 23 |
| 13.44 | 6.6 | s | 37 |
| 14.84 | 5.97 | vs | 100 |
| 16.75 | 5.29 | s | 65 |
| 16.93 | 5.23 | s | 59 |
| 17.26 | 5.13 | s | 54 |
| 17.59 | 5.04 | s | 61 |
| 18.02 | 4.92 | m | 16 |
| 19.11 | 4.64 | s | 40 |
| 19.80 | 4.48 | s | 48 |
| 20.93 | 4.24 | s | 34 |
| 21.96 | 4.05 | s | 36 |
| 22.32 | 3.98 | s | 35 |
| 22.78 | 3.90 | s | 44 |
| 23.27 | 3.82 | m | 29 |
| 24.14 | 3.68 | s | 35 |
| 24.81 | 3.59 | m | 18 |
| 25.49 | 3.49 | m | 25 |
| 27.11 | 3.29 | m | 27 |

TABLE 54-continued

X-ray powder diffraction pattern.

| Angle 2-Theta ° | d value Angstrom | Intensity (relative) | Intensity % |
|---|---|---|---|
| 28.37 | 3.14 | w | 15 |
| 30.38 | 2.94 | m | 17 |
| 31.38 | 2.85 | m | 17 |

In some embodiments, Form MLA-P3 is characterized by one or more peaks in its X-ray powder diffraction pattern selected from those in Table 55. In some embodiments, Form MLA-P3 is characterized by at least one, at least two, at least three, at least four, at least five, at least six, at least seven, at least eight, or at least nine peaks in its X-ray powder diffraction pattern selected from those in Table 55.

TABLE 55

X-ray powder diffraction pattern.

| Angle 2-Theta ° | d value Angstrom | Intensity (relative) | Intensity % |
|---|---|---|---|
| 6.72 | 13.1 | s | 62 |
| 7.83 | 11.3 | vs | 82 |
| 8.75 | 10.1 | s | 61 |
| 14.84 | 5.97 | vs | 100 |
| 16.75 | 5.29 | s | 65 |
| 16.93 | 5.23 | s | 59 |
| 17.26 | 5.13 | s | 54 |
| 17.59 | 5.04 | s | 61 |
| 19.80 | 4.48 | s | 48 |

Figure 49:
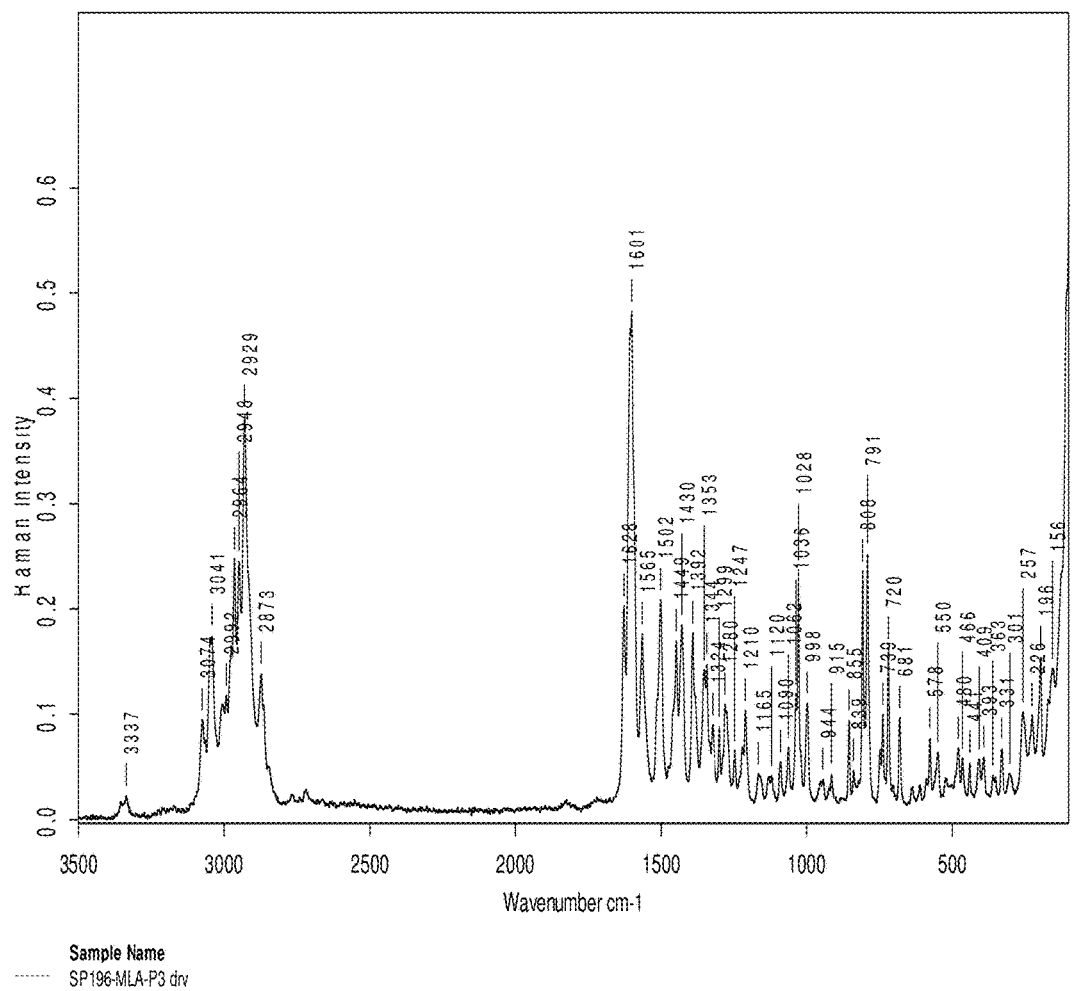
FIG. 49 depicts an FT-Raman spectrum of Form MLA-P3.

In some embodiments, Form MLA-P3 is characterized by a Raman spectrum substantially similar to the one depicted in FIG. 49. In some embodiments, Form MLA-P3 is characterized by one or more peaks in its Raman spectrum selected from those in Table 56. In some embodiments, Form MLA-P3 is characterized by having a Raman spectrum with characteristic peaks at about those in Table 56.

TABLE 56

Raman spectrum.

| Wavenumber (cm$^{-1}$) | Absolute Intensity | Normalized Intensity (%) |
|---|---|---|
| 3337 | 0.023 | 4.8 |
| 3074 | 0.095 | 19.7 |
| 3041 | 0.174 | 36.1 |
| 2992 | 0.117 | 24.3 |
| 2964 | 0.247 | 51.2 |
| 2948 | 0.245 | 50.8 |
| 2929 | 0.382 | 79.3 |
| 2873 | 0.138 | 28.6 |
| 1628 | 0.202 | 41.9 |
| 1601 | 0.482 | 100.0 |
| 1565 | 0.176 | 36.5 |
| 1502 | 0.208 | 43.2 |
| 1449 | 0.170 | 35.3 |
| 1430 | 0.185 | 38.4 |
| 1392 | 0.177 | 36.7 |
| 1353 | 0.142 | 29.5 |
| 1344 | 0.147 | 30.5 |
| 1324 | 0.090 | 18.7 |
| 1299 | 0.088 | 18.3 |
| 1280 | 0.109 | 22.6 |
| 1247 | 0.066 | 13.7 |
| 1210 | 0.103 | 21.4 |
| 1165 | 0.044 | 9.1 |
| 1119 | 0.042 | 8.7 |
| 1089 | 0.054 | 11.2 |

TABLE 56-continued

Raman spectrum.

| Wavenumber (cm$^{-1}$) | Absolute Intensity | Normalized Intensity (%) |
|---|---|---|
| 1062 | 0.069 | 14.3 |
| 1036 | 0.120 | 24.9 |
| 1028 | 0.237 | 49.2 |
| 998 | 0.110 | 22.8 |
| 944 | 0.038 | 7.9 |
| 915 | 0.043 | 8.9 |
| 854 | 0.094 | 19.5 |
| 839 | 0.046 | 9.5 |
| 808 | 0.236 | 49.0 |
| 791 | 0.252 | 52.3 |
| 739 | 0.100 | 20.7 |
| 720 | 0.162 | 33.6 |
| 681 | 0.096 | 19.9 |
| 578 | 0.077 | 16.0 |
| 550 | 0.064 | 13.3 |
| 480 | 0.068 | 14.1 |
| 466 | 0.058 | 12.0 |
| 441 | 0.054 | 11.2 |
| 409 | 0.057 | 11.8 |
| 393 | 0.059 | 12.2 |
| 363 | 0.042 | 8.7 |
| 331 | 0.067 | 13.9 |
| 301 | 0.043 | 8.9 |
| 257 | 0.102 | 21.2 |
| 226 | 0.099 | 20.5 |
| 196 | 0.154 | 32.0 |
| 155 | 0.143 | 29.7 |

In some embodiments, Form MLA-P3 is characterized by one or more peaks in its Raman spectrum selected from those in Table 57. In some embodiments, Form MLA-P3 is characterized by at least one, at least two, at least three, at least four, at least five, at least six, at least seven, at least eight, at least nine, at least ten, at least eleven, or at least twelve peaks in its Raman spectrum selected from those in Table 57.

TABLE 57

Raman spectrum.

| Wavenumber (cm$^{-1}$) | Absolute Intensity | Normalized Intensity (%) |
|---|---|---|
| 1628 | 0.202 | 41.9 |
| 1601 | 0.482 | 100.0 |
| 1565 | 0.176 | 36.5 |
| 1502 | 0.208 | 43.2 |
| 1449 | 0.170 | 35.3 |
| 1430 | 0.185 | 38.4 |
| 1392 | 0.177 | 36.7 |
| 1344 | 0.147 | 30.5 |
| 1028 | 0.237 | 49.2 |
| 808 | 0.236 | 49.0 |
| 791 | 0.252 | 52.3 |
| 720 | 0.162 | 33.6 |

Figure 50:
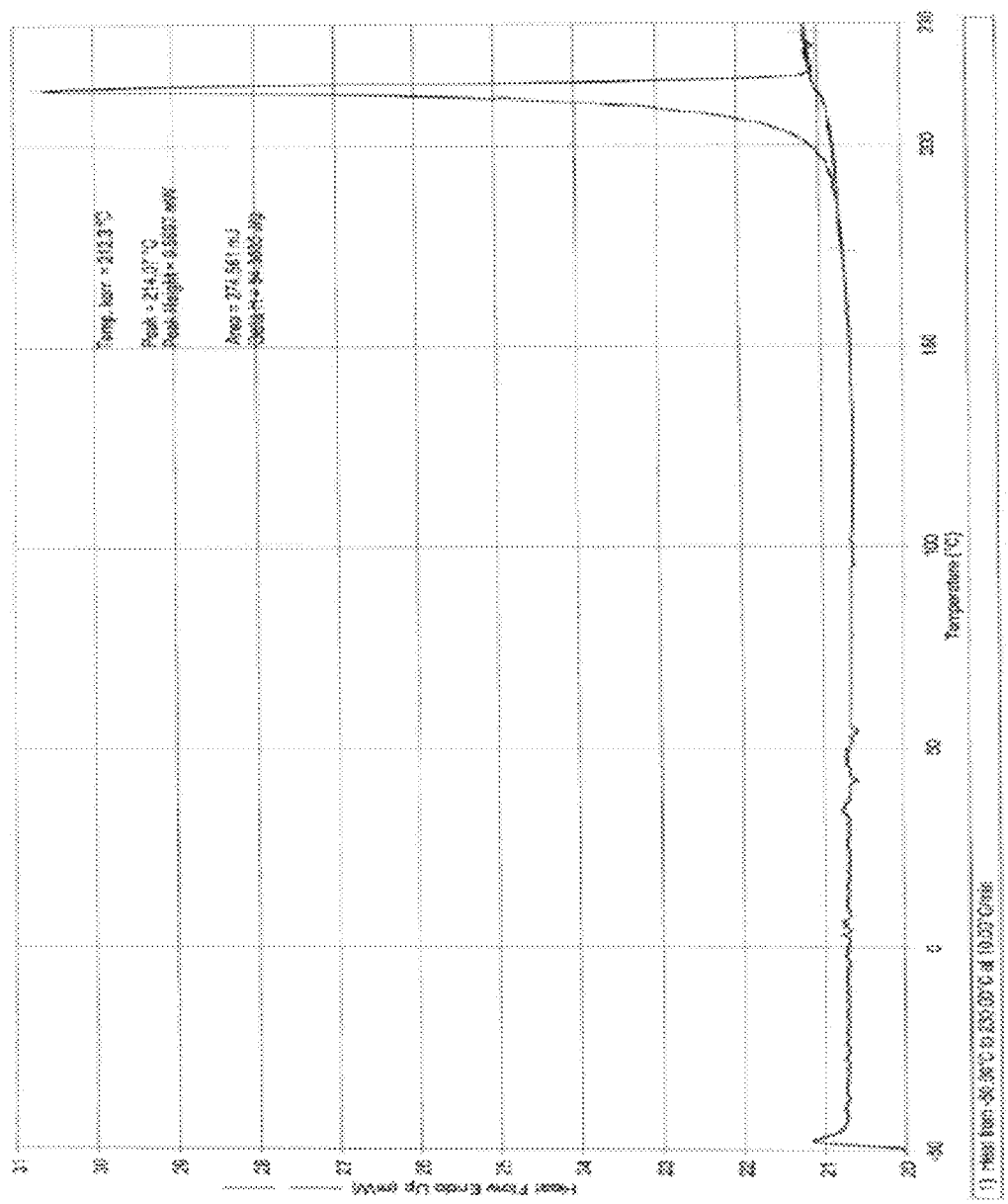
FIG. 50 depicts a DSC thermogram of Form MLA-P3.

In some embodiments, Form MLA-P3 has a DSC thermogram substantially similar to the one depicted in FIG. 50. In some embodiments, Form MLA-P3 has a DSC thermogram with an endotherm having a peak temperature ($T_{max}$) of about 212° C. In some embodiments, Form MLA-P3 has a DSC thermogram with a ΔH of about 94 J/g.

In some embodiments, Form MLA-P3 is substantially anhydrous. In some embodiments, Form MLA-P3 is obtained from acetone.

Form MLA-P4

In certain embodiments, the present invention provides crystalline Form MLA-P4 (Form MLA-P4) of compound 1.

In some embodiments, Form MLA-P4 is a salt of compound 1. In some embodiments, Form MLA-P4 is an L-malate salt of compound 1. In some embodiments, Form MLA-P4 is a mono-L-malate salt of compound 1. In some embodiments, Form MLA-P4 is a co-crystal of compound 1 and L-malic acid.

In certain embodiments, Form MLA-P4 is substantially fee of impurities. In certain embodiments, the impurity is compound 1 in free base form. In certain embodiments, Form MLA-P4 is 99% free of impurities by weight. In certain embodiments, Form MLA-P4 is 97% free of impurities by weight. In certain embodiments, Form MLA-P4 is 95% free of impurities by weight. In certain embodiments, Form MLA-P4 is substantially free of amorphous L-malic acid salt of compound 1. In certain embodiments, Form MLA-P4 is substantially free of other crystalline forms of compound 1.

Figure 51:
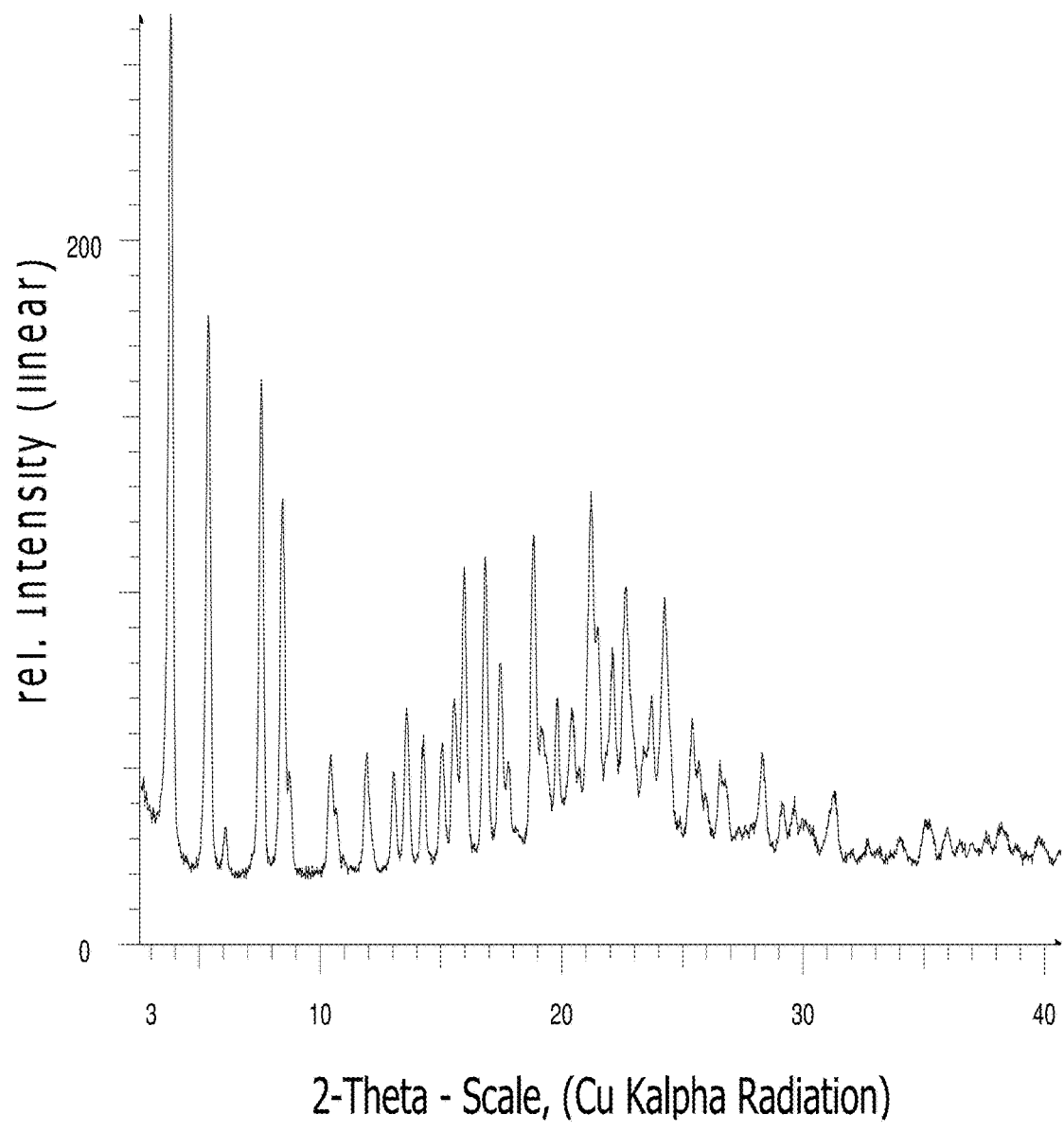
FIG. 51 depicts an XRPD pattern of Form MLA-P4.

Form MLA-P4 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form MLA-P4 is characterized by an X-ray powder diffraction pattern substantially similar to the one depicted in FIG. 51. In some embodiments, Form MLA-P4 is characterized in that it has one or more peaks in its X-ray powder diffraction pattern selected from those in Table 58. In some embodiments, Form MLA-P4 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, or at least twenty-nine peaks in its X-ray powder diffraction pattern selected from those in Table 58. In some embodiments, Form MLA-P4 of compound 1 is characterized in that it has one or more peaks in its X-ray powder diffraction pattern selected from the strong and very strong peaks in Table 58.

TABLE 58

X-ray powder diffraction pattern.

| Angle 2-Theta ° | d value Angstrom | Intensity (relative) | Intensity % |
|---|---|---|---|
| 3.78 | 23.4 | vs | 100 |
| 5.33 | 16.6 | vs | 75 |
| 6.03 | 14.6 | w | 14 |
| 7.52 | 11.7 | vs | 70 |
| 8.40 | 10.5 | s | 56 |
| 10.39 | 8.5 | m | 24 |
| 11.89 | 7.4 | m | 24 |
| 12.99 | 6.8 | m | 22 |
| 13.54 | 6.5 | m | 30 |
| 14.25 | 6.2 | m | 27 |
| 15.03 | 5.89 | m | 26 |
| 15.53 | 5.70 | s | 31 |
| 15.94 | 5.56 | s | 49 |
| 16.81 | 5.27 | s | 50 |
| 17.44 | 5.08 | s | 36 |
| 17.77 | 4.99 | m | 23 |
| 18.81 | 4.71 | s | 52 |
| 19.80 | 4.48 | s | 32 |
| 20.42 | 4.35 | s | 31 |
| 21.19 | 4.19 | s | 58 |
| 22.09 | 4.02 | s | 39 |

TABLE 58-continued

X-ray powder diffraction pattern.

| Angle 2-Theta ° | d value Angstrom | Intensity (relative) | Intensity % |
|---|---|---|---|
| 22.63 | 3.93 | s | 46 |
| 23.71 | 3.75 | s | 32 |
| 24.24 | 3.67 | s | 44 |
| 25.40 | 3.50 | m | 30 |
| 26.56 | 3.35 | m | 24 |
| 26.77 | 3.33 | m | 21 |
| 28.33 | 3.15 | m | 25 |
| 31.26 | 2.86 | m | 20 |

In some embodiments, Form MLA-P4 is characterized by one or more peaks in its X-ray powder diffraction pattern selected from those in Table 59. In some embodiments, Form MLA-P4 is characterized by at least one, at least two, at least three, at least four, at least five, at least six, at least seven, or at least eight peaks in its X-ray powder diffraction pattern selected from those in Table 59.

TABLE 59

X-ray powder diffraction pattern.

| Angle 2-Theta ° | d value Angstrom | Intensity (relative) | Intensity % |
|---|---|---|---|
| 5.33 | 16.6 | vs | 75 |
| 7.52 | 11.7 | vs | 70 |
| 8.40 | 10.5 | s | 56 |
| 16.81 | 5.27 | s | 50 |
| 18.81 | 4.71 | s | 52 |
| 21.19 | 4.19 | s | 58 |
| 22.63 | 3.93 | s | 46 |
| 24.24 | 3.67 | s | 44 |

Figure 52:
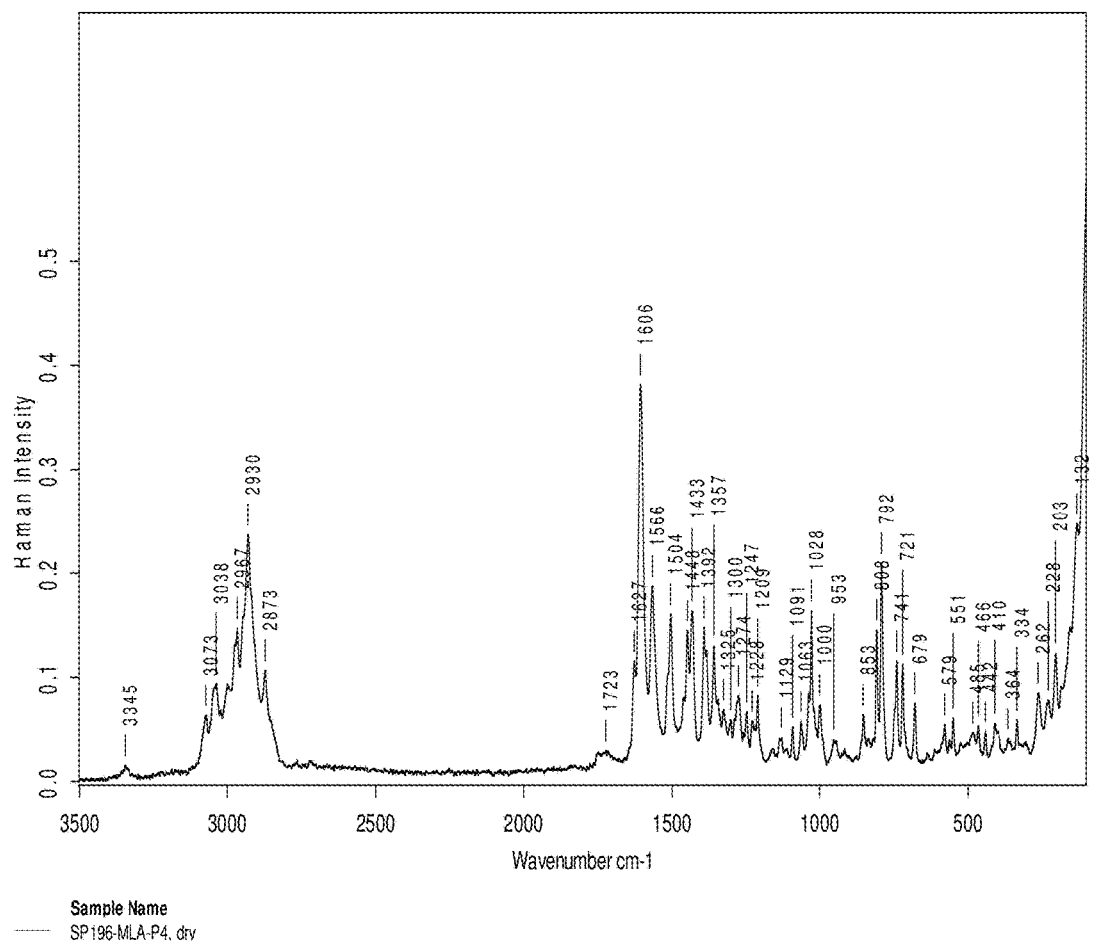
FIG. 52 depicts an FT-Raman spectrum of Form MLA-P4

In some embodiments, Form MLA-P4 is characterized by a Raman spectrum substantially similar to the one depicted in FIG. 52. In some embodiments, Form MLA-P4 is characterized by one or more peaks in its Raman spectrum selected from those in Table 60. In some embodiments, Form MLA-P4 is characterized by having a Raman spectrum with characteristic peaks at about those in Table 60.

TABLE 60

Raman spectrum.

| Wavenumber (cm$^{-1}$) | Absolute Intensity | Normalized Intensity (%) |
|---|---|---|
| 3345 | 0.015 | 3.9 |
| 3073 | 0.063 | 16.5 |
| 3038 | 0.093 | 24.4 |
| 2967 | 0.147 | 38.6 |
| 2930 | 0.237 | 62.2 |
| 2873 | 0.107 | 28.1 |
| 1723 | 0.029 | 7.6 |
| 1627 | 0.115 | 30.2 |
| 1606 | 0.381 | 100.0 |
| 1566 | 0.188 | 49.3 |
| 1504 | 0.160 | 42.0 |
| 1448 | 0.145 | 38.1 |
| 1433 | 0.164 | 43.0 |
| 1392 | 0.148 | 38.8 |
| 1357 | 0.130 | 34.1 |
| 1325 | 0.069 | 18.1 |
| 1300 | 0.059 | 15.5 |
| 1274 | 0.082 | 21.5 |
| 1246 | 0.066 | 17.3 |
| 1228 | 0.058 | 15.2 |
| 1209 | 0.082 | 21.5 |

TABLE 60-continued

Raman spectrum.

| Wavenumber (cm$^{-1}$) | Absolute Intensity | Normalized Intensity (%) |
|---|---|---|
| 1129 | 0.042 | 11.0 |
| 1091 | 0.052 | 13.6 |
| 1063 | 0.057 | 15.0 |
| 1028 | 0.164 | 43.0 |
| 1000 | 0.073 | 19.2 |
| 953 | 0.040 | 10.5 |
| 853 | 0.064 | 16.8 |
| 808 | 0.145 | 38.1 |
| 792 | 0.209 | 54.9 |
| 741 | 0.115 | 30.2 |
| 721 | 0.112 | 29.4 |
| 679 | 0.075 | 19.7 |
| 579 | 0.054 | 14.2 |
| 551 | 0.061 | 16.0 |
| 485 | 0.046 | 12.1 |
| 466 | 0.053 | 13.9 |
| 442 | 0.048 | 12.6 |
| 410 | 0.056 | 14.7 |
| 364 | 0.041 | 10.8 |
| 334 | 0.059 | 15.5 |
| 262 | 0.085 | 22.3 |
| 228 | 0.078 | 20.5 |
| 203 | 0.123 | 32.3 |
| 132 | 0.248 | 65.1 |

In some embodiments, Form MLA-P4 is characterized by one or more peaks in its Raman spectrum selected from those in Table 61. In some embodiments, Form MLA-P4 is characterized by at least one, at least two, at least three, at least four, at least five, at least six, at least seven, at least eight, at least nine, at least ten, at least eleven, or at least twelve peaks in its Raman spectrum selected from those in Table 61.

TABLE 61

Raman spectrum.

| Wavenumber (cm$^{-1}$) | Absolute Intensity | Normalized Intensity (%) |
|---|---|---|
| 1627 | 0.115 | 30.2 |
| 1606 | 0.381 | 100.0 |
| 1566 | 0.188 | 49.3 |
| 1504 | 0.160 | 42.0 |
| 1448 | 0.145 | 38.1 |
| 1433 | 0.164 | 43.0 |
| 1392 | 0.148 | 38.8 |
| 1357 | 0.130 | 34.1 |
| 1028 | 0.164 | 43.0 |
| 808 | 0.145 | 38.1 |
| 792 | 0.209 | 54.9 |
| 741 | 0.115 | 30.2 |

Figure 53:
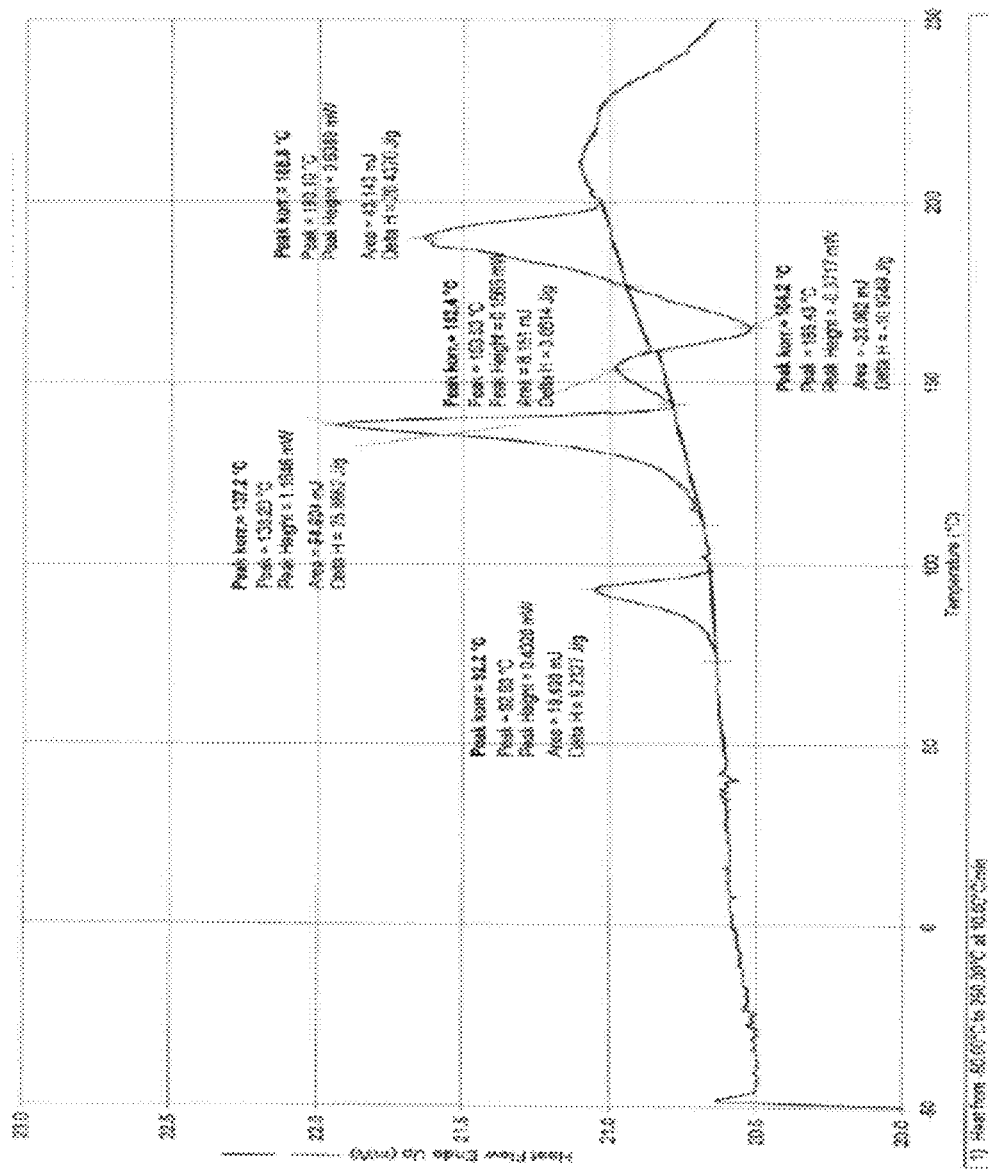
FIG. 53 depicts a DSC thermogram of Form MLA-P4.

In some embodiments, Form MLA-P4 has a DSC thermogram substantially similar to the one depicted in FIG. 53.

Figure 54:
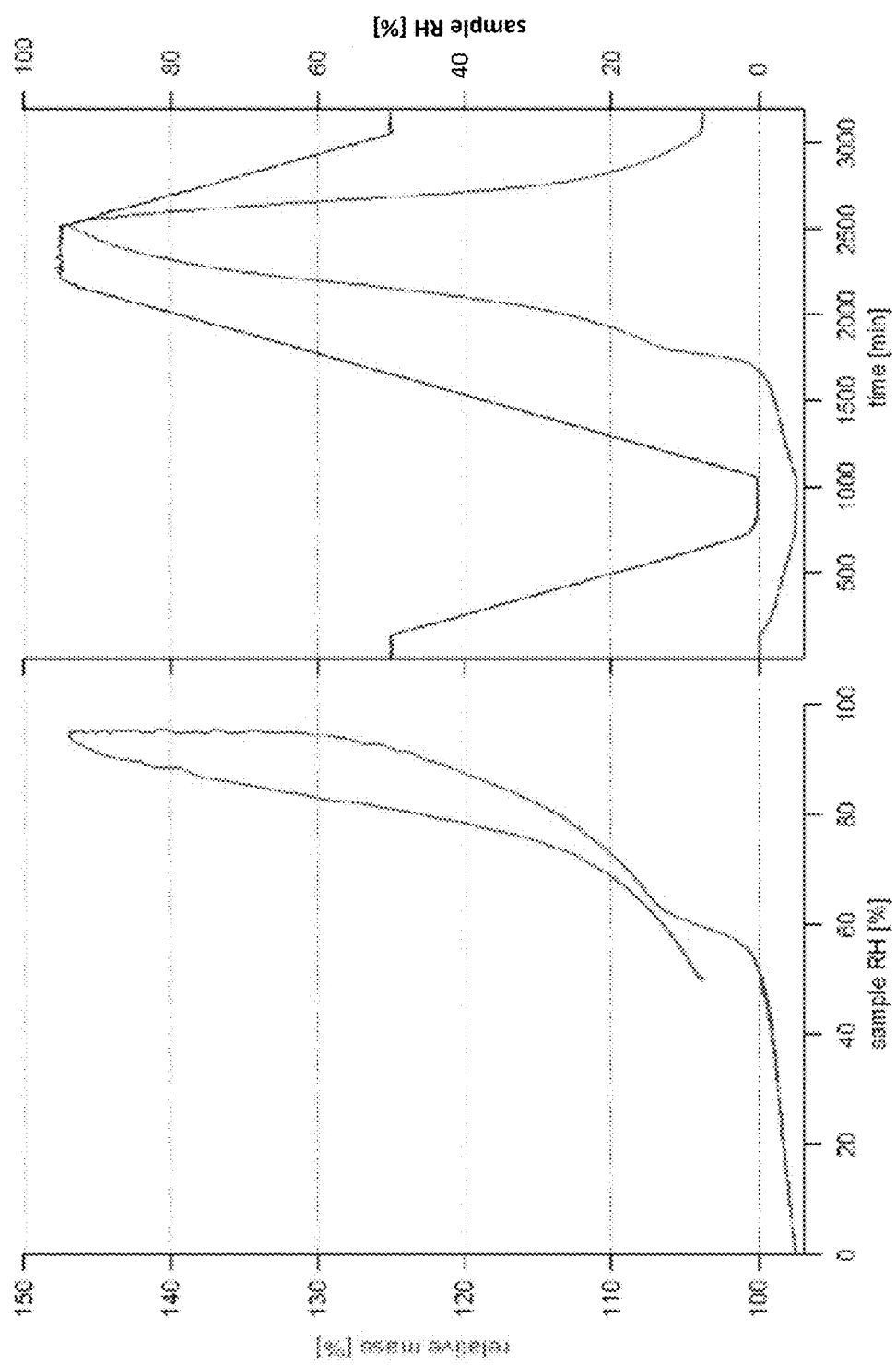
FIG. 54 depicts a DVS isotherm of Form MLA-P4.

In some embodiments, Form MLA-P4 has a DVS isotherm substantially similar to the one depicted in FIG. 54.

Figure 55:
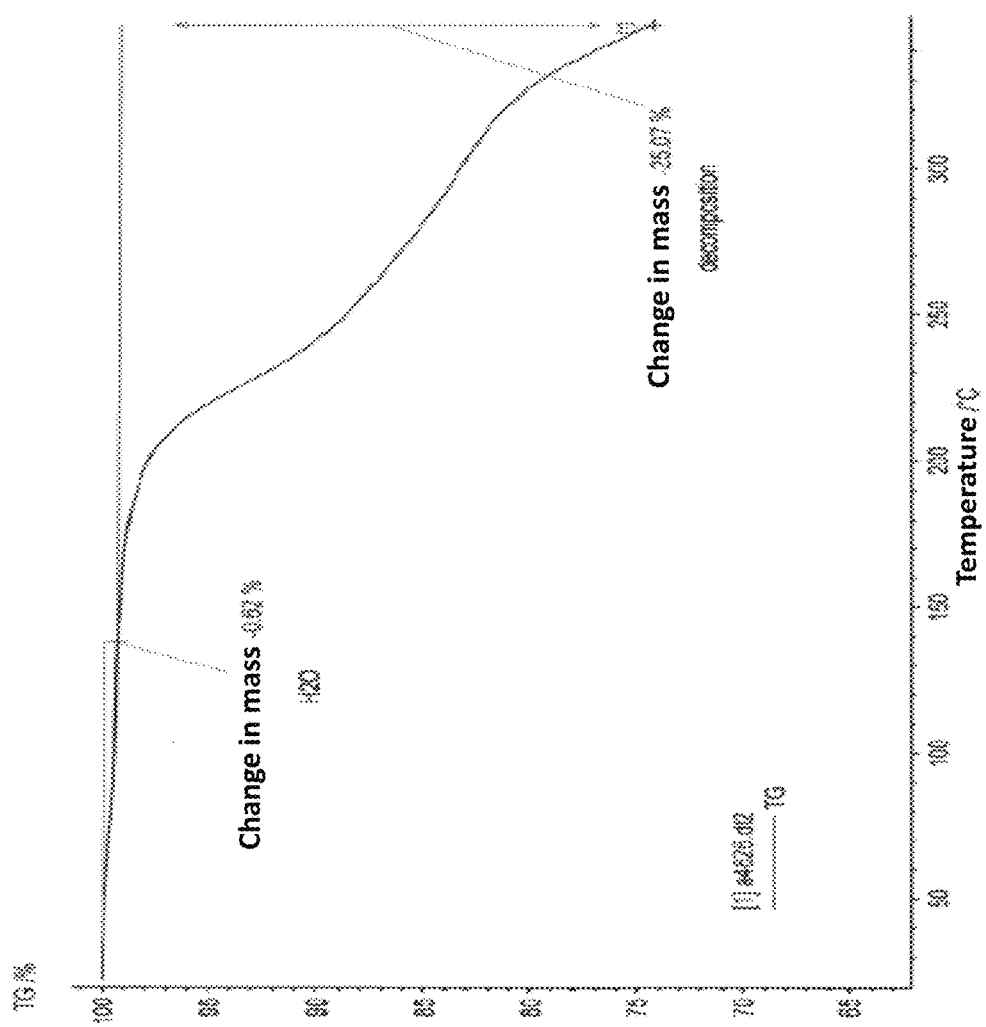
FIG. 55 depicts a TG-FTIR thermogram of Form MLA-P4.

In some embodiments, Form MLA-P4 has a TG-FTIR thermogram substantially similar to the one depicted in FIG. 55.

In some embodiments, Form MLA-P4 is substantially anhydrous. In some embodiments, Form MLA-P4 is obtained from crystallization from acetonitrile.

Succinate Salt, Co-Crystal, and Form SUC-P3

The invention also provides a succinate salt form of compound 1. The succinate salt may be amorphous or exist in one or more crystalline forms. In certain embodiments, the present invention provides crystalline Form SUC-P3 (Form SUC-P3) of compound 1. In some embodiments, Form SUC-P3 is a salt of compound 1. In some embodiments, Form SUC-P3 is a succinate salt of compound 1. In some embodiments, Form SUC-P3 is a mono-succinate salt of compound 1. In some embodiments, Form SUC-P3 is a co-crystal of compound 1 and succinic acid.

In certain embodiments, Form SUC-P3 is substantially free of impurities. In certain embodiments, the impurity is compound 1 in free base form. In certain embodiments, Form SUC-P3 is 99% free of impurities by weight. In certain embodiments, Form SUC-P3 is 97% free of impurities by weight. In certain embodiments, Form SUC-P3 is 95% free of impurities by weight. In certain embodiments, Form SUC-P3 is substantially free of amorphous succinic acid salt of compound 1. In certain embodiments, Form SUC-P3 is substantially free of other crystalline forms of compound 1.

Figure 56:
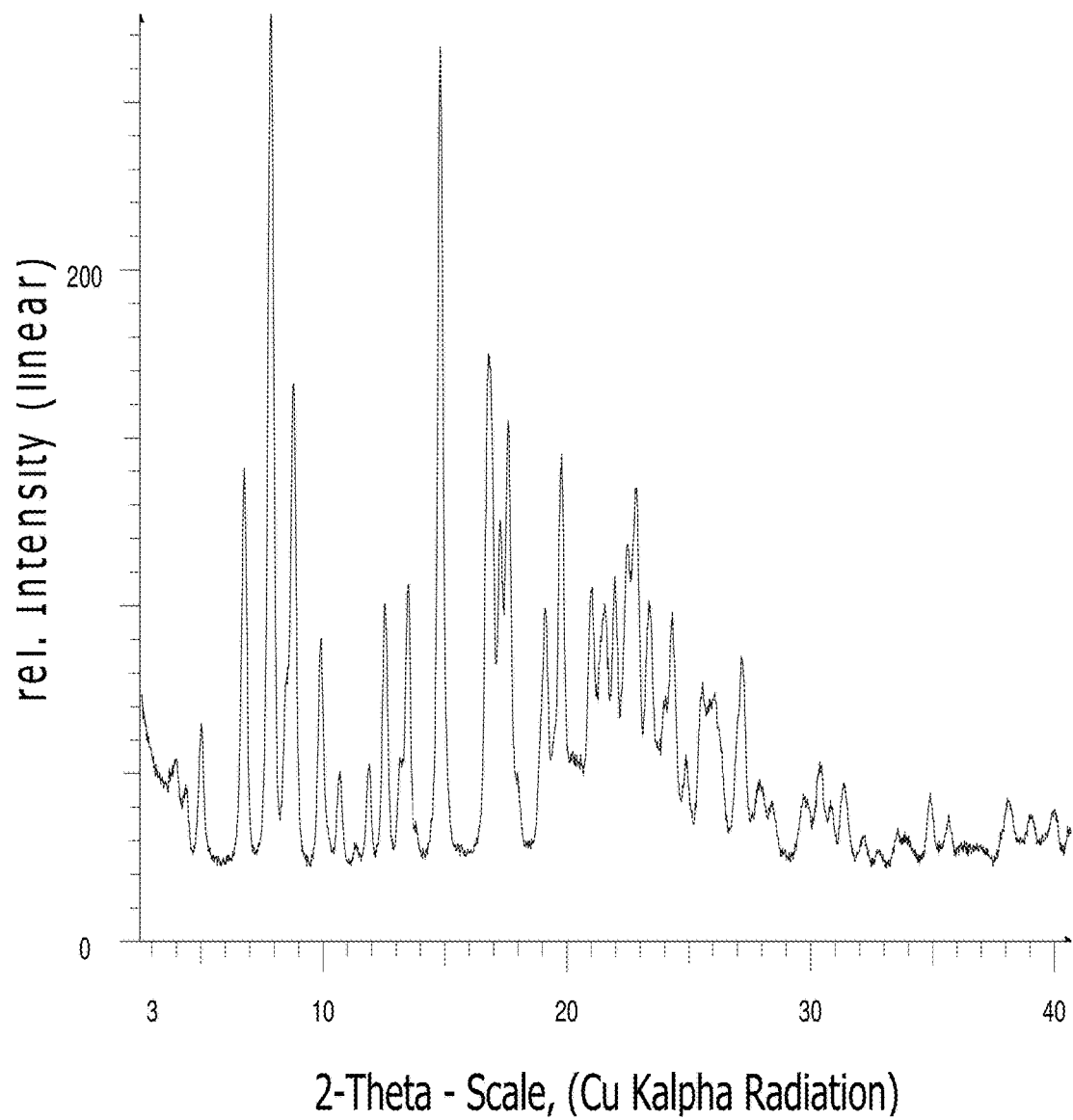
FIG. 56 depicts an XRPD pattern of Form SUC-P3.

Form SUC-P3 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form SUC-P3 is characterized by an X-ray powder diffraction pattern substantially similar to the one depicted in FIG. 56. In some embodiments, Form SUC-P3 is characterized in that it has one or more peaks in its X-ray powder diffraction pattern selected from those in Table 62. In some embodiments, Form SUC-P3 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, or at least twenty-eight peaks in its X-ray powder diffraction pattern selected from those in Table 62. In some embodiments, Form SUC-P3 of compound 1 is characterized in that it has one or more peaks in its X-ray powder diffraction pattern selected from the strong and very strong peaks in Table 62.

TABLE 62

X-ray powder diffraction pattern.

| Angle 2-Theta ° | d value Angstrom | Intensity (relative) | Intensity % |
|---|---|---|---|
| 4.98 | 17.7 | m | 22 |
| 6.73 | 13.1 | s | 50 |
| 7.82 | 11.3 | vs | 100 |
| 8.75 | 10.1 | s | 61 |
| 9.87 | 9.0 | s | 33 |
| 10.64 | 8.3 | m | 19 |
| 11.85 | 7.5 | m | 19 |
| 12.51 | 7.1 | s | 37 |
| 13.45 | 6.6 | s | 39 |
| 14.79 | 5.98 | vs | 99 |
| 16.81 | 5.27 | s | 63 |
| 17.25 | 5.14 | s | 46 |
| 17.58 | 5.04 | s | 57 |
| 19.10 | 4.64 | s | 37 |
| 19.76 | 4.49 | s | 53 |
| 20.98 | 4.23 | s | 38 |
| 21.56 | 4.12 | s | 36 |
| 21.95 | 4.05 | s | 40 |
| 22.46 | 3.96 | s | 44 |
| 22.82 | 3.89 | s | 51 |
| 23.37 | 3.80 | s | 38 |

TABLE 62-continued

X-ray powder diffraction pattern.

| Angle 2-Theta ° | d value Angstrom | Intensity (relative) | Intensity % |
|---|---|---|---|
| 24.30 | 3.66 | s | 36 |
| 24.87 | 3.58 | m | 21 |
| 25.57 | 3.48 | m | 29 |
| 27.19 | 3.28 | s | 33 |
| 30.44 | 2.93 | m | 19 |
| 31.37 | 2.85 | m | 17 |
| 34.90 | 2.57 | m | 16 |

In some embodiments, Form SUC-P3 is characterized by one or more peaks in its X-ray powder diffraction pattern selected from those in Table 63. In some embodiments, Form SUC-P3 is characterized by at least one, at least two, at least three, at least four, at least five, at least six, at least seven, or at least eight peaks in its X-ray powder diffraction pattern selected from those in Table 63.

TABLE 63

X-ray powder diffraction pattern.

| Angle 2-Theta ° | d value Angstrom | Intensity (relative) | Intensity % |
|---|---|---|---|
| 6.73 | 13.1 | s | 50 |
| 7.82 | 11.3 | vs | 100 |
| 8.75 | 10.1 | s | 61 |
| 14.79 | 5.98 | vs | 99 |
| 16.81 | 5.27 | s | 63 |
| 17.58 | 5.04 | s | 57 |
| 19.76 | 4.49 | s | 53 |
| 22.82 | 3.89 | s | 51 |

Figure 57:
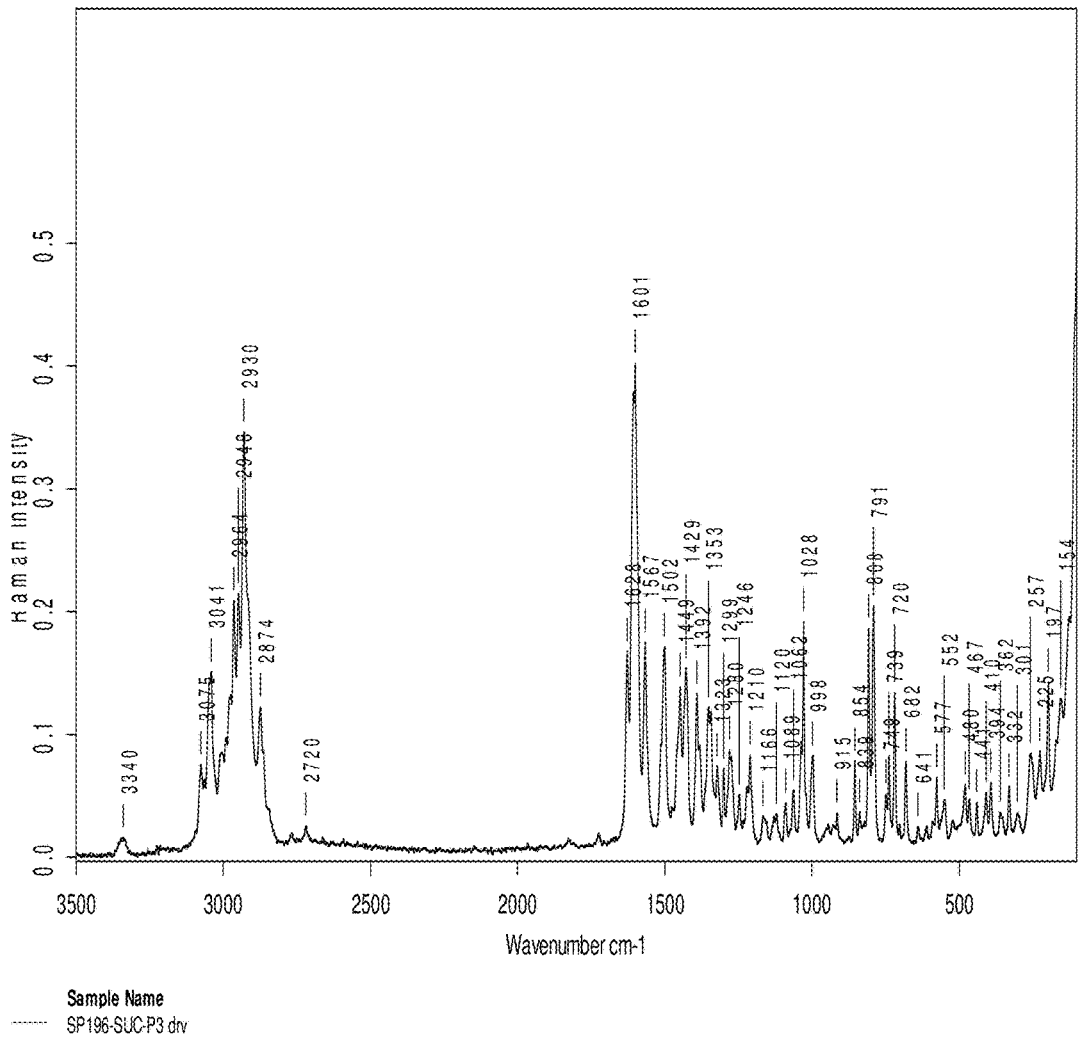
FIG. 57 depicts an FT-Raman spectrum of Form SUC-P3

In some embodiments, Form SUC-P3 is characterized by a Raman spectrum substantially similar to the one depicted in FIG. 57. In some embodiments, Form SUC-P3 is characterized by one or more peaks in its Raman spectrum selected from those in Table 64. In some embodiments, Form SUC-P3 is characterized by having a Raman spectrum with characteristic peaks at about those in Table 64.

TABLE 64

Raman spectrum.

| Wavenumber (cm$^{-1}$) | Absolute Intensity | Normalized Intensity (%) |
|---|---|---|
| 3340 | 0.016 | 4.0 |
| 3075 | 0.076 | 18.9 |
| 3041 | 0.151 | 37.6 |
| 2964 | 0.209 | 52.0 |
| 2948 | 0.215 | 53.5 |
| 2930 | 0.346 | 86.1 |
| 2874 | 0.122 | 30.3 |
| 2720 | 0.026 | 6.5 |
| 1628 | 0.168 | 41.8 |
| 1601 | 0.402 | 100.0 |
| 1567 | 0.175 | 43.5 |
| 1502 | 0.171 | 42.5 |
| 1449 | 0.139 | 34.6 |
| 1429 | 0.154 | 38.3 |
| 1392 | 0.133 | 33.1 |
| 1353 | 0.122 | 30.3 |
| 1323 | 0.074 | 18.4 |
| 1299 | 0.072 | 17.9 |
| 1280 | 0.087 | 21.6 |
| 1246 | 0.051 | 12.7 |
| 1209 | 0.083 | 20.6 |
| 1166 | 0.034 | 8.5 |

TABLE 64-continued

Raman spectrum.

| Wavenumber (cm$^{-1}$) | Absolute Intensity | Normalized Intensity (%) |
|---|---|---|
| 1120 | 0.036 | 9.0 |
| 1089 | 0.044 | 10.9 |
| 1062 | 0.055 | 13.7 |
| 1028 | 0.192 | 47.8 |
| 997 | 0.083 | 20.6 |
| 915 | 0.036 | 9.0 |
| 854 | 0.079 | 19.7 |
| 839 | 0.037 | 9.2 |
| 808 | 0.186 | 46.3 |
| 791 | 0.204 | 50.7 |
| 749 | 0.052 | 12.9 |
| 739 | 0.083 | 20.6 |
| 720 | 0.134 | 33.3 |
| 681 | 0.078 | 19.4 |
| 641 | 0.025 | 6.2 |
| 577 | 0.065 | 16.2 |
| 552 | 0.047 | 11.7 |
| 480 | 0.059 | 14.7 |
| 467 | 0.047 | 11.7 |
| 441 | 0.045 | 11.2 |
| 410 | 0.053 | 13.2 |
| 394 | 0.061 | 15.2 |
| 361 | 0.037 | 9.2 |
| 332 | 0.058 | 14.4 |
| 301 | 0.036 | 9.0 |
| 257 | 0.085 | 21.1 |
| 225 | 0.086 | 21.4 |
| 196 | 0.143 | 35.6 |
| 154 | 0.129 | 32.1 |

In some embodiments, Form SUC-P3 is characterized by one or more peaks in its Raman spectrum selected from those in Table 65. In some embodiments, Form SUC-P3 is characterized by at least one, at least two, at least three, at least four, at least five, at least six, at least seven, at least eight, at least nine, at least ten, at least eleven, or at least twelve peaks in its Raman spectrum selected from those in Table 65.

TABLE 65

Raman spectrum.

| Wavenumber (cm$^{-1}$) | Absolute Intensity | Normalized Intensity (%) |
|---|---|---|
| 1628 | 0.168 | 41.8 |
| 1601 | 0.402 | 100.0 |
| 1567 | 0.175 | 43.5 |
| 1502 | 0.171 | 42.5 |
| 1449 | 0.139 | 34.6 |
| 1429 | 0.154 | 38.3 |
| 1392 | 0.133 | 33.1 |
| 1353 | 0.122 | 30.3 |
| 1028 | 0.192 | 47.8 |
| 808 | 0.186 | 46.3 |
| 791 | 0.204 | 50.7 |
| 720 | 0.134 | 33.3 |

Figure 58:
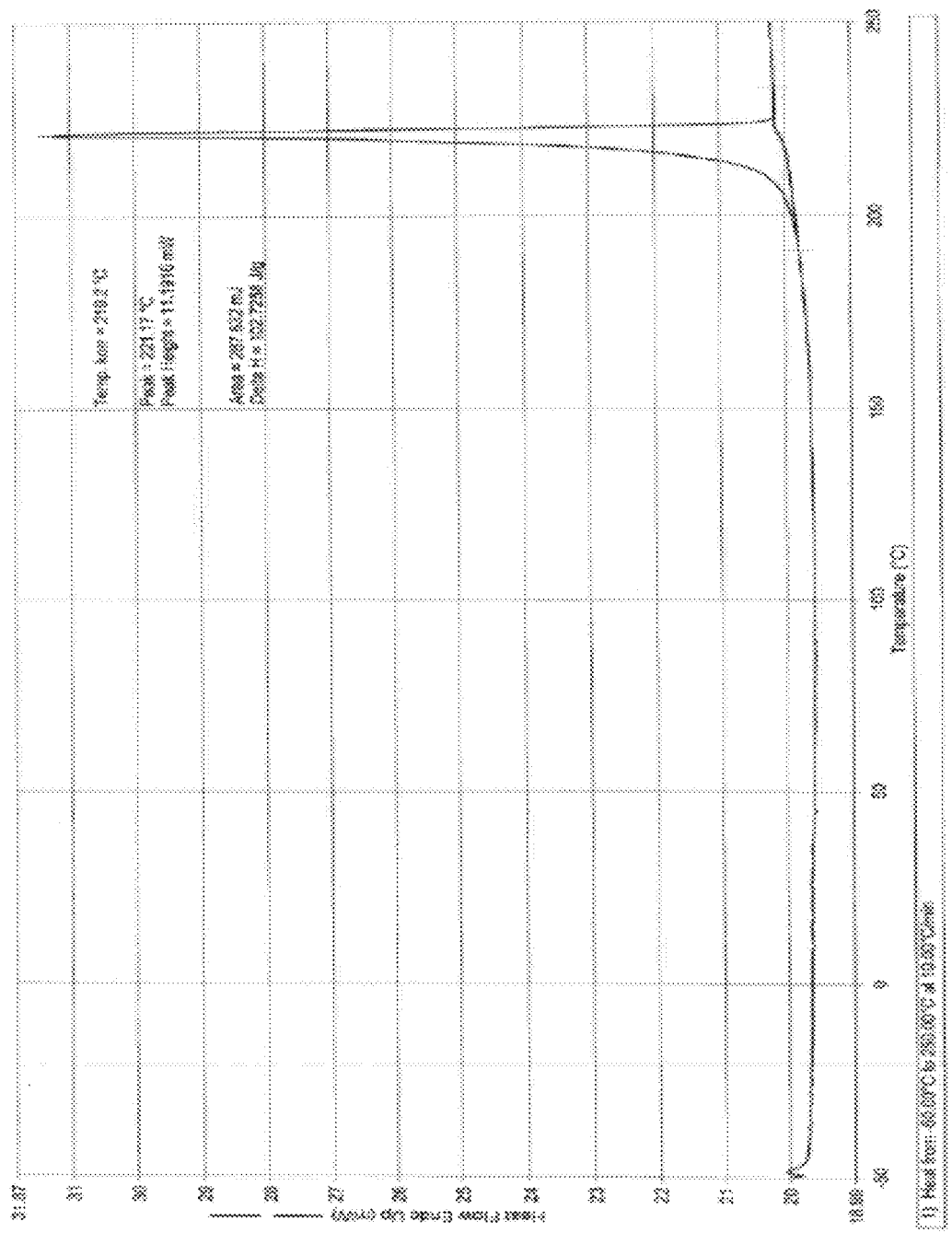
FIG. 58 depicts a DSC thermogram of Form SUC-P3.

In some embodiments, Form SUC-P3 has a DSC thermogram substantially similar to the one depicted in FIG. 58. In some embodiments, Form SUC-P3 has a DSC thermogram with an endotherm having a peak temperature ($T_{max}$) of about 219° C. In some embodiments, Form SUC-P3 has a DSC thermogram with a ΔH of about 103 J/g.

Figure 59:
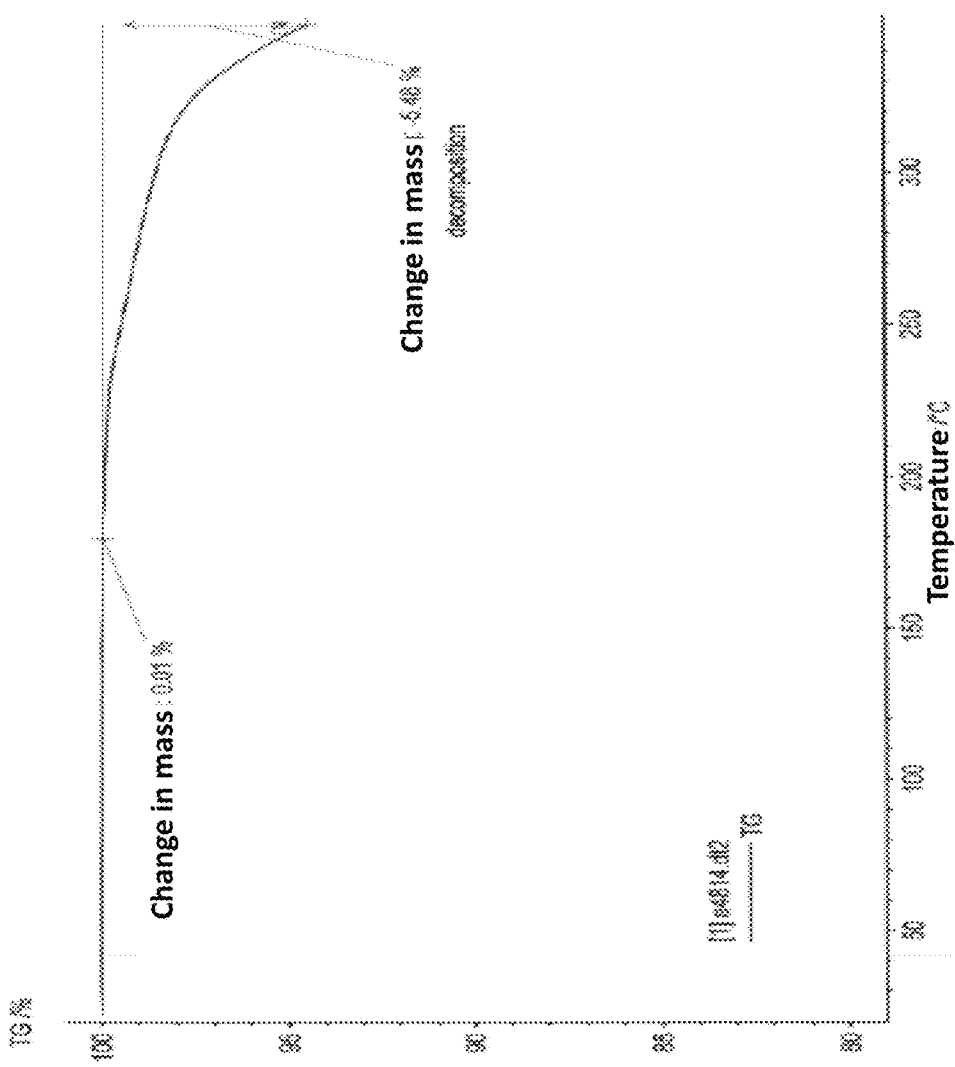
FIG. 59 depicts a TG-FTIR thermogram of Form SUC-P3.

In some embodiments, Form SUC-P3 has a TG-FTIR thermogram substantially similar to the one depicted in FIG. 59.

In some embodiments, Form SUC-P3 is substantially anhydrous. In some embodiments, Form SUC-P3 is obtained from recrystallization from acetone.

Form SUC-P4

In certain embodiments, the present invention provides crystalline Form SUC-P4 (SUC-P4) of compound 1. In some embodiments, Form SUC-P4 is a salt of compound 1. In some embodiments, Form SUC-P4 is a succinate salt of compound 1. In some embodiments, Form SUC-P4 is a non-stoichiometric succinate salt of compound 1. In some embodiments, Form SUC-P4 is a hemisuccinate salt of compound 1. In some embodiments, Form SUC-P4 is a co-crystal of compound 1 and succinic acid.

In certain embodiments, Form SUC-P4 is substantially free of impurities. In certain embodiments, the impurity is compound 1 in free base form. In certain embodiments, Form SUC-P4 is 99% free of impurities by weight. In certain embodiments, Form SUC-P4 is 97% free of impurities by weight. In certain embodiments, Form SUC-P4 is 95% free of impurities by weight. In certain embodiments, Form SUC-P4 is substantially free of amorphous succinic acid salt of compound 1. In certain embodiments, Form SUC-P4 is substantially free of other crystalline forms of compound 1.

Figure 60:
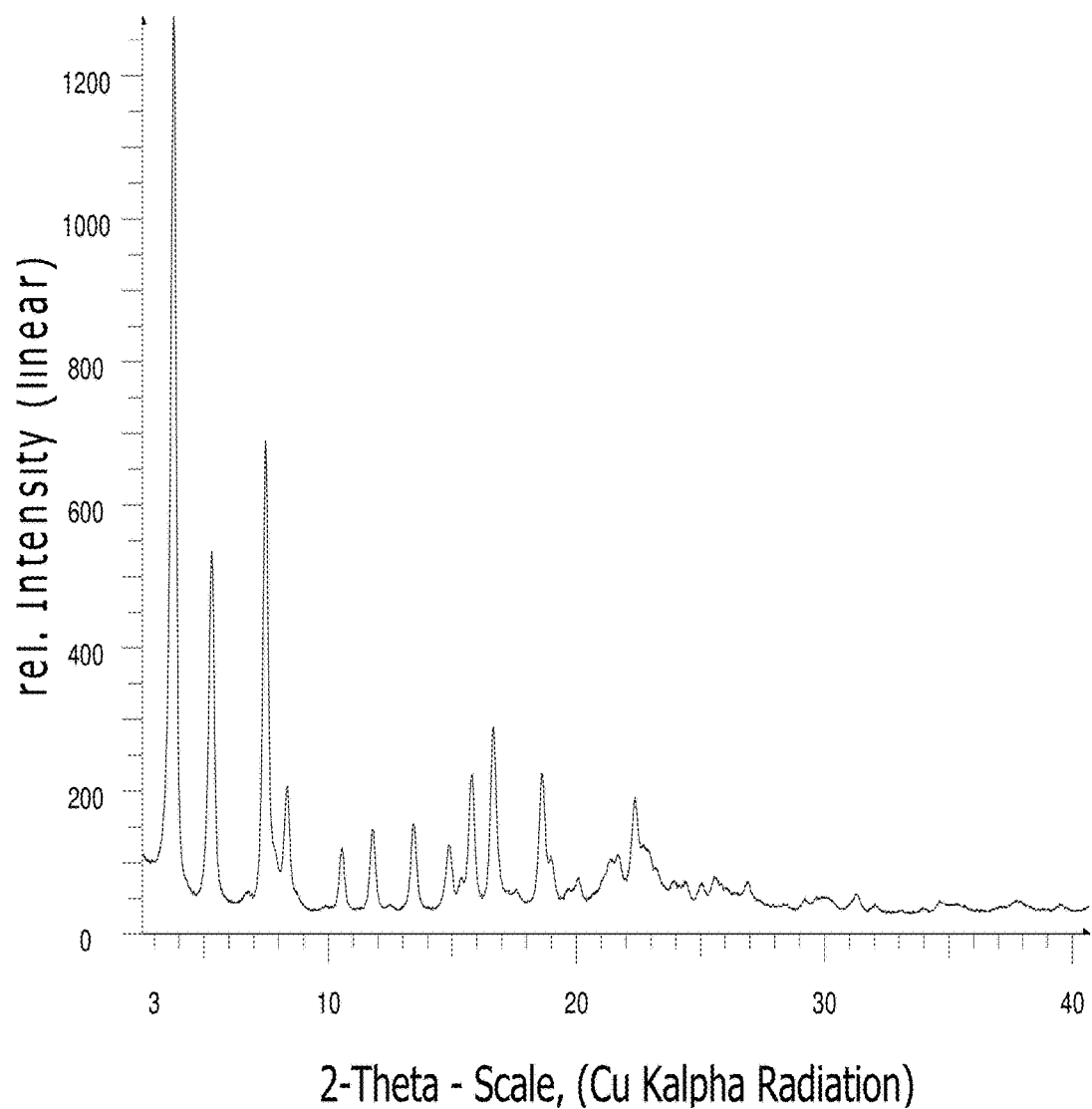
FIG. 60 depicts an XRPD pattern of Form SUC-P4.

Form SUC-P4 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form SUC-P4 is characterized by an X-ray powder diffraction pattern substantially similar to the one depicted in FIG. 60. In some embodiments, Form SUC-P4 is characterized in that it has one or more peaks in its X-ray powder diffraction pattern selected from those in Table 66. In some embodiments, Form SUC-P4 is characterized by at least one, at least two, at least three, at least four, at least five, at least six, at least seven, at least eight, at least nine, at least ten, at least eleven, at least twelve, at least thirteen, or at least fourteen peaks in its X-ray powder diffraction pattern selected from those in Table 66. In some embodiments, Form SUC-P4 of compound 1 is characterized in that it has one or more peaks in its X-ray powder diffraction pattern selected from the strong and very strong peaks in Table 66.

TABLE 66

X-ray powder diffraction pattern.

| Angle 2-Theta ° | d value Angstrom | Intensity (relative) | Intensity % |
|---|---|---|---|
| 3.74 | 23.6 | vs | 100 |
| 5.27 | 16.7 | s | 44 |
| 7.45 | 11.9 | s | 60 |
| 8.30 | 10.6 | m | 18 |
| 10.52 | 8.4 | w | 11 |
| 11.75 | 7.5 | w | 13 |
| 13.40 | 6.6 | w | 14 |
| 14.86 | 5.96 | w | 11 |
| 15.77 | 5.61 | m | 20 |
| 16.63 | 5.33 | m | 26 |
| 18.60 | 4.77 | m | 20 |
| 18.96 | 4.68 | w | 10 |
| 21.66 | 4.10 | w | 10 |
| 22.33 | 3.98 | m | 17 |

In some embodiments, Form SUC-P4 is characterized by one or more peaks in its X-ray powder diffraction pattern selected from those in Table 67. In some embodiments, Form SUC-P4 is characterized by at least one, at least two, at least three, at least four, at least five, or at least six peaks in its X-ray powder diffraction pattern selected from those in Table 67.

TABLE 67

X-ray powder diffraction pattern.

| Angle 2-Theta ° | d value Angstrom | Intensity (relative) | Intensity % |
|---|---|---|---|
| 5.27 | 16.7 | s | 44 |
| 7.45 | 11.9 | s | 60 |
| 8.30 | 10.6 | m | 18 |
| 15.77 | 5.61 | m | 20 |
| 16.63 | 5.33 | m | 26 |
| 18.60 | 4.77 | m | 20 |

Figure 61:
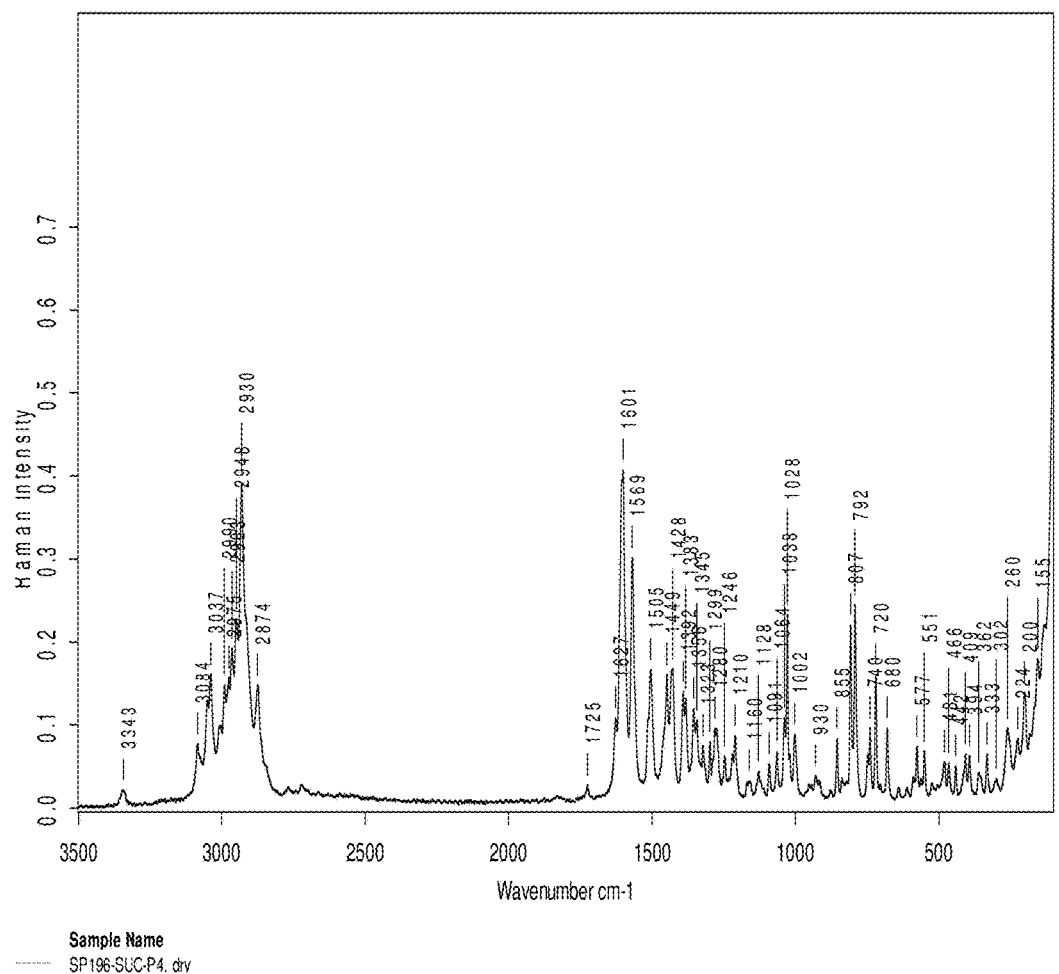
FIG. 61 depicts an FT-Raman spectrum of Form SUC-P4.

In some embodiments, Form SUC-P4 is characterized by a Raman spectrum substantially similar to the one depicted in FIG. 61. In some embodiments, Form SUC-P4 is characterized by one or more peaks in its Raman spectrum selected from those in Table 68. In some embodiments, Form SUC-P4 is characterized by having a Raman spectrum with characteristic peaks at about those in Table 68.

TABLE 68

Raman spectrum.

| Wavenumber (cm$^{-1}$) | Absolute Intensity | Normalized Intensity (%) |
|---|---|---|
| 3343 | 0.022 | 5.4 |
| 3084 | 0.077 | 18.9 |
| 3037 | 0.162 | 39.8 |
| 2990 | 0.148 | 36.4 |
| 2975 | 0.157 | 38.6 |
| 2963 | 0.193 | 47.4 |
| 2948 | 0.227 | 55.8 |
| 2930 | 0.392 | 96.3 |
| 2874 | 0.148 | 36.4 |
| 1725 | 0.027 | 6.6 |
| 1627 | 0.109 | 26.8 |
| 1601 | 0.407 | 100.0 |
| 1569 | 0.302 | 74.2 |
| 1505 | 0.167 | 41.0 |
| 1449 | 0.161 | 39.6 |
| 1428 | 0.168 | 41.3 |
| 1392 | 0.140 | 34.4 |
| 1383 | 0.132 | 32.4 |
| 1356 | 0.120 | 29.5 |
| 1345 | 0.105 | 25.8 |
| 1323 | 0.075 | 18.4 |
| 1299 | 0.080 | 19.7 |
| 1280 | 0.096 | 23.6 |
| 1246 | 0.063 | 15.5 |
| 1209 | 0.087 | 21.4 |
| 1160 | 0.033 | 8.1 |
| 1128 | 0.044 | 10.8 |
| 1091 | 0.053 | 13.0 |
| 1063 | 0.068 | 16.7 |
| 1038 | 0.109 | 26.8 |
| 1028 | 0.234 | 57.5 |
| 1002 | 0.089 | 21.9 |
| 930 | 0.039 | 9.6 |
| 855 | 0.083 | 20.4 |
| 807 | 0.221 | 54.3 |
| 792 | 0.245 | 60.2 |
| 740 | 0.096 | 23.6 |
| 720 | 0.162 | 39.8 |
| 680 | 0.096 | 23.6 |
| 577 | 0.074 | 18.2 |
| 551 | 0.068 | 16.7 |
| 481 | 0.055 | 13.5 |
| 466 | 0.054 | 13.3 |
| 442 | 0.050 | 12.3 |
| 409 | 0.065 | 16.0 |

TABLE 68-continued

Raman spectrum.

| Wavenumber (cm⁻¹) | Absolute Intensity | Normalized Intensity (%) |
|---|---|---|
| 394 | 0.063 | 15.5 |
| 362 | 0.043 | 10.6 |
| 333 | 0.065 | 16.0 |
| 302 | 0.035 | 8.6 |
| 260 | 0.096 | 23.6 |
| 224 | 0.083 | 20.4 |
| 200 | 0.139 | 34.2 |
| 155 | 0.180 | 44.2 |

In some embodiments, Form SUC-P4 is characterized by one or more peaks in its Raman spectrum selected from those in Table 69. In some embodiments, Form SUC-P4 is characterized by at least one, at least two, at least three, at least four, at least five, at least six, at least seven, at least eight, at least nine, at least ten, or at least eleven peaks in its Raman spectrum selected from those in Table 69.

TABLE 69

Raman spectrum.

| Wavenumber (cm⁻¹) | Absolute Intensity | Normalized Intensity (%) |
|---|---|---|
| 1601 | 0.407 | 100.0 |
| 1569 | 0.302 | 74.2 |
| 1505 | 0.167 | 41.0 |
| 1449 | 0.161 | 39.6 |
| 1428 | 0.168 | 41.3 |
| 1392 | 0.140 | 34.4 |
| 1383 | 0.132 | 32.4 |
| 1028 | 0.234 | 57.5 |
| 807 | 0.221 | 54.3 |
| 792 | 0.245 | 60.2 |
| 720 | 0.162 | 39.8 |

Figure 62:
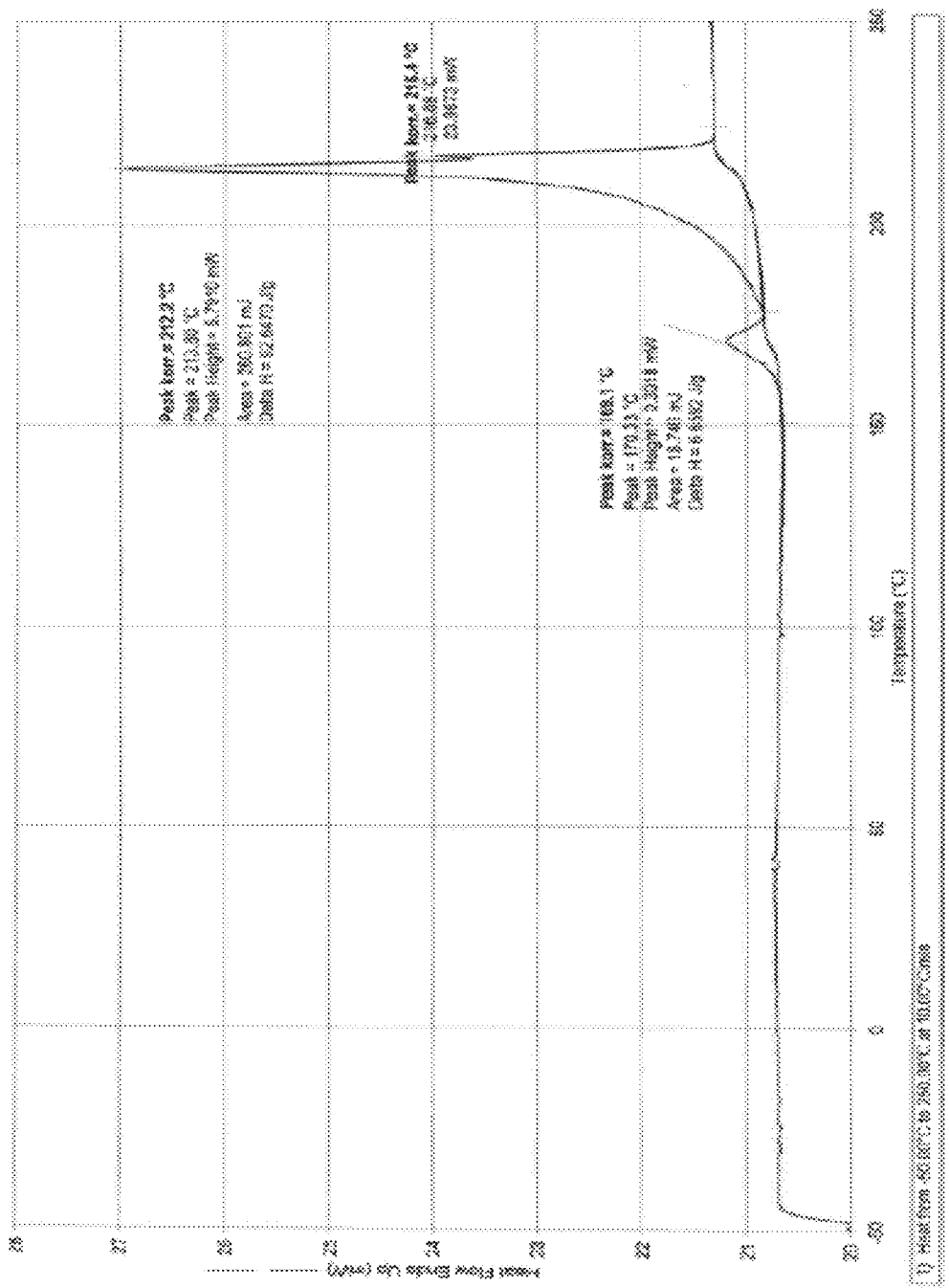
FIG. 62 depicts a DSC thermogram of Form SUC-P4.

In some embodiments, Form SUC-P4 has a DSC thermogram substantially similar to the one depicted in FIG. 62. In some embodiments, Form SUC-P4 has a DSC thermogram with an endotherm having a peak temperature ($T_{max}$) of about 169° C., about 212° C., or about 215° C. In some embodiments, Form SUC-P4 has a DSC thermogram with a ΔH of about 6.7 J/g or about 92.6 J/g.

Figure 63:
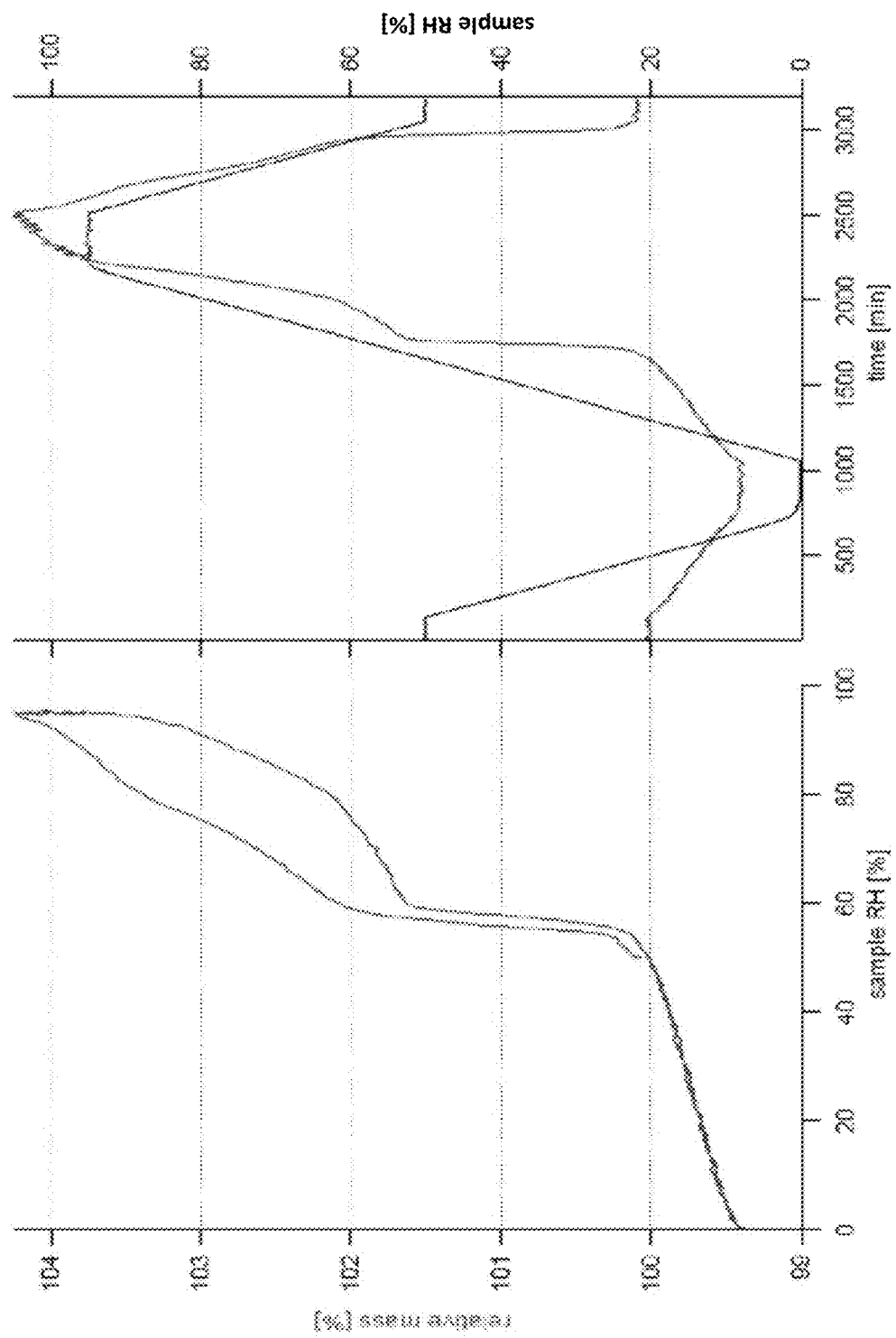
FIG. 63 depicts a DVS isotherm of Form SUC-P4.

In some embodiments, Form SUC-P4 has a DVS isotherm substantially similar to the one depicted in FIG. 63.

Figure 64:
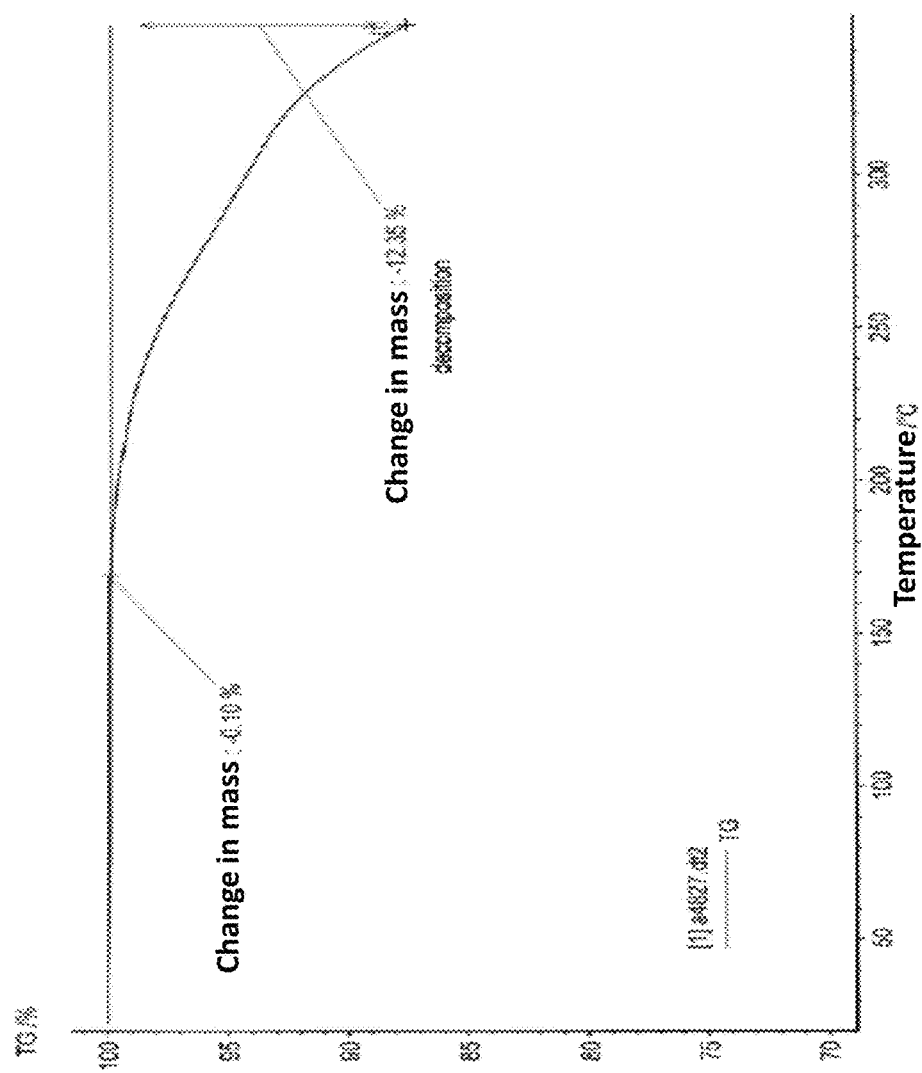
FIG. 64 depicts a TG-FTIR thermogram of Form SUC-P4.

In some embodiments, Form SUC-P4 has a TG-FTIR thermogram substantially similar to the one depicted in FIG. 64.

In some embodiments, Form SUC-P4 is substantially anhydrous. In some embodiments, Form SUC-P4 is obtained from recrystallization from acetonitrile.

Form SUC-P5

In certain embodiments, the present invention provides crystalline Form SUC-P5 (SUC-P5) of compound 1. In some embodiments, Form SUC-P5 is a salt of compound 1. In some embodiments, Form SUC-P5 is a succinate salt of compound 1. In some embodiments, Form SUC-P5 is a non-stoichiometric succinate salt of compound 1. In some embodiments, Form SUC-P5 is a hemisuccinate salt of compound 1. In some embodiments, Form SUC-P5 is a co-crystal of compound 1 and succinic acid.

In certain embodiments, Form SUC-P5 is substantially free of impurities. In certain embodiments, the impurity is compound 1 in free base form. In certain embodiments, Form SUC-P5 is 99% free of impurities by weight. In certain embodiments, Form SUC-P5 is 97% free of impurities by weight. In certain embodiments, Form SUC-P5 is 95% free of impurities by weight. In certain embodiments, Form SUC-P5 is substantially free of amorphous succinic acid salt of compound 1. In certain embodiments, Form SUC-P5 is substantially free of other crystalline forms of compound 1.

Figure 87:
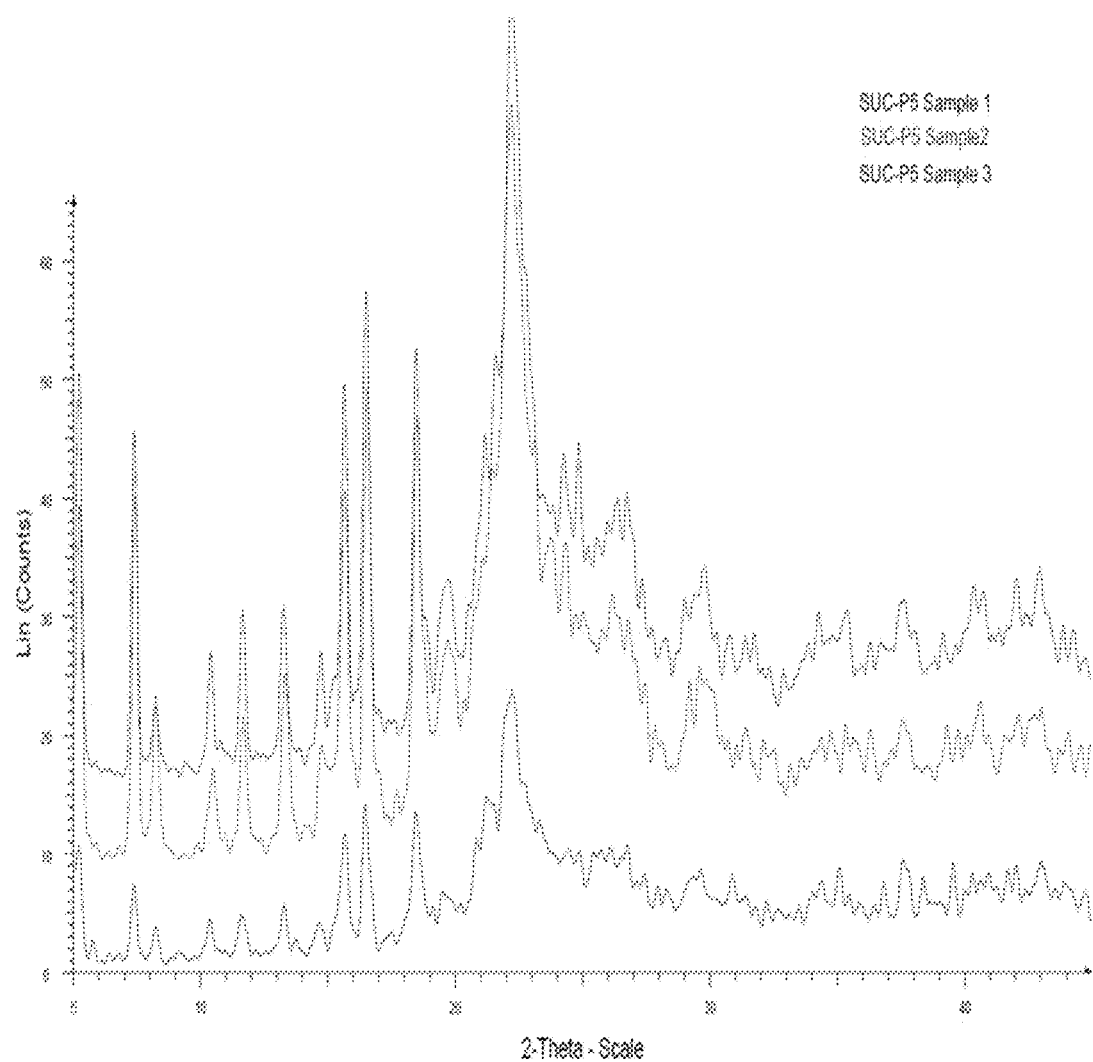
FIG. 87 depicts an XRPD pattern of Form SUC-P5.

Form SUC-P5 can be characterized by one or more of the characteristics described herein including, but not limited to, XRPD diffraction pattern and/or peaks, DSC thermogram, TGA thermogram, solubility, and stability. In some embodiments, Form SUC-P5 is characterized by an X-ray powder diffraction pattern substantially similar to the one depicted in FIG. 87. In some embodiments, Form SUC-P5 is characterized in that it has one or more peaks in its X-ray powder diffraction pattern selected from those in Table 76. In some embodiments, Form SUC-P5 is characterized by at least one, at least two, at least three, at least four, at least five, at least six, at least seven, at least eight or at least nine peaks in its X-ray powder diffraction pattern selected from those in Table 76. In some embodiments, Form SUC-P5 of compound 1 is characterized in that it has one or more peaks in its X-ray powder diffraction pattern selected from the strong and very strong peaks in Table 76.

TABLE 76

| X-ray powder diffraction pattern. Angle 2-Theta ° |
|---|
| 7.4 |
| 8.3 |
| 10.5 |
| 11.7 |
| 13.2 |
| 15.6 |
| 16.5 |
| 18.5 |
| 22.2 |

In some embodiments, Form SUC-P5 is characterized by one or more peaks in its X-ray powder diffraction pattern selected from those in Table 77. In some embodiments, Form SUC-P5 is characterized by at least one, at least two, at least three or at least four peaks in its X-ray powder diffraction pattern selected from those in Table 77.

TABLE 77

| X-ray powder diffraction pattern. Angle 2-Theta ° |
|---|
| 7.4 |
| 15.6 |
| 16.5 |
| 18.5 |
| 22.2 |

Figure 88:
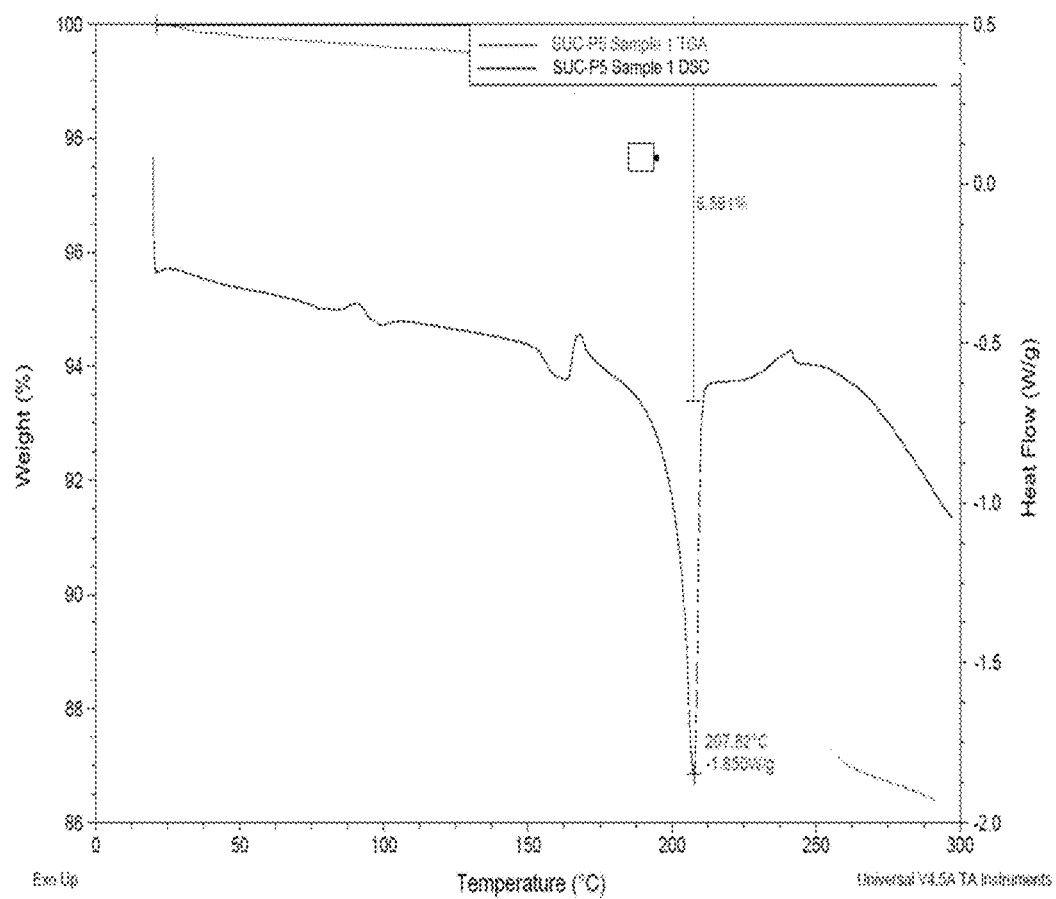
FIG. 88 depicts a DSC thermogram of Form SUC-P5.

In some embodiments, Form SUC-P5 has a DSC thermogram substantially similar to the one depicted in FIG. 88. In some embodiments, Form SUC-P5 has a DSC thermogram with an endotherm peak temperature of 207-208° C. In some embodiments, Form SUC-P5 has a DSC thermogram with an endotherm peak temperature of 207-208° C., with an approximately 7-8% weight loss up to that point.

In some embodiments, SUC-P5 is stable for at least about 1 month, at least about 2 months, at least about 4 months, at least about 6 months at about 40° C. and about 75% relative humidity. In some embodiments, SUC-P5 has substantially the same XRPD pattern post storage for at least about 1 month, at least about 2 months, at least about 4 months, at least about 6 months at about 40° C. and about 75% relative humidity. In some embodiments, SUC-P5 has substantially the same endothermic event with a peak at about $T_{max}$=205-210° C. in DSC of post storage for at least about 1 month, at least about 2 months, at least about 4 months, at least about 6 months at about 40° C. and about 75% relative humidity. In some embodiments, SUC-P5 is stable for at least about 1 month, at least about 2 months, at least about 4 months, at least about 6 months, at least about 12 months, at least about 18 months, at least about 2 years, or at least about 3 years at about 25° C. and about 60% relative humidity.

Maleate Salt, Co-Crystals, and Form MLE-P4

The invention also provides a maleate salt form of compound 1. The maleate salt may be amorphous or exist in one or more crystalline forms. In certain embodiments, the present invention provides crystalline Form MLE-P4 (Form MLE-P4) of compound 1. In some embodiments, Form MLE-P4 is a salt of compound 1. In some embodiments, Form MLE-P4 is a maleate salt of compound 1. In some embodiments, Form MLE-P4 is a non-stoichiometric maleate salt of compound 1. In some embodiments, Form MLE-P4 is a co-crystal of compound 1 and maleic acid.

In certain embodiments, Form MLE-P4 is substantially free of impurities. In certain embodiments, the impurity is compound 1 in free base form. In certain embodiments, Form MLE-P4 is 99% free of impurities by weight. In certain embodiments, Form MLE-P4 is 97% free of impurities by weight. In certain embodiments, Form MLE-P4 is 95% free of impurities by weight. In certain embodiments, Form MLE-P4 is substantially free of amorphous maleic acid salt of compound 1. In certain embodiments, Form MLE-P4 is substantially free of other crystalline forms of compound 1.

Figure 65:
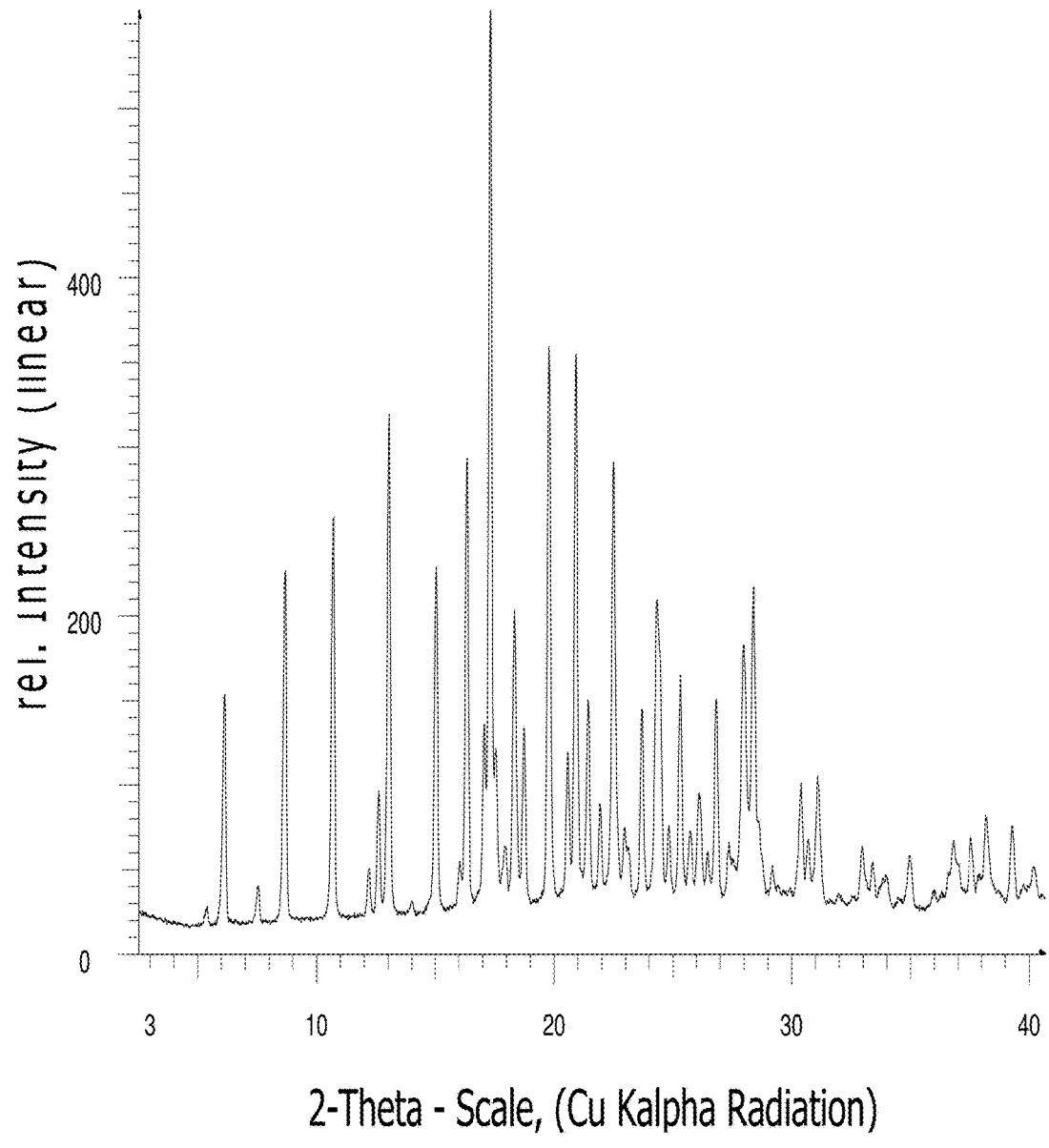
FIG. 65 depicts an XRPD pattern of Form MLE-P4.

Form MLE-P4 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form MLE-P4 is characterized by an X-ray powder diffraction pattern substantially similar to the one depicted in FIG. 65. In some embodiments, Form MLE-P4 is characterized in that it has one or more peaks in its X-ray powder diffraction pattern selected from those in Table 70. In some embodiments, Form MLE-P4 is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty-seven, at least thirty-eight, at least thirty-nine, at least forty, at least forty-one, or at least forty-two peaks in its X-ray powder diffraction pattern selected from those in Table 70. In some embodiments, Form MLE-P4 of compound 1 is characterized in that it has one or more peaks in its X-ray powder diffraction pattern selected from the strong and very strong peaks in Table 70.

TABLE 70

| X-ray powder diffraction pattern. | | | |
|---|---|---|---|
| Angle 2-Theta ° | d value Angstrom | Intensity (relative) | Intensity % |
| 6.09 | 14.5 | m | 26 |
| 7.51 | 11.8 | w | 7 |
| 8.63 | 10.2 | s | 40 |
| 10.67 | 8.3 | s | 47 |
| 12.16 | 7.3 | w | 9 |
| 12.57 | 7.0 | m | 18 |
| 13.01 | 6.8 | s | 58 |
| 15.01 | 5.90 | s | 41 |
| 16.02 | 5.53 | w | 10 |
| 16.32 | 5.43 | s | 53 |
| 17.04 | 5.20 | m | 25 |
| 17.29 | 5.12 | vs | 100 |
| 17.53 | 5.06 | m | 22 |
| 17.93 | 4.94 | w | 11 |
| 18.31 | 4.84 | s | 36 |
| 18.73 | 4.73 | m | 25 |
| 19.78 | 4.49 | s | 67 |
| 20.56 | 4.32 | m | 22 |
| 20.91 | 4.24 | s | 68 |
| 21.42 | 4.14 | m | 28 |
| 21.92 | 4.05 | m | 17 |
| 22.48 | 3.95 | s | 55 |
| 22.95 | 3.87 | w | 14 |
| 23.11 | 3.85 | w | 11 |
| 23.68 | 3.75 | m | 27 |
| 24.31 | 3.66 | s | 39 |
| 24.81 | 3.59 | w | 14 |
| 25.29 | 3.52 | s | 30 |
| 25.71 | 3.46 | w | 14 |
| 26.12 | 3.41 | m | 18 |
| 26.47 | 3.36 | w | 11 |
| 26.83 | 3.32 | m | 30 |
| 27.36 | 3.26 | w | 12 |
| 27.99 | 3.19 | s | 34 |
| 28.39 | 3.14 | s | 42 |
| 28.64 | 3.11 | m | 15 |
| 30.40 | 2.94 | m | 18 |
| 30.70 | 2.91 | w | 13 |
| 31.11 | 2.87 | m | 20 |
| 32.97 | 2.71 | w | 12 |
| 33.42 | 2.68 | w | 10 |
| 34.98 | 2.56 | w | 11 |

In some embodiments, Form MLE-P4 is characterized by one or more peaks in its X-ray powder diffraction pattern selected from those in Table 71. In some embodiments, Form MLE-P4 is characterized by at least one, at least two, at least three, at least four, at least five, at least six, at least seven, at least eight, at least nine, at least ten, at least eleven, or at least twelve peaks in its X-ray powder diffraction pattern selected from those in Table 71.

TABLE 71

| X-ray powder diffraction pattern. | | | |
|---|---|---|---|
| Angle 2-Theta ° | d value Angstrom | Intensity (relative) | Intensity % |
| 8.63 | 10.2 | s | 40 |
| 10.67 | 8.3 | s | 47 |
| 13.01 | 6.8 | s | 58 |
| 15.01 | 5.90 | s | 41 |
| 16.32 | 5.43 | s | 53 |
| 17.29 | 5.12 | vs | 100 |
| 18.31 | 4.84 | s | 36 |
| 19.78 | 4.49 | s | 67 |
| 20.91 | 4.24 | s | 68 |
| 22.48 | 3.95 | s | 55 |
| 24.31 | 3.66 | s | 39 |
| 28.39 | 3.14 | s | 42 |

Figure 66:
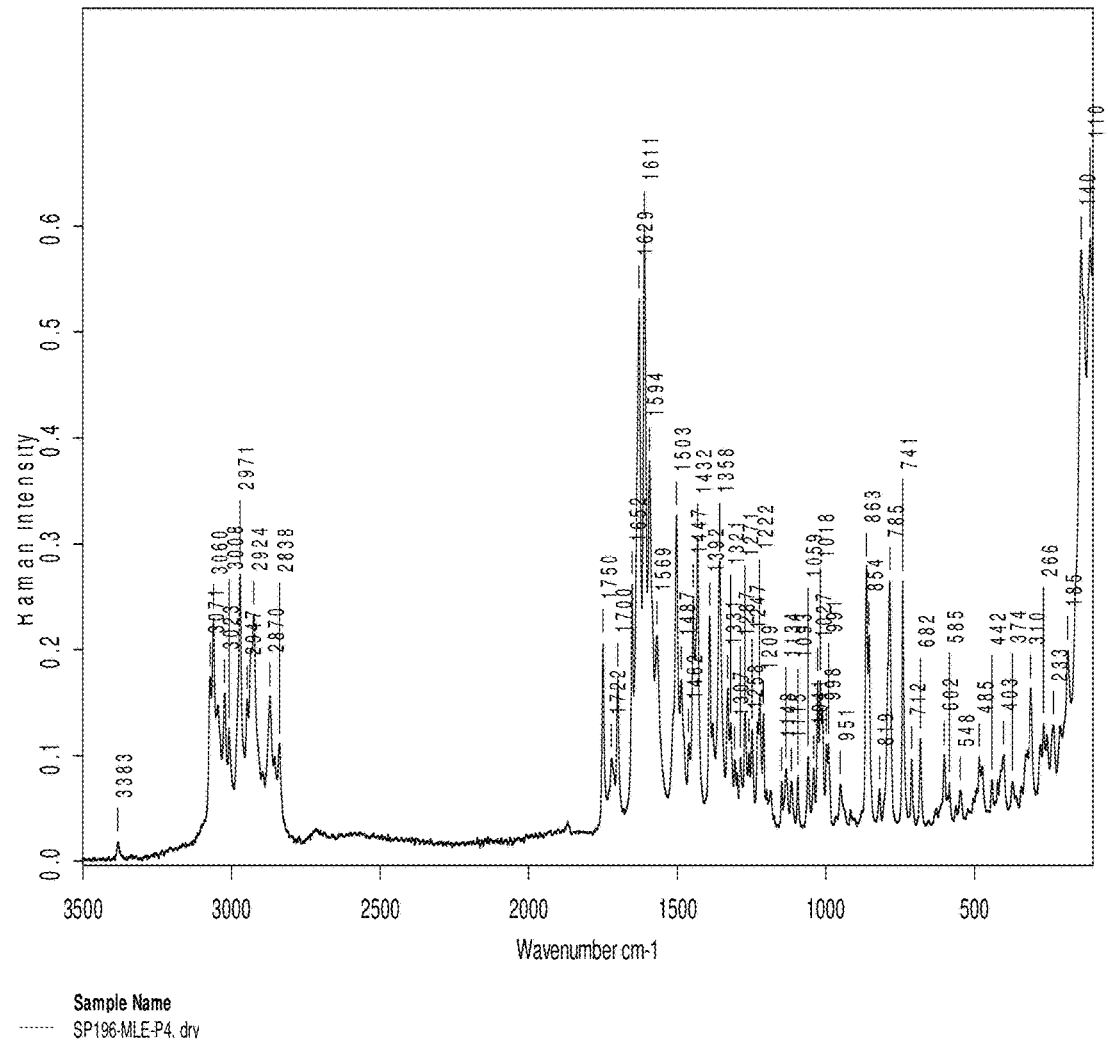
FIG. 66 depicts an FT-Raman spectrum of Form MLE-P4

In some embodiments, Form MLE-P4 is characterized by a Raman spectrum substantially similar to the one depicted in FIG. 66. In some embodiments, Form MLE-P4 is characterized by one or more peaks in its Raman spectrum selected from those in Table 72. In some embodiments, Form MLE-P4 is characterized by having a Raman spectrum with characteristic peaks at about those in Table 72.

TABLE 72

Raman spectrum.

| Wavenumber (cm$^{-1}$) | Absolute Intensity | Normalized Intensity (%) |
|---|---|---|
| 3383 | 0.019 | 3.2 |
| 3071 | 0.174 | 29.0 |
| 3060 | 0.229 | 38.1 |
| 3023 | 0.158 | 26.3 |
| 3007 | 0.126 | 21.0 |
| 2971 | 0.270 | 44.9 |
| 2947 | 0.153 | 25.5 |
| 2924 | 0.233 | 38.8 |
| 2870 | 0.156 | 26.0 |
| 2838 | 0.111 | 18.5 |
| 1750 | 0.206 | 34.3 |
| 1722 | 0.097 | 16.1 |
| 1700 | 0.174 | 29.0 |
| 1652 | 0.261 | 43.4 |
| 1629 | 0.531 | 88.4 |
| 1611 | 0.601 | 100.0 |
| 1594 | 0.378 | 62.9 |
| 1569 | 0.213 | 35.4 |
| 1503 | 0.327 | 54.4 |
| 1487 | 0.171 | 28.5 |
| 1462 | 0.112 | 18.6 |
| 1447 | 0.249 | 41.4 |
| 1432 | 0.306 | 50.9 |
| 1392 | 0.231 | 38.4 |
| 1358 | 0.283 | 47.1 |
| 1331 | 0.163 | 27.1 |
| 1321 | 0.130 | 21.6 |
| 1307 | 0.096 | 16.0 |
| 1287 | 0.098 | 16.3 |
| 1271 | 0.140 | 23.3 |
| 1258 | 0.103 | 17.1 |
| 1247 | 0.125 | 20.8 |
| 1222 | 0.158 | 26.3 |
| 1209 | 0.139 | 23.1 |
| 1148 | 0.076 | 12.6 |
| 1134 | 0.087 | 14.5 |
| 1115 | 0.075 | 12.5 |
| 1093 | 0.081 | 13.5 |
| 1059 | 0.099 | 16.5 |
| 1040 | 0.088 | 14.6 |
| 1027 | 0.170 | 28.3 |
| 1018 | 0.170 | 28.3 |
| 998 | 0.111 | 18.5 |
| 991 | 0.111 | 18.5 |
| 951 | 0.073 | 12.1 |
| 863 | 0.279 | 46.4 |
| 854 | 0.213 | 35.4 |
| 819 | 0.068 | 11.3 |
| 785 | 0.265 | 44.1 |
| 741 | 0.264 | 43.9 |
| 712 | 0.096 | 16.0 |
| 682 | 0.116 | 19.3 |
| 602 | 0.101 | 16.8 |
| 585 | 0.074 | 12.3 |
| 548 | 0.067 | 11.1 |
| 485 | 0.099 | 16.5 |
| 442 | 0.077 | 12.8 |
| 403 | 0.101 | 16.8 |
| 374 | 0.076 | 12.6 |
| 310 | 0.163 | 27.1 |
| 266 | 0.130 | 21.6 |
| 233 | 0.129 | 21.5 |
| 185 | 0.199 | 33.1 |
| 140 | 0.577 | 96.0 |
| 110 | 0.589 | 98.0 |

In some embodiments, Form MLE-P4 is characterized by one or more peaks in its Raman spectrum selected from those in Table 73. In some embodiments, Form MLE-P4 is characterized by at least one, at least two, at least three, at least four, at least five, at least six, at least seven, at least eight, at least nine, at least ten, or at least eleven peaks in its Raman spectrum selected from those in Table 73.

TABLE 73

Raman spectrum.

| Wavenumber (cm$^{-1}$) | Absolute Intensity | Normalized Intensity (%) |
|---|---|---|
| 1652 | 0.261 | 43.4 |
| 1629 | 0.531 | 88.4 |
| 1611 | 0.601 | 100.0 |
| 1594 | 0.378 | 62.9 |
| 1503 | 0.327 | 54.4 |
| 1447 | 0.249 | 41.4 |
| 1432 | 0.306 | 50.9 |
| 1358 | 0.283 | 47.1 |
| 863 | 0.279 | 46.4 |
| 785 | 0.265 | 44.1 |
| 741 | 0.264 | 43.9 |

Figure 67:
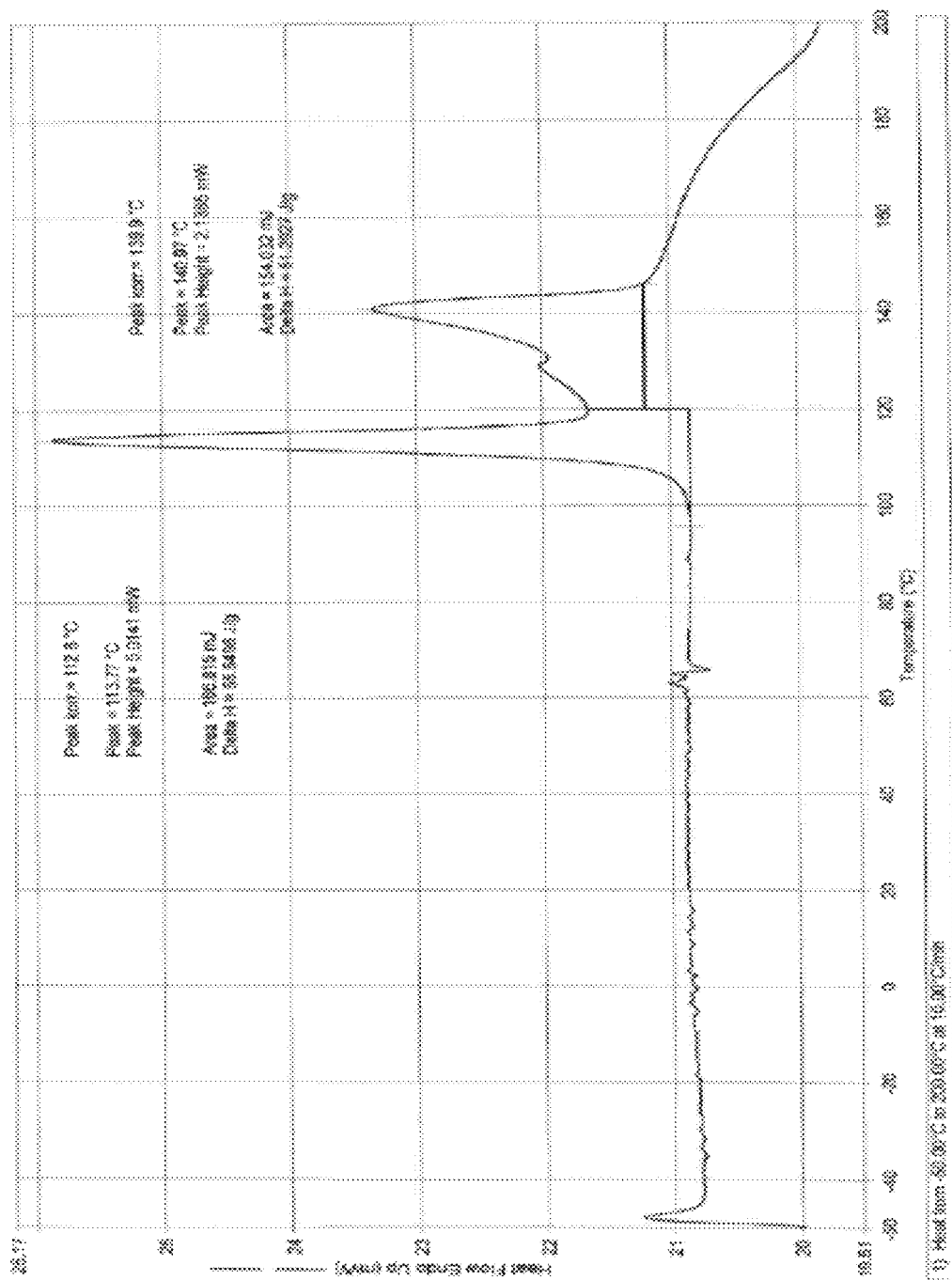
FIG. 67 depicts a DSC thermogram of Form MLE-P4.

In some embodiments, Form MLE-P4 has a DSC thermogram substantially similar to the one depicted in FIG. 67. In some embodiments, Form MLE-P4 has a DSC thermogram with an endotherm having a peak temperature ($T_{max}$) of about 112.8° C. or about 139.9° C. In some embodiments, Form MLE-P4 has a DSC thermogram with a ΔH of about 55.5 J/g or about 51.3 J/g)

Figure 68:
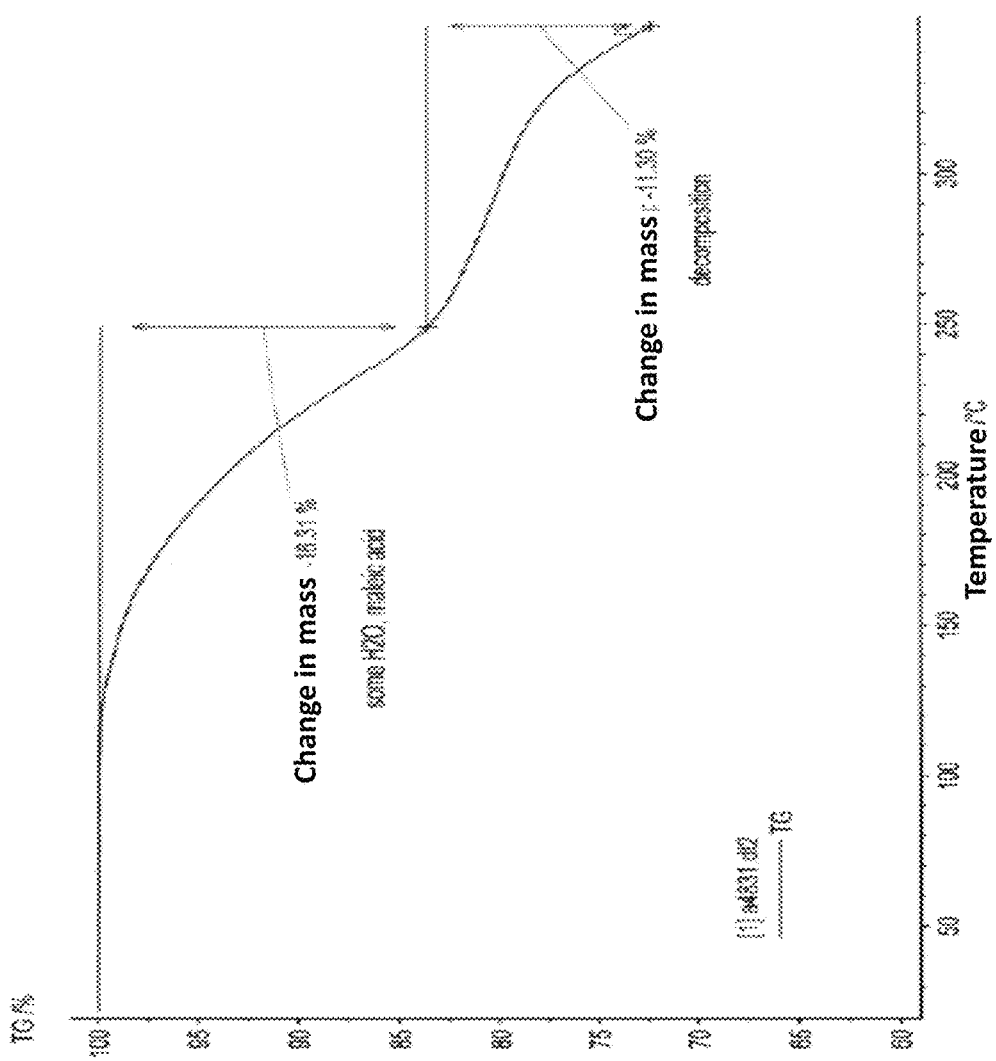
FIG. 68 depicts a TG-FTIR thermogram of Form MLE-P4.

In some embodiments, Form MLE-P4 has a TG-FTIR thermogram substantially similar to the one depicted in FIG. 68.

In certain embodiments, Form MLE-P4 has a melting point of about 140-150° C. In some embodiments, Form MLE-P4 is substantially anhydrous. In some embodiments, Form MLE-P4 is obtained from recrystallization from acetone.

Form MLE-P6

In certain embodiments, the present invention provides crystalline Form MLE-P6 of compound 1. In some embodiments, Form MLE-P6 is a salt of compound 1. In some embodiments, Form MLE-P6 is a maleate salt of compound 1. In some embodiments, Form MLE-P6 is a non-stoichiometric maleate salt of compound 1. In some embodiments, Form MLE-P6 is a co-crystal of compound 1 and maleic acid In certain embodiments, Form MLE-P6 is substantially free of impurities. In certain embodiments, Form MLE-P6 is 99% free of impurities by weight. In certain embodiments, Form MLE-P6 is 97% free of impurities by weight. In certain embodiments, Form MLE-P6 is 95% free of impurities by weight. In certain embodiments, Form MLE-P6 is substantially free of amorphous compound 1. In certain embodiments, Form MLE-P6 is substantially free of other crystalline forms of compound 1.

Figure 84:
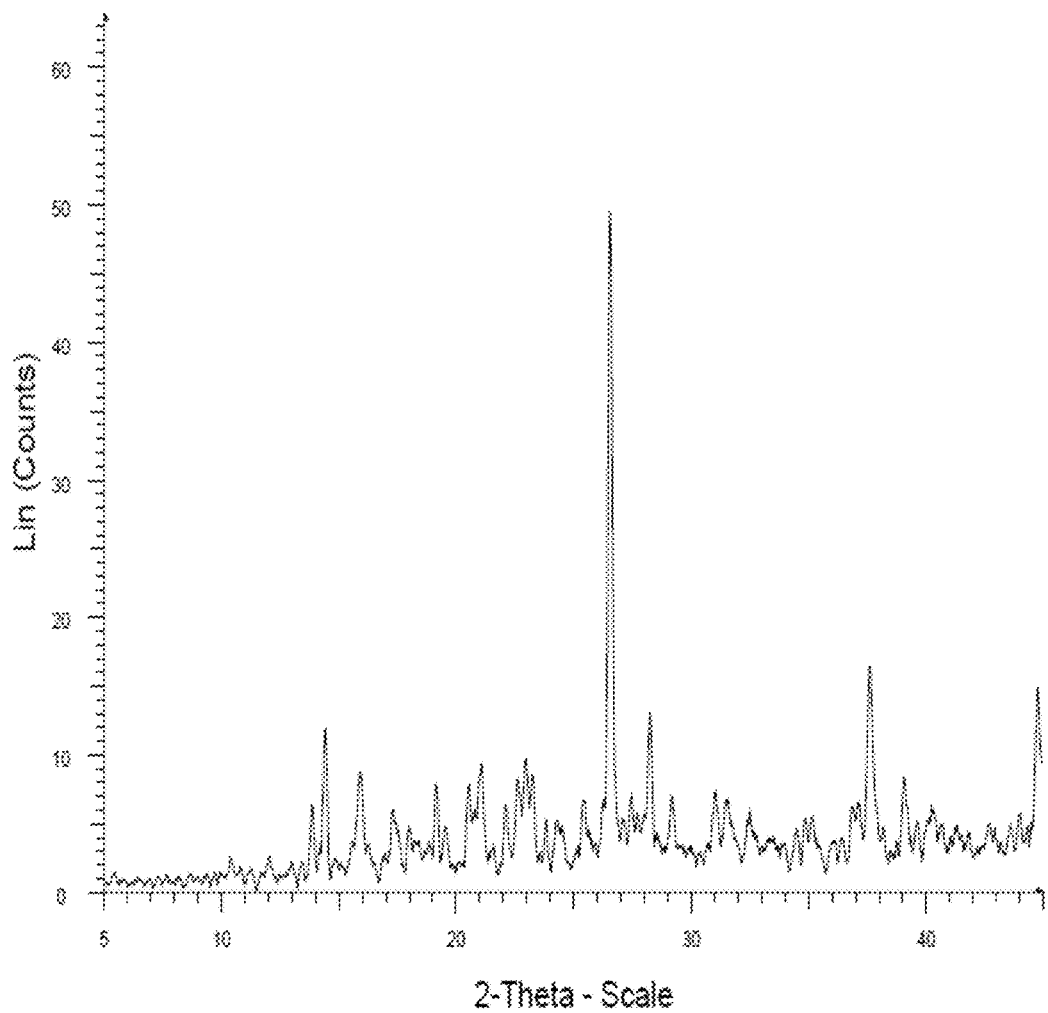
FIG. 84 depicts a XRPD pattern of Form MLE-P6.

Form MLE-P6 can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In some embodiments, Form MLE-P6 is characterized by an X-ray powder diffraction pattern substantially similar to the one depicted in FIG. 84.

In some embodiments, Form MLE-P6 is substantially anhydrous. In some embodiments, Form MLE-P6 is obtained from recrystallization from acetone.

Pharmaceutical Compositions

In some embodiments, the present invention provides a composition comprising a solid or salt form of compound 1 described herein and optionally a pharmaceutically acceptable excipient. In certain embodiments, the present invention provides a composition comprising a fumarate, L-malate, D-malate, succinate, maleate, thiocyanate, oxalate, benzoate, 2-oxoglutarate, or tartrate salt of compound 1 (e.g., a solid form of a fumarate, L-malate, D-malate, succinate, maleate, thiocyanate, oxalate, benzoate, 2-oxoglutarate, or tartrate salt of compound 1 described herein) and optionally a pharmaceutically acceptable excipient. In some embodiments, the amount of compound 1, or a fumarate, L-malate, D-malate, succinate, maleate, thiocyanate, oxalate, benzoate, 2-oxoglutarate, or tartrate salt of compound 1, in a composition described herein is such that it is effective to treat and/or prevent a disease, disorder, or condition. In certain embodiments, a provided composition is formulated for administration to a patent in need of such composition. In certain embodiments, a provided composition is formulated for oral administration to a patient. In certain embodiments, a provided composition is formulated into an oral dosage form. In certain embodiments, a provided composition is formulated into a tablet, powder, pill, capsule, or the like, for oral ingestion by a patient.

Suitable techniques, carriers, and excipients include those found within, for example, *Remington: The Science and Practice of Pharmacy*, 19$^{th}$ edition, Mack Publishing Company, Easton, Pa. 1995; Hoover, John E., *Remington's Pharmaceutical Sciences*, Mack Publishing Company, Easton, Pa. 1975; Liberman, H. A. and Lachman, L., Eds., *Pharmaceutical Dosage Forms*, Marcel Decker, New York, N.Y. 1980; and *Pharmaceutical Dosage Forms and Drug Delivery Systems*, 7$^{th}$ edition, Lippincott Williams & Wilkins, 1999, all of which are incorporated herein by reference in their entireties.

In general, doses of provided pharmaceutical compositions employed for adult human treatment are typically in the range of about 0.01 mg to about 5000 mg per day. In certain embodiments, doses employed for adult human treatment are from about 1 mg to about 1000 mg per day. In certain embodiments, a desired dose is conveniently presented in a single dose or in divided doses administered simultaneously (or over a short period of time) or at appropriate intervals, for example, as two, three, four or more sub-doses per day.

It will be understood that a specific dosage and treatment regimen for any particular patient may depend on a variety of factors, including the activity of the specific compound employed, age, body weight, general health, sex, diet, time of administration, rate of excretion, drug combination, and the judgment of the treating physician and the severity of the particular disease being treated. The amount of a provided compound in the composition may also depend upon the particular compound in the composition.

In some embodiments, a provided pharmaceutical composition comprises Form C. In some embodiments, a provided pharmaceutical composition comprises Form D. In some embodiments, a provided pharmaceutical composition comprises Form E. In some embodiments, a provided pharmaceutical composition comprises Form F. In some embodiments, a provided pharmaceutical composition comprises Form G. In some embodiments, a provided pharmaceutical composition comprises Form H. In some embodiments, a provided pharmaceutical composition comprises Form I. In some embodiments, a provided pharmaceutical composition comprises Form J. In some embodiments, a provided pharmaceutical composition comprises Form K. In some embodiments, a provided pharmaceutical composition comprises Form L. In some embodiments, a provided pharmaceutical composition comprises Form M. In some embodiments, a provided pharmaceutical composition comprises a fumarate salt of compound 1. In some embodiments, a provided pharmaceutical composition comprises Form FUM-P3. In some embodiments, a provided pharmaceutical composition comprises Form FUM-P4. In some embodiments, a provided pharmaceutical composition comprises an L-malate salt of compound 1. In some embodiments, a provided pharmaceutical composition comprises a D-malate salt of compound 1. In some embodiments, a provided pharmaceutical composition comprises Form MLA-P3. In some embodiments, a provided pharmaceutical composition comprises Form MLA-P4. In some embodiments, a provided pharmaceutical composition comprises a succinate salt of compound 1. In some embodiments, a provided pharmaceutical composition comprises Form SUC-P3. In some embodiments, a provided pharmaceutical composition comprises Form SUC-P4. In some embodiments, a provided pharmaceutical composition comprises Form SUC-P5. In some embodiments, a provided pharmaceutical composition comprises a maleate salt of compound 1. In some embodiments, a provided pharmaceutical composition comprises Form MLE-P4. In some embodiments, a provided pharmaceutical composition comprises a maleate salt of compound 1. In some embodiments, a provided pharmaceutical composition comprises Form MLE-P6. In some embodiments, a provided pharmaceutical composition comprises a thiocyanate salt of compound 1. In some embodiments, a provided pharmaceutical composition comprises an oxalate salt of compound 1. In some embodiments, a provided pharmaceutical composition comprises a benzoate salt of compound 1. In some embodiments, a provided pharmaceutical composition comprises a 2-oxoglutarate salt of compound 1. In some embodiments, a provided pharmaceutical composition comprises a tartrate salt of compound 1.

Methods of Treatment, Uses, and Administration

The present disclosure contemplates the treatment or prophylaxis of a disease of the central nervous system, such as mood disorders (e.g., depression), anxiety disorders, and neurodegenerative diseases. The term neurodegenerative disease encompasses a condition leading to the progressive loss of the structure or function of neurons, including the death of neurons. Examples of neurodegenerative diseases contemplated herein include, but are not limited to, AIDS dementia complex, adrenoleukodystrophy, alexander disease, Alpers' disease, arnyotrophic lateral sclerosis, ataxia telangiectasia, Batten disease, bovine spongiform encephalopathy, brainstem and cerebellun atrophy, Canavan disease, corticobasal degeneration, Creutzfeldt-Jakob disease, dementia with Lewy bodies, fatal familial insomnia, Friedrich's ataxia, familial spastic paraparesis, frontotemporal lobar degeneration, Huntington's disease, infantile Refsum disease, Kennedy's disease, Krabbe disease, Lyme disease, Machado-Joseph disease, monomelic amyotrophy, multiple sclerosis, multiple system atrophy, neuroacanthocytosis, Niemaum-Pick disease, neurodegeneration with brain iron accumulation, opsoclonus myoclonus, Parkinson's disease, Pick's disease, primary lateral sclerosis, progranulin, progressive multifocal leukoencephalopathy, progressive supranuclear palsy, protein aggregation, Refsum disease, Sandhoff disease, diffuse myeloclastic sclerosis, Shy-Drager syndrome, spinocerebellar ataxia, spinal muscular atrophy, spinal and bulbar muscular atrophy, subacute combined degeneration of spinal cord, Tabes dorsalis, Tay-Sachs disease, toxic encephalopathy, transmissible spongiform encephalopathy, and Wobbly hedgehog syndrome.

In certain embodiments, compound 1, and/or one or more salt forms or polymorphs of compound 1, can be used to treat, ameliorate the signs and/or symptoms of, prevent, or otherwise delay the onset or development of the CNS disease, disorder, or condition.

Taught herein, therefore, is the use of compound 1, and/or one or more salt forms or polymorphs of compound 1 described herein, or a pharmaceutically acceptable preparation thereof, in the manufacture of a medicament for treating and/or preventing central nervous system disorders, such as mood disorders (e.g., depression), anxiety disorders, or neurodegenerative diseases, in a subject in need thereof.

Also provided herein are methods of treating or preventing central nervous system disorders, such as mood disorders (e.g., depression), anxiety disorders, or neurodegenerative diseases comprising the administration of an effective amount of compound 1, and/or one or more salt forms or polymorphs of compound 1 described herein, or a pharmaceutically acceptable preparation thereof, to a subject in need thereof.

As used herein mood disorders are broadly recognized and clearly defined by the relevant DSM-IV-TR (Diagnostic and Statistical Manual of Mental Disorders, 4th Edition, Text Revision) criteria. Thus, there are depressive disorders of which the best known and most researched is major depressive disorder (MDD) commonly called clinical depression or major depression, and bipolar disorder (BD), formerly known as manic depression and characterized by intermittent episodes of mania or hypomania, usually interlaced with depressive episodes. Other depressive disorders include: atypical depression, melancholic depression, psychotic major depression, catatonic depression, postpartum depression, seasonal affective disorder, dysthymia, depressive disorder not otherwise specified (DD-NOS) (e.g., recurrent brief depression, minor depressive disorder), substance induced mood disorders (e.g., alcohol induced mood disorders, benzodiazepine induced mood disorders, interferon-alpha induced mood disorders).

Persons of skill in the art will be familiar with the lag period of traditional antidepressant medications, and with the heightened anxiety produced by the newer generation antidepressants, including SSRI's, SNRI's and NRI's in the early stages of treatment before the antidepressant effects are seen (within 2-4 weeks). Thus, in certain embodiments, the compounds described herein can be administered to a subject in need thereof as a substitute or replacement for traditional antidepressant medication. In other embodiments, compounds described herein can be administered to a subject in need thereof as a supplement to traditional antidepressant medication. In other embodiments, there is provided a method for treating or preventing depression in a subject, the method including the step of administering to said subject a compound (e.g., an amorphous or crystalline form of compound 1), or an embodiment thereof, described herein, or a salt form or pharmaceutical composition thereof, in the absence of adjunct antidepressant therapy.

Replacing traditional antidepressant medication with the present compounds can be advantageous, particularly where the traditional medication is associated with one or more adverse effects (e.g., anxiety, nausea, headaches, erectile dysfunction, early-onset suicidal tendencies, etc). Examples of traditional antidepressant medication would be known to those skilled in the art and include, but are not limited to, selective serotonin re-uptake inhibitors (SSRI), serotonin/noradrenalin re-uptake inhibitors, selective noradrenalin re-uptake inhibitors, monoamine oxidase inhibitors, tricyclic antidepressants, lithium and other mood stabilisers, atypical antidepressants, and hormones such as estrogen or progestogen.

In other embodiments, the present compounds are administered to a subject in need thereof, together with traditional antidepressants for a period of about 2-4 weeks, to address the symptoms of depression, with the option of discontinuing treatment with the present compounds whilst continuing with the traditional therapy. In other embodiments, the subject is treated with both a present compound and one or more traditional antidepressant medications (administered sequentially or in combination) for the duration of the treatment period. Such combination therapy may be particularly useful, for example, where the combination of a present compound and one or more traditional antidepressant medications provides relief from depression in the acute lag phase of the treatment period and/or where an additive or synergistic antidepressant therapeutic effect is desired.

Depression relapse can also occur in patients treated with traditional antidepressant medication. Many such compounds are administered for anywhere from months to years and a reduction in efficacy is often seen with such long-term use, leading to significant continuing depression and dysfunction. Depression relapse may be sudden onset for some patients, while for others it might be evident as a gradual decline in mood and function, which diminishes over time as the patient approaches the state of relapse. Thus, patients who experience sudden onset of depression relapse or a gradual depression relapse would benefit from the methods disclosed herein, as the present compound, or salt forms or polymorphs thereof, can offset the diminishing effect of traditional antidepressant therapy. Thus, the use of the present compound, or salt forms or polymorphs thereof may prevent or partly alleviate depression relapse often seen in patients taking traditional antidepressant medication.

Thus, in certain embodiments, provided herein are methods for treating or preventing relapse in a subject receiving antidepressant therapy, the method including the step of administering to said subject compound 1, or a salt form or polymorph thereof, or a pharmaceutical composition thereof.

The traditional antidepressant therapies that are associated with potential depression relapse in a subject would be known to those skilled in the art. Examples include, but are not limited to, dosage increases, alternative SSRIs or SNRIs, and non-SSRI antidepressants such as noradrenaline re-uptake inhibitors, monoamine oxidase inhibitors, tricyclic antidepressants, lithium and other mood stabilisers, atypical antidepressants and hormones such as estrogen and progestogen, also referred to herein as "second antidepressant compounds."

The desired therapeutic activity, or effect, will typically depend on the condition being treated. For example, where the subject is being treated for depression, the therapeutic effect may be a reduction in at least one clinical symptom of depression, including, but not limited to, cognitive impairment, loss of appetite, mood, and/or inactivity.

In certain embodiments, compound 1, or one or more salt forms or polymorphs thereof described herein, or a pharmaceutically acceptable preparation thereof, is administered to said subject sequentially (i.e., before or after) or in combination with a second antidepressant compound (e.g., with existing antidepressant therapy).

In certain embodiments, the present compound, or salt forms or polymorphs thereof, have the further added advantage over traditional therapy in that they exhibit reduced sedative side effects which may adversely affect a patient's quality of life. In certain embodiments, the present compound, or salt forms or polymorphs thereof, are free of measurable sedative side effects.

Sudden discontinuation of antidepressant medication may produce withdrawal effects caused by physical dependence on the drug. Compounds can be evaluated for physical dependence in a simple animal model where, following a period of chronic dosing (e.g., for 14-20 days), the study drug is stopped and measurements of food intake, body weight, and body temperature are taken over the next 5 days. The symptoms of abrupt discontinuation of the drug are manifest as significantly reduced appetite, weight loss, and drop in body temperature. This model is suitable for detecting the effects across a broad range of drug classes including opiates, antidepressants, and benzodiazepines. The compound, or salt forms or polymorphs thereof described herein also can be used as a combination therapy, e.g., combining the treatment with other antidepressants such as benzodiazepines (e.g., alprazolam, diazepam, lorazepam, clonezepam), selective serotonin re-uptake inhibitors (SSRI) (e.g., citalopram, dapoxetine, escitalopram, fluoxetine, fluvoxamine, indalpine, paroxetine, sertraline, zimelidine, vilaxodone), serotonin norepinephrine reuptake inhibitors (SNRI) (e.g., venlafaxine, duloxetine, desvenlafaxine, milnacipran), monoamine oxidase inhibitors (e.g., phenelzine, moclobemide), tricyclic antidepressants (e.g., trimipramine, imipramine), tetracyclic antidepressants (e.g., mertazepine, maprotiline), mood stabilisers (e.g. lithium, sodium valproate, valproic acid), atypical antidepressants (e.g., bupropion), acetylcholinesterase inhibitors (e.g., donepezil, galantamine, rivastigmine), atypical antipsychotics (e.g., risperidone, aripipizole, quetiapine, olanzapine), and hormones such as estrogen and progestogen.

It will thus be understood that compound 1, or salt forms or polymorphs thereof, can be used in the treatment and/or prevention of a disease, such as a disease responsive to or associated with neurite outgrowth. In certain embodiments, the neurite outgrowth-responsive disease being treated and/or prevented using compound 1, or a salt or polymorph thereof, is a neurodegenerative disease. In a certain embodiments, the neurodegenerative disease is multiple sclerosis or a Parkinsonian related disorder. In a further embodiment, the neurodegenerative disease is multiple sclerosis. In a further embodiment, the disease may involve a condition which involves neural damage including, but not limited to, wound healing, spinal cord injury, and peripheral nerve disorders.

Also contemplated herein is a sub-threshold disease, condition, state, disorder, or trauma. In an embodiment, the disease, condition, state, disorder, or trauma is defined by its symptoms. Hence, compound 1, or a salt form or polymorph thereof contemplated heroin, is useful in ameliorating the symptoms of a disease, condition, state, disorder, or trauma of the CNS. In certain embodiments, the trauma of the CNS includes stroke, brain hemorrhage, or another condition or event of the systemic vasculature which affects the CNS. The symptoms of a disease, condition, state, disorder, or trauma of the CNS would be familiar to those skilled in the art. Examples of such symptoms include mood disorders, such as depression. Thus, in certain embodiments, the compound forms described herein are used in the treatment of depression attributed to (or associated with) a neurodegenerative disease in the subject.

The compound forms described herein may also be used as therapy, e.g., combining the treatment with other neurodegenerative treatments, such as acetylcholineesterase inhibitors (e.g., Aricept, Exelon), and treatments for multiple sclerosis (e.g., Avonex, Betaseron, Copaxone, Tysabri, Gilenya).

In a further embodiment there is also provided a method of treatment of disorders of the central nervous system comprising the administration of an effective amount of compound 1, or a salt form or polymorph thereof, to a subject in need thereof.

It will be understood that compound 1, or a salt form or polymorph thereof as described herein, can be used in the treatment of anxiety or conditions/disease states associated with anxiety such as irritable bowel syndrome and fibromyalgia.

In certain embodiments, an anxiety disorder is classified as one of the following:
panic disorder,
obsessive-compulsive disorder (OCD),
post-traumatic stress disorder (PTSD),
social phobia (or social anxiety disorder (SAD),
specific phobias,
generalized anxiety disorder (GAD),
substance-induced anxiety disorder, and
acute stress disorder (ASD).

In certain embodiments, compound 1, or a salt form or polymorph thereof, as described herein may be used in the treatment of a panic disorder.

In certain embodiments, compound 1, or a salt form or polymorph thereof, as described herein may be used in the treatment of obsessive-compulsive disorder (OCD).

In certain embodiments, compound 1, or a salt form or polymorph thereof, as described herein may be used in the treatment of post-traumatic stress disorder (PTSD).

In an embodiment compound 1, or a salt form or polymorph thereof, as described herein may be used in the treatment of social phobia (or social anxiety disorder—SAD).

In certain embodiments, compound 1, or a salt form or polymorph thereof, as described herein may be used in the treatment of specific phobias. In certain embodiments, compound 1 or a salt form or polymorph thereof, as described herein may be used for agoraphobia or agoraphobia without history of panic disorder. In certain embodiments, compound 1 or a salt form or polymorph thereof, as described herein may be used for animal phobia.

In certain embodiments, compound 1, or a salt form or polymorph thereof, as described herein may be used in the treatment of substance-induced anxiety disorder.

In certain embodiments, compound 1, or a salt form or polymorph thereof, as described herein may be used in the treatment of acute stress disorder (ASD).

In certain embodiments, compound 1, or a salt form or polymorph thereof, as described herein may be used in the treatment of generalized anxiety disorder (GAD).

Generalised anxiety disorder criteria include:
(i) At least 6 months of "excessive anxiety and worry" about a variety of events and situations. Generally, "excessive" can be interpreted as more than would be expected for a particular situation or event. Most people become anxious over certain things, but the intensity of the anxiety typically corresponds to the situation.
(ii) There is significant difficulty in controlling the anxiety and worry. If someone has a very difficult struggle to regain control, relax, or cope with the anxiety and worry, then this requirement is met.

(iii) The presence for most days over the previous six months of 3 or more (only 1 for children) of the following symptoms:
  1. Feeling wound-up, tense, or restless
  2. Easily becoming fatigued or worn-out
  3. Concentration problems
  4. Irritability
  5. Significant tension in muscles
  6. Difficulty with sleep
(iv) The symptoms are not part of another mental disorder.
(v) The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.
(vi) The condition is not due to a substance or medical issue.

In certain embodiments, a subject to be treated with compound 1, or a salt form or polymorph thereof, as described herein may be identified by one or more of the above criteria for generalized anxiety disorder.

In certain embodiments, compound 1, or a salt form or polymorph thereof, as described herein may be used to treat or prevent one or more symptoms associated with an anxiety disorder.

Each anxiety disorder has different symptoms, but all the symptoms cluster around excessive, irrational fear and dread.

In another embodiment compound 1, or a salt form or polymorph thereof, as described herein may be used in the treatment of depression, for instance, major depressive disorder.

Major depressive disorder criteria include:
(i) At least five of the following symptoms have been present during the same 2-week period and represent a change from previous functioning: at least one of the symptoms is either
  1) depressed mood, or
  2) loss of interest or pleasure.
(ii) Depressed mood most of the day, nearly every day, as indicated either by subjective report (e.g., feels sad or empty) or observation made by others (e.g., appears tearful).
(iii) Markedly diminished interest or pleasure in all, or almost all, activities most of the day, nearly every day (as indicated either by subjective account or observation made by others).
(iv) Significant weight loss when not dieting or weight gain (e.g., a change of more than 5% of body weight in a month), or decrease or increase in appetite nearly every day.
(v) Insomnia or hypersomnia nearly every day.
(vi) Psychomotor agitation or retardation nearly every day (observable by others, not merely subjective feelings of restlessness or being slowed down).
(vii) Fatigue or loss of energy nearly every day.
(viii) Feelings of worthlessness or excessive or inappropriate guilt (which may be delusional) nearly every day (not merely self-reproach or guilt about being sick).
(ix) Diminished ability to think or concentrate, or indecisiveness, nearly every day (either by subjective account or as observed by others).
(x) Recurrent thoughts of death (not just fear of dying), recurrent suicidal ideation without a specific plan, or a suicide attempt or specific plan for committing suicide
(xi) The symptoms do not meet criteria for a mixed episode.
(xii) The symptoms cause clinically significant distress or impairment in social, occupational, or other important areas of functioning.
(xiii) The symptoms are not due to the direct physiological effects of a substance (e.g. a drug of abuse, a medication) or a general medical condition (e.g., hypothyroidism).
(xiv) The symptoms are not better accounted for by bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

The above criteria have been sourced from the American Psychiatric Association (2000) Diagnostic and Statistical Manual of Mental Disorders (4th Ed., Text Revision). Washington D.C.: American Psychiatric Association.

In certain embodiments, a subject to be treated with compound 1, or a salt form or polymorph thereof, as described herein may be identified by one or more of the above criteria for major depressive disorder.

In another embodiment compound 1, or a salt form or polymorph thereof, as described herein may be used to treat or prevent one or more symptoms associated with depression.

Further disorders for which compound 1, or a salt form or polymorph thereof, as described herein may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal, neuroses, convulsions, migraine, depressive disorder, bipolar disorder, psychotic disorder, neurodegeneration arising from cerebral ischemia, attention deficit hyperactivity disorder, Tourette's syndrome, speech disorder, disorders of circadian rhythm, single-episode or recurrent major depressive disorder, dysthymic disorder, bipolar I or bipolar II manic disorder, cyclothymic disorder, schizophrenia, and stuttering.

In an embodiment compound 1, or a salt form or polymorph thereof, as described herein may be used in the treatment of cerebral ischemia. In certain embodiments, compound 1, or a salt form or polymorph thereof, as described herein may be used in the treatment of neurodegeneration arising from cerebral ischemia.

In an embodiment compound 1, or a salt form or polymorph thereof, as described herein may be used in the treatment of disorders of the circadian rhythm.

In an embodiment compound 1, or a salt form or polymorph thereof, as described herein may be used in the treatment of pain and nociception.

In an embodiment compound 1, or a salt form or polymorph thereof, as described herein may be used in the treatment of Alzheimer's disease.

It should be appreciated that compound 1, or a salt form or polymorph thereof, a described herein can be administered to a subject in a treatment effective amount. In some embodiments, a treatment effective amount is a therapeutically effective amount or a prophylactically effective amount.

Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

In certain embodiments, a provided method comprises administering to a subject in need thereof the present compound, or salt form or polymorph thereof, in a dosage to provide an effective amount in vivo that will enhance neurite outgrowth (neurogenesis), including, but not limited to the acute stages of treatment (e.g., within 1, 2, 3, or 4 weeks from the commencement of treatment). In an embodiment, an effective amount in vivo has an in vitro equivalent concentration that is sufficient to increase neurite outgrowth by at least 5%, at least 10%, at least 20%, or at least 50% in a neurite outgrowth assay, for example, a neurite outgrowth assay described herein. Methods of determining an in vitro equivalent concentration of the present compounds would be familiar to the skilled artisan. For example, at from about 10 minutes to about 60 minutes after administration of the present compounds to a subject, a blood sample is taken and assayed by HPLC, ELISA, gas chromatography, or by other suitable assay to determine the concentration per ml of blood. An equivalent effective concentration can then be used in an in vitro assay once factors such as the weight of the subject, the appropriate blood volume of the subject and the appropriate rate of diffusion of the present compound across the blood-brain barrier are taken into account. In another embodiment, when the present compound is found to stimulate neurite outgrowth in vitro (as compared to a control), an approximate in vivo effective amount can be determined for a subject by extrapolating the in vitro concentration to an in vivo equivalent. Factors such as the weight of the subject, the appropriate blood volume of the subject and the appropriate rate of diffusion of the present compound across the blood-brain barrier may be used to extrapolate an in vivo effective amount and hence the appropriate dosage amount that would give rise to said in vivo effective amount.

Thereafter, treatment with the compound 1, or a salt form or polymorph thereof, may be continued throughout the treatment period or it may be ceased or replaced with traditional therapeutic compounds. Methods of determining the effective amount of compound 1, or a salt form or polymorph thereof, that is required for enhancing neurite outgrowth (neurogenesis) in vivo would be familiar to those skilled in the art. For example, enhancement of neurogenesis can be determined by measuring a symptom of the CNS disorder including, but not limited to, cognitive impairment, degree and frequency of seizures or tremors, motordysfunction, headaches and mood (e.g., degree of happiness).

In certain embodiments, an effective amount of compound 1, or a salt form or polymorph thereof, for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, compound 1, or a salt form or polymorph thereof, may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds, salts, polymorphs, and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another anti-anxiety or anti-depressant medication, an effective amount of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When combination therapy is employed, an effective amount can be achieved using a first amount of compound 1, or a salt or polymorph thereof, and a second amount of an additional suitable therapeutic agent.

In certain embodiments, compound 1 or a salt or polymorph thereof as described herein, or a pharmaceutically acceptable salt thereof, and the additional therapeutic agent are each administered in an effective amount (i.e., each in an amount which would be therapeutically effective if administered alone). In other embodiments, compound 1, or a salt or polymorph thereof as described herein, or a pharmaceutically acceptable salt thereof, and the additional therapeutic agent are each administered in an amount which alone does not provide a therapeutic effect (a sub-therapeutic dose). In yet other embodiments, compound 1, or a salt or polymorph thereof as described herein, can be administered in an effective amount, while the additional therapeutic agent is administered in a sub-therapeutic dose. In still other embodiments, compound 1, or a salt or polymorph thereof as described herein, can be administered in a sub-therapeutic dose, while the additional therapeutic agent is administered in an effective amount.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of compound 1 or a salt or polymorph thereof as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, compound 1, or a salt or polymorph thereof as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with compound 1, or a salt form or polymorph thereof, either administered separately or in the same pharmaceutical composition, include, but are not limited to, muscle relaxants, anticonvulsants, hypnotics, anaesthetics, analgesics, cholinergics, antidepressants, mood stabilisers, and anxiolytics.

In certain embodiments, a second therapeutic agent is a SSRI selected from the following: citalopram (Celexa, Cipramil, Cipram, Dalsan, Recital, Emocal, Sepram, Seropmm, Citox, Cital), dapoxetine (Priligy), escitalopram (Lexapro, Cipralex, Seroplex, Esertia), fluoxetine (Prozac, Fontex, Seromex, Seronil, Sarafem, Ladose, Motivest, Flutop, Fluctin (EUR), Fluox (NZ), Depress (UZB), Lovan (AUS), Prodep (IND)), fluvoxamine (Luvox, Fevarin, Faverin, Dumyrox, Favoxil, Movox), paroxetine (Paxil, Seroxat, Sereupin, Aropax, Deroxat, Divarius, Rexetin, Xetanor, Paroxat, Loxamine, Deparoc), sertraline (Zoloft, Lustral, Serlain, Asentra), and vilazodone (Viibryd).

In certain embodiments, a second therapeutic agent is a tetracyclic antidepressant (TeCA) selected from the group consisting of: amoxapine (Amokisan, Asendin, Asendis, Defanyl, Demolox, Moxadil), maprotiline (Deprilept, Ludiomil, Psymion), mazindol (Mazanor, Sanorex), mianselin (Bolvidon, Depnon, Norval, Tolvon), mirtazapine (Remeron, Avanza, Zispin, Miro), and setiptiline (Tecipul).

In certain embodiments, a second therapeutic agent is a serotonin-noradrenaline reuptake inhibitor (SNRI) selected from the group consisting of: desvenlafaxine (Pristiq), duloxetine (Cymbalta, Ariclaim, Xeristar, Yentreve, Duzela), milnacipran (Ixel, Savella, Dalcipran, Toledomin), and venlafaxine (Effexor, Efexor).

In certain embodiments, a second therapeutic agent is a Noradrenaline reuptake inhibitor (NRI) selected from the group consisting of: atomoxetine (Tomoxetine, Strattera, Attentin), mazindol (Mazanor, Sanorex), reboxetine (Edronax, Norebox, Prolift, Solvex, Davedax, Vestra), and viloxazine (Vivalan, Emovit, Vivarint, Vicilan).

In certain embodiments, a second therapeutic agent is a monoamine oxidase inhibitor (MAOI) selected from the group consisting of: benmoxin (Nerusil, Neuralex), hydralazine (Apresoline), iproclozide (Sursum), iproniazid (Marsilid, prozid, Ipronid, Rivivol, Propilniazida), isocarboxazid (Marplan), isoniazid (Laniazid, Nydrazid), mebanazine (Actomol), nialamide (Niamid), octamoxin (Ximaol, Nimaol), phenelzine (Nardil, Nardelzine), pheniprazine (Catron), phenoxypropazine (Drazine), pivalylbenzhydrazine (Tersavid), procarbazine (Matulane, Natulan, Indicarb), caroxazone (Surodil, Timostenil), echinopsidine (Adepren), furazolidone (Furoxone, Dependal-M), linezolid (Zyvox, Zyvoxam, Zyvoxid), tranylcypromine (Parnate, Jatrosom), brofaromine (Consonar), metralindole (Inkazan), minaprine (Cantor), moclobemide (Aurorix, Manerix), pirlindole (Pirazidol), toloxatone (Humoryl), lazabemide (Pakio, Tempium), pargyline (Eutonyl), rasagiline (Azilect), and selegiline (Deprenyl, Eldepryl, Emsam).

In certain embodiments, a second therapeutic agent is a tricyclic antidepressant (TCA) selected from the group consisting of: amitriptyline (Tryptomer, Elavil, Tryptizol, Laroxyl, Sarotex, Lentizol), butriptyline (Evadene, Evadyne, Evasidol, Centrolese), clomipramine (Anafranil), desipramine (Norpramin, Pertofrane), dosulepin (Prothiaden, Dothep, Thaden and Dopress), doxepin (Aponal, Adapine, Doxal, Deptran, Sinquan, Sinequan, Zonalon, Xepin, Silenor), imipramine (Antideprin, Deprimin, Deprinol, Depsol, Depsonil, Dynaprin, Eupramin, hnipramil, Irmin, Janimine, Melipramin, Surplix, Tofranil), lofepramine (Gamanil, Tymelyt, Lomont), nortriptyline (Sensoval, Aventyl, Pamelor, Norpress, Allegron, Noritren, Nortrilen), Protriptyline (Vivactil), and trimipramine (Sunnontil, Rhotrimine, Stangyl).

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

EXAMPLES

In order that the invention described herein may be more fully understood, the following examples are set forth. These examples are for illustrative purposes only and are not to be construed as limiting this invention in any manner.

Example 1. General Methods of Instrumental Measurements

FT-Raman Spectroscopy. Bruker RFS100 with OPUS 6.5 software or Multi-RAM with OPUS 7.0 software; Nd:YAG 1064-nm excitation, Ge detector, 3500-100 $cm^{-1}$ range; typical measurement conditions: 50-300 mW nominal laser power, 64-128 scans, 2 $cm^{-1}$ resolution.

XRPD. Broker D8; reflection geometry, Bragg-Brentano; Cu—$K_\alpha$ radiation, 40 kV/40 mA; variable divergence slit; LynxEye detector with 3° window; 0.02° 2θ step size; 37 s step time. The samples were rotated during the measurement. Sample preparation: The samples were generally prepared without any special treatment other than the application of slight pressure to get a flat surface. Silicon single crystal sample holder, 0.1 mm deep.

$^1$H-NMR. Bruker DPX300 spectrometer; proton frequency of 300.13 MHz; 30° excitation pulse; recycle delay of 1 s; accumulation of 16 scans; deuterated DMSO as the solvent; solvent peak used for referencing; chemical shifts reported on the TMS scale.

TG-FTIR. Netzsch Thermo-Microbalance TG 209 with Bruker FT-IR Spectrometer Vector 22; aluminum crucible (with micro-hole), $N_2$ atmosphere, 10 K/min heating rate, 25-250° C. or 25-350° C. range.

DSC. Perkin Elmer DSC 7; closed gold crucibles, sample filled in an $N_2$ environment, 10 K/min heating rate, −50 to 250° C. range, at times quench cooling (at −200 K $min^{-1}$) to −50° C. between scans.

DVS. Projekt Messtechnik Sorptions Prüf system SPS 11-100 n or Surface Measurement Systems DVS-1. The sample was placed on an aluminum or platinum holder on top of a microbalance and allowed to equilibrate for 2 h at 50% r.h. before starting one of two pre-defined humidity programs:
(1) 2 h at 50% r.h.;
(2) 50→0% r.h. (5%/h); 5 h at 0% r.h.;
(3) 0→95% r.h. (5%/h); 5 h at 95% r.h.; and
(4) 95→50% r.h. (5%/h); 2 h at 50% r.h.;
or
(1) 2 h at 50% r.h.;
(2) 50→95% r.h. (5%/h); 5 h at 95% r.h.;
(3) 95→0% r.h. (5/o/h); 5 h at 0% r.h.; and
(4) 0→50% r.h. (5%/h); 2 h at 50% r.h.

The hygroscopicity was classified based on the mass gain at 85% r.h. relative to the initial mass as follows: deliquescent (sufficient water adsorbed to form a liquid), very hygroscopic (mass increase of ≥15%), hygroscopic (mass increase <15% and ≥2%), slightly hygroscopic (mass increase <2% and ≥0.2%), or non-hygroscopic (mass increase <0.2%).

Solvents. For all experiments, Fluka, Merck or ABCR analytical grade solvents were used.

Approximate Solubility Determination. Approximate solubilities were determined by a stepwise dilution of a suspension of about 10 mg of substance in 0.05 mL of solvent. If the substance was not dissolved by addition of a total of >10 mL solvent, the solubility is indicated as <1 mg/mL. Due to the experimental error inherent in this method, the solubility values are intended to be regarded as rough estimates and are to be used solely for the design of crystallization experiments.

Aqueous Solubility Determination. Approximately 0.3 mL of doubly distilled water was added to 3-10 mg of the substance to be measured. The resulting suspension/solution was equilibrated in a temperature-controlled Eppendorf Thermomixer Comfort shaker for 2 h at 25° C. at a shaking rate of 500 rpm. The solid phase was recovered by filter centrifugation (0.10-μm PVDF membrane) and examined by FT-Raman spectroscopy. The pH of the corresponding solution was determined with a Metrohm 713 pH meter. The concentration of the solution was determined by HPLC (see below).

HPLC: For the aqueous solubility measurements the HPLC method given in Table 77 was used. Standard solutions of the SP196-FD-P1 free drug of compound 1 and the L-malate salt of compound 1 (SP196-MLA-P4) were prepared in the concentration range of 0.2-0.05 mg/mL for the construction of a calibration curve.

TABLE 77

HPLC method used for solubility determinations.

| Instrument | Agilent 1100 series | | |
|---|---|---|---|
| Column | Waters Xterra C18, 100 × 4.6 mm, 5 μm (FK-CC01E) | | |
| Mobile Phase A | $H_2O$ + 0.1% TFA | | |
| Mobile Phase B | MeCN | | |
| Reference conc. | 0.2-0.05 mg/mL | | |
| Retention time | 10.48 min | | |
| Gradient | 0 min | 95% A | 5% B |
| | 20 min | 5% A | 95% B |
| | 20.5 min | 95% A | 5% B |
| | 22 min | 95% A | 5% B |
| Flow | 1.00 mL/min | | |
| Injection Volume | 10 μL | | |
| Column temp. | 25° C. | | |
| Wavelength | 240 nm | | |

Example 2. General Methods of Crystallization and Drying

Sixty solvent-based crystallization and drying experiments were carried out with the aim of identifying the thermodynamically stable polymorph at room temperature as well as hydrates, solvates, and the most relevant metastable forms.

Several different crystallization methods were used including suspension equilibration (Example 3), cooling crystallization (Example 4), evaporation (Example 5), precipitation (Example 6), vapor diffusion (Example 7), and reverse vapor diffusion (Example 7). Experiments involving drying and desolvation of solvates/hydrates were also performed (Example 8).

A crystalline form of compound 1 was provided; PP445-P1 is an exemplary batch. The amorphous form of compound 1 was prepared (Example 10) and was used as a starting material for crystallization experiments in addition to crystalline compound 1.

Solvents were chosen with respect to a diversity of their physico-chemical parameters such as solubility, polarity, proticity/aproticity, volatility, etc. Several experiments were carried out in water/solvent mixtures with various water activities to search for hydrates. Other experiments were carried out in solvents that had been dried over molecular sieves, in order to ensure that they were free of water.

Special care was taken to ensure that a large variety of crystallization techniques and solvent properties was explored.

The obtained solid forms of compound 1 were characterized by XRPD, FT-Raman, DSC, DVS, TG-FTIR, $^1$H-NMR, melting point, solubility, and/or stability. In addition, the peaks in the XRPD patterns were determined and the patterns then classified using the PANalytical X'Pert (Highscore Plus) software.

Example 3. General Methods of Suspension Equilibration

Suspension equilibration experiments in a variety of different solvents and solvent mixtures were carried out at various temperatures.

This solvent-based crystallization method is aimed at obtaining the thermodynamically stable polymorphic form (or hydrate or solvate) under the applied conditions (solvent system and temperature).

The solvents and solvent mixtures were chosen based on the solubility of the compound (ideally about 2-30 mg/mL) and the physicochemical properties of the solvents.

Several experiments were carried out in water/solvent mixtures with various water activities in the search for hydrates. For other experiments solvents that had been dried over molecular sieves were used in order to ensure that they were free of water.

The goal of the experiments (22-23° C., 14-day duration, solvent=MeOH, EtOH, MeCN, acetone, EtOAc, THF, 2-PrOH, 9:1 THF/H$_2$O, 93:7 MeCN/H$_2$O, or 95:5 2-PrOH/H$_2$O) was to find the most stable polymorphic form of compound 1 at room temperature with a high probability.

The experiments at elevated temperatures (50° C., 4-day duration, solvent=acetone, DMF, THF, or EtOH) should provide an indication of whether a different form is more stable at this temperature, which can be particularly important for developing a controlled cooling crystallization process for the final step of API production. In addition, the use of high temperatures can help overcome kinetic barriers to polymorphic interconversion.

The experiments at 5° C. were carried out to search for solvated (and additional hydrated) forms of compound 1 since experiments at low temperatures are conducive to solvate and hydrate formation.

The amorphous material was used as the starting material for several suspension equilibration experiments (temperature=5° C., 30° C., 75° C., or 90° C.; duration=1 d, 5 d, or 7 d; solvent=THF, 96:4 acetone/H$_2$O, 98.5/1.5 acetone/H$_2$O, 2-PrOH, or water). Since the amorphous form is in a higher energy state than the crystalline form of the starting material compound 1, potential kinetic barriers might not poses as much of a hindrance for a transformation. The amorphous form of compound 1 was used as starting material for experiments to determine the stability range of compound 1 by equilibration at various water activity levels.

Upon completion of the suspension equilibration experiments, the recovered products were examined by Raman spectroscopy both immediately after filtration and after 30 min of drying under vacuum at room temperature. Such a procedure can permit the identification of labile solvates that rapidly convert into other forms on the laboratory scale.

Example 4. General Methods of Cooling Crystallizations from Hot Solutions

Cooling crystallizations from hot solutions can not only yield the thermodynamically stable form but also produce metastable forms when the crystallization occurs spontaneously and rapidly. In addition, application of heat can change the energetics and mobility of the molecules in solution. Thus different configurations (i.e., conformations and solution-based clusters) might be accessible, leading to the crystallization of different polymorphic forms.

Solvents and solvent mixtures with known (or estimated) low solubilities (e.g., 1-5 mg/mL) at room temperature are ideal for this type of experiment. In addition, as $T_{max}$ is limited by the boiling point of the solvent (or by the lowest boiling point from a mixture of solvents), solvents with different boiling points were used in order to explore a larger temperature range.

A summary is given in Table 78.

TABLE 78

| Cooling experiments starting with PP445-P1. | | | |
|---|---|---|---|
| Solvent/Mixture[a] | $T_{max}$ | $T_{min}$ | Cooling |
| dioxane/toluene | 90° C. | 0° C. | 0.15 K/min |
| 2PrOH/H$_2$O | 75° C. | 0° C. | 0.125 K/min |
| EtOH/heptane | 75° C. | 0° C. | 0.125 K/min |
| THF/IPE | 60° C. | 0° C. | 0.10 K/min |
| Dioxane | 85° C. | 0° C. | fast |
| MeCN | 80° C. | 0° C. | fast[b] |
| EtOAc | 75° C. | 0° C. | fast[b] |

[a]Organic solvents were dried over molecular sieves.
[b]Precipitation only after partial evaporation of solvent.

Example 5. General Methods of Evaporation

Evaporation is another crystallization method that can lead to either fast or slow precipitation depending on the speed of solvent removal. Thus, evaporations were carried out under N$_2$ flow or ambient conditions (open vial).

All evaporation experiments were carried out using the amorphous form of compound 1 as the starting material (under N$_2$ flow or in open vial; temperature=room temperature (r.t.); solvent=MeCN, EtOAc, DCM, or methyl ethyl ketone (MEK)).

Example 6. General Methods of Precipitation

Precipitation experiments can be carried out either by adding an antisolvent (AS) slowly or quickly into a solution of the compound or by adding a solution of the compound slowly or quickly into a bath of antisolvent. These different techniques can potentially lead to different forms even when using the same solvent mixture.

Solvents with a relative high solubility (ideally about 10-50 mg/mL) and antisolvents with a low solubility (e.g., <1 mg/mL) were chosen. In addition, the solvent and antisolvent pair should be freely miscible. To avoid possible solvate and/or hydrate formation, precipitation experiments can also be carried out at elevated temperatures. Precipitation experiments were carried out with the crystalline compound 1 starting material (Table 79).

TABLE 79

Precipitation experiments with the crystalline starting material compound 1 (sample PP445-P1).

| Solvent | Antisolvent | T | Conditions |
|---|---|---|---|
| pyridine | TBME | r.t. | AS added to solution |
| dioxane | heptane | 40° C. | AS added to solution |
| 1BuOH | toluene | 40° C. | AS added to solution |
| DCM | hexane | r.t. | solution added to AS |
| acetone | DEE | 5° C. | solution added to AS |

In addition, attempts were made to reproduce Form SUC-P3 (solvent=acetone, temperature=r.t., duration=1 d). The experiments SP196-SUC-P3 and SP196-MLA-P3 were repeated without the use of the succinic acid or L-malic acid salt former (as PP445-P38). The spontaneous precipitation from a saturated acetone solution resulted in Form C.

Next, in experiment PP445-P39, a saturated acetone solution was seeded with a small amount of From SUC-P3. A suspension formed. However, the obtained solid material also corresponds to Form C and not to Form SUC-P3. Thus, reproduction of Form SUC-P3 without the use of a salt former was not possible.

Considering all results and data, it was concluded that Form SUC-P3 is not a polymorph of the free drug but a succinate salt with a similar lattice structure to a malate salt.

Example 7. General Methods of Vapor Diffusion and Reverse Vapor Diffusion

Vapor diffusion is a slow crystallization method aimed at obtaining crystalline material of the stable form under the applied conditions (solvent system and temperature). A volatile antisolvent is allowed to slowly diffuse into a solution of the compound and thereby to gradually reduce the solubility in the solvent mixture, leading to saturation, supersaturation, and, ultimately, crystallization. This type of crystallization experiment can take place over the course of several weeks.

Reverse vapor diffusion experiments are performed by dissolving the API in a solvent/antisolvent mixture in which the solvent is the more volatile component. Partial evaporation is then allowed to occur, and since the more volatile solvent evaporates faster, the solubility should decrease over time, leading to a slow build-up of supersaturation and precipitation.

By using both complementary techniques, a wide solvent space can be explored. Solvent/antisolvent pairs with a large difference in their vapor pressures were chosen. Solvents ideally have a relatively high solubility (e.g., about 10 mg/mL), while antisolvents have a low solubility (e.g., <1 mg/mL).

The vapor diffusion and reverse vapor diffusion experiments are summarized in Table 80 and Table 81, respectively.

TABLE 80

Vapor diffusion experiments starting with PP445-P1.

| Solvent | Antisolvent | Condition |
|---|---|---|
| DMSO | TBME | r.t. → 4° C. |
| DMF | DEE | r.t. |

TABLE 80-continued

Vapor diffusion experiments starting with PP445-P1.

| Solvent | Antisolvent | Condition |
|---|---|---|
| pyridine | hexane | r.t. |
| 1BuOH | heptane | r.t. → 4° C. |

TABLE 81

Reverse vapor diffusion experiments starting with PP445-P1.

| Solvent | Antisolvent | Condition |
|---|---|---|
| THF | $H_2O$ | r.t. |
| DCM | toluene | r.t. |
| MEK | heptane | 70° C. |
| MeOH | toluene | 60° C. |
| acetone | hexane | 15° C. |

Example 8. General Methods of Drying and Desolvation

Drying and desolvation experiments were carried out with at least one sample of each obtained solvate and hydrate (including the starting material compound 1).

The solvated/hydrated forms were either dried under vacuum (<5 mbar) at r.t. or elevated temperatures, or suspended and equilibrated in a non-solvate forming solvent/solvent mixture at various temperatures.

Using a variety of starting materials (i.e., different solvates) with possibly varying conformations and/or different intra- and intermolecular interactions, can lead to the formation of new anhydrous polymorphic forms.

Summaries of the experiments are provided in Table 82 and Table 83.

TABLE 82

Drying under vacuum of the obtained solvates/hydrates.

| Form | Temperature | Condition |
|---|---|---|
| E (MeOH solvate) | r.t. | overnight |
| F (EtOH solvate) | r.t. | overnight |
| G (2-PrOH solvate) | r.t. | overnight |
| H (1-BuOH solvate) | r.t. | 3 d |
| I (THF solvate) | 40° C. | overnight |
| J (EtOAc solvate) | r.t. | overnight |
| K (dioxane solvate) | r.t. | 3 d |
| L (pyridine solvate) | 40° C. | overnight |

TABLE 83

Desolvation experiment by suspension of the solvates/hydrates in non-solvate forming solvents.

| Form | Conditions | Solvent |
|---|---|---|
| M (DMSO solvate) | 5 d at 35° C. | 1:1 acetone/TBME |
| L (pyridine solvate) | 5 d at 35° C. | 1:1 DCM/hexane |
| I (THF solvate) | 5 d at 35° C. | EtOAc |
| F (EtOH solvate) | 7 d at 90° C. | heptane |
| G (2-PrOH solvate) | 7 d at 110° C. | i-BuOAc |
| G (2-PrOH solvate) | 2 d at 130° C. | aniline |

Example 9. General Methods of Salt Screening

For the salt screening evaporation experiment stock solutions of the free drug compound 1 were prepared in THF, MeCN, 2-PrOH, and acetone. Stock solutions of most salt formers were also prepared in THF, MeCN, 2-PrOH, and acetone. Due to low solubility in organic solvents, stock solutions of some salt formers were prepared in $H_2O$ only (Table 84).

TABLE 84

Concentrations (in mol/l) of the free drug 1 and the salt formers (FUM, MLA, MLE, and SUC) instock solutions.

|  | THF | MeCN | 2-PrOH | acetone |
| --- | --- | --- | --- | --- |
| Free drug 1 | 0.038 | 0.019 | 0.021 | 0.021 |
| FUM (fumaric acid) | 0.050 | — | 0.050 | 0.037 |
| MLA (L-malic acid) | 0.050 | 0.050 | 0.050 | 0.050 |
| MLE (maleic acid) | 0.050 | 0.050 | 0.050 | 0.050 |
| SUC (succinic acid) | 0.050 | 0.043 | 0.050 | 0.050 |

Salts were prepared by mixing the stoichiometric volumes of each stock solution (free drug and corresponding salt former) according to the microtiter plate layout with a total sample volume about 200 μL.

Crystallization was performed by evaporation of the solvents under $N_2$ flow at room temperature. The resulting solids were examined by Raman microscopy. Two Raman spectra and microscopic images were collected for each obtained residue.

For the phase equilibration (slurry) experiments, a second set of four solvents was selected: heptane, EtOAc, diisopropyl ether (IPE), and toluene. To the residues of the evaporation experiments 100 μL of solvent were added: heptane to columns 1 to 3 (wells A1 to H3), EtOAc to columns 4 to 6 (wells A4 to H6), IPE to columns 7-9 (wells A7 to H9), and toluene to columns 10 to 12 (wells A10 to H12). The microtiter plate was shaken on an Eppendorf Thermo-Mixer at 500 rpm for 3 days, with a temperature cycling program (20-30° C.). The solvents were again evaporated at r.t. under controlled $N_2$ flow. The resulting solids were examined by Raman microscopy. Two Raman spectra and microscopic images were collected for each residue.

Example 10. Preparation of Form A

Figure 2:
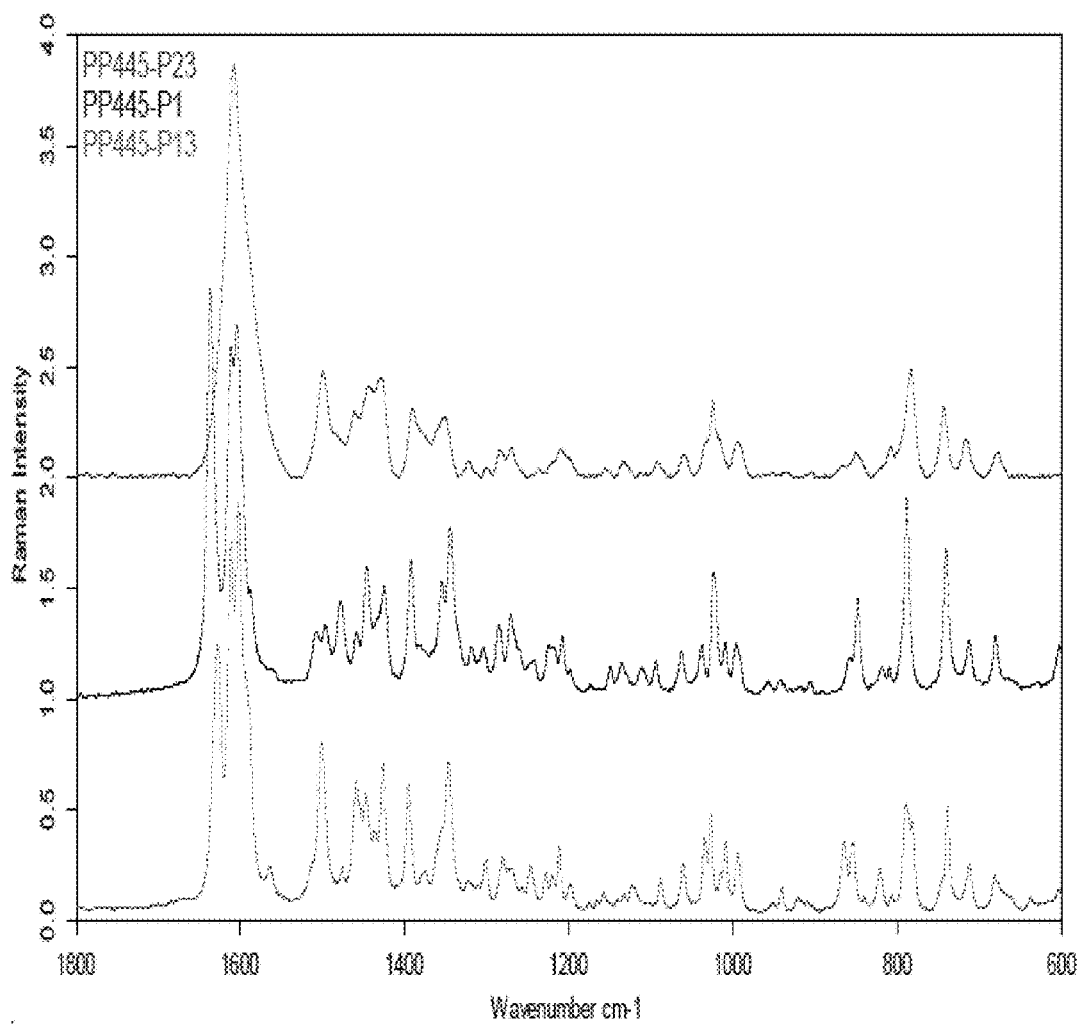
FIG. 2 depicts Fourier-Transform Raman (FT-Raman) spectrum of Form A (top curve).

Methods of preparing amorphous Form A are illustrated in Table 85. The solid material obtained from a fast evaporation experiment using compound 1 under $N_2$ flow at r.t. (PP442-P22) shows a diffractogram with several broad, unresolved features from −3°2θ to 30° 2θ on top of a broad halo from ~10° 2θ to 30° 2θ which is characteristic for amorphous material (FIG. 1). Some structure might have been retained in this sample.

TABLE 85

Experiments aimed at preparing Form A of compound 1.

| Sample | Method | Conditions | Result |
| --- | --- | --- | --- |
| PP445-P22 | fast evaporation from DCM | under $N_2$ at r.t. | mainly amorphous |
| PP445-P23 | quench cooling of melt | heated to 180° C.; cooled in ice | amorphous |

Amorphous Form A was successfully prepared by quench cooling the melt (PP445-P23) (Table 1). The diffractogram of the obtained glassy substance (FIG. 1) shows no distinct peaks but only the broad halo from ~10° 2θ to 30° 2θ that is characteristic for amorphous material.

The FT-Raman spectrum of PP445-P23 (FIG. 2) shows relatively broad peaks compared to the crystalline Form C. It is defined as the reference spectrum of Form A.

The amorphous material appears to be stable for at least 5 days under ambient conditions, as it was unchanged after re-examination by XRPD (data not shown).

Example 11. Preparation and Characterization of Form C

Form C may be prepared according to the following method: A sample of compound 1 (10 mg) was placed in a small glass test tube (approx. 8 mm diameter), EtOH (250 μL; AR grade at r.t.) was added, and the resulting mixture was warmed (hair dryer) until all of the solid material was fully dissolved. The solution was then diluted with warm water (250 μL Milli-Q, pre-warmed to 30-40° C.). The resulting clear solution was allowed to cool to room temperature, leading to the formation of a solid. The solid was isolated by decanting the mother liquor and then washing the remaining solid with a small amount (100 μL) of 50% aqueous ethanol (50:50 mix of AR grade EtOH and Milli-Q water; r.t.). The final solid material was dried in a vacuum desiccator to yield Form C.

Form C may alternatively be prepared according to the following method. 20 g of compound 1 was suspended in 200 ml of acetone (reagent grade) and heated to 50-55° C. with vigorous stirring (using magnetic bar in a 2000-ml flask). Within 30 m of stirring at 50-55° C. the suspension turned into a very thick cake. 100 ml of acetone was added to the cake while keeping reaction temperature to 50-55° C. (stirring started again). Addition of acetone was repeated three times within 30 minutes (about 8 min interval). The resulting suspension was stirred for 2 h at 50-55° C. The reaction vessel was removed from oil-bath and cooled to r.t. (~30 min) and solid separated was filtered, dried, and powdered to yield Form C.

An FT-Raman spectrum is shown in FIG. 4.

Figure 3:
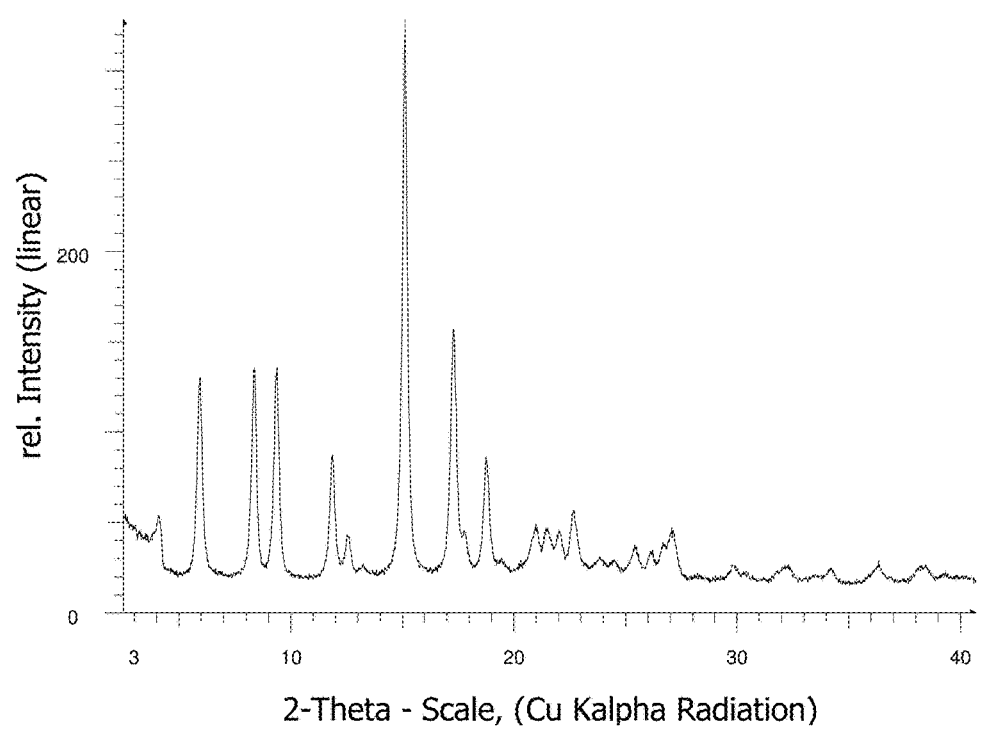
FIG. 3 depicts an XRPD pattern of Form C.

The XRPD patterns are shown in FIG. 3.

The TG-FTIR (sample PP445-P13, FIG. 7) shows the loss of ~0.7 wt % DMF (<0.05 eq.) gradually from 50° C. to 250° C., most likely residual solvent due to incomplete drying (the sample was dried under vacuum for 1 h). Decomposition starts at temperatures >250° C.

Figure 69:
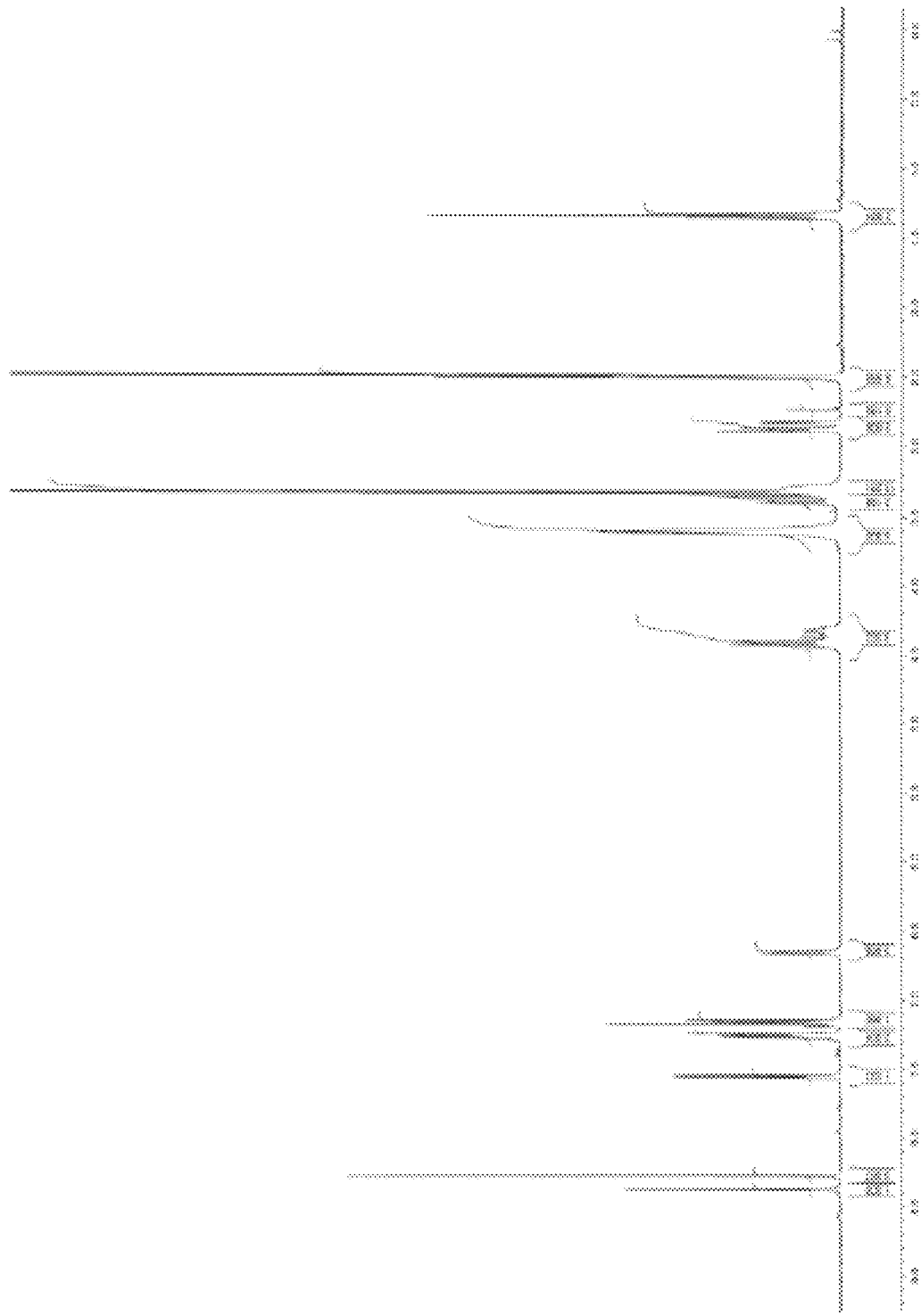
FIG. 69 depicts a Proton Nuclear Magnetic Resonance ($^1$H-NMR) spectrum of Form C.

The $^1$H-NMR spectrum agrees with the structure of compound 1 (FIG. 69).

The microscopic image of a sample of Form C (sample PP445-P38, FIG. 8) shows very fine hair or needles.

The DSC thermogram (sample PP445-P13, FIG. 5) shows a sharp endothermic event with a peak at $T_{max}$=212.4° C. (ΔH=99.0 J/g), likely corresponding to melting, and no further events up to 250° C.

The DVS isotherm (sample PP445-P13, FIG. 6) shows a reversible mass loss of ~0.3 wt % upon decreasing the relative humidity (r.h.) from 50% r.h. to 0%. Equilibrium was reached at 0% r.h. Upon increasing the relative humidity from 50% r.h. to 95% r.h. a mass increase of ~0.6 wt % is observed. Equilibrium was reached at 95% r.h. Upon decreasing the relative humidity from 95% r.h. to 50% r.h., a mass loss occurred and the final mass is equal to the starting mass.

The mass increase of ~0.2 wt % from 50% to 85% r.h. classifies the material as slightly hygroscopic.

The FT-Raman spectrum of the material after the DVS measurement corresponds to the spectrum of the material before the DVS measurement.

The aqueous solubility of Form C (sample PP445-P43) is 0.04 mg/mL (at pH=7.5 of saturated solution) after 2 h equilibration at 25° C. The FT-Raman spectrum of the solid residue is unchanged.

Thus, Form C corresponds to a crystalline, anhydrous, slightly hygroscopic polymorph of compound 1. Form C is a thermodynamically stable polymorph of compound 1 at least in the temperature range from 25° C. to 60° C.

Example 12. Preparation and Characterization of Form D

Form D (such as sample PP445-P2-T1) was obtained by drying Form E under vacuum (<5 mbar) at r.t. overnight.

The FT-Raman spectrum of Form D is given in FIG. 10.

The XRPD pattern (FIG. 9) is changed compared to the methanol solvate (Form E) and does not correspond to the starting material (compound 1) or to the anhydrous Form C.

The TG-FTIR thermogram (FIG. 12) shows no significant mass loss (~0.2 wt % $H_2O$) from 50° C. to 180° C., and decomposition at temperatures >250° C.

Figure 70:
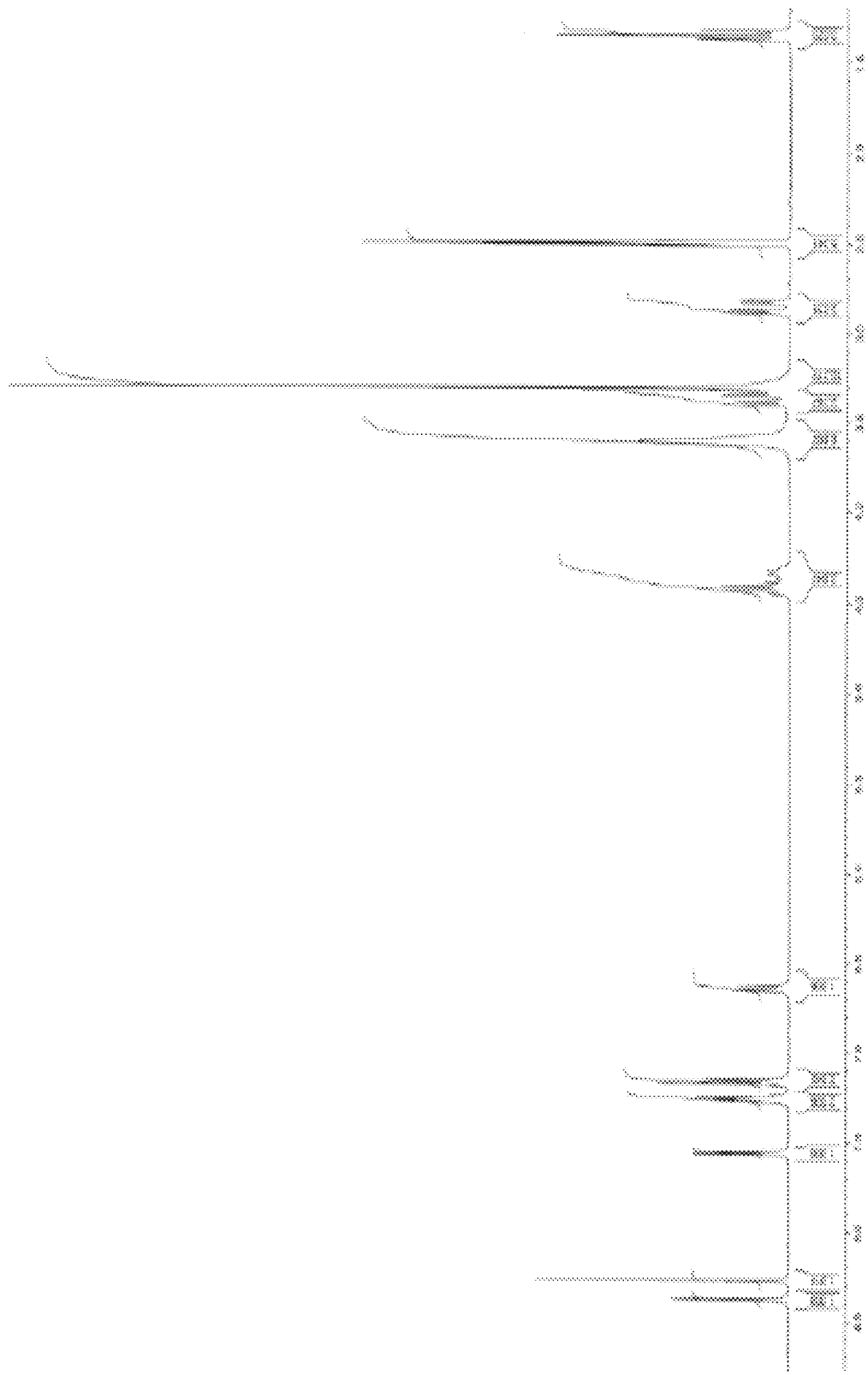
FIG. 70 depicts a $^1$H-NMR spectrum of Form D.

The $^1$H-NMR spectrum (FIG. 70) agrees with the given structure of compound 1 without any solvent content.

The DSC thermogram (FIG. 11) shows two overlapping endothermic events with peaks at $T_{max}$=162.0° C. (ΔH≈27.8 J/g) and $T_{max}$=175.6° C. (ΔH≈24.3 J/g), followed by a third endothermic event with a peak at $T_{max}$=204.5° C. (ΔH=13.7 J/g).

Thus, Form D corresponds to a crystalline, anhydrous polymorph of compound 1. Form D may be thermodynamically less stable than Form C at least in the temperature range from 25° C. to 60° C.

Example 13. Preparation and Characterization of Form E

Form E (such as sample PP445-P2) was prepared from a suspension equilibration experiment on compound 1 at 23° C. in MeOH. In one set of experiments, 99.2 mg of compound 1 (sample PP445-P1) were suspended in 0.5 mL of MeOH; the suspension was equilibrated at 23° C. and 500 rpm; after 14 days a solid was recovered by filter centrifugation (0.2-μm PTFE membrane) to yield Form E (sample PP445-P2).

Figure 13:
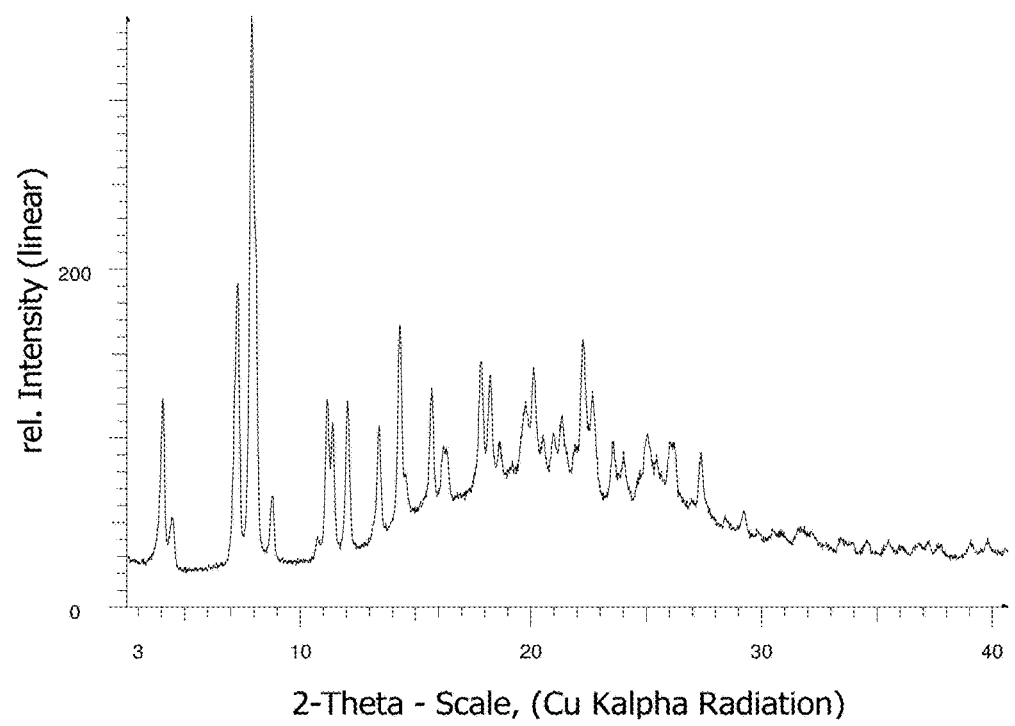
FIG. 13 depicts an XRPD pattern of Form E.

The FT-Raman spectrum and XRPD pattern of Form E are given in FIG. 14 and FIG. 13, respectively.

The TG-FTIR thermogram (FIG. 15) shows the loss of ~4.8 wt % MeOH and $H_2O$ (≤0.65 eq. MeOH) from 50° C. to 200° C. and decomposition at temperatures >250° C.

These results indicate that Form B is a methanol solvate of compound 1.

Example 14. Dying Experiments on Form E

A sample of Form E (PP445-P2) was dried in an attempt to desolvate it (as sample PP445-P2-T1). The solid material PP445-P2 was stored under vacuum (<5 mbar) at r.t. overnight. The solvents included in Form E before drying were 4.8% MeOH and $H_2O$. The solvent included in the sample of Form E after drying was 0.2% $H_2O$. The FT-Raman spectrum and XRPD pattern of the dried sample corresponded to Form D.

Example 15. Preparation and Characterization of Form F

Form F (such as samples PP445-P3 and PP445-P27) was obtained from suspension equilibration experiments on compound 1 at 23° C. or 50° C. in EtOH. In one set of experiments, 99.2 mg of compound 1 (sample PP445-P1) were suspended in 0.5 mL of EtOH; suspension at 23° C. and 500 rpm; after 14 days recovered solid by filter centrifugation (0.2-μm PTFE membrane to yield Form F (sample PP445-P3).

Figure 16:
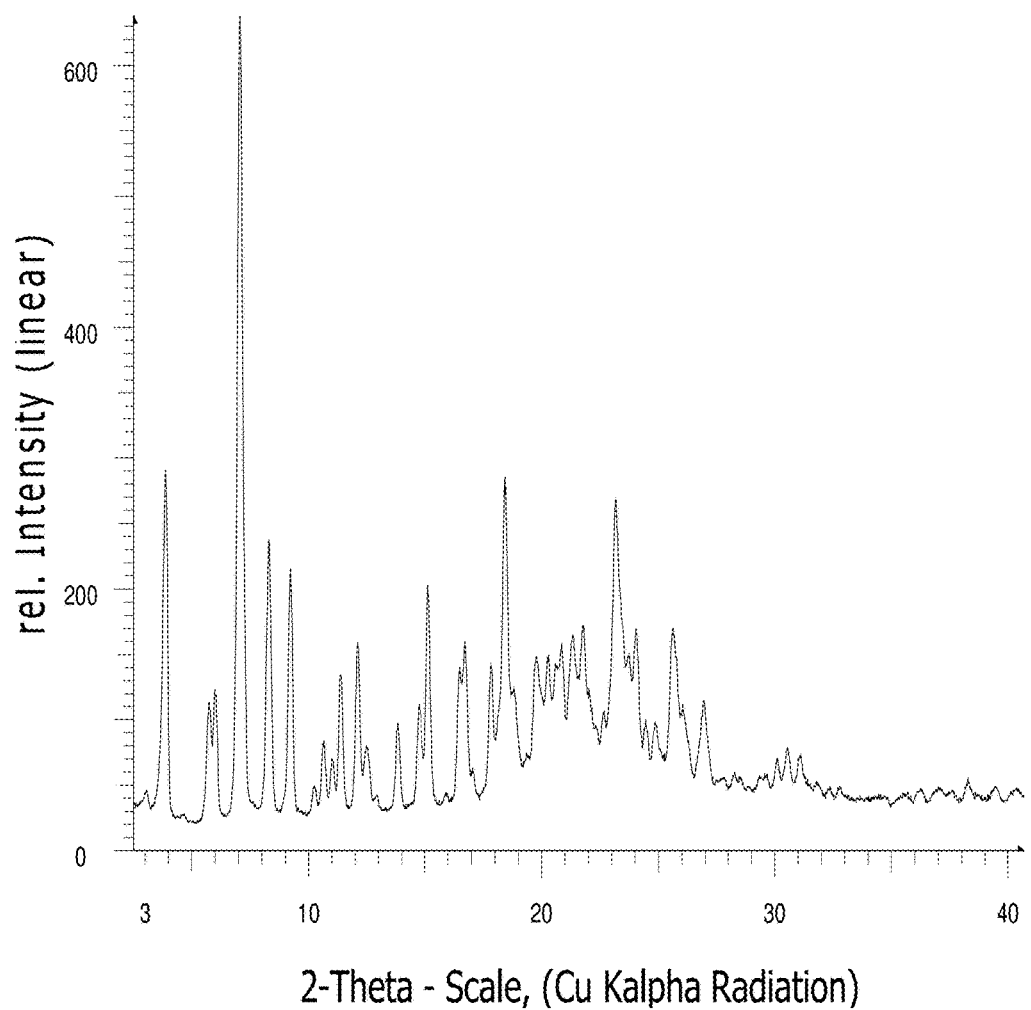
FIG. 16 depicts an XRPD pattern of Form F.

The FT-Raman spectrum is given in FIG. 17. The XRPD pattern is shown in FIG. 16.

The TG-FTIR (sample PP445-P27, FIG. 18) shows the loss of ~7.5 wt % EtOH (~0.75 eq.) from 50° C. to 180° C., further loss of ~1.4 wt % EtOH from 170° C. to 250° C. and decomposition at temperatures >250° C. The sample had been dried under vacuum at r.t, for 1 h before the measurement. Thus, most of the EtOH content (boiling point=78° C.) is likely bound within the structure.

These results indicate Form F is an ethanol solvate of compound 1.

Example 16. Drying Experiments on Form F

A sample of Form F (PP445-P27) was dried in an attempt to desolvate it (as sample PP445-P27-T1). The solid material PP445-P27 was stored under vacuum (<5 mbar) at r.t. overnight. The solvent included in the sample before and after drying was 8.9% EtOH and 2.7% EtOH, respectively.

The XRPD pattern of the dried sample shows only a few broad peaks indicating that the dried sample is of lower crystallinity compared to the material before drying.

The TG-FTIR thermogram shows the loss of ~2.2 wt % EtOH (and some $H_2O$) from 50° C. to 160° C. and a second loss of ~0.5 wt % EtOH from 160° C. to 240° C. Decomposition starts at temperatures >250° C.

Thus, a partial desolvation has likely occurred parallel to a break-down of the crystal structure of Form F. No transformation into a known or new anhydrous form was observed.

Example 17. Preparation and Characterization of Form G

Form G (such as sample PP445-P8) was prepared from a suspension equilibration experiment on compound 1 at 23° C. in 2-PrOH. In one set of experiments, 99.0 mg of compound 1 (sample PP445-P1) were suspended in 0.5 mL of 2PrOH; equilibrated suspension at 23° C. and 500 rpm; after several days added 0.5 mL solvent; after a total of 14 days recovered solid by filter centrifugation (0.2-μm PTFE membrane) to yield Form G (sample PP445-P8).

Figure 19:
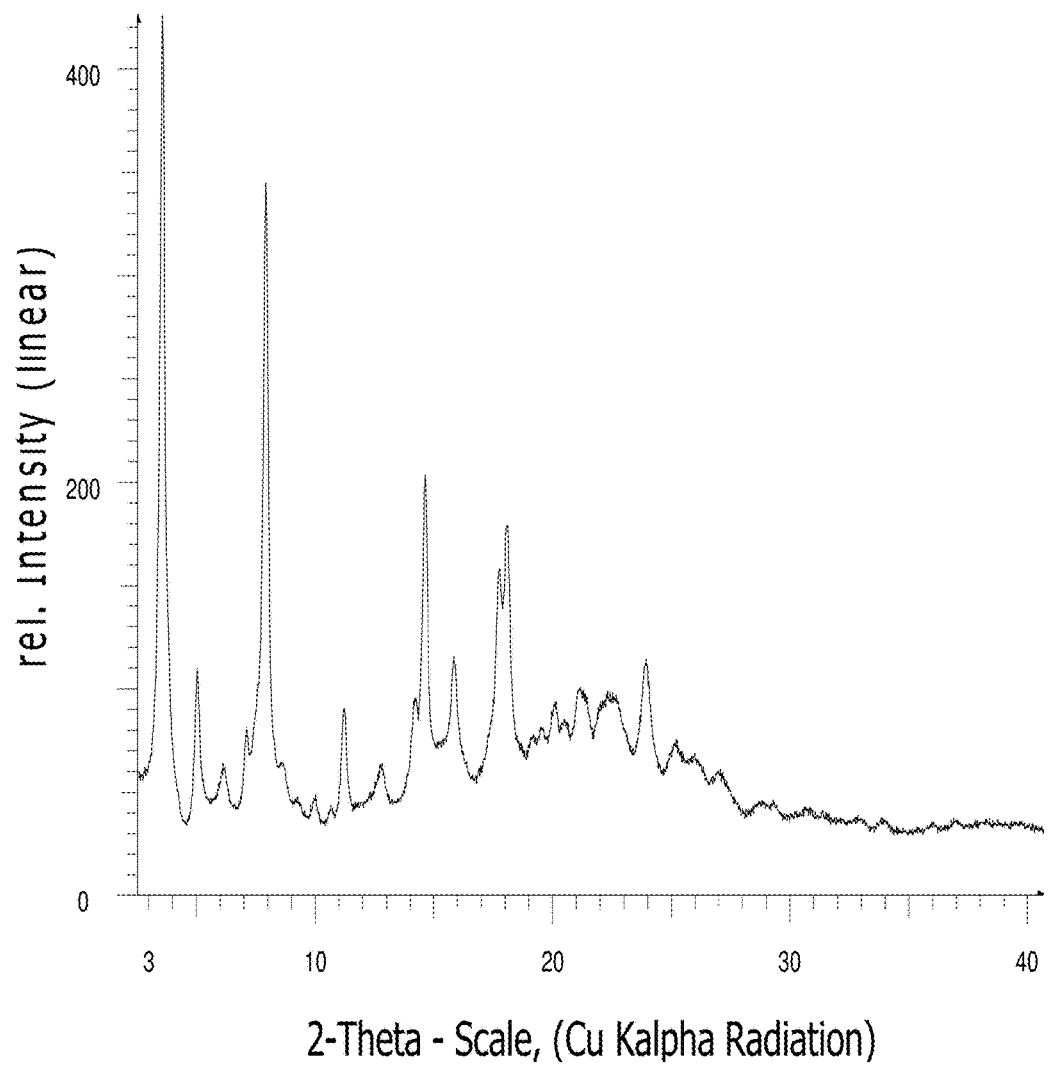
FIG. 19 depicts an XRPD pattern of Form G.

The FT-Raman spectrum and XRPD pattern of Form G are given in FIG. 20 and FIG. 19, respectively.

The TG-FTIR thermogram (FIG. 21) shows the loss of ~4.5 wt % 2-PrOH (~0.3 eq.) from 50° C. to 220° C. and decomposition at temperatures >280° C. The sample was dried under vacuum at r.t. for 1 h before the measurement. Thus, most of the 2-PrOH content (boiling point (b.p.)=82° C.) is likely bound within the structure.

These results indicate that Form G is a 2-propanol solvate of compound 1.

Example 18. Drying Experiments on Form G

A sample of Form G (PP445-P8) was dried in an attempt to desolvate it (as sample PP445-P8-T1). The solid material PP445-P8 was stored under vacuum (<5 mbar) at r.t. overnight. The solvent included in the sample before and after drying was 4.5% 2-PrOH (with some H$_2$O) and 4.0% 2-PrOH (with traces of H$_2$O), respectively.

The XRPD pattern of the dried sample shows only a few broad peaks indicating the dried sample is of lower crystallinity compared to the material before drying.

The TG-FTIR thermogramshows the loss of ~4.0 wt % 2-PrOH (with traces of H$_2$O) from 50° C. to 200° C. Decomposition starts at temperatures T>200° C.

Thus, a partial desolvation has likely occurred parallel to a break-down of the crystal structure of Form G. No transformation into a known or new anhydrous form was observed.

Example 19. Preparation and Characterization of Form H

Form H (such as sample PP445-P37) was obtained from a precipitation/cooling/evaporation experiment on compound 1 in ~1:6 1-butanol/toluene. In one set of experiments, 98.8 mg of compound 1 (sample PP445-P1) were suspended in 2.5 mL of 1-BuOH, and the suspension was heated to 40° C. Added stepwise 2.5 mL of 1BuOH to obtain clear solution, and stirred solution at 40° C. After 1 h added slowly and stepwise 30.0 mL of toluene (solution remained clear), stirred solution at 40° C., and after 2 d observed no changes. Stored solution at 4-5° C., and after 8 d observed no changes. Evaporated solvent under N2 flow at r.t. to obtain Form H as a yellow solid material (sample PP445-P37).

Figure 22:
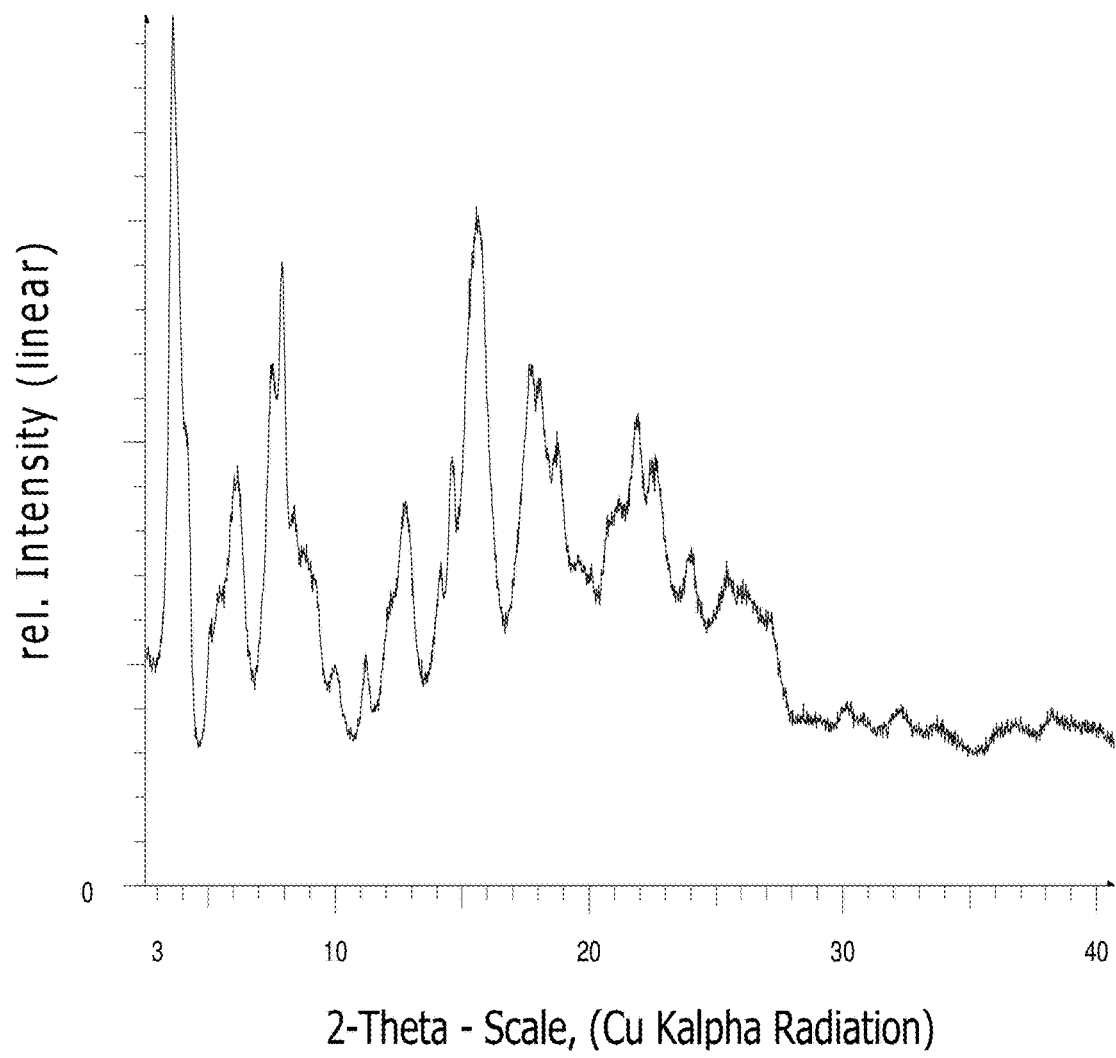
FIG. 22 depicts an XRPD pattern of Form H.

The FT-Raman spectrum and XRPD pattern of Form H are given in FIG. 23 and FIG. 22, respectively.

The TG-FTIR thermogram (FIG. 24) shows the loss of ~6.0 wt % 1-BuOH (~0.4 eq.) from 50° C. to 220° C. and decomposition at temperatures >250° C. Most of the 1-BuOH content (boiling point=117° C.) is likely bound within the structure.

Figure 71:
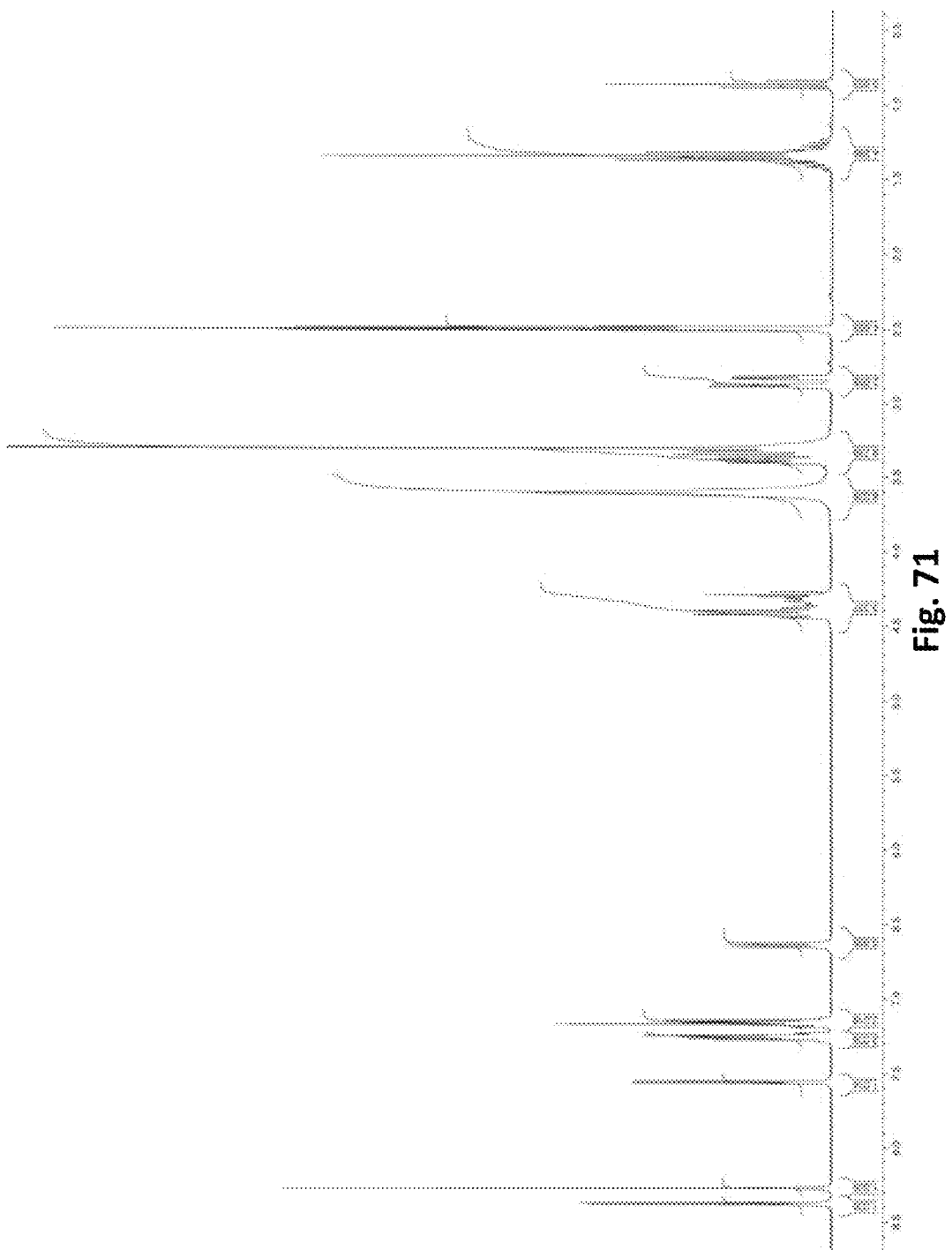
FIG. 71 depicts a $^1$H-NMR spectrum of Form H.

The $^1$H-NMR measurement (FIG. 71) agrees with the given structure. The measured sample contains ~0.3 eq. 1-BuOH which is in good agreement with the TG-FTIR measurement.

Thus, Form H is likely a 1-butanol solvate of compound 1.

Example 20. Drying Experiments on Form H

A sample of Form H (PP445-P37) was dried in an attempt to desolvate it (as sample PP445-P37-T1). The solid material PP445-P37 was stored under vacuum (<5 mbar) at r.t, for 3 days. The solvent included in the sample before and after drying was 6.0% 1-BuOH and 5.4% 1-BuOH, respectively.

The XRPD pattern of the dried sample shows some intensity changes compared to the pattern of the material before drying, but no other significant differences.

The TG-FTIR thermogram shows the loss of ~5.4 wt % 1-BuOH (with some H$_2$O) from 50° C. to 250° C. Decomposition starts at temperatures >250° C.

Thus, no significant desolvation has occurred. No transformation into a known or new crystalline form was observed.

Example 21. Preparation and Characterization of Form I

Form I (such as sample PP445-P28) was obtained from a suspension equilibration experiment at 5° C. in THF starting with the amorphous form of compound 1. In one set of experiments, 98.1 mg of compound 1 (sample PP445-P1) were heated to 190° C. and a yellow melt was obtained. Vial was quickly cooled with molten material in ice bath to obtain a yellow glassy material that was proposed to be the amorphous form. Added 0.5 mL of THF (dried over 4 Å MS) to obtain light yellow suspension, equilibrated suspension at 5° C. while stirring (as suspension became too thick for stirring), and added 2×0.5 mL solvent. After 5 d recovered solid by filter centrifugation (0.2-µm PTFE membrane) to obtain Form I (sample PP445-P28).

Figure 25:
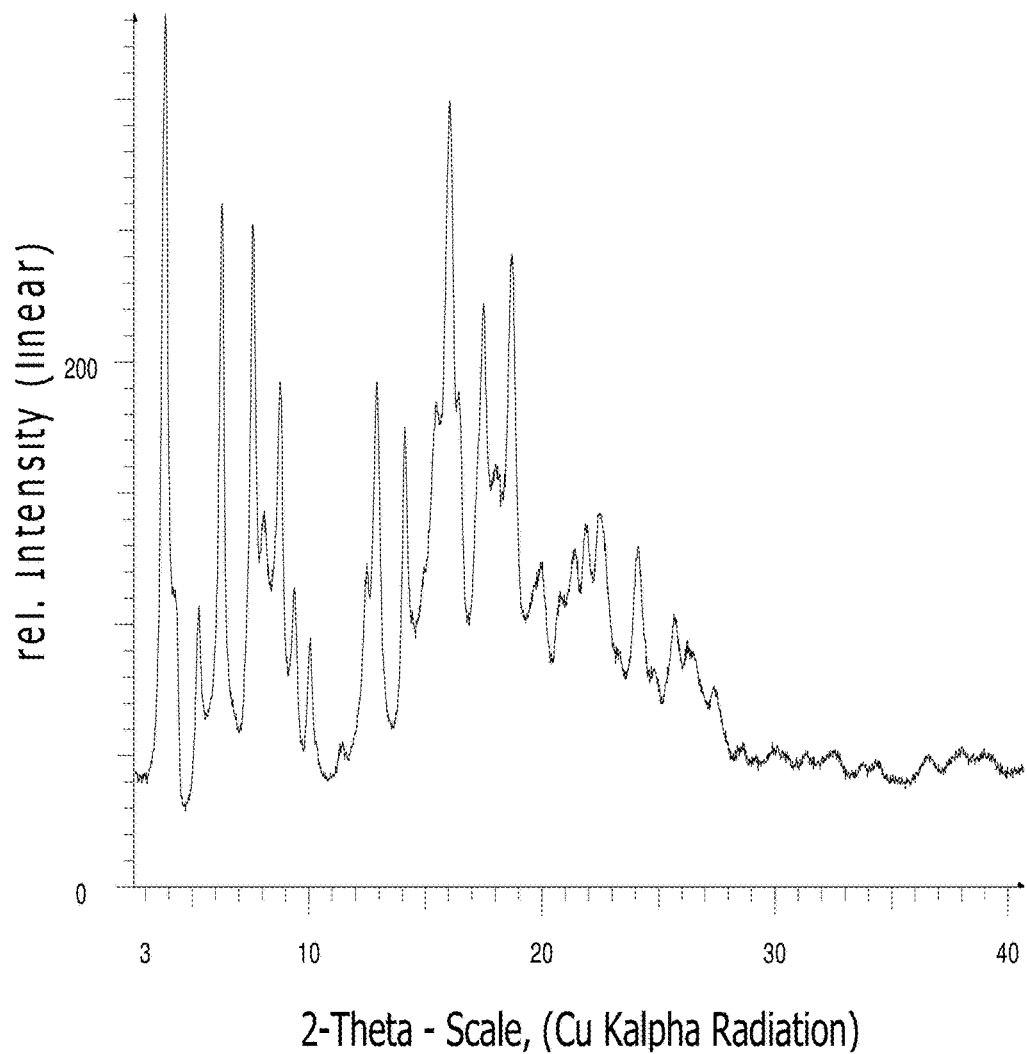
FIG. 25 depicts an XRPD pattern of Form I.

The FT-Raman spectrum and XRPD pattern of Form I are given in FIG. 26 and FIG. 25, respectively.

The TG-FTIR thermogram (FIG. 27) shows the loss of ~6.3 wt % THF (~0.4 eq.) from 50° C. to 250° C. and decomposition at temperatures>250° C. The sample was dried under vacuum at r.t. for 2 h before the measurement. Thus, most, if not all, of the THF content (b.p.=66° C.) is likely bound within the structure.

Figure 72:
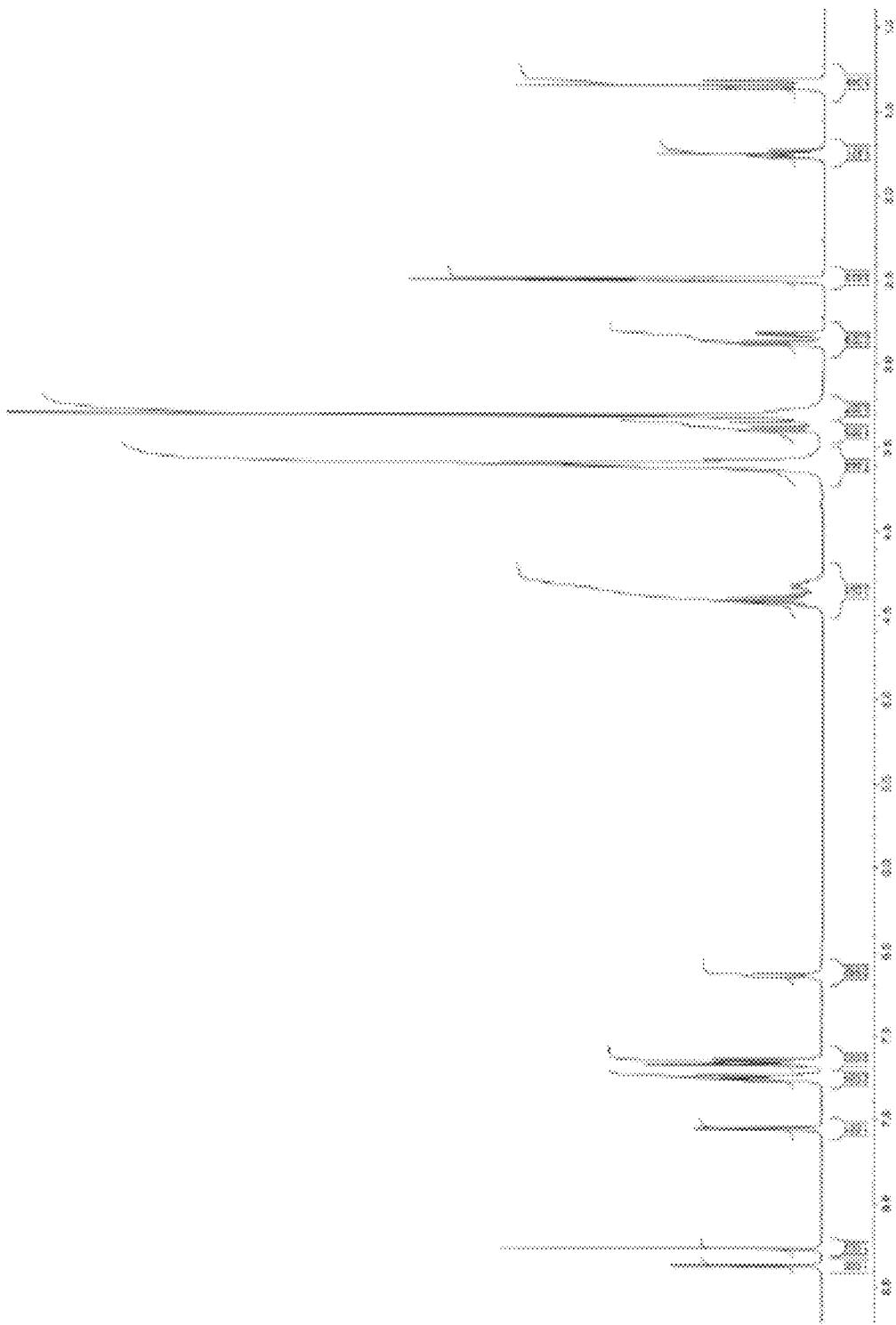
FIG. 72 depicts a $^1$H-NMR spectrum of Form 1.

The $^1$H-NMR spectrum (FIG. 72) agrees with the given structure. The measured sample contains ~0.4 eq. THF which is in good agreement with the TG-FTIR measurement.

Thus, Form I is likely a THF solvate of compound 1.

Example 22. Drying Experiments on Form I

A sample of Form I (PP445-P28) was dried in an attempt to desolvate it (as sample PP445-P28-T1). The solid material PP445-P28 was stored under vacuum (<5 mbar) at 40° C. overnight. The solvent included in the sample before and after drying was 6.3 wt % THF and 5.0 wt % THF, respectively.

The XRPD pattern of the dried sample shows broader peaks of lower intensity, indicating that the dried material has lower crystallinity compared to the sample before drying.

The TG-FTIR thermogram shows the loss of ~5.0 wt % THF (with traces of 1-120) from 50° C. to 250° C. Decomposition starts at temperatures T>250° C.

Thus, a partial desolvation has likely occurred parallel to a partial break-down of the crystal structure of Form 1. No transformation into a known or new anhydrous form was observed.

Example 23. Preparation and Characterization of Form J

Form J (such as sample PP445-P48) was obtained from a cooling crystallization of compound 1 in EtOAc. In one set of experiments, 99.2 mg of compound 1 (sample PP445-P1) were suspended in 1.0 mL of EtOAc and the suspension was heated to 75° C. Added stepwise 19.0 mL of EtOAc to obtain a clear solution. Held clear solution at 75° C. for 30 min, then cooled vial with solution quickly in ice bath. Stored sample for ~4 h in ice-bath and overnight at 5° C. Observed clear solution. Partially evaporated solvent under N$_2$ flow in ice-bath and observed no precipitation. Stored solution overnight at 5° C. Partially evaporated solvent under N$_2$ flow in ice-bath and observed no precipitation. Stored solution again overnight at 5° C., and observed light yellow suspension. Recovered solid material by vacuum filtration (P4 pore size) to obtain Form J (sample PP445-P48) as a bright yellow material.

Figure 28:
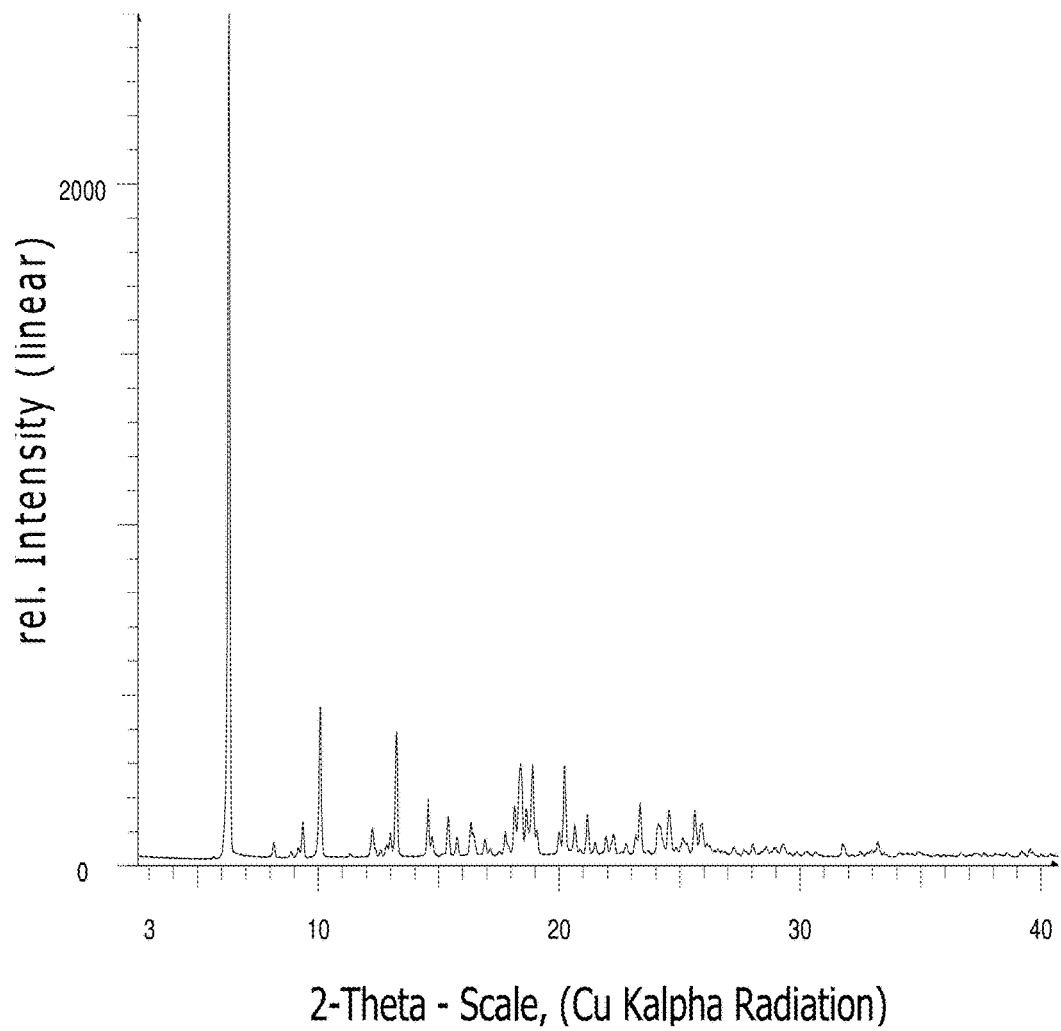
FIG. 28 depicts an XRPD pattern of Form J.

The FT-Raman spectrum and XRPD pattern of Form J are given in FIG. 29 and FIG. 28, respectively.

The TG-FTIR thermogram (FIG. 30) shows the loss of ~2.0 wt % EtOAc in a step from 100° C. to 160° C., further loss of ~1.8 wt % EtOAc from 160° C. to 240° C., and decomposition at temperatures T>250° C. The sample was dried under vacuum at r.t. for 1 h before the measurement. Thus, the EtOAc content (b.p.=76° C.) is likely bound within the structure, 4 wt % EtOAc correspond to 0.2 eq.

Figure 73:
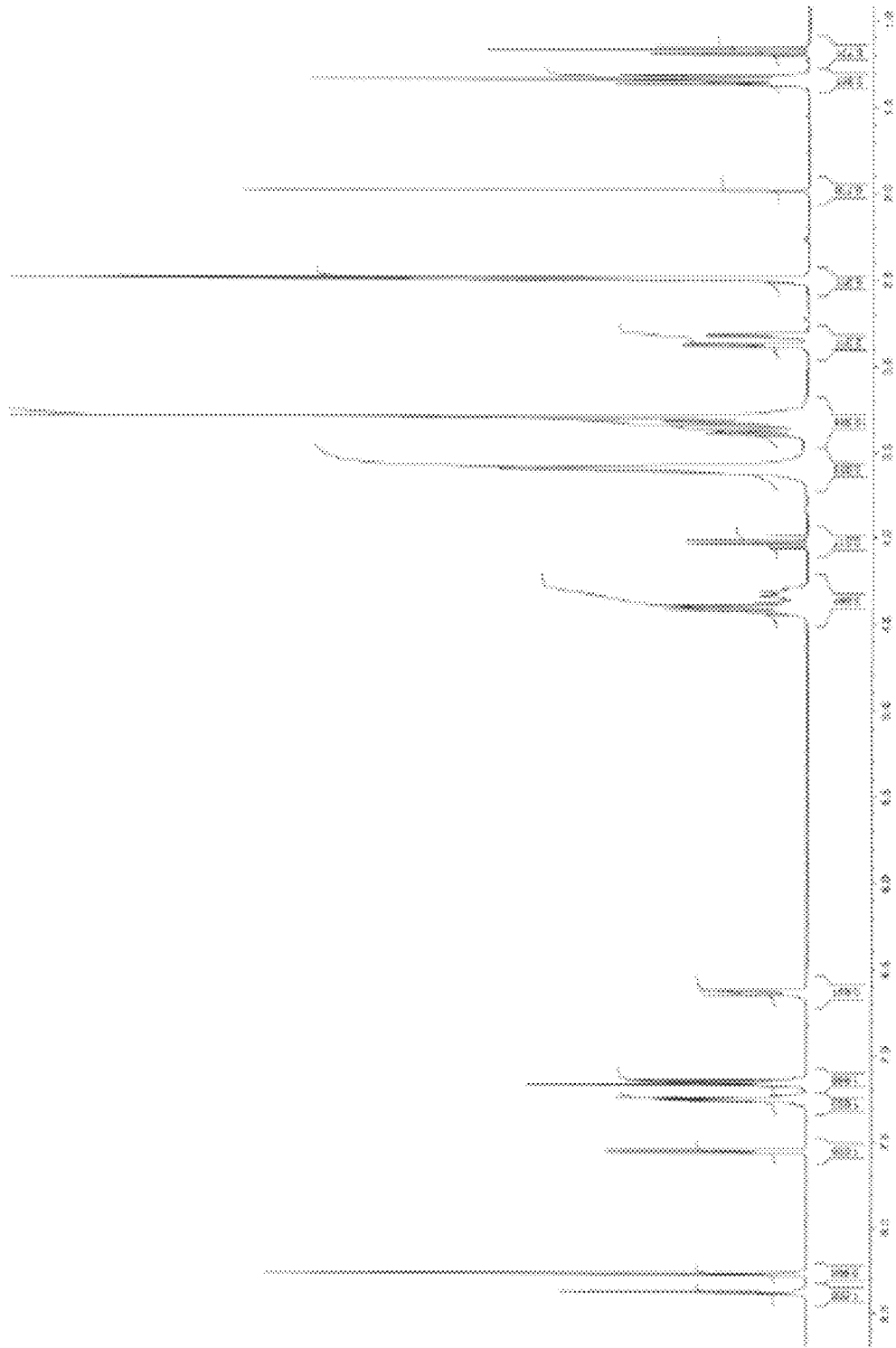
FIG. 73 depicts a $^1$H-NMR spectrum of Form J.

The $^1$H-NMR spectrum (FIG. 73) agrees with the given structure. The measured sample contains ~0.2-0.3 eq. EtOAc which is in good agreement with the TG-FTIR measurement.

Thus, Form J is likely an EtOAc solvate of compound 1.

Example 24. Drying Experiments on Form J

A sample of Form J (PP445-P48) was dried in an attempt to desolvate it (as sample PP445-P48-T1). The solid material PP445-P48 was stored under vacuum (<5 mbar) at r.t. overnight. The solvent included in the sample before and after drying was 3.8% EtOAc (with traces of H$_2$O) and 4.7% EtOAc (with some H$_2$O), respectively.

The XRPD pattern of the dried sample is unchanged compared to the pattern of the material before drying.

The TG-FTIR thermogram shows the loss of ~4.7 wt % EtOAc (with some water) from ~130° C. to 250° C.

Example 25. Preparation and Characterization of Form K

Form K (such as sample PP445-P46) was obtained from a cooling crystallization of compound 1 in dioxane. In one set of experiments, 99.8 mg of compound 1 (sample PP445-P1) were suspended in 1.0 mL of dioxane, and the suspension was heated to 80° C. to obtain a clear solution. Heated clear solution to 85° C., held clear solution at 85° C. for 30 min, and cooled vial with solution quickly in ice bath. Stored sample for 30 min in ice-bath, then warmed to r.t. to obtain a suspension. Stirred suspension at r.t, for 2 h and recovered solid material by filter centrifugation (0.2-µm PTFE membrane) to yield Form K (sample PP445-P46).

Figure 31:
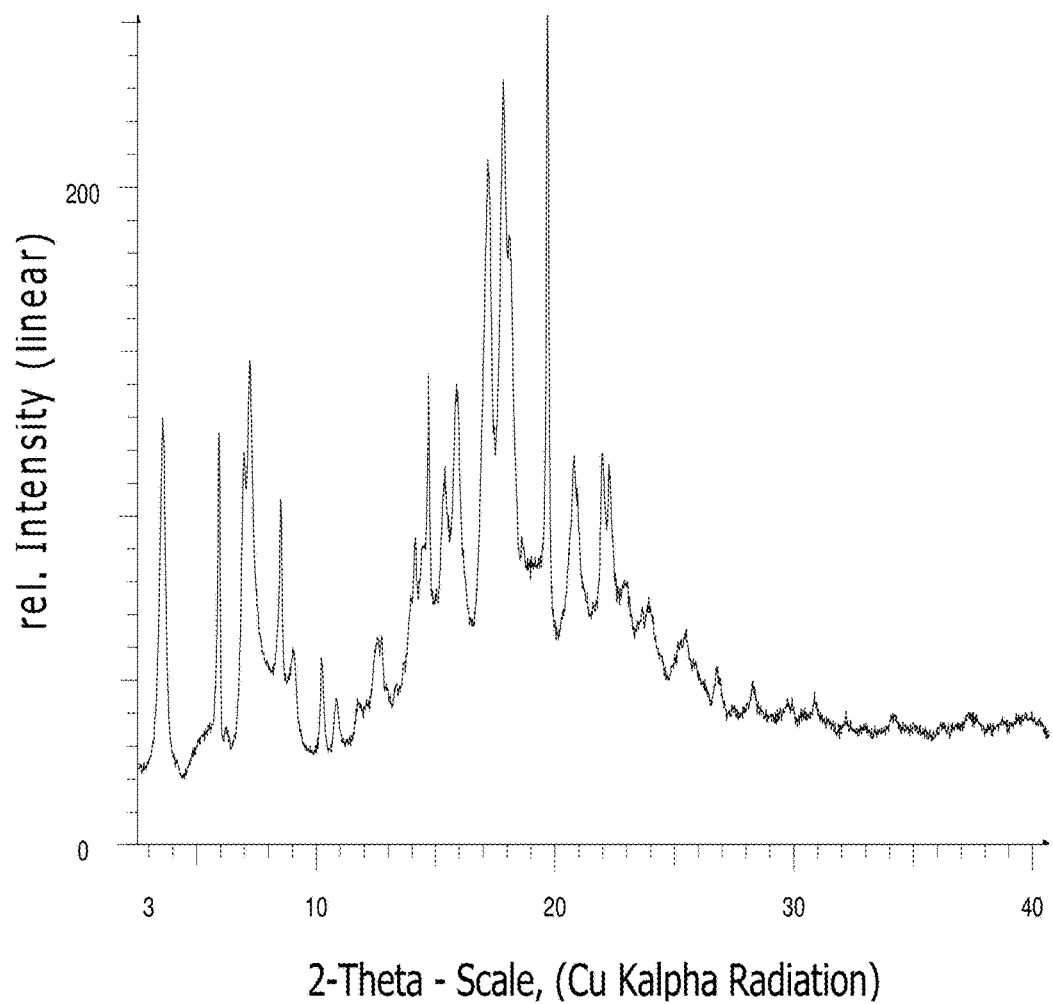
FIG. 31 depicts an XRPD pattern of Form K.

The FT-Raman spectrum and XRPD pattern of Form K are given in FIG. 32 and FIG. 31, respectively.

The TG-FTIR thermogram (FIG. 33) shows the loss of ~16.1 wt % dioxane (~0.9 eq.) from 25° C. to 240° C. and decomposition at temperatures T>250° C. The sample was dried under vacuum at r.t. for 2 h before the measurement. Thus, most of the dioxane content (b.p.=100° C.) is likely bound within the structure.

Figure 74:
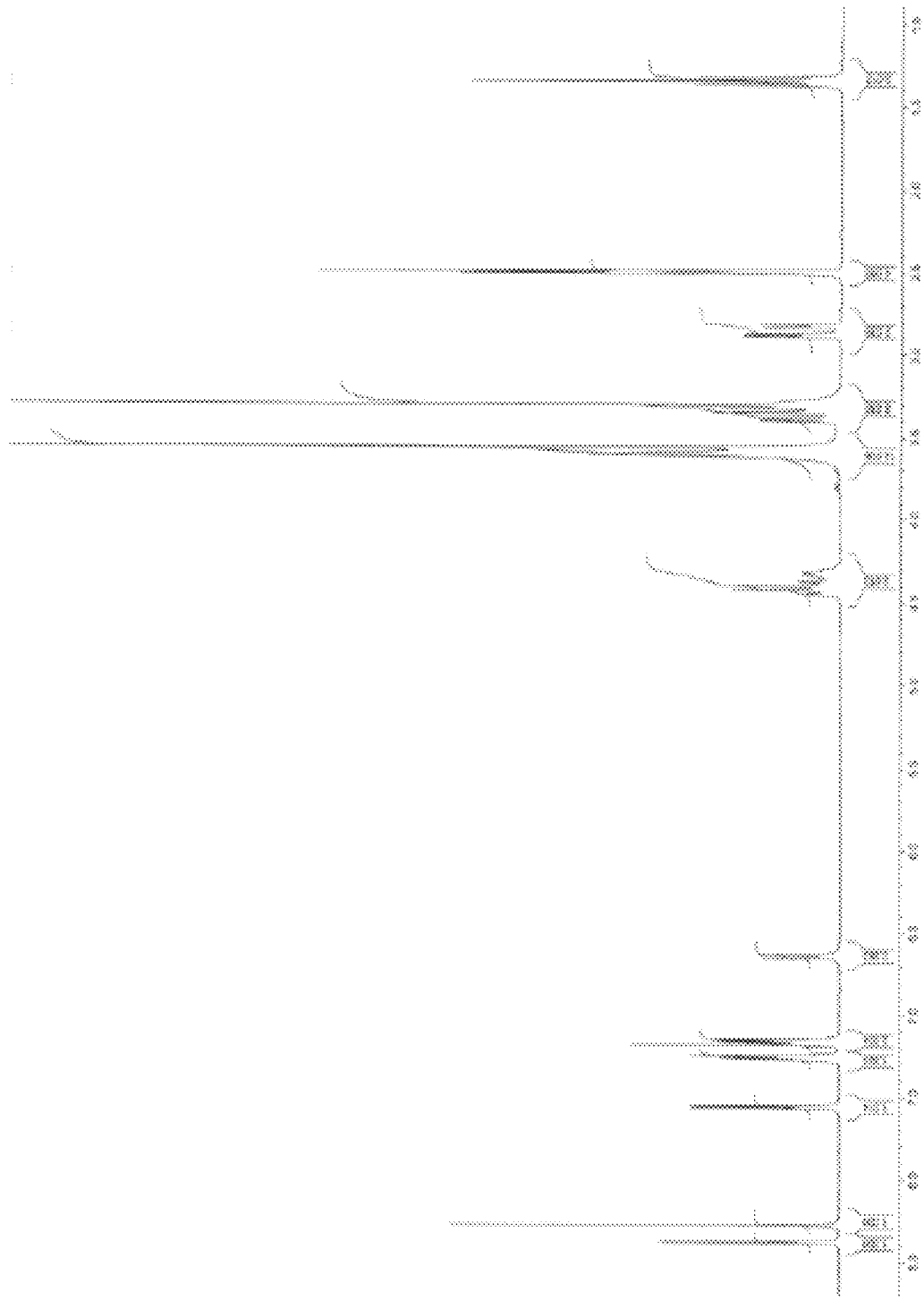
FIG. 74 depicts a $^1$H-NMR spectrum of Form K.

The $^1$H-NMR spectrum (FIG. 74) agrees with the given structure. The measured sample contains ~1 eq. dioxane which is in good agreement with the TG-FTIR measurement.

Thus, Form K is likely a dioxane solvate of compound 1.

Example 26. Drying Experiments on Form K

A sample of Form K (PP445-P46) was dried in an attempt to desolvate it (as sample PP445-P46-T1). The solid material PP445-P46 was stored under vacuum (<5 mbar) at r.t. for 3 days. The solvent included in the sample before and after drying was 16.1% dioxane and 7.7% dioxane (with some water), respectively.

The XRPD pattern of the dried sample shows only few broad peaks of low intensity indicating that the dried sample is of lower crystallinity compared to the material before drying.

The TG-FTIR thermogram shows the loss of ~7.7 wt % dioxane (with some water) from 50° C. to 230° C. Decomposition starts at temperatures T>230° C.

Thus, a partial desolvation has likely occurred parallel to a break-down of the crystal structure of Form K. No transformation into a known or new crystalline form was observed.

Example 27. Preparation and Characterization of Form L

Form L (such as sample PP445-P14) was obtained from a vapor diffusion experiment on compound 1 involving pyridine and hexane. In one set of experiments, 99.7 mg of compound 1 (sample PP445-P1) were dissolved in 0.7 mL of pyridine to obtain an almost clear, light yellow solution. Filtered solution through 0.2-µm PTFE membrane and stored open vial in atmosphere saturated with hexane at r.t. Observed white precipitate after 2 d. Removed liquid phase to give Form L (sample PP445-P14).

Figure 34:
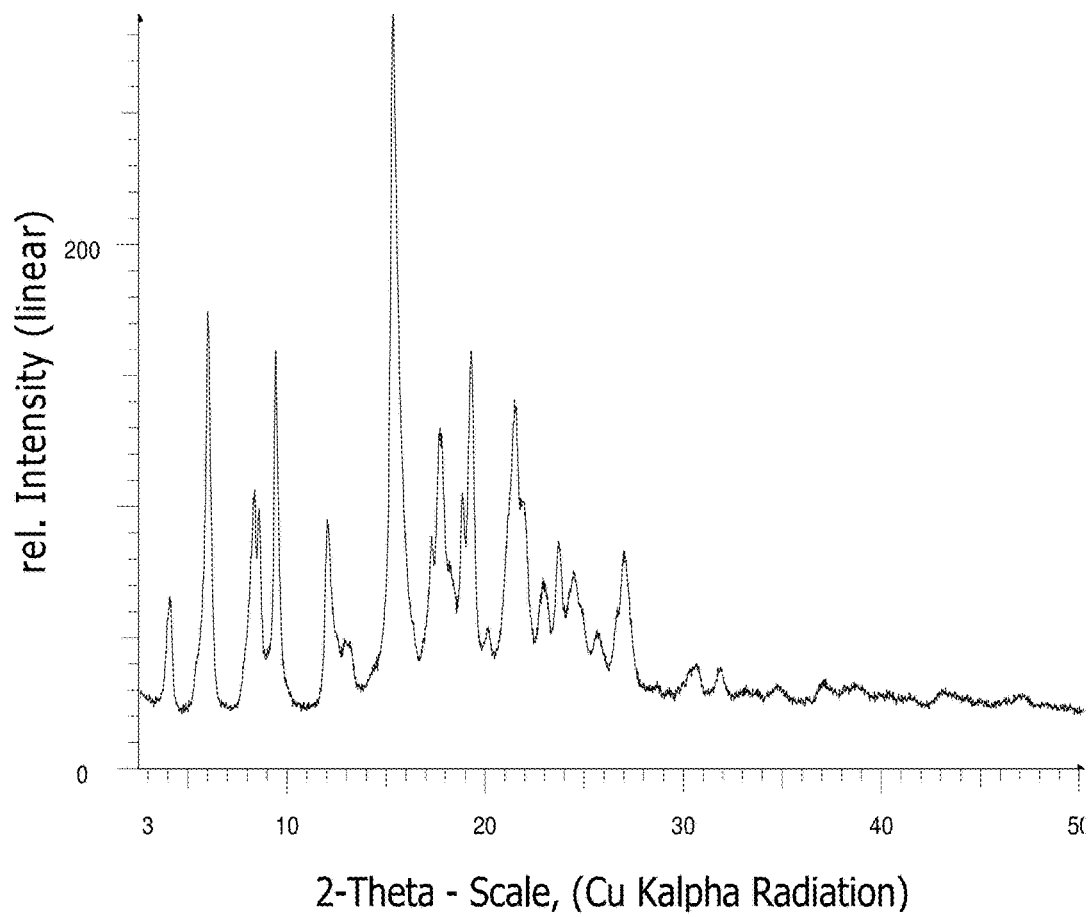
FIG. 34 depicts an XRPD pattern of Form L.

The FT-Raman spectrum and XRPD pattern of Form L are given in FIG. 35 and FIG. 34, respectively.

The TG-FTIR thermogram (FIG. 36) shows the loss of ~5.1 wt % pyridine (~0.3 eq.) from 50° C. to 200° C. and decomposition at temperatures T>200° C. The sample was dried under vacuum for 1 h before the measurement. It is likely that at least some of the pyridine content (boiling point of 115° C.) is bound within the structure and this Form L corresponds to a pyridine solvate.

Figure 75:
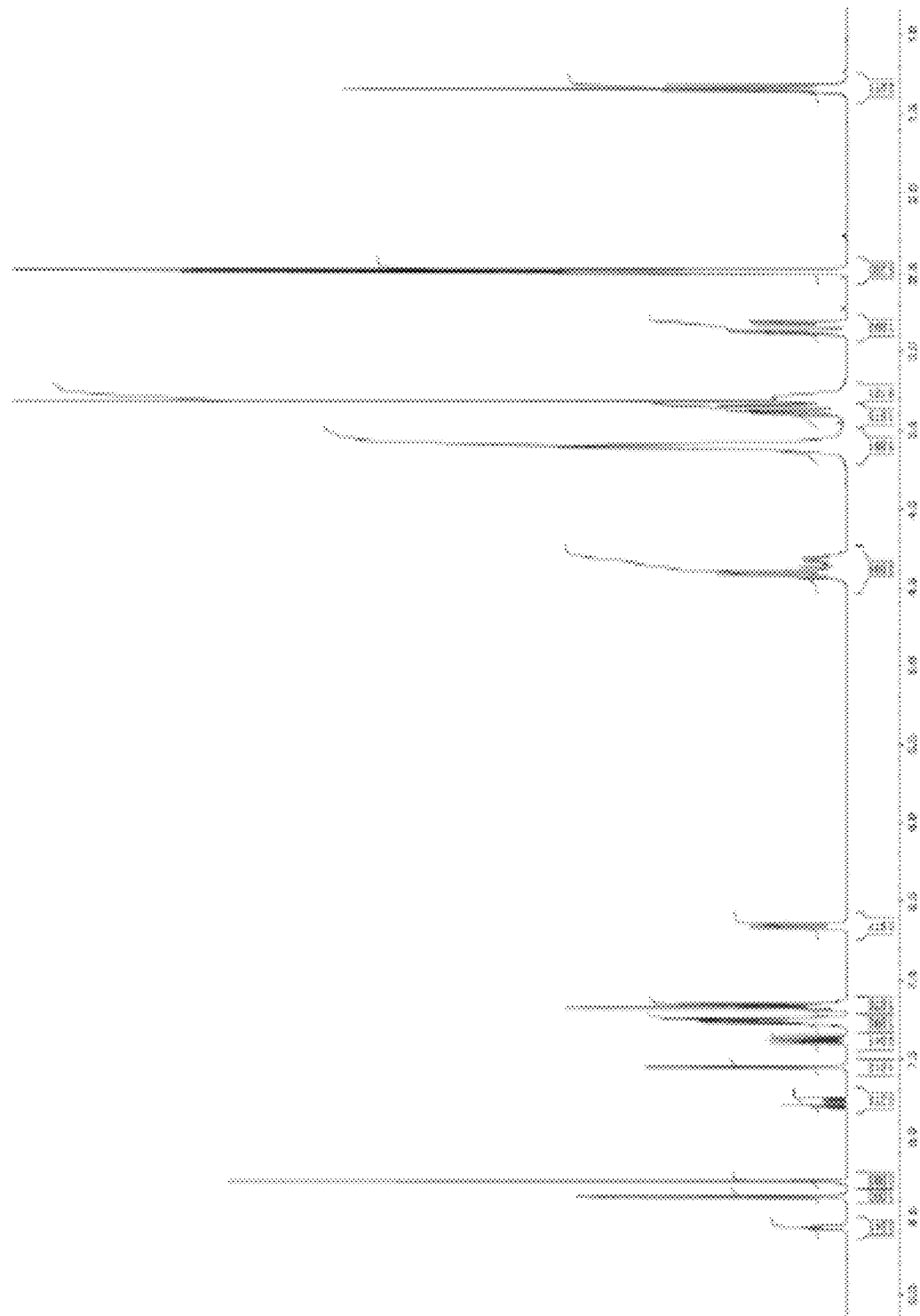
FIG. 75 depicts a $^1$H-NMR spectrum of Form L.

The $^1$H-NMR spectrum (FIG. 75) agrees with the given structure and a pyridine content of ~0.3 eq, in good agreement with the TG-FTIR measurement.

Thus, Form L is likely a pyridine solvate of compound 1.

Example 28. Drying Experiments on Form L

A sample of Form L (PP445-P14) was dried in an attempt to desolvate it (as sample PP445-P14-T1). The solid material was stored under vacuum (<5 mbar) at 40° C. overnight. The solvent included in the sample before and after drying was 5.1% pyridine and 1.4% pyridine, respectively.

The XRPD pattern of the dried sample is unchanged compared to the pattern of the material before drying.

The TG-FTIR thermogram shows the loss of ~1.4 wt % pyridine from 50° C. to 240° C.

Thus, a partial desolvation has likely occurred, and no change in structure was observed.

The pyridine loss in this dried sample occurs at temperatures significantly above the boiling point of 115° C., indicating that at least some of the pyridine of Form L is bound within the structure. Thus, Form L is likely a pyridine solvate.

Example 29. Preparation and Characterization of Form M

Form M (such as sample PP445-P12) was obtained from a vapor diffusion experiment on compound 1 involving DMSO and TBME (t-butyl methyl ether). In one set of experiments, 99.7 mg of compound 1 (sample PP445-P1) were dissolved in 5.0 mL of DMSO to obtain an almost clear, light yellow solution. Filtered solution through 0.2-µm PTFE membrane. Stored open vial in atmosphere saturated with TBME at r.t. and after one month observed clear solution. Stored clear solution at 4° C. and after 3 d observed light yellow precipitate. Let sample warm to r.t. and recovered precipitate by vacuum filtration (P4 pore size) to yield Form M (sample PP445-P12) as a light yellow solid material.

Figure 37:
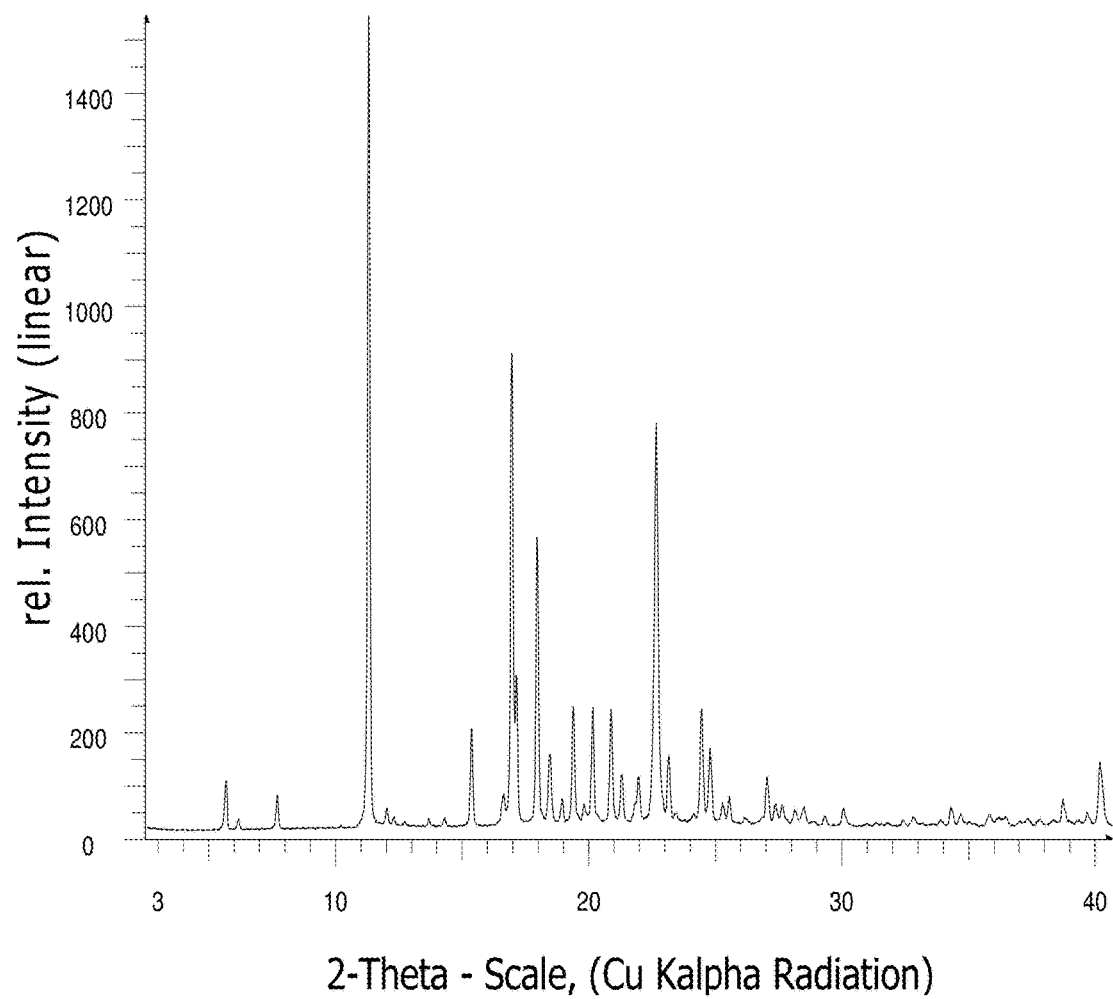
FIG. 37 depicts an XRPD pattern of Form M.

The FT-Raman spectrum and XRPD pattern of Form M are given in FIG. 38 and FIG. 37, respectively.

The TG-FTIR thermogram (FIG. 39) shows the loss of 17.8 wt % DMSO (with traces of $H_2O$) from 50° C. to 350° C. As most of the solvent content (corresponding to ~1.2 eq.) is lost significantly above the boiling point of DMSO (b.p.=189° C.), it is likely that Form M corresponds to a DMSO solvate.

Figure 76:
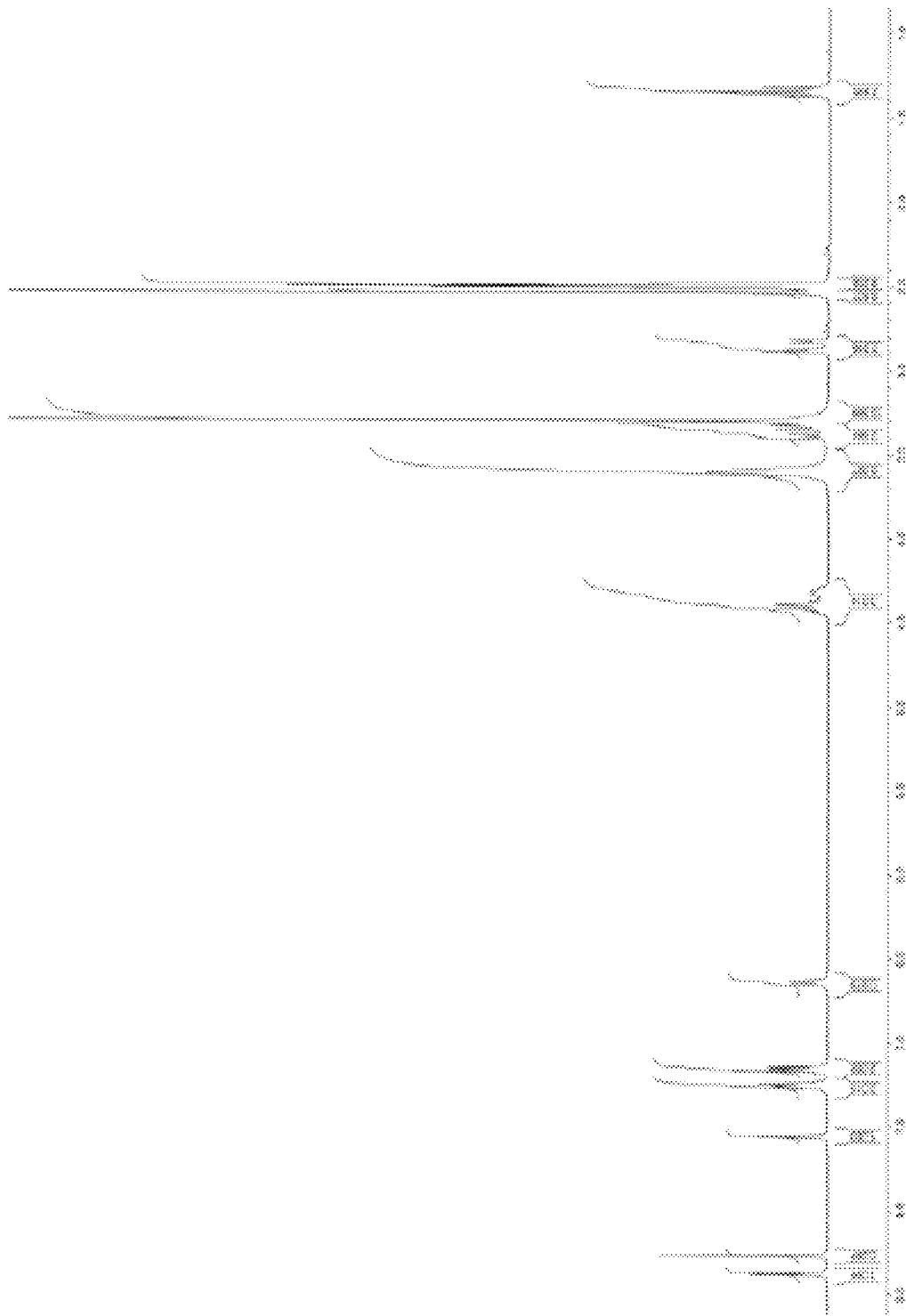
FIG. 76 depicts a $^1$H-NMR spectrum of Form M.

The $^1$H-NMR spectrum (FIG. 76) agrees with the structure of the compound 1 and contains (in addition to the deuterated $d_6$-DMSO solvent) ~1.5 eq. non-deuterated DMSO.

Thus, Form M is likely a DMSO solvate of compound 1.

Example 30. Preparation and Characterization of Form FUM-P3

Form FUM-P3 (such as sample SP196-FUM-P3) was prepared by combining concentrated solutions of the fumaric acid (a salt former) and of compound 1 (free drug) in acetone (1:1 ratio of fumaric acid to compound 1). Spontaneous precipitation of a crystalline solid occurred. The solvent was partially evaporated under $N_2$ flow. The resulting suspension was equilibrated between 40° C. and 20° C. overnight. The solid material was recovered, dried under vacuum and characterized. In one set of experiments, 27.8 mg of fumaric acid were dissolved in 6.0 mL of acetone to obtain a clear solution. Added 9.6 mL of SP196-FD-stock solution (1:1 ratio of FD to sf) to obtain a light yellow solution. The SP196-FD-stock solution was prepared by dissolving 438.5 mg of compound 1 (sample PP445-P1=sample SP196-FD-P1) in 42.0 mL of acetone, obtaining a clear solution, and filtering the solution through a 0.2-μm PTFE membrane. Stirred solution at r.t. and after 2 h observed yellow suspension. Partially evaporated solvent under $N_2$ flow, sonicated suspension for 5 min, and equilibrated suspension with temperature cycling (holding for 1 h at 20° C., heating in 1 h to 30° C., holding for 1 h at 30° C., cooling in 1 h to 20° C., repeating) overnight. Recovered solid by filter centrifugation (0.45-μm PTFE membrane) to yield Form FUM-P3 (sample SP196-FUM-P3).

The FT-Raman spectrum of product of the scale-up experiment SP196-FUM-P3 corresponds reasonably well to the spectrum of the salt screening lead (SP196-FUM-P2-F1b, FIG. 41).

The XRPD pattern of SP196-FUM-P3 (FIG. 40) confirms the crystallinity of the material.

Figure 77:
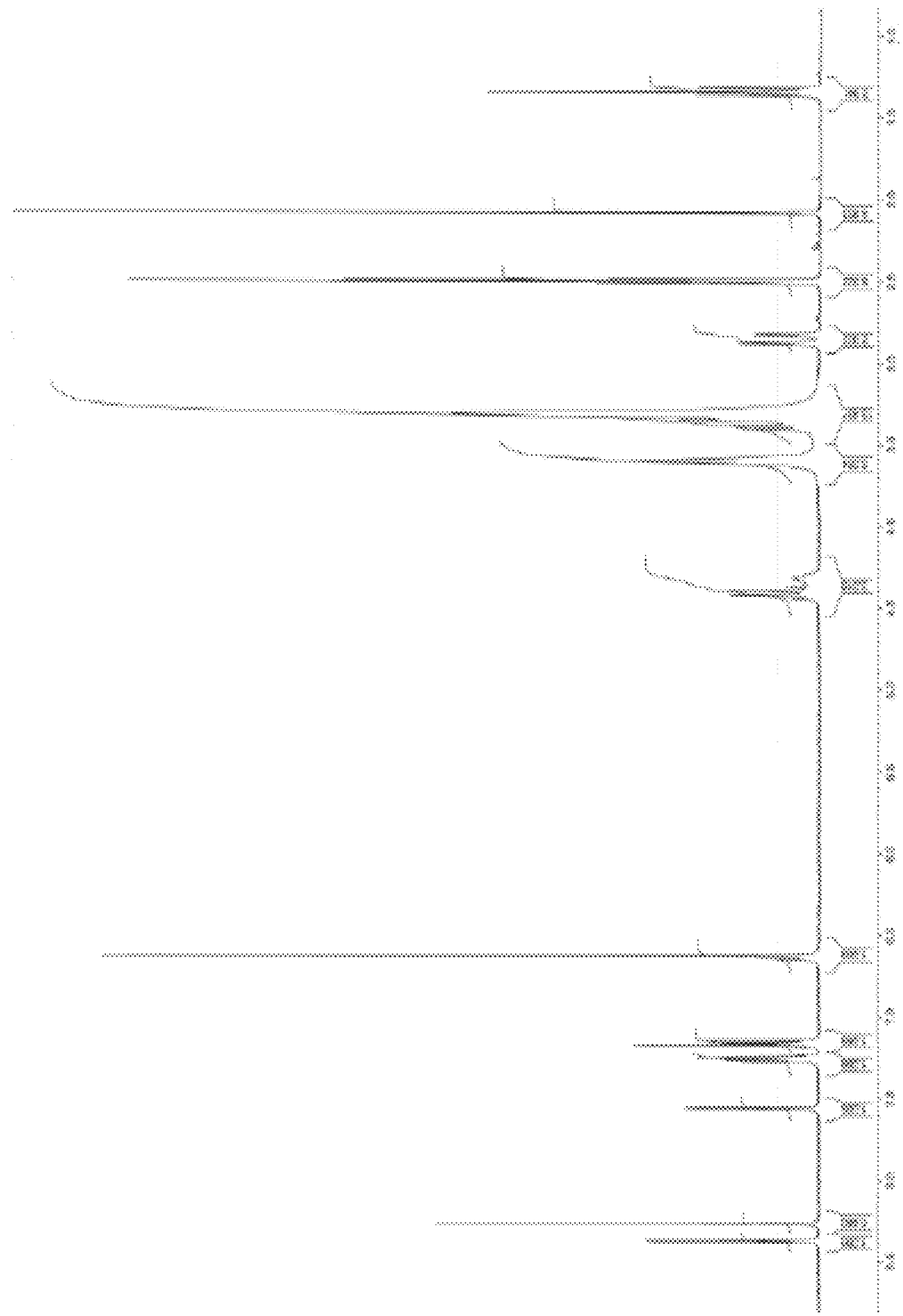
FIG. 77 depicts a $^1$H-NMR spectrum of Form FUM-P3.

The $^1$H-NMR spectrum of SP196-FUM-P3 agrees with the structure of the free drug and a fumaric acid content of 0.5 eq. (FIG. 77). The sample also contains ~0.8 eq. acetone.

The TG-FTIR thermogram of SP196-FUM-P3 (FIG. 44) shows the loss of ~8.9 wt % acetone from 50° C. to 200° C. and decomposition at temperatures T>200° C. The loss seems to occur in two steps and corresponds to 0.8 eq. of acetone assuming a hemi-fumarate salt (2:1 ratio of free drug to salt former) in agreement with the $^1$H-NMR spectrum. As the solvent loss occurs significantly above the boiling point of acetone (b.p.=56° C.), the solvent is most likely bound within the structure.

The elemental composition analysis complies with a 1:0.5:0.5 ratio of free drug to salt former to acetone solvent content (Table 74).

TABLE 74

Elemental analysis results of SP196-FUM-P3.

| | % C | % H | % N | % O | Σ |
|---|---|---|---|---|---|
| SP196-FUM-P3 (experimental) | 64.7 | 6.1 | 11.0 | 17.5 | 99.3 |
| SP196-FUM-P3 (exp., normalized to 100% $C_{24}H_{26}N_4O_3$, $C_4H_4O_4$ (theoretical 1:1 salt) | 65.2 | 6.1 | 11.1 | 17.6 | 100.0 |
| | 62.9 | 5.7 | 10.5 | 20.9 | 100.0 |
| difference (exp. (norm.) — theo.) | 2.3[a] | 0.4[a] | 0.6[a] | −3.3[a] | — |
| $C_{24}H_{26}N_4O_3$, 0.5 × $C_4H_4O_4$, 0.5 × $C_3H_6O$ (theoretical 1:0.5 salt with 0.5 eq. acetone) | 65.3 | 6.2 | 11.1 | 17.4 | 100.0 |
| difference (exp. (norm) — theo.) | −0.1 | −0.1 | 0.0 | 0.2 | — |

[a]Differences that exceed a measurement error of ±0 3%.

Thus, Form FUM-P3 may be a hemi-acetone solvate (0.5 eq. acetone) of a hemi fumarate salt (0.5 eq. salt former).

The DSC thermogram of SP196-FUM-P3 (FIG. 42) shows several endothermic and exothermic events, starting at about 114° C., which are difficult to interpret and assign at this point. The melting point of the free fumaric acid salt former is at about 287° C.

At the beginning of the DVS experiment (FIG. 43), the sample mass decreased by 1.2 wt % after 2 h equilibration at 50% r.h. Upon increasing the relative humidity to 95% r.h., the sample mass decreased further by 2.9 wt % (with a total mass loss relative to the starting weight of 4.1 wt %). No equilibrium was reached at 95% r.h. after 5 h equilibration. Upon decreasing the relative humidity from 95% r.h. to 0% r.h. the sample lost 1.7 wt % gradually (with a total mass loss relative to the starting weight of 5.7 wt %). After 5 h equilibration at 0% r.h. the mass remained stable and equilibrium was reached. Increasing the relative humidity back to 50%, the mass increased by 0.8 wt %. Thus, the final mass remained 4.9 wt % below the starting mass.

The FT-Raman spectrum of the material after the DVS measurement (FIG. 41) corresponds mainly to the spectrum of the free drug starting material (SP196-FD-P1=PP445-P1, corresponding to a hydrate), with additional components of the fumarate salt SP196-FUM-P3 and of the free fumaric acid salt former.

Thus, it is conceivable that most (or all) of the acetone (0.5 eq. correspond to 5.7 wt %), and maybe also some of fumaric acid salt former (0.5 eq. correspond to 11.5 wt %) is lost during the DVS cycle (with a total mass loss of 5.7 wt % at 0% r.h.) and partially replaced by water to partially transform the salt into the free drug hydrate.

Example 31. Preparation and Characterization of Form FUM-P4

Form FUM-P4 (such as sample SP196-FUM-P4) was prepared by adding compound 1 (free drug) to a saturated solution of the fumaric acid (salt former) in THF at 40° C. (in order to prevent formation of a THF solvate of the free drug). The resulting suspension was equilibrated at 40° C. for two days. The solid material was recovered, dried under vacuum, and characterized. In one set of experiments, 100.6 mg of fumaric acid were dissolved at 40° C. in 2.0 mL of THE to obtain a clear solution. Added stepwise solid compound 1 (sample SP196-FD-P1) until light yellow suspension formed. Equilibrated suspension at 40° C. while stirring overnight. Observed very thin suspension the next day. Added spatula tip of solid SP196-FD-P1 material, continued equilibration at 40° C., and after 1 d recovered solid by filter centrifugation (0.2-µm PTFE membrane) to yield Form FUM-P4 (sample SP196-FUM-P4).

The FT-Raman spectrum of the scale-up experiment SP196-FUM-P4 could correspond to the spectrum of the scale-up sample SP196-FUM-P3 with some small shifts and differences. The spectrum also contains THF peaks (FIG. 46).

Figure 45:
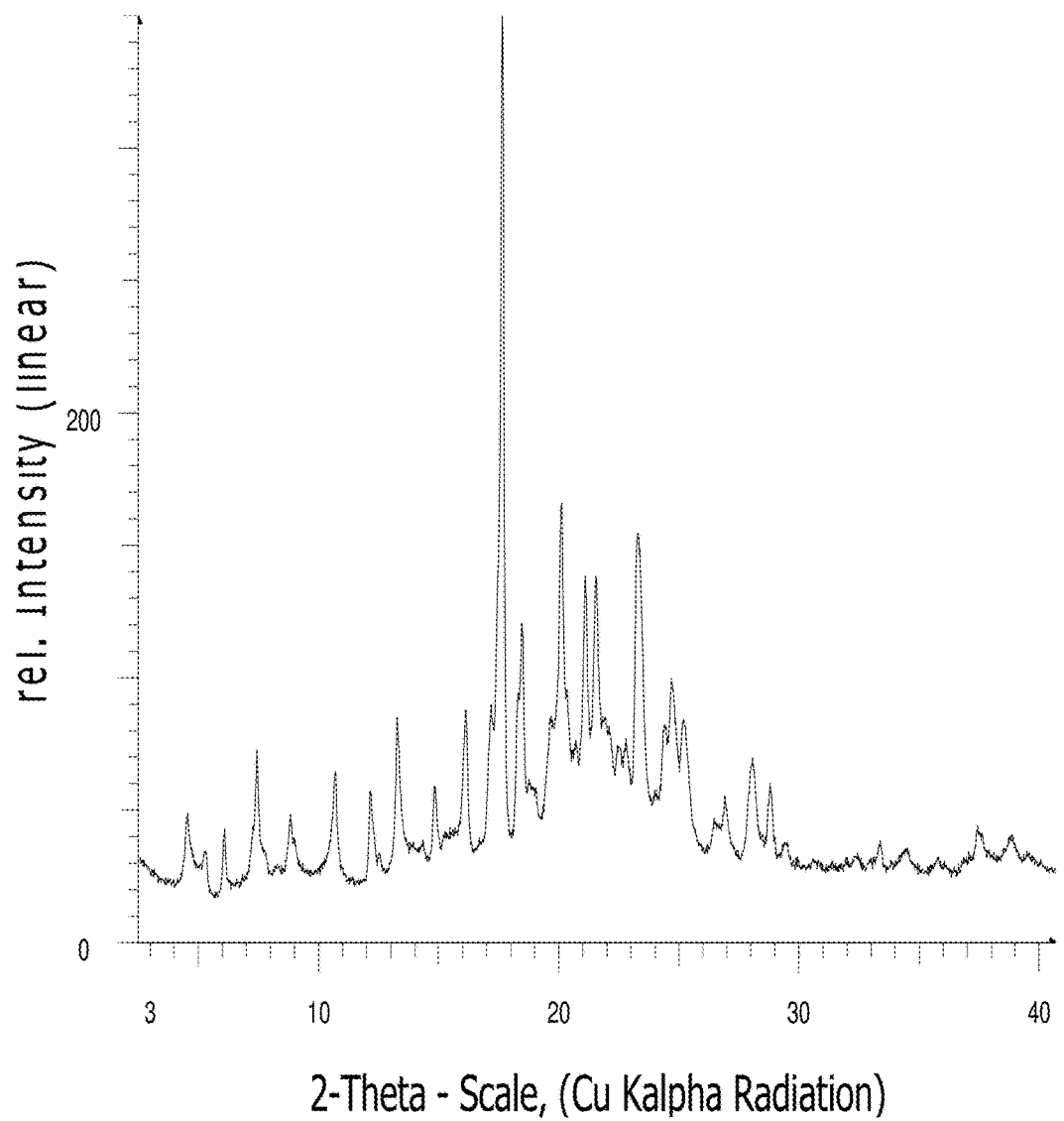
FIG. 45 depicts an XRPD pattern of Form FUM-P4.

The XRPD pattern of the scale-up experiment SP196-FUM-P4 shows broad peaks with a low resolution. The pattern could correspond to the pattern of the scale-up sample SP196-FUM-P3 with some small shifts and differences (FIG. 45).

Figure 78:
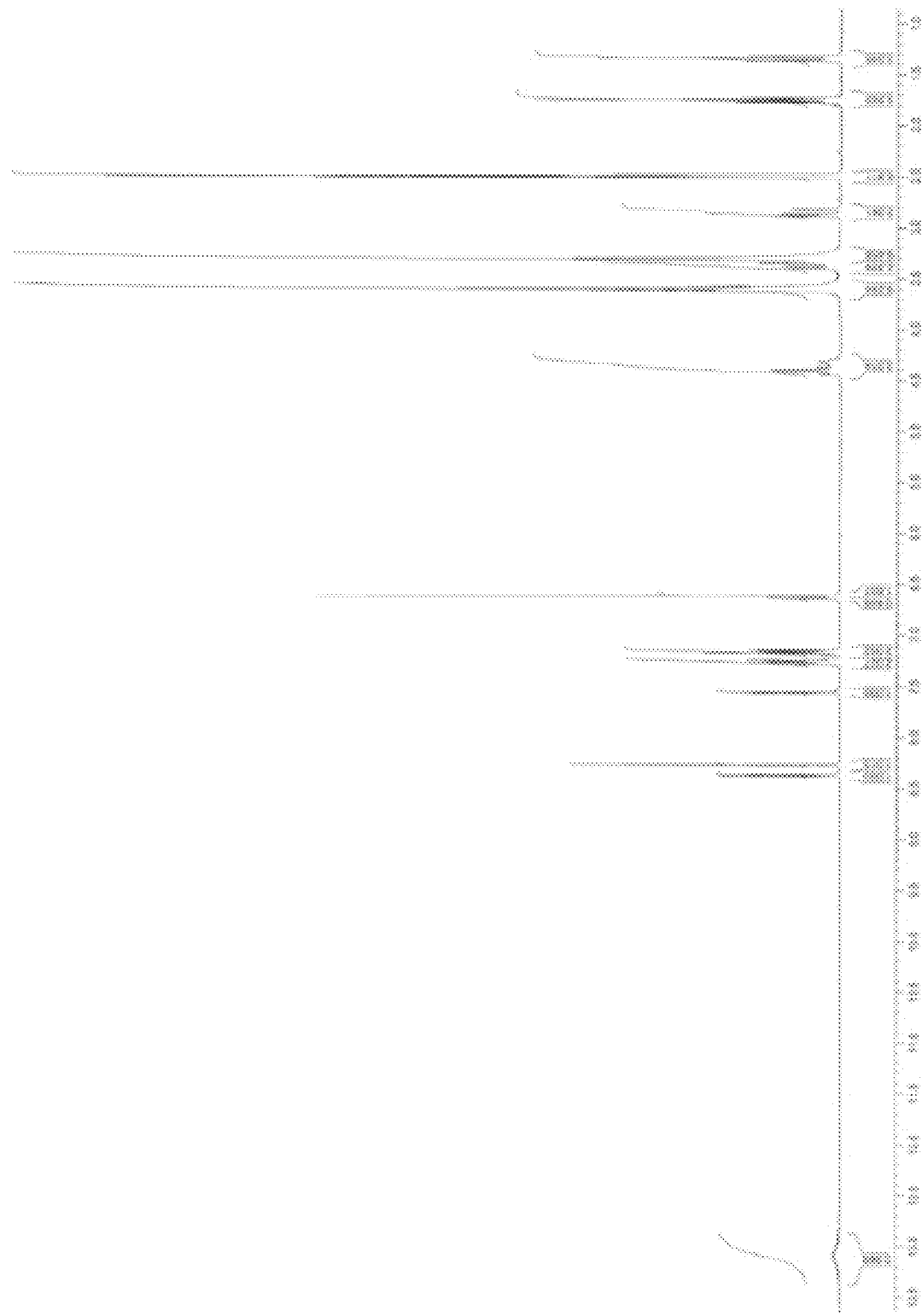
FIG. 78 depicts a $^1$H-NMR spectrum of Form FUM-P4.

The $^1$H-NMR spectrum of the scale-up sample SP196-FUM-P4 agrees with the structure of the free drug and a fumaric acid salt former content of ~1.0 eq. (FIG. 78). The sample also contains ~0.8 eq. THF.

The TG-FTIR thermogram of the scale-up sample SP196-FUM-P4 (FIG. 47) shows the loss of ~11.3 wt % THF from 50° C. to 200° C. and decomposition at temperatures T>200° C. The loss corresponds to 0.8 eq. of a fumarate salt (1:1 ratio of free drug to salt former) in agreement with the $^1$H-NMR spectrum. As the solvent loss occurs significantly above the boiling point of THF (b.p.=66° C.), the solvent is most likely bound within the structure.

Thus, the material likely corresponds to a THF solvate of a mono-fumarate salt. As the FT-Raman spectrum and XRPD pattern of this THF solvate are very similar to the spectrum/pattern of the acetone solvate (SP196-FUM-P3), these two solvates could be isomorphous/isostructural. However, it is interesting to note, that the acetone solvate (FUM-P3) seems to correspond to a hemi-salt (with 0.5 eq. solvent content), while the THF solvate (FUM-P4) is likely a mono-salt (with ~0.8 to ~1.0 eq. solvent content).

Example 32. Preparation and Characterization of Form MLA-P3

Form MLA-P3 (e.g., sample SP196-MLA-P3) was prepared by combining concentrated solutions of L-malic acid (salt former) and of compound 1 (free drug) in acetone. The solvent was partially evaporated under $N_2$ flow. After spontaneous precipitation of a crystalline solid, the suspension was equilibrated between 40° C. and 20° C. overnight. The solid material was recovered, dried under vacuum, and characterized. In one set of experiments, 32.1 mg of L-malic acid were dissolved in 0.3 mL of acetone to obtain a clear solution. Added 9.6 mL of SP196-FD-stock solution (1:1 ratio of FD to sf) to obtain a light yellow solution. Stirred solution at r.t. and after 2 h observed yellow suspension. Partially evaporated solvent under $N_2$ flow, sonicated suspension for 5 min, and equilibrated suspension with temperature cycling (holding for 1 h at 20° C., heating in 1 h to 30° C., holding for 1 h at 30° C., cooling in 1 h to 20° C., repeating) overnight. Recovered solid by filter centrifugation (0.2-µm PTFE membrane) to yield Form MLA-P3 (sample SP196-MLA-P3).

The FT-Raman spectrum is shown in FIG. 49.

The XRPD pattern of the salt scale-up sample SP196-MLA-P3 (FIG. 48) is very similar to the pattern of sample SP196-SUC-P3, suggesting that these two forms are isomorphic/isostructural. The pattern does not correspond to any known pattern of the free drug.

Figure 79:
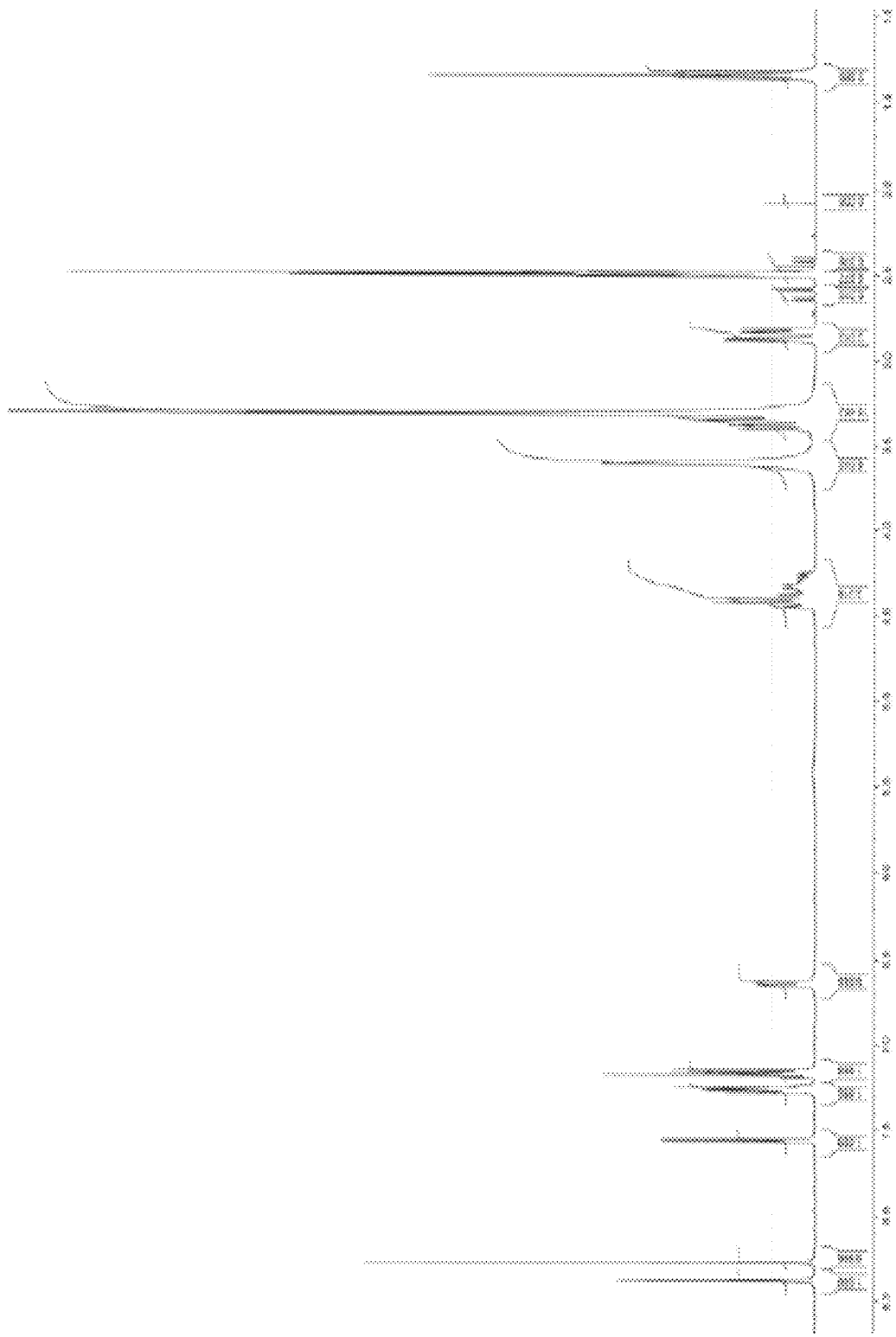
FIG. 79 depicts a $^1$H-NMR spectrum of Form MLA-P3.

The $^1$H-NMR spectrum of SP196-MLA-P3 (FIG. 79) agrees with the structure of the free drug. The sample contains ~0.3 eq. L-malic acid salt former and <0.01 eq. acetone solvent residue.

The DSC thermogram (FIG. 50) shows a sharp endothermic event with a peak at $T_{max}$=212.3° C. ($\Delta$H=94.4 J/g), likely corresponding to melting, and no further event up to 230° C. It has to be noted, that the peak maximum is shifted compared to the DSC thermogram of sample SP196-SUC-P3 (peak at $T_{max}$=219.1° C.) by ~7° C.

The similar XRPD patterns of the SP196-MLA-P3 and SP196-SUC-P3 samples suggested that both correspond not to salts but to one and the same form of the free drug. However, the differences of peaks maxima in the DSC thermograms indicate that these two sample indeed correspond to two different salts (that have nearly identical lattice structures, i.e., are isomorphic). The similar structure of the L-malic acid and succinic acid salt formers can possibly provide an explanation for the similarity of the XRPD patterns.

Example 33. Preparation and Characterization of Form MLA-P4

Form MLA-P4 (e.g., sample SP196-MLA-P4) was prepared by adding solid compound 1 (free drug) to a saturated solution of the L-malic acid (salt former) in MeCN. The resulting suspension was equilibrated under temperature cycling (20° C.-30° C.) for two days. The solid material was recovered, dried under vacuum, and characterized. In one set of experiments, 47.2 mg of L-malic acid salt former were dissolved in 1.0 mL of acetone to obtain a clear solution. Added stepwise several spatula tips of solid SP196-FD-P1 until light suspension formed, sonicated suspension for 1 min, and obtained thicker suspension. Equilibrated suspension with temperature cycling (holding for 1 h at 20° C., heating in 1 h to 30° C., holding for 1 h at 30° C., cooling in 1 h to 20° C., repeating) for 2 d. Recovered solid by filter centrifugation (0.2-µm PTFE membrane) to yield Form MLA-P4 (sample SP196-MLA-P4).

The FT-Raman spectrum of the scale-up sample SP196-MLA-P4 is shown in FIG. 52.

The XRPD pattern (FIG. 51) confirms the crystallinity of the material. The pattern does not correspond to any known pattern of the free drug.

Figure 80:
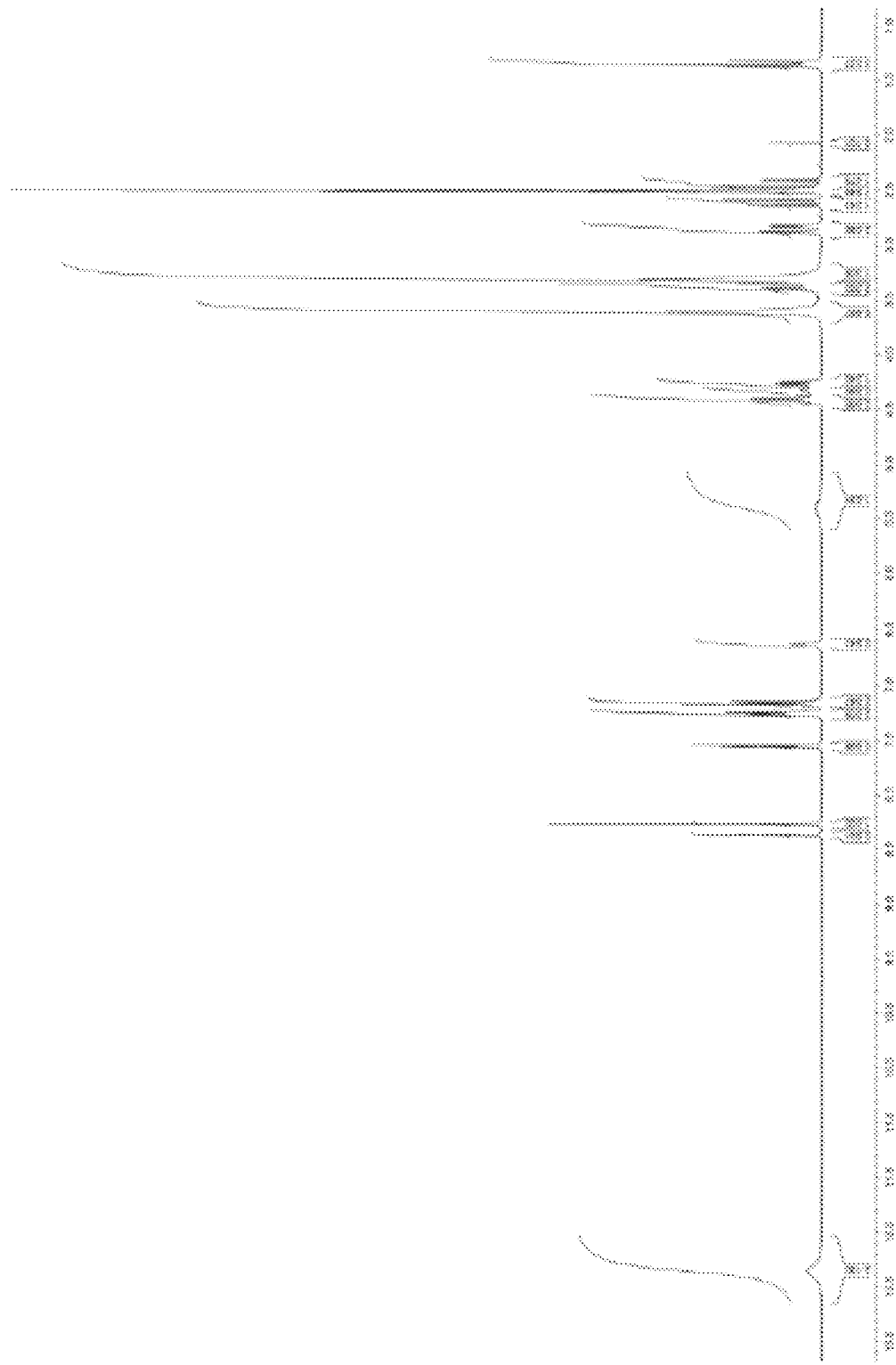
FIG. 80 depicts a $^1$H-NMR spectrum of Form MLA-P4.

The $^1$H-NMR spectrum (FIG. 80) agrees with the structure of the free drug, a L-malic acid salt former content of ~1.0-1.2 eq., and no solvent contributions.

The elemental composition analysis complies with a 1:2 ratio of free drug to salt former with ~0.6 wt % $H_2O$ (~0.2 eq.), in agreement with the TG-FTIR and NMR results.

The TG-FTIR thermogram (FIG. 55) shows the loss of ~0.6 wt % $H_2O$ from 50° C. to 140° C. and decomposition at temperatures T>140° C. The sample likely corresponds to an anhydrous form and not a hydrate, as the small amount of water is likely unbound.

The DSC thermogram (FIG. 53) shows several endothermic and exothermic events starting at about 92° C.

The DVS isotherm (FIG. 54) shows a reversible mass loss of ~2.5 wt % upon decreasing the relative humidity from 50% r.h. to 0%. Equilibrium was reached at 0% r.h. Upon increasing the relative humidity from 50% r.h. to 95% r.h. a sudden mass increase of ~6.4 wt % is observed between ~52% and 62% r.h., followed by a more gradual mass increase just above 62% r.h. and then again an increase in the rate up to 95% r.h. (total mass increase of ~46.6 wt % from 50% r.h. to 95% r.h.). No equilibrium was reached at 95% r.h. Upon decreasing the relative humidity from 95% r.h. to 50% r.h., a gradual mass loss occurred and the final mass remained ~4.2 wt % above the starting mass.

The mass increase of ~17.6 wt % from 50% to 85% r.h. indicates that Form MLA-P4 is very hygroscopic.

The FT-Raman spectrum of the material after the DVS measurement corresponds to the spectrum of the material before the DVS measurement.

Example 34. Preparation and Characterization of Form SUC-P3

Form SUC-P3 (e.g., sample SP196-SUC-P3) was prepared by combining concentrated solutions of succinic acid (salt former) and of compound 1 (flee drug) in acetone. The solvent was partially evaporated under $N_2$ flow. After spontaneous precipitation of a crystalline solid, the suspension was equilibrated between 40° C. and 20° C. overnight. The solid material was recovered, dried under vacuum, and characterized. In one set of experiments, 28.2 mg of succinic acid were dissolved in 1.2 mL of acetone to obtain a clear solution. Added 9.6 mL of SP196-FD-stock solution (1:1 ratio of FD to sf) to obtain a light yellow solution. Stirred solution at r.t. and after 2 h observed yellow suspension. Partially evaporated solvent under $N_2$ flow, sonicated suspension for 5 min, and added 0.5 mL of acetone. Equilibrated suspension with temperature cycling (holding for 1 h at 20° C., heating in 1 h to 30° C., holding for 1 h at 30° C., cooling in 1 h to 20° C., repeating) overnight. Recovered solid by filter centrifugation (0.2-μm PTFE membrane) to yield Form SUC-P3 (sample SP196-SUC-P3).

The FT-Raman spectrum is shown in FIG. 57.

The XRPD pattern (FIG. 56) is very similar to the pattern of sample SP196-MLA-P3. The pattern does not correspond to any known pattern of the free drug.

Figure 81:
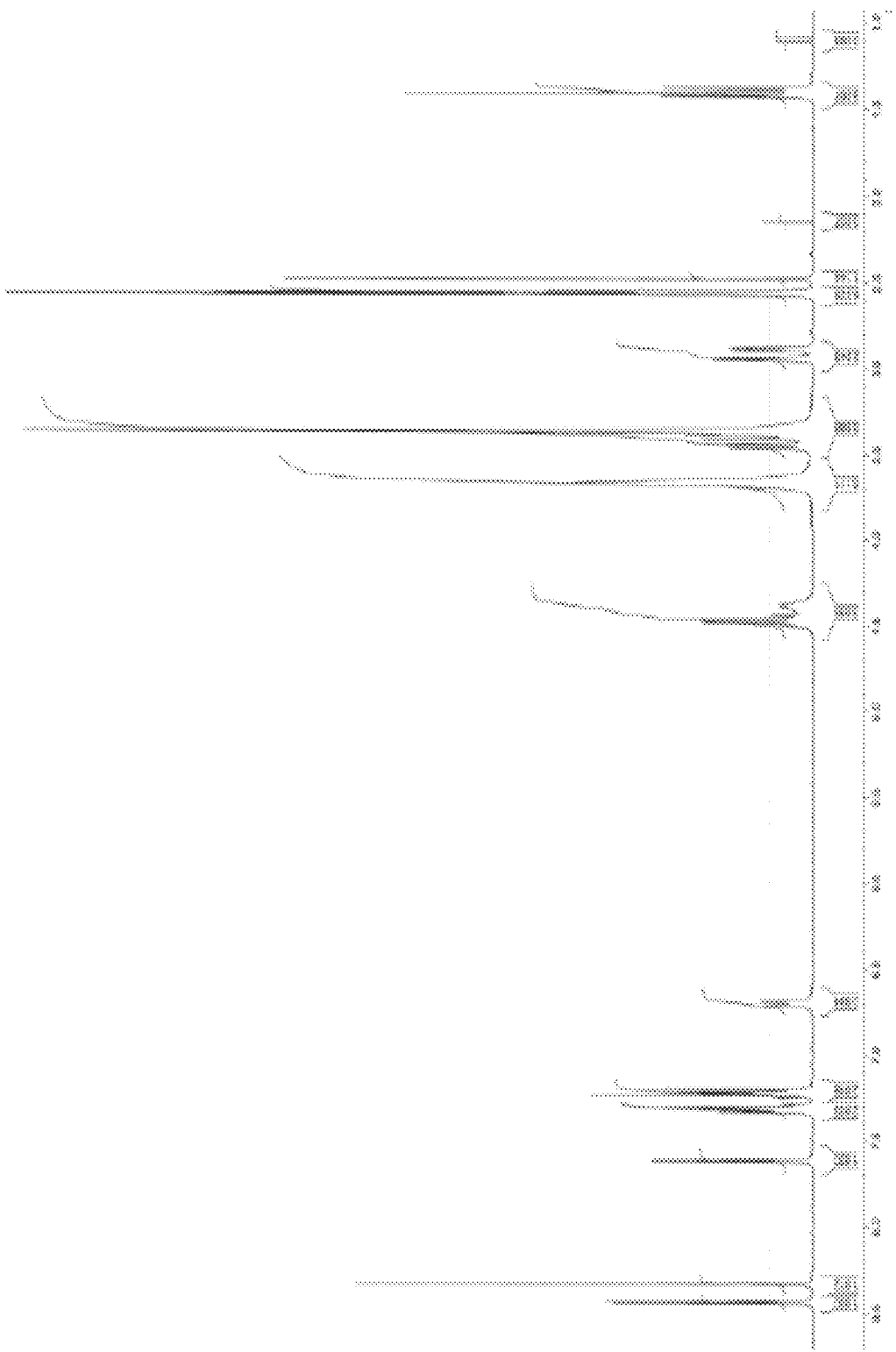
FIG. 81 depicts a $^1$H-NMR spectrum of Form SUC-P3.

The $^1$H-NMR spectrum (FIG. 81) agrees with the structure of a succinate of compound 1. The sample contains ~0.3 eq. succinic acid salt former and <0.01 eq. acetone solvent residue.

The TG-FTIR thermogram (FIG. 59) shows no mass loss from 50° C. to 180° C. and decomposition at temperatures T>180° C.

The DSC thermogram (FIG. 58) shows a sharp endothermic event with a peak at $T_{max}$=219.2° C. (ΔH=102.7 J/g), likely corresponding to melting, and no further event up to 250° C. The peak maximum is shifted compared to the DSC thermogram of sample SP196-MLA-P3 (peak at $T_{max}$=212.3° C.) by ~7° C.

The similar XRPD patterns of the SP196-MLA-P3 and SP196-SUC-P3 samples at first suggested that both correspond not to salts but rather to one and the same form of the free drug. However, the difference between the peak maxima in the DSC thermograms indicates that these two samples indeed correspond to two different salt forms with nearly identical lattice structures. The similar structures of the L-malic acid and succinic acid salt formers can maybe provide an explanation for the similarity of the XRPD patterns.

Example 35. Preparation and Characterization of Form SUC-P4

Form SUC-P4 (e.g., sample SP196-SUC-P4) was prepared by combining concentrated solutions of succinic acid (salt former) and of compound 1 (free drug) in MeCN. Spontaneous precipitation of a crystalline solid occurred. The suspension was equilibrated for 2 h. The solid material was recovered, dried under vacuum, and characterized. In one set of experiments, 102.1 mg of compound 1 (sample SP196-FD-P1) were dissolved in 13.0 mL of MeCN, and the solution was filtered through 0.2-μm PTFE membrane to obtain a clear solution. Dissolved 28.0 mg of succinic acid salt former in 4.6 mL of MeCN and filtered solution through 0.2-μm PTFE membrane. Combined the two solutions and sonicated solution for 1 h. Solution remained clear. Stirred solution at r.t. and after 1 h observed light yellow suspension. Equilibrated suspension for 2 h; recovered solid by vacuum filtration (P4 pore size) to yield Form SUC-P4 (sample SP196-SUC-P4).

The FT-Raman spectrum of the scale-up sample SP196-SUC-P4 is shown in FIG. 61.

The XRPD pattern of SP196-SUC-P4 (FIG. 60) confirms the crystallinity of the material. The pattern does not correspond to any known pattern of the free drug.

Figure 82:
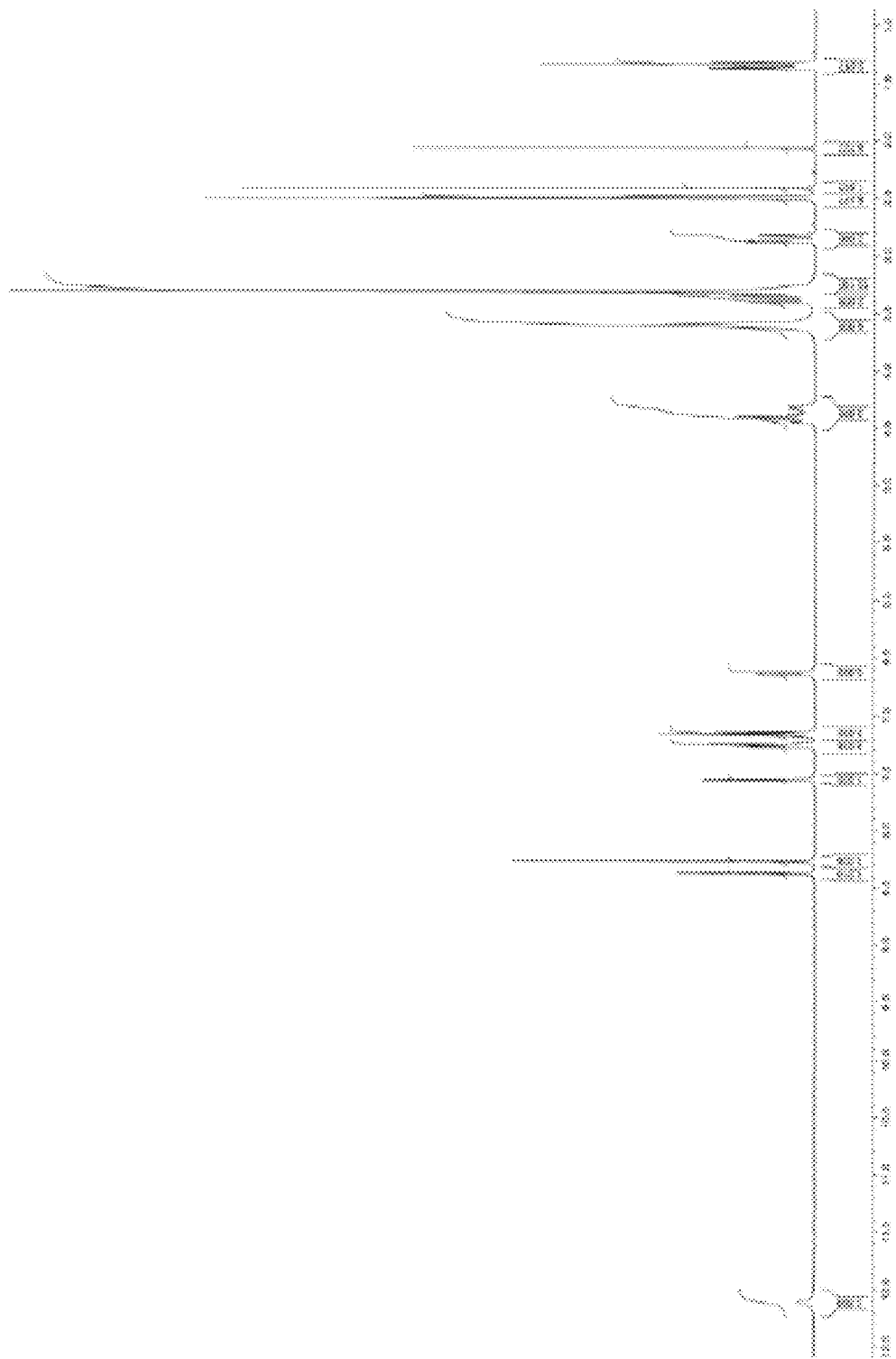
FIG. 82 depicts a $^1$H-NMR spectrum of Form SUC-P4.

The $^1$H-NMR spectrum of SP196-SUC-P4 (FIG. 82) agrees with the structure of a succinate of compound 1. The sample contains ~0.45 eq. succinic acid salt former and ~0.24 eq. MeCN solvent residues.

The TG-FTIR thermogram of SP196-SUC-P4 (data not shown) shows the gradual loss of ~2.1 wt % $H_2O$ and MeCN from 25° C. to 150° C. Most of this loss, however, occurs before or at the boiling point of the solvents. Thus, the solvent content is likely due to unbound surface water/solvent. To confirm this hypothesis, the sample was dried under vacuum at r.t. and re-analyzed (as sample SUC-P4a) by XRPD and TG-FTIR. The XRPD pattern (data not shown) is unchanged.

The TG-FTIR thermogram of this dried sample SP196-SUC-P4a (FIG. 64) shows no significant mass loss from 25° C. to 170° C. and decomposition at temperatures T>170° C. Thus, this sample likely corresponds to an anhydrous form.

The elemental composition analysis (sample SP196-SUC-P4a) complies with a 1:0.5 ratio of free drug to salt former (Table 75).

TABLE 75

Elemental analysis results of SP196-SUC-P4a.

| | % C | % H | % N | % O | Σ |
|---|---|---|---|---|---|
| SP196-SUC-P4a (experimental) | 65.3 | 5.8 | 12.0 | 16.4 | 99.5 |
| SP196-SUC-P4a (exp., normalized to 100%) | 65.6 | 5.9 | 12.0 | 16.5 | 100.0 |
| $C_{24}H_{26}N_4O_3$, $C_4H_4O_4$ (theoretical 1:1 salt) | 62.7 | 6.0 | 10.4 | 20.9 | 100.0 |
| difference (exp. (norm.) — theo.) | 2.9[a] | −0.1 | 1.6[a] | −4.4[a] | — |
| $C_{24}H_{26}N_4O_3$, 0.5 × $C_4H_4O_4$ (theoretical 1:0.5 salt) | 65.6 | 6.1 | 11.8 | 16.5 | 100.0 |
| difference (exp. (norm) — theo.) | 0.0 | −0.2 | 0.2 | 0.0 | — |

[a]Differences that exceed a measurement error of ±0.3%.

Thus, the material of SUC-P4/P4a likely corresponds to an anhydrous hemi-succinate salt of compound 1 (1:0.5 ratio of free drug to salt former).

The DSC thermogram (FIG. 62) shows a small endothermic event with a peak at $T_{max}$=169.1° C. (ΔH=6.7 J/g) and a larger endothermic event with two peaks at $T_{max}$=212.2° C. and $T_{max}$=215.4° C. (total ΔH=92.6 J/g), and no further event up to 250° C. The melting point of free succinic acid salt former is at about 184° C.

The DVS isotherm (FIG. 63) shows a reversible mass loss of ~0.6 wt % upon decreasing the relative humidity from 50% r.h. to 0%. Equilibrium was reached at 0% r.h. Upon increasing the relative humidity from 50% r.h. to 95% r.h. a sudden mass increase of ~1.6 wt % is observed between 50% and 60% r.h., afterwards a more gradual mass increase of ~2.6 wt % between 60% and 95% r.h. (total mass increase of ~4.2 wt % from 50% r.h. to 95% r.h.). No equilibrium was reached at 95% r.h. Upon decreasing the relative humidity from 95% r.h. to 50% r.h., a gradual mass loss of ~2.1 wt % occurred between 95% r.h. and 60% r.h., and a more sudden mass loss of ~2.0 wt % between 60% and 50% r.h. The final mass remained ~0.1 wt % above the starting mass.

The mass increase of ~2.5 wt % from 50% to 85% r.h. indicates that Form SUC-P4 is hygroscopic.

The FT-Raman spectrum of the material after the DVS measurement corresponds to the spectrum of the material before the DVS measurement.

Example 36. Preparation and Characterization of Form SUC-P5

Form SUC-P5 (e.g., SUC-P5 Sample 1) was prepared by combining hot solutions of succinic acid (salt former) and of compound 1 (free drug) in EtOAc, followed by slowly cooling to room temperature. Spontaneous precipitation of a crystalline solid occurred at 50° C. The suspension was equilibrated for 1 h. The solid material was recovered, dried under vacuum, and characterized. In scale-up experiment, form SUC-P5 (e.g., SUC-P5 Sample 1) was prepared by mixing the hot solutions of succinic acid (salt former) and of compound 1 (free drug) in EtOAc at about 70° C., followed by cooling to 65° C. and addition of slurry of seeds (SUC-P5 Sample 1) in EtOAc. The mixture was then stirred at 55-65° C. for 1 hour and then slowly cooled to room temperature and the suspension was equilibrated for 16 h. The solid material was recovered, dried under vacuum, and characterized.

The XRPD pattern of SUC-P5 (three different batches SUC-P5 Sample 1, SUC-P5 Sample 2, SUC-P5 Sample 3) (FIG. 87) confirms the crystallinity of the material. The pattern does not correspond to any known pattern of the free drug.

Figure 89:
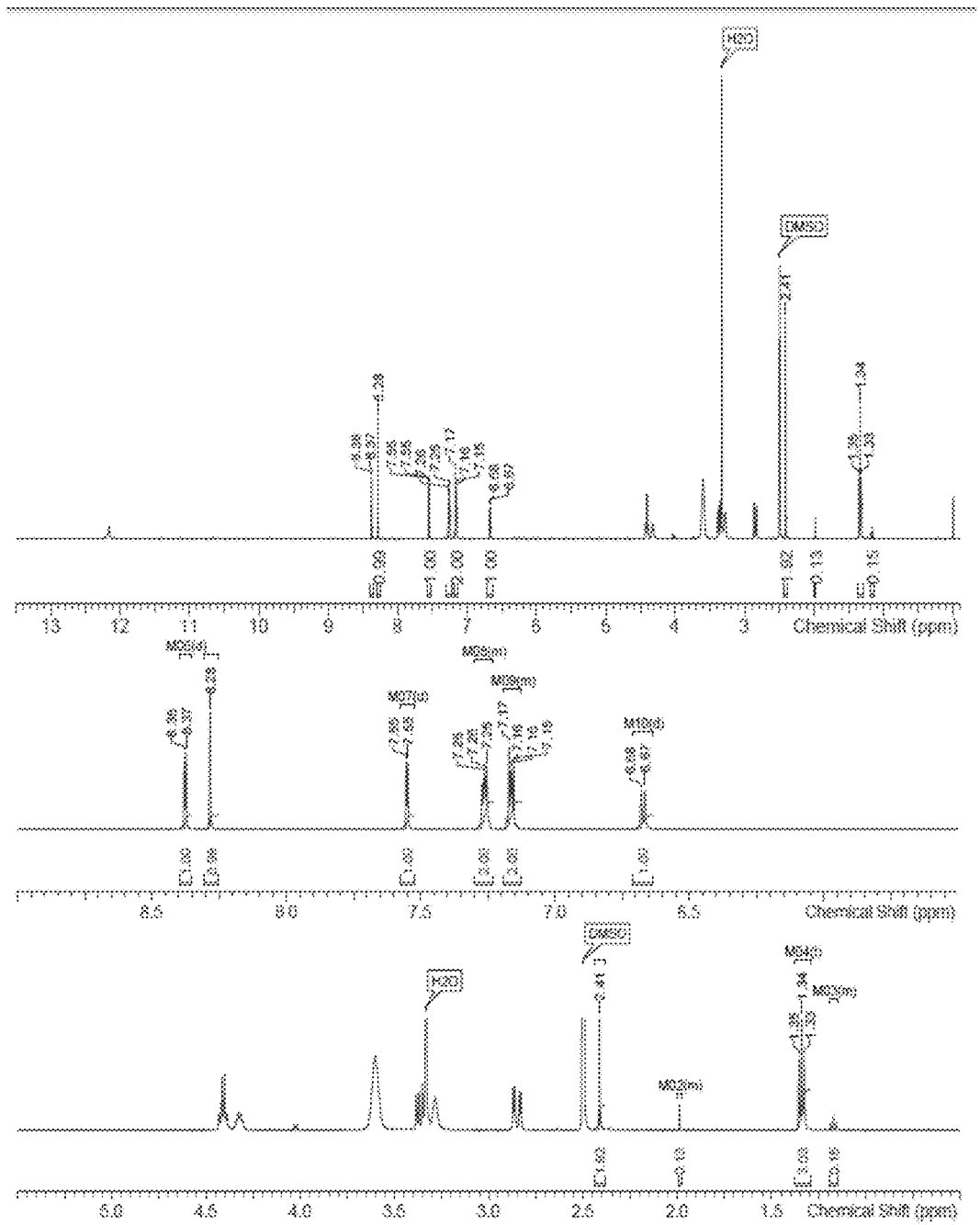
FIG. 89 depicts a 1H-NMR spectrum of Form SUC-P5.

The $^1$H-NMR spectrum of SUC-P5 Sample 1 (FIG. 89) agrees with the structure of a succinate of compound 1. The sample contains ~0.5 eq. succinic acid salt former and ~0.1 eq. EtOAc solvent residues. The $^1$H-NMR spectrum of dried sample SUC-P5 Sample 1 shows the loss of the significant amount of EtOAc.

The DSC thermogram (FIG. 88) shows an endothermic event with a peak at 207-208° C., with an approximately 7-8% weight loss up to that point. No further event occurred to 300° C. The melting point of free succinic acid salt former is at about 184° C.

Example 37. Preparation and Characterization of Form MLE-P4

The FT-Raman spectrum of the salt scale-up sample SP196-MLE-P4 is shown in FIG. 66. The sample could contain a small amount of free maleic acid salt former. In one set of experiments, 106.2 mg of maleic acid salt former were dissolved in 1.0 mL of MeCN to obtain a clear solution. Added stepwise several spatula tips of solid compound 1 (sample SP196-FD-P1) until light suspension formed. Sonicated suspension for 1 min to obtain a thicker suspension. Equilibrated suspension with temperature cycling (holding for 1 h at 20° C., heating in 1 h to 30° C., holding for 1 h at 30° C., cooling in 1 h to 20° C., repeating) for 2 d. Recovered solid by filter centrifugation (0.2-μm PTFE membrane) to yield Form MLE-P4 (sample SP196-MLE-P4).

The XRPD pattern (FIG. 65) confirms the crystallinity of the material. The pattern does not correspond to any known pattern of the compound 1 free drug. The sample could contain a small amount of free maleic acid salt former.

Figure 83:
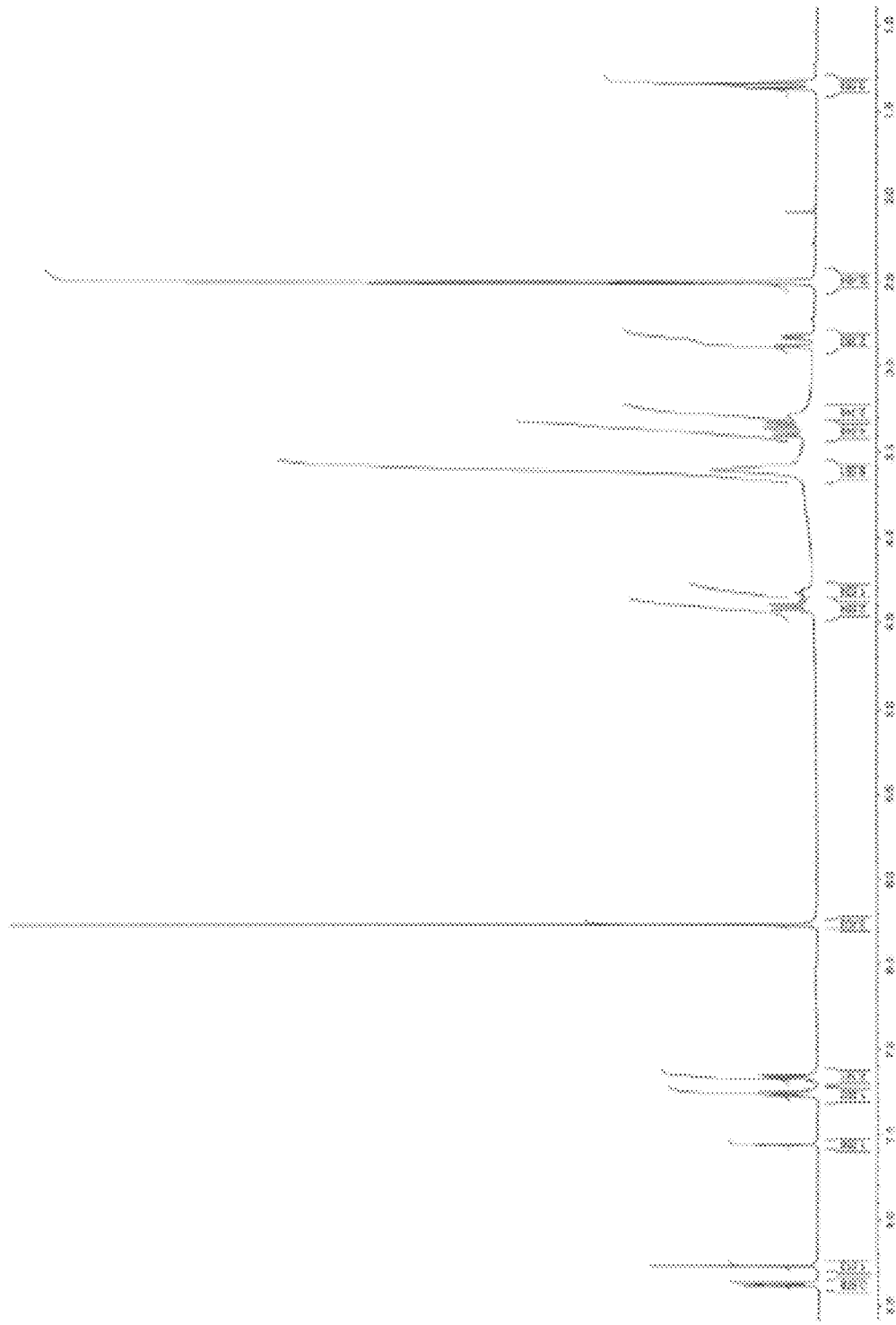
FIG. 83 depicts a $^1$H-NMR spectrum of Form MLE-P4.

The $^1$H-NMR spectrum (FIG. 83) agrees with the structure of a maleate of compound 1 (maleic acid salt former content: ~1.7 eq.; no solvent content).

The TG-FTIR thermogram (FIG. 68) shows no mass loss from 25° C. to 120° C., the loss of ~16.3 wt % (~0.7 eq.) maleic acid (with some water) from 120° C. to 250° C. and decomposition at temperatures T>250° C. Thus, the sample likely corresponds to an anhydrous form with low thermal stability.

The DSC thermogram (FIG. 67) shows a sharp endotherm with a peak at $T_{max}$=112.8° C. ($\Delta H \approx 55.5$ J/g), followed by further endothermic events with a second significant peak at $T_{max}$=139.9° C. (total $\Delta H$=51.3 J/g). Decomposition likely starts at T>145° C. The free maleic acid salt former decomposes before melting at about 135° C.

Example 38. Preparation and Characterization of Form MLE-P6

Form MLE-P6 was prepared according to the following method. In a 25 ml conical flask, compound 1 (100 mg) was dissolved in acetone at 50-55° C., and maleic acid (30 mg) was added to the solution. The solution becomes clear by shaking at 50-55° C. for 5 min. The solution was quickly filtered through a filter paper (e.g., in a second) into a clean 25 ml conical flask and left undisturbed at ambient temperature with very slight evaporation. The sharp needles separated were filtered and dried by passing air and then under high vacuum for 1 hour.

The melting point Form MLE-P6 was about 140-150° C. $^1$HNMR (CDCl$_3$): δ 8.37 (d, 1H, J=3.0 Hz), 8.28 (s, 1H), 7.55 (d, 1H, J=3.0 Hz), 7.28-7.15 (m, 4H), 6.29 (bs, 1H), 6.26 (s, 1H), 4.44-4.31 (m, 3H), 3.40-3.28 (m, 9H), 2.88-2.81 (m, 2H), 2.08 (s, 1.5H), 1.34 (t, 3H, J=6.9 Hz) ppm.

Example 39. Preparation and Characterization of Tartrate Salt

The tartrate salt of compound 1 was prepared according to the following method. In a 25 ml conical flask compound 1 (418 mg) was dissolved in acetone (15 ml) at about 50-55° C., and tartaric acid (150 mg, 1.0 equivalent) was added to the solution. The solution was heated with shaking at about 50-55° C. for 10 min to dissolve all solids. The hot solution was quickly filtered through a filter paper in to a clean 25 ml conical flask and left undisturbed at ambient temperature with very slight evaporation. The resulting rod-shaped crystals were filtered, dried by passing air, and then subject to high vacuum for 1 hour.

The melting point of the tartrate salt was about 140-200° C. (decomposition).

$^1$HNMR (DMSO-d$_6$): δ8.41 (d, 1-t, J=3.3 Hz), 8.32 (s, 1H), 7.59 (d, 1H, J=3.0 Hz), 7.32-7.18 (m, 4H), 6.29 (bd, 1H, J=6.6 Hz), 5.14 (bs, 1H), 4.83-4.41 (m, 5H), 3.44-3.30 (m, 9H), 2.92-2.85 (m, 2H), 2.12 (s, 2H), 1.38 (t, 3H, J=6.9 Hz) ppm.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A hemi-succinate salt of the crystalline Form SUC-P5 of compound 1:

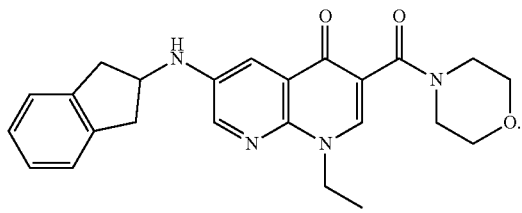

2. The crystalline Form SUC-P5 of claim 1, wherein the crystalline Form SUC-P5 is substantially free of impurities.

3. The crystalline Form SUC-P5 of claim 1, wherein the crystalline Form SUC-P5 is substantially free of amorphous compound 1.

4. The crystalline Form SUC-P5 of claim 1, wherein the crystalline Form SUC-P5 has two or more peaks in its x-ray powder diffraction (XRPD) pattern selected from those in the following table:

| Angle 2-Theta ° |
|---|
| 7.4 |
| 15.6 |
| 16.5 |
| 18.5 |
| 22.2 |

5. The crystalline Form SUC-P5 of claim 1, wherein the crystalline Form SUC-P5 has four or more peaks in its XRPD pattern selected from those in the following table:

| Angle 2-Theta ° |
|---|
| 7.4 |
| 8.3 |
| 10.5 |
| 11.7 |
| 13.2 |
| 15.6 |
| 16.5 |
| 18.5 |
| 22.2 |

6. The crystalline Form SUC-P5 of claim 1, wherein the crystalline Form SUC-P5 is characterized by a differential scanning calorimetry (DSC) thermogram with an endotherm having a peak temperature ($T_{max}$) of about 207° C.

7. The crystalline Form SUC-P5 of claim 1, wherein the crystalline Form SUC-P5 is characterized by a DSC thermogram with a ΔH of about 6.7 J/g or about 92.6 J/g.

8. A pharmaceutical composition comprising the crystalline form SUC-P5 of claim 1, and optionally a pharmaceutically acceptable excipient.

9. The pharmaceutical composition of claim 8, wherein the crystalline form SUC-P5 is of a therapeutically effective amount.

10. A method of treating an anxiety disorder or depression in a subject in need thereof, the method comprising administering to the subject a therapeutically effective amount of a pharmaceutical composition of claim 8.

11. The method of claim 10, wherein the depression is major depressive disorder (MDD), bipolar disorder (BD), atypical depression, melancholic depression, psychotic major depression, catatonic depression, postpartum depression, seasonal affective disorder, dysthymia, a depressive disorder not otherwise specified (DD-NOS), or a substance induced mood disorder.

12. The method of claim 10, wherein the anxiety disorder is panic disorder, obsessive-compulsive disorder (OCD), post-traumatic stress disorder (PTSD), generalized anxiety disorder (GAD), substance-induced anxiety disorder, acute stress disorder (ASD), irritable bowel syndrome, or fibromyalgia.

13. The method of claim 10, wherein the anxiety disorder is a phobia.

14. The method of claim 10, wherein the phobia is social phobia, agoraphobia, or animal phobia.

15. The method of claim 10, wherein the subject is a human.

* * * * *